(12) United States Patent
Witschel et al.

(10) Patent No.: US 7,115,545 B1
(45) Date of Patent: Oct. 3, 2006

(54) TRICYCLIC BENZOYLPYRAZOLE DERIVATIVES USED AS A HERBICIDE

(75) Inventors: Matthias Witschel, Ludwigshafen (DE); Steffen Kudis, Mannheim (DE); Klaus Langemann, Worms (DE); Ernst Baumann, Dudenhofen (DE); Wolfgang von Deyn, Neustadt (DE); Guido Mayer, Neustadt (DE); Ulf Misslitz, Neustadt (DE); Ulf Neidlein, Mannheim (DE); Martina Otten, Ludwigshafen (DE); Karl-Otto Westphalen, Speyer (DE); Helmut Walter, Obrigheim (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 09/936,356

(22) PCT Filed: Mar. 8, 2000

(86) PCT No.: PCT/EP00/02010

§ 371 (c)(1),
(2), (4) Date: Sep. 11, 2001

(87) PCT Pub. No.: WO00/55158

PCT Pub. Date: Sep. 21, 2000

(30) Foreign Application Priority Data

Mar. 12, 1999 (DE) ................................ 199 11 219

(51) Int. Cl.
*A01N 43/80* (2006.01)
*A61K 31/423* (2006.01)
*C07D 261/20* (2006.01)

(52) U.S. Cl. ........................ 504/271; 548/241; 514/379
(58) Field of Classification Search ............... 514/379; 548/241; 504/271
See application file for complete search history.

(56) References Cited

U.S. PATENT DOCUMENTS 5,049,564 A 9/1991 DeBernardis

FOREIGN PATENT DOCUMENTS

| EP | 365 201 | 4/1990 |
| EP | 860 441 | 8/1998 |
| JP | 10130267 | 8/1996 |
| WO | 97/08164 | 3/1997 |
| WO | 97/19087 | 5/1997 |

OTHER PUBLICATIONS

Database Crossfile XP-0021425478,Kim et al. J. Pharm. Sci. 82(4), 355 (1933) and 82 (5), 521 (1993) Database Crossfile XP-002142549 De et al., Synth.Comm. 18 (5), 481 (1988).

*Primary Examiner*—Kamal A. Saeed
*Assistant Examiner*—Rebecca Anderson
(74) *Attorney, Agent, or Firm*—Novak Druce & Quigg LLP

(57) ABSTRACT

Tricyclic benzoylpyrazole derivatives of the formula I

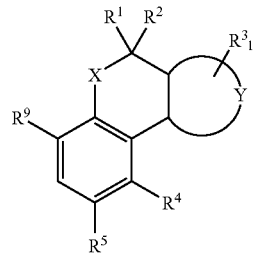

wherein X, Y, $R^1$, $R^2$, $R^6$, $R^7$, $R^3$, $R^4$, $R^5$, 1, $R^8$ and $R^9$ are as defined in the disclosure and their agriculturally useful salts; processes and intermediates for preparing the tricyclic benzoylpyrazole derivatives; compositions comprising them and the use of these derivatives or of the compositions comprising them for controlling undesirable plants are described.

18 Claims, No Drawings

TRICYCLIC BENZOYLPYRAZOLE DERIVATIVES USED AS A HERBICIDE

This application is a 371 of PCT/EP00/02010 filed Mar. 8, 2000.

The present invention relates to novel tricyclic benzoylpyrazole derivatives of the formula I

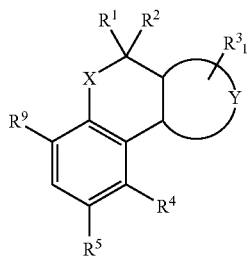

where:
X is oxygen, sulfur, S=O, S(=O)$_2$, CR$^6$R$^7$, NR$^8$ or a bond;
Y together with the two carbons to which it is attached forms a saturated, partially saturated or unsaturated 5- or 6-membered heterocycle which contains one to three identical or different heteroatoms selected from the following group:
oxygen, sulfur or nitrogen;
R$^1$,R$^2$,R$^6$,R$^7$ are hydrogen, C$_1$–C$_6$-alkyl, C$_1$–C$_6$-haloalkyl, C$_1$–C$_6$-alkoxy or C$_1$–C$_6$-haloalkoxy;
R$^3$ is halogen, C$_1$–C$_6$-alkyl, C$_1$–C$_6$-haloalkyl, C$_1$–C$_6$-alkoxy or C$_1$–C$_6$-haloalkoxy;
R$^4$ is hydrogen, nitro, halogen, cyano, C$_1$–C$_6$-alkyl, C$_1$–C$_6$-haloalkyl, C$_1$–C$_6$-alkoxy, C$_1$–C$_6$-haloalkoxy, C$_1$–C$_6$-alkylthio, C$_1$–C$_6$-haloalkylthio, C$_1$–C$_6$-alkylsulfinyl, C$_1$–C$_6$-haloalkylsulfinyl, C$_1$–C$_6$-alkylsulfonyl, C$_1$–C$_6$-haloalkylsulfonyl, aminosulfonyl, N-(C$_1$–C$_6$-alkyl)aminosulfonyl, N,N-di(C$_1$–C$_6$-alkyl)aminosulfonyl, N-(C$_1$–C$_6$-alkylsulfonyl)amino, N-(C$_1$–C$_6$-haloalkylsulfonyl)amino, N-(C$_1$–C$_6$-alkyl)-N-(C$_1$–C$_6$-alkylsulfonyl)amino or N-(C$_1$–C$_6$-alkyl)-N-(C$_1$–C$_6$-haloalkylsulfonyl)amino;
R$^5$ is hydrogen, C$_1$–C$_6$-alkyl or halogen;
R$^8$ is hydrogen, C$_1$–C$_6$-alkyl, C$_1$–C$_6$-haloalkyl, C$_1$–C$_6$-alkylcarbonyl, formyl, C$_1$–C$_6$-alkoxycarbonyl, C$_1$–C$_6$-haloalkoxycarbonyl, C$_1$–C$_6$-alkylsulfonyl or C$_1$–C$_6$-haloalkylsulfonyl;
l is 0, 1 or 2;
R$^9$ is a radical IIa or IIb

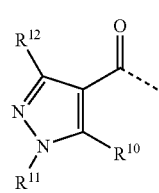

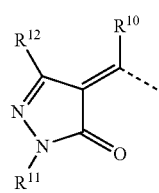

where
R$^{10}$ is hydroxyl, mercapto, halogen, OR$^{13}$, SR$^{13}$, SO$_2$R$^{14}$, NR$^{15}$R$^{16}$ or N-bonded heterocyclyl, where the heterocyclyl radical may be partially or fully halogenated and/or may carry one to three of the following radicals:
nitro, cyano, C$_1$–C$_4$-alkyl, C$_1$–C$_4$-haloalkyl, C$_1$–C$_4$-alkoxy or C$_1$–C$_4$-haloalkoxy;
R$^{11}$ is hydrogen, C$_1$–C$_6$-alkyl, C$_1$–C$_6$-haloalkyl, C$_3$–C$_6$-cycloalkyl, hydroxyl, C$_1$–C$_6$-alkoxy or C$_1$–C$_6$-haloalkoxy;
R$^{12}$ is hydrogen, halogen, C$_1$–C$_6$-alkyl, C$_1$–C$_6$-haloalkyl, hydroxyl, C$_1$–C$_6$-alkoxy, C$_1$–C$_6$-haloalkoxy, C$_1$–C$_6$-alkylthio or C$_1$–C$_6$-haloalkylthio;
R$^{13}$ is C$_1$–C$_6$-alkyl, C$_3$–C$_6$-alkenyl, C$_3$–C$_6$-haloalkenyl, C$_3$–C$_6$-alkynyl, C$_3$–C$_6$-haloalkynyl, C$_3$–C$_6$-cycloalkyl, C$_1$–C$_{20}$-alkylcarbonyl, C$_2$–C$_{20}$-alkenylcarbonyl, C$_2$–C$_6$-alkynylcarbonyl, C$_3$–C$_6$-cycloalkylcarbonyl, C$_1$–C$_6$-alkoxycarbonyl, C$_3$–C$_6$-alkenyloxycarbonyl, C$_3$–C$_6$-alkynyloxycarbonyl, C$_1$–C$_6$-alkylthiocarbonyl, C$_1$–C$_6$-alkylaminocarbonyl, C$_3$–C$_6$-alkenylaminocarbonyl, C$_3$–C$_6$-alkynylaminocarbonyl, N,N-di(C$_1$–C$_6$-alkyl)aminocarbonyl, N-(C$_3$–C$_6$-alkenyl)-N-(C$_1$–C$_6$-alkyl)aminocarbonyl, N-(C$_3$–C$_6$-alkynyl)-N-(C$_1$–C$_6$-alkyl)aminocarbonyl, N-(C$_1$–C$_6$-alkoxy)-N-(C$_1$–C$_6$-alkyl)aminocarbonyl, N-(C$_3$–C$_6$-alkenyl)-N-(C$_1$–C$_6$-alkoxy)aminocarbonyl, N-(C$_3$–C$_6$-alkynyl)-N-(C$_1$–C$_6$-alkoxy)aminocarbonyl, di(C$_1$–C$_6$-alkyl)aminothiocarbonyl, C$_1$–C$_6$-alkylcarbonyl-C$_1$–C$_6$-alkyl, C$_1$–C$_6$-alkoxyimino-C$_1$–C$_6$-alkyl, N-(C$_1$–C$_6$-alkylamino)imino-C$_1$–C$_6$-alkyl or N,N-di(C$_1$–C$_6$-alkylamino)imino-C$_1$–C$_6$-alkyl, where the abovementioned alkyl, cycloalkyl and alkoxy radicals may be partially or fully halogenated and/or may carry one to three of the following groups:
cyano, C$_1$–C$_4$-alkoxy, C$_1$–C$_4$-alkylthio, di(C$_1$–C$_4$-alkyl)amino, C$_1$–C$_4$-alkylcarbonyl, C$_1$–C$_4$-akoxycarbonyl, C$_1$–C$_4$-alkoxy-C$_1$–C$_4$-alkoxycarbonyl, di(C$_1$–C$_4$-alkyl)amino-C$_1$–C$_4$-alkoxycarbonyl, hydroxycarbonyl, C$_1$–C$_4$-alkylaminocarbonyl, di(C$_1$–C$_4$-alkyl)aminocarbonyl, aminocarbonyl, C$_1$–C$_4$-alkylcarbonyloxy or C$_3$–C$_6$-cycloalkyl;
is phenyl, heterocyclyl, phenyl-C$_1$–C$_6$-alkyl, heterocyclyl-C$_1$–C$_6$-alkyl, phenylcarbonyl-C$_1$–C$_6$-alkyl, heterocyclylcarbonyl-C$_1$–C$_6$-alkyl, phenylcarbonyl, heterocyclylcarbonyl, phenoxycarbonyl, phenyloxythiocarbonyl, heterocyclyloxycarbonyl, heterocyclyloxythiocarbonyl, phenylaminocarbonyl, N-(C$_1$–C$_6$-alkyl)-N-(phenyl)aminocarbonyl, heterocyclylaminocarbonyl, N-(C$_1$–C$_6$-alkyl)-N-(heterocyclyl)aminocarbonyl, phenyl-C$_2$–C$_6$-alkenylcarbonyl or heterocyclyl-C$_2$–C$_6$-alkenylcarbonyl, where the phenyl and the heterocyclyl radical of the 18 lastmentioned substituents may be partially or fully halogenated and/or may carry one to three of the following radicals:
nitro, cyano, C$_1$–C$_4$-alkyl, C$_1$–C$_4$-haloalkyl, C$_1$–C$_4$-alkoxy, C$_1$–C$_4$-haloalkoxy, heterocyclyl or N-bonded heterocyclyl, where the two lastmentioned substituents for their part may be partially or fully halogenated and/or may carry one to three of the following radicals:
nitro, cyano, C$_1$–C$_4$-alkyl, C$_1$–C$_4$-haloalkyl, C$_1$–C$_4$-alkoxy or C$_1$–C$_4$-haloalkoxy;
R$^{14}$ is C$_1$–C$_6$-alkyl, C$_3$–C$_6$-alkenyl, C$_3$–C$_6$-haloalkenyl, C$_3$–C$_6$-alkynyl, C$_3$–C$_6$-haloalkynyl, C$_3$–C$_6$-cycloalkyl, C$_1$–C$_6$-alkoxy, di(C$_1$–C$_6$-alkyl)amino or di(C$_1$–C$_6$-haloalkyl)amino, where the abovementioned alkyl, cycloalkyl and alkoxy radicals may be partially or fully halogenated and/or may carry one to three of the following groups:

cyano, $C_1$–$C_4$-alkoxy, $C_1$–$C_4$-alkylthio, di($C_1$–$C_4$-alkyl)amino, $C_1$–$C_4$-alkylcarbonyl, $C_1$–$C_4$-alkoxycarbonyl, $C_1$–$C_4$-alkoxy-$C_1$–$C_4$-alkoxycarbonyl, di($C_1$–$C_4$-alkyl)amino-$C_1$–$C_4$-alkoxycarbonyl, hydroxycarbonyl, $C_1$–$C_4$-alkylaminocarbonyl, di($C_1$–$C_4$-alkyl)aminocarbonyl, aminocarbonyl, $C_1$–$C_4$-alkylcarbonyloxy or $C_3$–$C_6$-cycloalkyl;

is phenyl, heterocyclyl, phenyl-$C_1$–$C_6$-alkyl, heterocyclyl-$C_1$–$C_6$-alkyl, phenoxy, heterocyclyloxy, where the phenyl and the heterocyclyl radical of the lastmentioned substituents may be partially or fully halogenated and/or may carry one to three of the following radicals:

nitro, cyano, $C_1$–$C_4$-alkyl, $C_1$–$C_4$-haloalkyl, $C_1$–$C_4$-alkoxy or $C_1$–$C_4$-haloalkoxy;

$R^{15}$ is $C_1$–$C_6$-alkyl, $C_3$–$C_6$-alkenyl, $C_3$–$C_6$-haloalkenyl, $C_3$–$C_6$-alkynyl, $C_3$–$C_6$-haloalkynyl, $C_3$–$C_6$-cycloalkyl, $C_1$–$C_6$-alkoxy, $C_3$–$C_6$-alkenyloxy, $C_3$–$C_6$-alkynyloxy, di($C_1$–$C_6$-alkyl)amino or $C_1$–$C_6$-alkylcarbonylamino, where the abovementioned alkyl, cycloalkyl and alkoxy radicals may be partially or fully halogenated and/or may carry one to three radicals of the following group:

cyano, $C_1$–$C_4$-alkoxy, $C_1$–$C_4$-alkylthio, di($C_1$–$C_4$-alkyl)amino, $C_1$–$C_4$-alkylcarbonyl, $C_1$–$C_4$-alkoxycarbonyl, $C_1$–$C_4$-alkoxy-$C_1$–$C_4$-alkoxycarbonyl, di($C_1$–$C_4$-alkyl)amino-$C_1$–$C_4$-alkoxycarbonyl, hydroxycarbonyl, $C_1$–$C_4$-alkylaminocarbonyl, di($C_1$–$C_4$-alkyl)aminocarbonyl, aminocarbonyl, $C_1$–$C_4$-alkylcarbonyloxy or $C_3$–$C_6$-cycloalkyl;

is phenyl, heterocyclyl, phenyl-$C_1$–$C_6$-alkyl or heterocyclyl-$C_1$–$C_6$-alkyl, where the phenyl or heterocyclyl radical of the four lastmentioned substituents may be partially or fully halogenated and/or may carry one to three of the following radicals:

nitro, cyano, $C_1$–$C_4$-alkyl, $C_1$–$C_4$-haloalkyl, $C_1$–$C_4$-alkoxy or $C_1$–$C_4$-haloalkoxy;

$R^{16}$ is $C_1$–$C_6$-alkyl, $C_3$–$C_6$-alkenyl, $C_3$–$C_6$-alkynyl or $C_1$–$C_6$-alkylcarbonyl;

and their agriculturally useful salts.

Moreover, the invention relates to processes and intermediates for preparing compounds of the formula I, to compositions comprising them, and to the use of these derivatives or of the compositions comprising them for controlling harmful plants.

WO 97/19087 and EP-A 860 441 disclose tricyclic compounds which are characterized in that the respective benzoyl unit that they contain is fused via positions 3 and 4 with a bicycle. However, the herbicidal properties of the prior-art compounds and their compatibility with crop plants are not entirely satisfactory. It is an object of the present invention to provide novel, biologically, in particular herbicidally, active compounds having improved properties.

We have found that this object is achieved by the tricyclic benzoylpyrazole derivatives of the formula I and their herbicidal action.

Furthermore, we have found processes and intermediates for synthesizing the compounds of the formula I. Likewise, we have found herbicidal compositions which comprise the compounds I and have very good herbicidal action. Moreover, we have found processes for preparing these compositions and methods for controlling undesirable vegetation using the compounds I.

Depending on the substitution pattern, the compounds of the formula I can contain one or more chiral centers, in which case they are present as enantiomers or diastereomer mixtures. The invention provides both the pure enantiomers or diastereomers and their mixtures.

The compounds of the formula I can also be present in the form of their agriculturally useful salts, the type of salt generally being immaterial. Generally suitable are the salts of those cations or the acid addition salts of those acids whose cations and anions, respectively, do not negatively affect the herbicidal action of the compounds I.

Suitable cations are, in particular, ions of the alkali metals, preferably lithium, sodium and potassium, of the alkaline earth metals, preferably calcium and magnesium, and of the transition metals, preferably manganese, copper, zinc and iron, and also ammonium, where, if desired, one to four hydrogen atoms may be replaced by $C_1$–$C_4$-alkyl, hydroxy-$C_1$–$C_4$-alkyl, $C_1$–$C_4$-alkoxy-$C_1$–$C_4$-alkyl, hydroxy-$C_1$–$C_4$-alkoxy-$C_1$–$C_4$-alkyl, phenyl or benzyl, preferably ammonium, dimethylammonium, diisopropylammonium, tetramethylammonium, tetrabutylammonium, 2-(2-hydroxyeth-1-oxy)eth-1-ylammonium, di(2-hydroxyeth-1-yl) ammonium, trimethylbenzylammonium, furthermore phosphonium ions, sulfonium ions, preferably tri($C_1$–$C_4$-alkyl)sulfonium, and sulfoxonium ions, preferably tri($C_1$–$C_4$-alkyl)sulfoxonium.

Anions of useful acid addition salts are primarily chloride, bromide, fluoride, hydrogen sulfate, sulfate, dihydrogen phosphate, hydrogen phosphate, nitrate, hydrogen carbonate, carbonate, hexafluorosilicate, hexafluorophosphate, benzoate and the anions of $C_1$–$C_4$-alkanoic acids, preferably formate, acetate, propionate and butyrate.

In the case of $R^{10}$=hydroxyl or mercapto, IIa also represents the tautomeric forms IIa' and IIa''

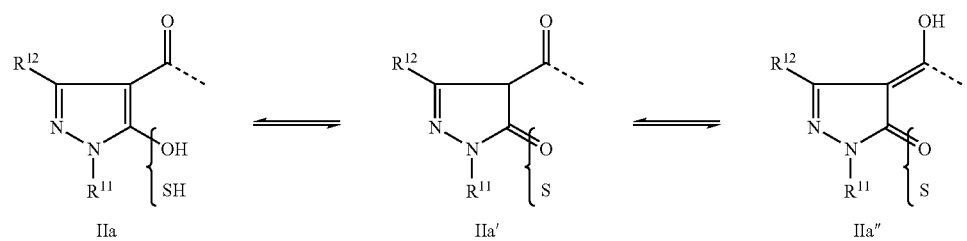

Likewise, in the case of $R^{10}$=hydroxyl or mercapto, IIb also represents the tautomeric forms IIb' and IIb"

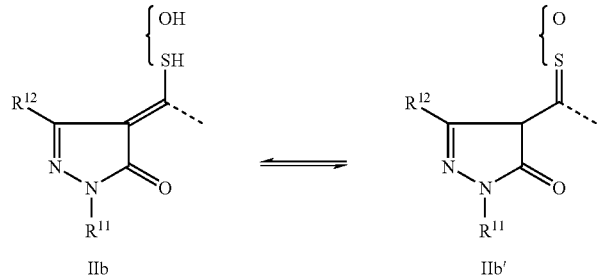

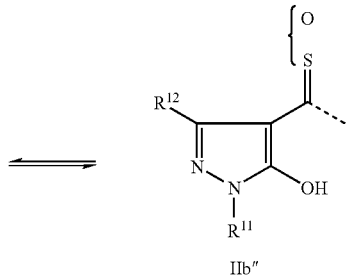

The organic molecular moieties mentioned for the substituents $R^1$–$R^{17}$ or as radicals on phenyl and heterocyclyl radicals are collective terms for individual enumerations of the individual group members. All hydrocarbon chains, i.e. all alkyl, haloalkyl, hydroxyalkyl, alkoxy, haloalkoxy, alkylthio, haloalkylthio, alkylsulfinyl, haloalkylsulfinyl, alkylsulfonyl, haloalkylsulfonyl, N-alkylaminosulfonyl, N,N-dialkylaminosulfonyl, N-alkylamino, N,N-dialkylamino, N-haloalkylamino, N,N-dihaloalkylamino, N-alkylsulfonylamino, N-haloalkylsulfonylamino, N-alkyl-N-alkylsulfonylamino, N-alkyl-N-haloalkylsulfonylamino, alkylcarbonyl, alkoxycarbonyl, haloalkoxycarbonyl, alkylthiocarbonyl, alkylcarbonyloxy, alkylaminocarbonyl, dialkylaminocarbonyl, dialkylaminothiocarbonyl, alkoxyalkyl, hydroxyalkoxyalkyl, alkylcarbonylalkyl, alkoxyiminoalkyl, N-(alkylamino)iminoalkyl, N-(dialkylamino)iminoalkyl, phenylalkenylcarbonyl, heterocyclylalkenylcarbonyl, N-alkoxy-N-alkylaminocarbonyl, N-alkyl-N-phenylaminocarbonyl, N-alkyl-N-heterocyclylaminocarbonyl, phenylalkyl, heterocyclylalkyl, phenylcarbonylalkyl, heterocyclylcarbonylalkyl, dialkylaminoalkoxycarbonyl, alkoxyalkoxycarbonyl, alkenylcarbonyl, alkenyloxycarbonyl, alkenylaminocarbonyl, N-alkenyl-N-alkylaminocarbonyl, N-alkenyl-N-alkoxyaminocarbonyl, alkynylcarbonyl, alkynyloxycarbonyl, alkynylaminocarbonyl, N-alkynyl-N-alkylaminocarbonyl, N-alkynyl-N-alkoxyaminocarbonyl, alkenyl, alkynyl, haloalkenyl, haloalkynyl, alkenyloxy and alkynyloxy moieties, may be straight-chain or branched. Unless indicated otherwise, halogenated substituents preferably carry one to five identical or different halogen atoms. The term halogen denotes in each case fluorine, chlorine, bromine or iodine.

Examples of other meanings are:

$C_1$–$C_4$-alkyl and the alkyl moieties of hydroxy-$C_1$–$C_4$-alkyl: for example methyl, ethyl, propyl, 1-methylethyl, butyl, 1-methylpropyl, 2-methylpropyl or 1,1-dimethylethyl;

$C_1$–$C_6$-alkyl, and the alkyl moieties of $C_1$–$C_6$-alkylcarbonyl-$C_1$–$C_6$-alkyl, $C_1$–$C_6$-alkoxyimino-$C_1$–$C_6$-alkyl, N-($C_1$–$C_6$-alkylamino)imino-$C_1$–$C_6$-alkyl, N-(di-$C_1$–$C_6$-alkylamino)imino-$C_1$–$C_6$-alkyl, N-($C_1$–$C_6$-alkoxy)-N-($C_1$–$C_6$-alkyl)aminocarbonyl, N-($C_3$–$C_6$-alkenyl)-N-($C_1$–$C_6$-alkyl)aminocarbonyl, N-($C_3$–$C_6$-alkynyl)-N-($C_1$–$C_6$-alkyl)aminocarbonyl, N-($C_1$–$C_6$-alkyl)-N-phenylaminocarbonyl, N-($C_1$–$C_6$-alkyl)-N-heterocyclylaminocarbonyl, phenyl-$C_1$–$C_6$-alkyl, N-($C_1$–$C_6$-alkyl)-N-($C_1$–$C_6$-alkylsulfonyl)amino, N-($C_1$–$C_6$-alkyl)-N-($C_1$–$C_6$-haloalkylsulfonyl)amino, heterocyclyl-$C_1$–$C_6$-alkyl, phenylcarbonyl-$C_1$–$C_6$-alkyl, heterocyclylcarbonyl-$C_1$–$C_6$-alkyl: $C_1$–$C_4$-alkyl as mentioned above, and also, for example, pentyl, 1-methylbutyl, 2-methylbutyl, 3-methylbutyl, 2,2-dimethylpropyl, 1-ethylpropyl, hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1-ethyl-1-methylpropyl or 1-ethyl-3-methylpropyl;

$C_1$–$C_4$-haloalkyl: a $C_1$–$C_4$-alkyl radical as mentioned above which is partially or fully substituted by fluorine, chlorine, bromine and/or iodine, i.e., for example, chloromethyl, dichloromethyl, trichloromethyl, fluoromethyl, difluoromethyl, trifluoromethyl, chlorofluoromethyl, dichlorofluoromethyl, chlorodifluoromethyl, 2-fluoroethyl, 2-chloroethyl, 2-bromoethyl, 2-iodoethyl, 2,2-difluoroethyl, 2,2,2-trifluoroethyl, 2-chloro-2-fluoroethyl, 2-chloro-2,2-difluoroethyl, 2,2-dichloro-2-fluoroethyl, 2,2,2-trichloroethyl, pentafluoroethyl, 2-fluoropropyl, 3-fluoropropyl, 2,2-difluoropropyl, 2,3-difluoropropyl, 2-chloropropyl, 3-chloropropyl, 2,3-dichloropropyl, 2-bromopropyl, 3-bromopropyl, 3,3,3-trifluoropropyl, 3,3,3-trichloropropyl, 2,2,3,3,3-pentafluoropropyl, heptafluoropropyl, 1-(fluoromethyl)-2-fluoroethyl, 1-(chloromethyl)-2-chloroethyl, 1-(bromomethyl)-2-bromoethyl, 4-fluorobutyl, 4-chlorobutyl, 4-bromobutyl or nonafluorobutyl;

$C_1$–$C_6$-haloalkyl, and the haloalkyl moieties of N-$C_1$–$C_6$-haloalkylamino and N,N-(di-$C_1$–$C_6$-haloalkyl)amino: $C_1$–$C_4$-haloalkyl as mentioned above, and also, for example, 5-fluoropentyl, 5-chloropentyl, 5-bromopentyl, 5-iodopentyl, undecafluoropentyl, 6-fluorohexyl, 6-chlorohexyl, 6-bromohexyl, 6-iodohexyl or dodecafluorohexyl;

$C_1$–$C_4$-alkoxy: for example methoxy, ethoxy, propoxy, 1-methylethoxy, butoxy, 1-methylpropoxy, 2-methylpropoxy or 1,1-dimethylethoxy;

$C_1$–$C_6$-alkoxy, and the alkoxy moieties of $C_1$–$C_6$-alkoxyimino-$C_1$–$C_6$-alkyl, N-($C_1$–$C_6$-alkoxy)-N-($C_1$–$C_6$-alkyl)aminocarbonyl, N-($C_3$–$C_6$-alkenyl)-N-($C_1$–$C_6$-alkoxy)aminocarbonyl and N-($C_3$–$C_6$-alkynyl)-N-($C_1$–$C_6$-alkoxy)aminocarbonyl: $C_1$–$C_4$-alkoxy as mentioned above, and also, for example, pentoxy, 1-methylbutoxy, 2-methylbutoxy, 3-methylbutoxy, 1,1-dimethylpropoxy, 1,2-dimethylpropoxy, 2,2-dimethylpropoxy, 1-ethylpropoxy, hexoxy, 1-methylpentoxy, 2-methylpentoxy, 3-methylpentoxy, 4-methylpentoxy, 1,1-dimethylbutoxy, 1,2-dimethylbutoxy, 1,3-dimethylbutoxy, 2,2-dimethylbutoxy, 2,3-dimethylbutoxy, 3,3-dimethylbutoxy, 1-ethylbutoxy, 2-ethylbutoxy, 1,1,2-trimethylpropoxy, 1,2,2-trimethylpropoxy, 1-ethyl-1-methylpropoxy or 1-ethyl-2-methylpropoxy;

$C_1$–$C_4$-haloalkoxy: a $C_1$–$C_4$-alkoxy radical as mentioned above which is partially or fully substituted by fluorine, chlorine, bromine and/or iodine, i.e., for example, fluoromethoxy, difluoromethoxy, trifluoromethoxy, chlorodifluoromethoxy, bromodifluoromethoxy, 2-fluoroethoxy, 2-chloroethoxy, 2-bromoethoxy, 2-iodoethoxy, 2,2-difluoroethoxy, 2,2,2-trifluoroethoxy, 2-chloro-2-fluoroethoxy, 2-chloro-2,2-difluoroethoxy, 2,2-dichloro-2-fluoroethoxy, 2,2,2-trichloroethoxy, pentafluoroethoxy, 2-fluoropropoxy, 3-fluoropropoxy, 2-chloropropoxy, 3-chloropropoxy, 2-bromopropoxy, 3-bromopropoxy, 2,2-difluoropropoxy, 2,3-difluoropropoxy, 2,3-dichloropropoxy, 3,3,3-trifluoropropoxy, 3,3,3-trichloropropoxy, 2,2,3,3,3-pentafluoropropoxy, heptafluoropropoxy, 1-(fluoromethyl)-2-fluoroethoxy, 1-(chloromethyl)-2-chloroethoxy, 1-(bromomethyl)-2-bromoethoxy, 4-fluorobutoxy, 4-chlorobutoxy, 4-bromobutoxy or nonafluorobutoxy;

$C_1$–$C_6$-haloalkoxy: $C_1$–$C_4$-haloalkoxy as mentioned above, and also, for example, 5-fluoropentoxy, 5-chloropentoxy, 5-bromopentoxy, 5-iodopentoxy, undecafluoropentoxy, 6-fluorohexoxy, 6-chlorohexoxy, 6-bromohexoxy, 6-iodohexoxy or dodecafluorohexoxy;

$C_1$–$C_4$-alkylthio: for example methylthio, ethylthio, propylthio, 1-methylethylthio, butylthio, 1-methylpropylthio, 2-methylpropylthio or 1,1-dimethylethylthio;

$C_1$–$C_6$-alkylthio, and the alkylthio moieties of $C_1$–$C_6$-alkylthiocarbonyl: $C_1$–$C_4$-alkylthio as mentioned above and also, for example, pentylthio, 1-methylbutylthio, 2-methylbutylthio, 3-methylbutylthio, 2,2-dimethylpropylthio, 1-ethylpropylthio, hexylthio, 1,1-dimethylpropylthio, 1,2-dimethylpropylthio, 1-methylpentylthio, 2-methylpentylthio, 3-methylpentylthio, 4-methylpentylthio, 1,1-dimethylbutylthio, 1,2-dimethylbutylthio, 1,3-dimethylbutylthio, 2,2-dimethylbutylthio, 2,3-dimethylbutylthio, 3,3-dimethylbutylthio, 1-ethylbutylthio, 2-ethylbutylthio, 1,1,2-trimethylpropylthio, 1,2,2-trimethylpropylthio, 1-ethyl-1-methylpropylthio or 1-ethyl-2-methylpropylthio;

$C_1$–$C_6$-haloalkylthio: a $C_1$–$C_6$-alkylthio radical as mentioned above which is partially or fully substituted by fluorine, chlorine, bromine and/or iodine, i.e., for example, fluoromethylthio, difluoromethylthio, trifluoromethylthio, chlorodifluoromethylthio, bromodifluoromethylthio, 2-fluoroethylthio, 2-chloroethylthio, 2-bromoethylthio, 2-iodoethylthio, 2,2-difluoroethylthio, 2,2,2-trifluoroethylthio, 2,2,2-trichloroethylthio, 2-chloro-2-fluoroethylthio, 2-chloro-2,2-difluoroethylthio, 2,2-dichloro-2-fluoroethylthio, pentafluoroethylthio, 2-fluoropropylthio, 3-fluoropropylthio, 2-chloropropylthio, 3-chloropropylthio, 2-bromopropylthio, 3-bromopropylthio, 2,2-difluoropropylthio, 2,3-difluoropropylthio, 2,3-dichloropropylthio, 3,3,3-trifluoropropylthio, 3,3,3-trichloropropylthio, 2,2,3,3,3-pentafluoropropylthio, heptafluoropropylthio, 1-(fluoromethyl)-2-fluoroethylthio, 1-(chloromethyl)-2-chloroethylthio, 1-(bromomethyl)-2-bromoethylthio, 4-fluorobutylthio, 4-chlorobutylthio, 4-bromobutylthio, nonafluorobutylthio, 5-fluoropentylthio, 5-chloropentylthio, 5-bromopentylthio, 5-iodopentylthio, undecafluoropentylthio, 6-fluorohexylthio, 6-chlorohexylthio, 6-bromohexylthio, 6-iodohexylthio or dodecafluorohexylthio;

$C_1$–$C_6$-alkylsulfinyl ($C_1$–$C_6$-alkyl-S(=O)—): for example methylsulfinyl, ethylsulfinyl, propylsulfinyl, 1-methylethylsulfinyl, butylsulfinyl, 1-methylpropylsulfinyl, 2-methylpropylsulfinyl, 1,1-dimethylethylsulfinyl, pentylsulfinyl, 1-methylbutylsulfinyl, 2-methylbutylsulfinyl, 3-methylbutylsulfinyl, 2,2-dimethylpropylsulfinyl, 1-ethylpropylsulfinyl, 1,1-dimethylpropylsulfinyl, 1,2-dimethylpropylsulfinyl, hexylsulfinyl, 1-methylpentylsulfinyl, 2-methylpentylsulfinyl, 3-methylpentylsulfinyl, 4-methylpentylsulfinyl, 1,1-dimethylbutylsulfinyl, 1,2-dimethylbutylsulfinyl, 1,3-dimethylbutylsulfinyl, 2,2-dimethylbutylsulfinyl, 2,3-dimethylbutylsulfinyl, 3,3-dimethylbutylsulfinyl, 1-ethylbutylsulfinyl, 2-ethylbutylsulfinyl, 1,1,2-trimethylpropylsulfinyl, 1,2,2-trimethylpropylsulfinyl, 1-ethyl-1-methylpropylsulfinyl or 1-ethyl-2-methylpropylsulfinyl;

$C_1$–$C_6$-haloalkylsulfinyl: a $C_1$–$C_6$-alkylsulfinyl radical as mentioned above which is partially or fully substituted by fluorine, chlorine, bromine and/or iodine, i.e., for example, fluoromethylsulfinyl, difluoromethylsulfinyl, trifluoromethylsulfinyl, chlorodifluoromethylsulfinyl, bromodifluoromethylsulfinyl, 2-fluoroethylsulfinyl, 2-chloroethylsulfinyl, 2-bromoethylsulfinyl, 2-iodoethylsulfinyl, 2,2-difluoroethylsulfinyl, 2,2,2-trifluoroethylsulfinyl, 2,2,2-trichloroethylsulfinyl, 2-chloro-2-fluoroethylsulfinyl, 2-chloro-2,2-difluoroethylsulfinyl, 2,2-dichloro-2-fluoroethylsulfinyl, pentafluoroethylsulfinyl, 2-fluoropropylsulfinyl, 3-fluoropropylsulfinyl, 2-chloropropylsulfinyl, 3-chloropropylsulfinyl, 2-bromopropylsulfinyl, 3-bromopropylsulfinyl, 2,2-difluoropropylsulfinyl, 2,3-difluoropropylsulfinyl, 2,3-dichloropropylsulfinyl, 3,3,3-trifluoropropylsulfinyl, 3,3,3-trichloropropylsulfinyl, 2,2,3,3,3-pentafluoropropylsulfinyl, heptafluoropropylsulfinyl, 1-(fluoromethyl)-2-fluoroethylsulfinyl, 1-(chloromethyl)-2-chloroethylsulfinyl, 1-(bromomethyl)-2-bromoethylsulfinyl, 4-fluorobutylsulfinyl, 4-chlorobutylsulfinyl, 4-bromobutylsulfinyl, nonafluorobutylsulfinyl, 5-fluoropentylsulfinyl, 5-chloropentylsulfinyl, 5-bromopentylsulfinyl, 5-iodopentylsulfinyl, undecafluoropentylsulfinyl, 6-fluorohexylsulfinyl, 6-chlorohexylsulfinyl, 6-bromohexylsulfinyl, 6-iodohexylsulfinyl or dodecafluorohexylsulfinyl;

$C_1$–$C_6$-alkylsulfonyl ($C_1$–$C_6$-alkyl-S(=O)$_2$—), and the alkylsulfonyl radicals of N-($C_1$–$C_6$-alkylsulfonyl)amino and N-($C_1$–$C_6$-alkyl)-N-($C_1$–$C_6$-alkylsulfonyl)amino: for example methylsulfonyl, ethylsulfonyl, propylsulfonyl, 1-methylethylsulfonyl, butylsulfonyl, 1-methylpropylsulfonyl, 2-methylpropylsulfonyl, 1,1-dimethylethylsulfonyl, pentylsulfonyl, 1-methylbutylsulfonyl, 2-methylbutylsulfonyl, 3-methylbutylsulfonyl, 1,1-dimethylpropylsulfonyl, 1,2-dimethylpropylsulfonyl, 2,2-dimethylpropylsulfonyl, 1-ethylpropylsulfonyl, hexylsulfonyl, 1-methylpentylsulfonyl, 2-methylpentylsulfonyl, 3-methylpentylsulfonyl, 4-methylpentylsulfonyl, 1,1-dimethylbutylsulfonyl, 1,2-dimethylbutylsulfonyl, 1,3-dimethylbutylsulfonyl, 2,2-dimethylbutylsulfonyl, 2,3-dimethylbutylsulfonyl, 3,3-dimethylbutylsulfonyl, 1-ethylbutylsulfonyl, 2-ethylbutylsulfonyl, 1,1,2-trimethylpropylsulfonyl, 1,2,2-trimethylpropylsulfonyl, 1-ethyl-1-methylpropylsulfonyl or 1-ethyl-2-methylpropylsulfonyl;

$C_1$–$C_6$-haloalkylsulfonyl, and the haloalkylsulfonyl radicals of N-($C_1$–$C_6$-haloalkylsulfonyl)amino and N-($C_1$–$C_6$-alkyl)-N-($C_1$–$C_6$-haloalkylsulfonyl)amino:

a $C_1$–$C_6$-alkylsulfonyl radical as mentioned above which is partially or fully substituted by fluorine, chlorine, bromine and/or iodine, i.e., for example, fluoromethylsulfonyl, difluoromethylsulfonyl, trifluoromethylsulfonyl, chlorodifluoromethylsulfonyl, bromodifluoromethylsulfonyl, 2-fluoroethylsulfonyl, 2-chloroethylsulfonyl, 2-bromoethylsulfonyl, 2-iodoethylsulfonyl, 2,2-difluoroethylsulfonyl, 2,2,2-trifluoroethylsulfonyl, 2-chloro-2-fluoroethylsulfonyl, 2-chloro-2,2-difluoroethylsulfonyl, 2,2-dichloro-2-fluoroethylsulfonyl, 2,2,2-trichloroethylsulfonyl, pentafluoroethylsulfonyl, 2-fluoropropylsulfonyl, 3-fluoropropylsulfonyl, 2-chloropropylsulfonyl, 3-chloropropylsulfonyl, 2-bromopropylsulfonyl, 3-bromopropylsulfonyl, 2,2-difluoropropylsulfonyl, 2,3-difluoropropylsulfonyl, 2,3-dichloropropylsulfonyl, 3,3,3-trifluoropropylsulfonyl, 3,3,3-trichloropropylsulfonyl, 2,2,3,3,3-pentafluoropropylsulfonyl, heptafluoropropylsulfonyl, 1-(fluoromethyl)-2-fluoroethylsulfonyl, 1-(chloromethyl)-2-chloroethylsulfonyl, 1-(bromomethyl)-2-bromoethylsulfonyl, 4-fluorobutylsulfonyl, 4-chlorobutylsulfonyl, 4-bromobutylsulfonyl, nonafluorobutylsulfonyl, 5-fluoropentylsulfonyl, 5-chloropentylsulfonyl, 5-bromopentylsulfonyl, 5-iodopentylsulfonyl, 6-fluorohexylsulfonyl, 6-bromohexylsulfonyl, 6-iodohexylsulfonyl or dodecafluorohexylsulfonyl;

$C_1$–$C_6$-alkylamino, and the alkylamino radicals of N-($C_1$–$C_6$-alkylamino)imino-$C_1$–$C_6$-alkyl: for example methylamino, ethylamino, propylamino, 1-methylethylamino, butylamino, 1-methylpropylamino, 2-methylpropylamino, 1,1-dimethylethylamino, pentylamino, 1-methylbutylamino, 2-methylbutylamino, 3-methylbutylamino, 2,2-dimethylpropylamino, 1-ethylpropylamino, hexylamino, 1,1-dimethylpropylamino, 1,2-dimethylpropylamino, 1-methylpentylamino, 2-methylpentylamino, 3-methylpentylamino, 4-methylpentylamino, 1,1-dimethylbutylamino, 1,2-dimethylbutylamino, 1,3-dimethylbutylamino, 2,2-dimethylbutylamino, 2,3-dimethylbutylamino, 3,3-dimethylbutylamino, 1-ethylbutylamino, 2-ethylbutylamino, 1,1,2-trimethylpropylamino, 1,2,2-trimethylpropylamino, 1-ethyl-1-methylpropylamino or 1-ethyl-2-methylpropylamino;

($C_1$–$C_6$-alkylamino)sulfonyl: for example methylaminosulfonyl, ethylaminosulfonyl, propylaminosulfonyl, 1-methylethylaminosulfonyl, butylaminosulfonyl, 1-methylpropylaminosulfonyl, 2-methylpropylaminosulfonyl, 1,1-dimethylethylaminosulfonyl, pentylaminosulfonyl, 1-methylbutylaminosulfonyl, 2-methylbutylaminosulfonyl, 3-methylbutylaminosulfonyl, 2,2-dimethylpropylaminosulfonyl, 1-ethylpropylaminosulfonyl, hexylaminosulfonyl, 1,1-dimethylpropylaminosulfonyl, 1,2-dimethylpropylaminosulfonyl, 1-methylpentylaminosulfonyl, 2-methylpentylaminosulfonyl, 3-methylpentylaminosulfonyl, 4-methylpentylaminosulfonyl, 1,1-dimethylbutylaminosulfonyl, 1,2-dimethylbutylaminosulfonyl, 1,3-dimethylbutylaminosulfonyl, 2,2-dimethylbutylaminosulfonyl, 2,3-dimethylbutylaminosulfonyl, 3,3-dimethylbutylaminosulfonyl, 1-ethylbutylaminosulfonyl, 2-ethylbutylaminosulfonyl, 1,1,2-trimethylpropylaminosulfonyl, 1,2,2-trimethylpropylaminosulfonyl, 1-ethyl-1-methylpropylaminosulfonyl or 1-ethyl-2-methylpropylaminosulfonyl;

di($C_1$–$C_6$-alkyl)aminosulfonyl: for example N,N-dimethylaminosulfonyl, N,N-diethylaminosulfonyl, N,N-di(1-methylethyl)aminosulfonyl, N,N-dipropylaminosulfonyl, N,N-dibutylaminosulfonyl, N,N-di(1-methylpropyl)aminosulfonyl, N,N-di(2-methylpropyl)aminosulfonyl, N,N-di(1,1-dimethylethyl)aminosulfonyl, N-ethyl-N-methylaminosulfonyl, N-methyl-N-propylaminosulfonyl, N-methyl-N-(1-methylethyl)aminosulfonyl, N-butyl-N-methylaminosulfonyl, N-methyl-N-(1-methylpropyl)aminosulfonyl, N-methyl-N-(2-methylpropyl)aminosulfonyl, N-(1,1-dimethylethyl)-N-methylaminosulfonyl, N-ethyl-N-propylaminosulfonyl, N-ethyl-N-(1-methylethyl)aminosulfonyl, N-butyl-N-ethylaminosulfonyl, N-ethyl-N-(1-methylpropyl)aminosulfonyl, N-ethyl-N-(2-methylpropyl)aminosulfonyl, N-ethyl-N-(1,1-dimethylethyl)aminosulfonyl, N-(1-methylethyl)-N-propylaminosulfonyl, N-butyl-N-propylaminosulfonyl, N-(1-methylpropyl)-N-propylaminosulfonyl, N-(2-methylpropyl)-N-propylaminosulfonyl, N-(1,1-dimethylethyl)-N-propylaminosulfonyl, N-butyl-N-(1-methylethyl)aminosulfonyl, N-(1-methylethyl)-N-(1-methylpropyl)aminosulfonyl, N-(1-methylethyl)-N-(2-methylpropyl)aminosulfonyl, N-(1,1-dimethylethyl)-N-(1-methylethyl)aminosulfonyl, N-butyl-N-(1-methylpropyl)aminosulfonyl, N-butyl-N-(2-methylpropyl)aminosulfonyl, N-butyl-N-(1,1-dimethylethyl)aminosulfonyl, N-(1-methylpropyl)-N-(2-methylpropyl)aminosulfonyl, N-(1,1-dimethylethyl)-N-(1-methylpropyl)aminosulfonyl, N-(1,1-dimethylethyl)-N-(2-methylpropyl)aminosulfonyl, N-methyl-N-pentylaminosulfonyl, N-methyl-N-(1-methylbutyl)aminosulfonyl, N-methyl-N-(2-methylbutyl)aminosulfonyl, N-methyl-N-(3-methylbutyl)aminosulfonyl, N-methyl-N-(2,2-dimethylpropyl)aminosulfonyl, N-methyl-N-(1-ethylpropyl)aminosulfonyl, N-methyl-N-hexylaminosulfonyl, N-methyl-N-(1,1-dimethylpropyl)aminosulfonyl, N-methyl-N-(1,2-dimethylpropyl)aminosulfonyl, N-methyl-N-(1-methylpentyl)aminosulfonyl, N-methyl-N-(2-methylpentyl)aminosulfonyl, N-methyl-N-(3-methylpentyl)aminosulfonyl, N-methyl-N-(4-methylpentyl)aminosulfonyl, N-methyl-N-(1,1-dimethylbutyl)aminosulfonyl, N-methyl-N-(1,2-dimethylbutyl)aminosulfonyl, N-methyl-N-(1,3-dimethylbutyl)aminosulfonyl, N-methyl-N-(2,2-dimethylbutyl)aminosulfonyl, N-methyl-N-(2,3-dimethylbutyl)aminosulfonyl, N-methyl-N-(3,3-dimethylbutyl)aminosulfonyl, N-methyl-N-(1-ethylbutyl)aminosulfonyl, N-methyl-N-(2-ethylbutyl)aminosulfonyl, N-methyl-N-(1,1,2-trimethylpropyl)aminosulfonyl, N-methyl-N-(1,2,2-trimethylpropyl)aminosulfonyl, N-methyl-N-(1-ethyl-1-methylpropyl)aminosulfonyl, N-methyl-N-(1-ethyl-2-methylpropyl)aminosulfonyl, N-ethyl-N-pentylaminosulfonyl, N-ethyl-N-(1-methylbutyl)aminosulfonyl, N-ethyl-N-(2-methylbutyl)aminosulfonyl, N-ethyl-N-(3-methylbutyl)aminosulfonyl, N-ethyl-N-(2,2-dimethylpropyl)aminosulfonyl, N-ethyl-N-(1-ethylpropyl)aminosulfonyl, N-ethyl-N-hexylaminosulfonyl, N-ethyl-N-(1,1-dimethylpropyl)aminosulfonyl, N-ethyl-N-(1,2-dimethylpropyl)aminosulfonyl, N-ethyl-N-(1-methylpentyl)aminosulfonyl, N-ethyl-N-(2-methylpentyl)aminosulfonyl, N-ethyl-N-(3-methylpentyl)aminosulfonyl, N-ethyl-N-(4-methylpentyl)

aminosulfonyl, N-ethyl-N-(1,1-dimethylbutyl)aminosulfonyl, N-ethyl-N-(1,2-dimethylbutyl)aminosulfonyl, N-ethyl-N-(1,3-dimethylbutyl)aminosulfonyl, N-ethyl-N-(2,2-dimethylbutyl)aminosulfonyl, N-ethyl-N-(2,3-dimethylbutyl)aminosulfonyl, N-ethyl-N-(3,3-dimethylbutyl)aminosulfonyl, N-ethyl-N-(1-ethylbutyl)aminosulfonyl, N-ethyl-N-(2-ethylbutyl)aminosulfonyl, N-ethyl-N-(1,1,2-trimethylpropyl)aminosulfonyl, N-ethyl-N-(1,2,2-trimethylpropyl)aminosulfonyl, N-ethyl-N-(1-ethyl-1-methylpropyl)aminosulfonyl, N-ethyl-N-(1-ethyl-2-methylpropyl)aminosulfonyl, N-propyl-N-pentylaminosulfonyl, N-butyl-N-pentylaminosulfonyl, N,N-dipentylaminosulfonyl, N-propyl-N-hexylaminosulfonyl, N-butyl-N-hexylaminosulfonyl, N-pentyl-N-hexylaminosulfonyl or N,N-dihexylaminosulfonyl;

di($C_1$–$C_4$-alkyl)amino, and the dialkylamino radicals of di($C_1$–$C_4$-alkyl)amino-$C_1$–$C_4$-alkoxycarbonyl and N-(di-$C_1$–$C_4$-alkylamino)imino-$C_1$–$C_6$-alkyl: for example N,N-dimethylamino, N,N-diethylamino, N,N-dipropylamino, N,N-di(1-methylethyl)amino, N,N-dibutylamino, N,N-di(1-methylpropyl)amino, N,N-di(2-methylpropyl)amino, N,N-di(1,1-dimethylethyl)amino, N-ethyl-N-methylamino, N-methyl-N-propylamino, N-methyl-N-(1-methylethyl)amino, N-butyl-N-methylamino, N-methyl-N-(1-methylpropyl)amino, N-methyl-N-(2-methylpropyl)amino, N-(1,1-dimethylethyl)-N-methylamino, N-ethyl-N-propylamino, N-ethyl-N-(1-methylethyl)amino, N-butyl-N-ethylamino, N-ethyl-N-(1-methylpropyl)amino, N-ethyl-N-(2-methylpropyl)amino, N-ethyl-N-(1,1-dimethylethyl)amino, N-(1-methylethyl)-N-propylamino, N-butyl-N-propylamino, N-(1-methylpropyl)-N-propylamino, N-(2-methylpropyl)-N-propylamino, N-(1,1-dimethylethyl)-N-propylamino, N-butyl-N-(1-methylethyl)amino, N-(1-methylethyl)-N-(1-methylpropyl)amino, N-(1-methylethyl)-N-(2-methylpropyl)amino, N-(1,1-dimethylethyl)-N-(1-methylethyl)amino, N-butyl-N-(1-methylpropyl)amino, N-butyl-N-(2-methylpropyl)amino, N-butyl-N-(1,1-dimethylethyl)amino, N-(1-methylpropyl)-N-(2-methylpropyl)amino, N-(1,1-dimethylethyl)-N-(1-methylpropyl)amino or N-(1,1-dimethylethyl)-N-(2-methylpropyl)amino;

di($C_1$–$C_6$-alkyl)amino, and the dialkylamino radicals of di($C_1$–$C_6$-alkyl)aminoimino-$C_1$–$C_6$-alkyl: di($C_1$–$C_4$-alkyl)amino as mentioned above, and also N,N-dipentylamino, N,N-dihexylamino, N-methyl-N-pentylamino, N-ethyl-N-pentylamino, N-methyl-N-hexylamino or N-ethyl-N-hexylamino;

$C_1$–$C_4$-alkylcarbonyl: for example methylcarbonyl, ethylcarbonyl, propylcarbonyl, 1-methylethylcarbonyl, butylcarbonyl, 1-methylpropylcarbonyl, 2-methylpropylcarbonyl or 1,1-dimethylethylcarbonyl;

$C_1$–$C_6$-alkylcarbonyl, and the alkylcarbonyl radicals of $C_1$–$C_6$-alkylcarbonyl-$C_1$–$C_6$-alkyl: $C_1$–$C_4$-alkylcarbonyl as mentioned above, and also, for example, pentylcarbonyl, 1-methylbutylcarbonyl, 2-methylbutylcarbonyl, 3-methylbutylcarbonyl, 2,2-dimethylpropylcarbonyl, 1-ethylpropylcarbonyl, hexylcarbonyl, 1,1-dimethylpropylcarbonyl, 1,2-dimethylpropylcarbonyl, 1-methylpentylcarbonyl, 2-methylpentylcarbonyl, 3-methylpentylcarbonyl, 4-methylpentylcarbonyl, 1,1-dimethylbutylcarbonyl, 1,2-dimethylbutylcarbonyl, 1,3-dimethylbutylcarbonyl, 2,2-dimethylbutylcarbonyl, 2,3-dimethylbutylcarbonyl, 3,3-dimethylbutylcarbonyl, 1-ethylbutylcarbonyl, 2-ethylbutylcarbonyl, 1,1,2-trimethylpropylcarbonyl, 1,2,2-trimethylpropylcarbonyl, 1-ethyl-1-methylpropylcarbonyl or 1-ethyl-2-methylpropylcarbonyl;

$C_1$–$C_{20}$-alkylcarbonyl: $C_1$–$C_6$-alkylcarbonyl as mentioned above, and also heptylcarbonyl, octylcarbonyl, pentadecylcarbonyl or heptadecylcarbonyl;

$C_1$–$C_4$-alkoxycarbonyl, and the alkoxycarbonyl moieties of di($C_1$–$C_4$-alkyl)amino-$C_1$–$C_4$-alkoxycarbonyl: for example methoxycarbonyl, ethoxycarbonyl, propoxycarbonyl, 1-methylethoxycarbonyl, butoxycarbonyl, 1-methylpropoxycarbonyl, 2-methylpropoxycarbonyl or 1,1-dimethylethoxycarbonyl;

($C_1$–$C_6$-alkoxy)carbonyl: ($C_1$–$C_4$-alkoxy)carbonyl as mentioned above, and also, for example, pentoxycarbonyl, 1-methylbutoxycarbonyl, 2-methylbutoxycarbonyl, 3-methylbutoxycarbonyl, 2,2-dimethylpropoxycarbonyl, 1-ethylpropoxycarbonyl, hexoxycarbonyl, 1,1-dimethylpropoxycarbonyl, 1,2-dimethylpropoxycarbonyl, 1-methylpentoxycarbonyl, 2-methylpentoxycarbonyl, 3-methylpentoxycarbonyl, 4-methylpentoxycarbonyl, 1,1-dimethylbutoxycarbonyl, 1,2-dimethylbutoxycarbonyl, 1,3-dimethylbutoxycarbonyl, 2,2-dimethylbutoxycarbonyl, 2,3-dimethylbutoxycarbonyl, 3,3-dimethylbutoxycarbonyl, 1-ethylbutoxycarbonyl, 2-ethylbutoxycarbonyl, 1,1,2-trimethylpropoxycarbonyl, 1,2,2-trimethylpropoxycarbonyl, 1-ethyl-1-methyl-propoxycarbonyl or 1-ethyl-2-methyl-propoxycarbonyl;

$C_1$–$C_6$-haloalkoxycarbonyl: a $C_1$–$C_6$-alkoxycarbonyl radical as mentioned above which is partially or fully substituted by fluorine, chlorine, bromine and/or iodine, i.e., for example, fluoromethoxycarbonyl, difluoromethoxycarbonyl, trifluoromethoxycarbonyl, chlorodifluoromethoxycarbonyl, bromodifluoromethoxycarbonyl, 2-fluoroethoxycarbonyl, 2-chloroethoxycarbonyl, 2-bromoethoxycarbonyl, 2-iodoethoxycarbonyl, 2,2-difluoroethoxycarbonyl, 2,2,2-trifluoroethoxycarbonyl, 2-chloro-2-fluoroethoxycarbonyl, 2-chloro-2,2-difluoroethoxycarbonyl, 2,2-dichloro-2-fluoroethoxycarbonyl, 2,2,2-trichloroethoxycarbonyl, pentafluoroethoxycarbonyl, 2-fluoropropoxycarbonyl, 3-fluoropropoxycarbonyl, 2-chloropropoxycarbonyl, 3-chloropropoxycarbonyl, 2-bromopropoxycarbonyl, 3-bromopropoxycarbonyl, 2,2-difluoropropoxycarbonyl, 2,3-difluoropropoxycarbonyl, 2,3-dichloropropoxycarbonyl, 3,3,3-trifluoropropoxycarbonyl, 3,3,3-trichloropropoxycarbonyl, 2,2,3,3,3-pentafluoropropoxycarbonyl, heptafluoropropoxycarbonyl, 1-(fluoromethyl)-2-fluoroethoxycarbonyl, 1-(chloromethyl)-2-chloroethoxycarbonyl, 1-(bromomethyl)-2-bromoethoxycarbonyl, 4-fluorobutoxycarbonyl, 4-chlorobutoxycarbonyl, 4-bromobutoxycarbonyl, nonafluorobutoxycarbonyl, 5-fluoropentoxycarbonyl, 5-chloropentoxycarbonyl, 5-bromopentoxycarbonyl, 5-iodopentoxycarbonyl, 6-fluorohexoxycarbonyl, 6-bromohexoxycarbonyl, 6-iodohexoxycarbonyl or dodecafluorohexoxycarbonyl;

($C_1$–$C_4$-alkyl)carbonyloxy: acetyloxy, ethylcarbonyloxy, propylcarbonyloxy, 1-methylethylcarbonyloxy, butylcarbonyloxy, 1-methylpropylcarbonyloxy, 2-methylpropylcarbonyloxy or 1,1-dimethylethylcarbonyloxy;

($C_1$–$C_4$-alkylamino)carbonyl: for example methylaminocarbonyl, ethylaminocarbonyl, propylaminocarbonyl, 1-methylethylaminocarbonyl, butylaminocarbonyl, 1-methylpropylaminocarbonyl, 2-methylpropylaminocarbonyl or 1,1-dimethylethylaminocarbonyl;

($C_1$–$C_6$-alkylamino)carbonyl: ($C_1$–$C_4$-alkylamino)carbonyl as mentioned above, and also, for example, pentylaminocarbonyl, 1-methylbutylaminocarbonyl, 2-methylbutylaminocarbonyl, 3-methylbutylaminocarbonyl, 2,2-dimethylpropylaminocarbonyl, 1-ethylpropylaminocarbonyl, hexylaminocarbonyl, 1,1-dimethylpropylaminocarbonyl, 1,2-dimethylpropylaminocarbonyl, 1-methylpentylaminocarbonyl, 2-methylpentylaminocarbonyl, 3-methylpentylaminocarbonyl, 4-methylpentylaminocarbonyl, 1,1-dimethylbutylaminocarbonyl, 1,2-dimethylbutylaminocarbonyl, 1,3-dimethylbutylaminocarbonyl, 2,2-dimethylbutylaminocarbonyl, 2,3-dimethylbutylaminocarbonyl, 3,3-dimethylbutylaminocarbonyl, 1-ethylbutylaminocarbonyl, 2-ethylbutylaminocarbonyl, 1,1,2-trimethylpropylaminocarbonyl, 1,2,2-trimethylpropylaminocarbonyl, 1-ethyl-1-methylpropylaminocarbonyl or 1-ethyl-2-methylpropylaminocarbonyl;

di($C_1$–$C_4$-alkyl)aminocarbonyl: for example N,N-dimethylaminocarbonyl, N,N-diethylaminocarbonyl, N,N-di(1-methylethyl)aminocarbonyl, N,N-dipropylaminocarbonyl, N,N-dibutylaminocarbonyl, N,N-di(1-methylpropyl)aminocarbonyl, N,N-di(2-methylpropyl)aminocarbonyl, N,N-di(1,1-dimethylethyl)aminocarbonyl, N-ethyl-N-methylaminocarbonyl, N-methyl-N-propylaminocarbonyl, N-methyl-N-(1-methylethyl)aminocarbonyl, N-butyl-N-methylaminocarbonyl, N-methyl-N-(1-methylpropyl)aminocarbonyl, N-methyl-N-(2-methylpropyl)aminocarbonyl, N-(1,1-dimethylethyl)-N-methylaminocarbonyl, N-ethyl-N-propylaminocarbonyl, N-ethyl-N-(1-methylethyl)aminocarbonyl, N-butyl-N-ethylaminocarbonyl, N-ethyl-N-(1-methylpropyl)aminocarbonyl, N-ethyl-N-(2-methylpropyl)aminocarbonyl, N-ethyl-N-(1,1-dimethylethyl)aminocarbonyl, N-(1-methylethyl)-N-propylaminocarbonyl, N-butyl-N-propylaminocarbonyl, N-(1-methylpropyl)-N-propylaminocarbonyl, N-(2-methylpropyl)-N-propylaminocarbonyl, N-(1,1-dimethylethyl)-N-propylaminocarbonyl, N-butyl-N-(1-methylethyl)aminocarbonyl, N-(1-methylethyl)-N-(1-methylpropyl)aminocarbonyl, N-(1-methylethyl)-N-(2-methylpropyl)aminocarbonyl, N-(1,1-dimethylethyl)-N-(1-methylethyl)aminocarbonyl, N-butyl-N-(1-methylpropyl)aminocarbonyl, N-butyl-N-(2-methylpropyl)aminocarbonyl, N-butyl-N-(1,1-dimethylethyl)aminocarbonyl, N-(1-methylpropyl)-N-(2-methylpropyl)aminocarbonyl, N-(1,1-dimethylethyl)-N-(1-methylpropyl)aminocarbonyl or N-(1,1-dimethylethyl)-N-(2-methylpropyl)aminocarbonyl;

di($C_1$–$C_6$-alkyl)aminocarbonyl: di($C_1$–$C_4$-alkyl)aminocarbonyl as mentioned above, and also, for example, N-methyl-N-pentylaminocarbonyl, N-methyl-N-(1-methylbutyl)aminocarbonyl, N-Methyl-N-(2-methylbutyl)aminocarbonyl, N-methyl-N-(3-methylbutyl)aminocarbonyl, N-methyl-N-(2,2-dimethylpropyl)aminocarbonyl, N-methyl-N-(1-ethylpropyl)aminocarbonyl, N-methyl-N-hexylaminocarbonyl, N-methyl-N-(1,1-dimethylpropyl)aminocarbonyl, N-methyl-N-(1,2-dimethylpropyl)aminocarbonyl, N-methyl-N-(1-methylpentyl)aminocarbonyl, N-methyl-N-(2-methylpentyl)aminocarbonyl, N-methyl-N-(3-methylpentyl)aminocarbonyl, N-methyl-N-(4-methylpentyl)aminocarbonyl, N-methyl-N-(1,1-dimethylbutyl)aminocarbonyl, N-methyl-N-(1,2-dimethylbutyl)aminocarbonyl, N-methyl-N-(1,3-dimethylbutyl)aminocarbonyl, N-methyl-N-(2,2-dimethylbutyl)aminocarbonyl, N-methyl-N-(2,3-dimethylbutyl)aminocarbonyl, N-methyl-N-(3,3-dimethylbutyl)aminocarbonyl, N-methyl-N-(1-ethylbutyl)aminocarbonyl, N-methyl-N-(2-ethylbutyl)aminocarbonyl, N-methyl-N-(1,1,2-trimethylpropyl)aminocarbonyl, N-methyl-N-(1,2,2-trimethylpropyl)aminocarbonyl, N-methyl-N-(1-ethyl-1-methylpropyl)aminocarbonyl, N-methyl-N-(1-ethyl-2-methylpropyl)aminocarbonyl, N-ethyl-N-pentylaminocarbonyl, N-ethyl-N-(1-methylbutyl)aminocarbonyl, N-ethyl-N-(2-methylbutyl)aminocarbonyl, N-ethyl-N-(3-methylbutyl)aminocarbonyl, N-ethyl-N-(2,2-dimethylpropyl)aminocarbonyl, N-ethyl-N-(1-ethylpropyl)aminocarbonyl, N-ethyl-N-hexylaminocarbonyl, N-ethyl-N-(1,1-dimethylpropyl)aminocarbonyl, N-ethyl-N-(1,2-dimethylpropyl)aminocarbonyl, N-ethyl-N-(1-methylpentyl)aminocarbonyl, N-ethyl-N-(2-methylpentyl)aminocarbonyl, N-ethyl-N-(3-methylpentyl)aminocarbonyl, N-ethyl-N-(4-methylpentyl)aminocarbonyl, N-ethyl-N-(1,1-dimethylbutyl)aminocarbonyl, N-ethyl-N-(1,2-dimethylbutyl)aminocarbonyl, N-ethyl-N-(1,3-dimethylbutyl)aminocarbonyl, N-ethyl-N-(2,2-dimethylbutyl)aminocarbonyl, N-ethyl-N-(2,3-dimethylbutyl)aminocarbonyl, N-ethyl-N-(3,3-dimethylbutyl)aminocarbonyl, N-ethyl-N-(1-ethylbutyl)aminocarbonyl, N-ethyl-N-(2-ethylbutyl)aminocarbonyl, N-ethyl-N-(1,1,2-trimethylpropyl)aminocarbonyl, N-ethyl-N-(1,2,2-trimethylpropyl)aminocarbonyl, N-ethyl-N-(1-ethyl-1-methylpropyl)aminocarbonyl, N-ethyl-N-(1-ethyl-2-methylpropyl)aminocarbonyl, N-propyl-N-pentylaminocarbonyl, N-butyl-N-pentylaminocarbonyl, N,N-dipentylaminocarbonyl, N-propyl-N-hexylaminocarbonyl, N-butyl-N-hexylaminocarbonyl, N-pentyl-N-hexylaminocarbonyl or N,N-dihexylaminocarbonyl;

di($C_1$–$C_6$-alkyl)aminothiocarbonyl: for example N,N-dimethylaminothiocarbonyl, N,N-diethylaminothiocarbonyl, N,N-di(1-methylethyl)aminothiocarbonyl, N,N-dipropylaminothiocarbonyl, N,N-dibutylaminothiocarbonyl, N,N-di(1-methylpropyl)aminothiocarbonyl, N,N-di(2-methylpropyl)aminothiocarbonyl, N,N-di(1,1-dimethylethyl)aminothiocarbonyl, N-ethyl-N-methylaminothiocarbonyl, N-methyl-N-propylaminothiocarbonyl, N-methyl-N-(1-methylethyl)aminothiocarbonyl, N-butyl-N-methylaminothiocarbonyl, N-methyl-N-(1-methylpropyl)aminothiocarbonyl, N-methyl-N-(2-methylpropyl)aminothiocarbonyl, N-(1,1-dimethylethyl)-N-methylaminothiocarbonyl, N-ethyl-N-propylaminothiocarbonyl, N-ethyl-N-(1-methylethyl)aminothiocarbonyl, N-butyl-N-ethylaminothiocarbonyl, N-ethyl N-(1-methylpropyl) aminothiocarbonyl, N-ethyl-N-(2-methylpropyl) aminothiocarbonyl, N-ethyl-N-(1,1-dimethylethyl) aminothiocarbonyl, N-(1-methylethyl)-N-propylaminothiocarbonyl, N-butyl-N-propylaminothiocarbonyl, N-(1-methylpropyl)-N-propylaminothiocarbonyl, N-(2-methylpropyl)-N-propylaminothiocarbonyl, N-(1,1-dimethylethyl)-N- propylaminothiocarbonyl, N-butyl-N-(1-methylethyl) aminothiocarbonyl, N-(1-methylethyl)-N-(1-methylpropyl)aminothiocarbonyl, N-(1-methylethyl)-N-(2-methylpropyl)aminothiocarbonyl, N-(1,1-dimethylethyl)-N-(1-methylethyl)aminothiocarbonyl, N-butyl-N-(1-methylpropyl)aminothiocarbonyl, N-butyl-N-(2-methylpropyl)aminothiocarbonyl, N-butyl-N-(1,1-dimethylethyl)aminothiocarbonyl, N-(1-methylpropyl)-N-(2-methylpropyl)aminothiocarbonyl, N-(1,1-dimethylethyl)-N-(1-methylpropyl) aminothiocarbonyl, N-(1,1-dimethylethyl)-N-(2-methylpropyl)aminothiocarbonyl, N-methyl-N-pentylaminothiocarbonyl, N-methyl-N-(1-methylbutyl)aminothiocarbonyl, N-methyl-N-(2-methylbutyl)aminothiocarbonyl, N-methyl-N-(3-methylbutyl)aminothiocarbonyl, N-methyl-N-(2,2-dimethylpropyl)aminothiocarbonyl, N-methyl-N-(1-ethylpropyl)aminothiocarbonyl, N-methyl-N-hexylaminothiocarbonyl, N-methyl-N-(1,1-dimethylpropyl)aminothiocarbonyl, N-methyl-N-(1,2-dimethylpropyl)aminothiocarbonyl, N-methyl-N-(1-methylpentyl)aminothiocarbonyl, N-methyl-N-(2-methylpentyl)aminothiocarbonyl, N-methyl-N-(3-methylpentyl)aminothiocarbonyl, N-methyl-N-(4-methylpentyl)aminothiocarbonyl, N-methyl-N-(1,1-dimethylbutyl)aminothiocarbonyl, N-methyl-N-(1,2-dimethylbutyl)aminothiocarbonyl, N-methyl-N-(1,3-dimethylbutyl)aminothiocarbonyl, N-methyl-N-(2,2-dimethylbutyl)aminothiocarbonyl, N-methyl-N-(2,3-dimethylbutyl)aminothiocarbonyl, N-methyl-N-(3,3-dimethylbutyl)aminothiocarbonyl, N-methyl-N-(1-ethylbutyl)aminothiocarbonyl, N-methyl-N-(2-ethylbutyl)aminothiocarbonyl, N-methyl-N-ethyl-N-(1,1,2-trimethylpropyl)aminothiocarbonyl, N-methyl-N-(1,2,2-trimethylpropyl)aminothiocarbonyl, N-methyl-N-(1-ethyl-1-methylpropyl)aminothiocarbonyl, N-methyl-N-(1-ethyl-2-methylpropyl)aminothiocarbonyl, N-ethyl-N-pentylaminothiocarbonyl, N-ethyl-N-(1-methylbutyl)aminothiocarbonyl, N-ethyl-N-(2-methylbutyl)aminothiocarbonyl, N-ethyl-N-(3-methylbutyl)aminothiocarbonyl, N-ethyl-N-(2,2-dimethylpropyl)aminothiocarbonyl, N-ethyl-N-(1-ethylpropyl)aminothiocarbonyl, N-ethyl-N-hexylaminothiocarbonyl, N-ethyl-N-(1,1-dimethylpropyl)aminothiocarbonyl, N-ethyl-N-(1,2-dimethylpropyl)aminothiocarbonyl, N-ethyl-N-(1-methylpentyl)aminothiocarbonyl, N-ethyl-N-(2-methylpentyl)aminothiocarbonyl, N-ethyl-N-(3-methylpentyl)aminothiocarbonyl, N-ethyl-N-(4-methylpentyl)aminothiocarbonyl, N-ethyl-N-(1,1-dimethylbutyl)aminothiocarbonyl, N-ethyl-N-(1,2-dimethylbutyl)aminothiocarbonyl, N-ethyl-N-(1,3-dimethylbutyl)aminothiocarbonyl, N-ethyl-N-(2,2-dimethylbutyl)aminothiocarbonyl, N-ethyl-N-(2,3-dimethylbutyl)aminothiocarbonyl, N-ethyl-N-(3,3-dimethylbutyl)aminothiocarbonyl, N-ethyl-N-(1-ethylbutyl)aminothiocarbonyl, N-ethyl-N-(2-ethylbutyl)aminothiocarbonyl, N-ethyl-N-(1,1,2-trimethylpropyl)aminothiocarbonyl, N-ethyl-N-(1,2,2-trimethylpropyl)aminothiocarbonyl, N-ethyl-N-(1-ethyl-1-methylpropyl)aminothiocarbonyl, N-ethyl-N-(1-ethyl-2-methylpropyl)aminothiocarbonyl, N-propyl-N-pentylaminothiocarbonyl, N-butyl-N-pentylaminothiocarbonyl, N,N-dipentylaminothiocarbonyl, N-propyl-N-hexylaminothiocarbonyl, N-butyl-N-hexylaminothiocarbonyl, N-pentyl-N-hexylaminothiocarbonyl or N,N-dihexylaminothiocarbonyl;

$C_1$–$C_4$-alkoxy-$C_1$–$C_4$-alkyl and the alkoxyalkyl moieties of hydroxy-$C_1$–$C_4$-alkoxy-$C_1$–$C_4$-alkyl: $C_1$–$C_4$-alkyl which is substituted by $C_1$–$C_4$-alkoxy as mentioned above, i.e., for example, methoxymethyl, ethoxymethyl, propoxymethyl, (1-methylethoxy)methyl, butoxymethyl, (1-methylpropoxy)methyl, (2-methylpropoxy)methyl, (1,1-dimethylethoxy)methyl, 2-(methoxy)ethyl, 2-(ethoxy)ethyl, 2-(propoxy)ethyl, 2-(1-methylethoxy)ethyl, 2-(butoxy)ethyl, 2-(1-methylpropoxy)ethyl, 2-(2-methylpropoxy)ethyl, 2-(1,1-dimethylethoxy)ethyl, 2-(methoxy)propyl, 2-(ethoxy)propyl, 2-(propoxy)propyl, 2-(1-methylethoxy)propyl, 2-(butoxy)propyl, 2-(1-methylpropoxy)propyl, 2-(2-methylpropoxy)propyl, 2-(1,1-dimethylethoxy)propyl, 3-(methoxy)propyl, 3-(ethoxy)propyl, 3-(propoxy)propyl, 3-(1-methylethoxy)propyl, 3-(butoxy)propyl, 3-(1-methylpropoxy)propyl, 3-(2-methylpropoxy)propyl, 3-(1,1-dimethylethoxy)propyl, 2-(methoxy)butyl, 2-(ethoxy)butyl, 2-(propoxy)butyl, 2-(1-methylethoxy)butyl, 2-(butoxy)butyl, 2-(1-methylpropoxy)butyl, 2-(2-methylpropoxy)butyl, 2-(1,1-dimethylethoxy)butyl, 3-(methoxy)butyl, 3-(ethoxy)butyl, 3-(propoxy)butyl, 3-(1-methylethoxy)butyl, 3-(butoxy)butyl, 3-(1-methylpropoxy)butyl, 3-(2-methylpropoxy)butyl, 3-(1,1-dimethylethoxy)butyl, 4-(methoxy)butyl, 4-(ethoxy)butyl, 4-(propoxy)butyl, 4-(1-methylethoxy)butyl, 4-(butoxy)butyl, 4-(1-methylpropoxy)butyl, 4-(2-methylpropoxy)butyl or 4-(1,1-dimethylethoxy)butyl;

$C_1$–$C_4$-alkoxy-$C_1$–$C_4$-alkoxy as alkoxyalkoxy moieties of $C_1$–$C_4$-alkoxy-$C_1$–$C_4$-alkoxycarbonyl: $C_1$–$C_4$-alkoxy which is substituted by $C_1$–$C_4$-alkoxy as mentioned above, i.e., for example, methoxymethoxy, ethoxymethoxy, propoxymethoxy, (1-methylethoxy)methoxy, butoxymethoxy, (1-methylpropoxy)methoxy, (2-methylpropoxy)methoxy, (1,1-dimethylethoxy)methoxy, 2-(methoxy)ethoxy, 2-(ethoxy)ethoxy, 2-(propoxy)ethoxy, 2-(1-methylethoxy)ethoxy, 2-(butoxy)ethoxy, 2-(1-methylpropoxy)ethoxy, 2-(2-methylpropoxy)ethoxy, 2-(1,1-dimethylethoxy)ethoxy, 2-(methoxy)propoxy, 2-(ethoxy)propoxy, 2-(propoxy)propoxy, 2-(1-methylethoxy)propoxy, 2-(butoxy)propoxy, 2-(1-methylpropoxy)propoxy, 2-(2-methylpropoxy)propoxy, 2-(1,1-dimethylethoxy)propoxy, 3-(methoxy)propoxy, 3-(ethoxy)propoxy, 3-(propoxy)propoxy, 3-(1-methylethoxy)propoxy, 3-(butoxy)propoxy, 3-(1-methylpropoxy)propoxy, 3-(2-methylpropoxy)propoxy, 3-(1,1-dimethylethoxy)propoxy, 2-(methoxy)butoxy, 2-(ethoxy)butoxy, 2-(propoxy)butoxy, 2-(1-methylethoxy)butoxy, 2-(butoxy)butoxy, 2-(1-methylpropoxy)butoxy, 2-(2-methylpropoxy)butoxy, 2-(1,1-dimethylethoxy)butoxy, 3-(methoxy)butoxy, 3-(ethoxy)butoxy, 3-(propoxy)butoxy, 3-(1-methylethoxy)butoxy, 3-(butoxy)butoxy, 3-(1-methylpropoxy)butoxy, 3-(2-methylpropoxy)butoxy, 3-(1,1-dimethylethoxy)butoxy, 4-(methoxy)butoxy, 4-(ethoxy)butoxy, 4-(propoxy)butoxy, 4-(1-methylethoxy)butoxy, 4-(butoxy)butoxy, 4-(1-methylpropoxy)butoxy, 4-(2-methylpropoxy)butoxy or 4-(1,1-dimethylethoxy)butoxy;

$C_3$–$C_6$-alkenyl, and the alkenyl moieties of $C_3$–$C_6$-alkenylcarbonyl, $C_3$–$C_6$-alkenyloxy, $C_3$–$C_6$-alkenyloxycarbonyl, $C_3$–$C_6$-alkenylaminocarbonyl, N-($C_3$–$C_6$-alkenyl)-N-($C_1$–$C_6$-alkyl)aminocarbonyl, N-($C_3$–$C_6$-alkenyl)-N-($C_1$–$C_6$-alkoxy)aminocarbonyl: for example prop-2-en-1-yl, but-1-en-4-yl, 1-methylprop-2-en-1-yl, 2-methylprop-2-en-1-yl, 2-buten-1-yl, 1-penten-3-yl, 1-penten-4-yl, 2-penten-4-yl, 1-methylbut-2-en-1-yl, 2-methylbut-2-en-1-yl, 3-methylbut-2-en-1-yl, 1-methylbut-3-en-1-yl, 2-methylbut-3-en-1-yl, 3-methylbut-3-en-1-yl, 1,1-dimethylprop-2-en-1-yl, 1,2-dimethylprop-2-en-1-yl, 1-ethylprop-2-en-1-yl, hex-3-en-1-yl, hex-4-en-1-yl, hex-5-en-1-yl, 1-methylpent-3-en-1-yl, 2-methylpent-3-en-1-yl, 3-methylpent-3-en-1-yl, 4-methylpent-3-en-1-yl, 1-methylpent-4-en-1-yl, 2-methylpent-4-en-1-yl, 3-methylpent-4-en-1-yl, 4-methylpent-4-en-1-yl, 1,1-dimethylbut-2-en-1-yl, 1,1-dimethylbut-3-en-1-yl, 1,2-dimethylbut-2-en-1-yl, 1,2-dimethylbut-3-en-1-yl, 1,3-dimethylbut-2-en-1-yl, 1,3-dimethylbut-3-en-1-yl, 2,2-dimethylbut-3-en-1-yl, 2,3-dimethylbut-2-en-1-yl, 2,3-dimethylbut-3-en-1-yl, 3,3-dimethylbut-2-en-1-yl, 1-ethylbut-2-en-1-yl, 1-ethylbut-3-en-1-yl, 2-ethylbut-2-en-1-yl, 2-ethylbut-3-en-1-yl, 1,1,2-trimethylprop-2-en-1-yl, 1-ethyl-1-methylprop-2-en-1-yl or 1-ethyl-2-methylprop-2-en-1-yl;

$C_2$–$C_6$-alkenyl, and the alkenyl moieties of $C_2$–$C_6$-alkenylcarbonyl, phenyl-$C_2$–$C_6$-alkenylcarbonyl and heterocyclyl-$C_2$–$C_6$-alkenylcarbonyl: $C_3$–$C_6$-alkenyl as mentioned above, and also ethenyl;

$C_2$–$C_{20}$-alkenyl as alkenyl moiety of $C_2$–$C_{20}$-alkenylcarbonyl: $C_2$–$C_6$-alkenyl as mentioned above, and also pentadecenyl or heptadecenyl;

$C_3$–$C_6$-haloalkenyl: a $C_3$–$C_6$-alkenyl radical as mentioned above which is partially or fully substituted by fluorine, chlorine, bromine and/or iodine, i.e., for example, 2-chloroallyl, 3-chloroallyl, 2,3-dichloroallyl, 3,3-dichloroallyl, 2,3,3-trichloroallyl, 2,3-dichlorobut-2-enyl, 2-bromoallyl, 3-bromoallyl, 2,3-dibromoallyl, 3,3-dibromoallyl, 2,3,3-tribromoallyl or 2,3-dibromobut-2-enyl;

$C_3$–$C_6$-alkynyl, and the alkynyl moieties of $C_3$–$C_6$-alkynylcarbonyl, $C_3$–$C_6$-alkynyloxy, $C_3$–$C_6$-alkynyloxycarbonyl, $C_3$–$C_6$-alkynylaminocarbonyl, N-($C_3$–$C_6$-alkynyl)-N-($C_1$–$C_6$-alkyl)aminocarbonyl, N-($C_3$–$C_6$-alkynyl)-N-($C_1$–$C_6$-alkoxyamino)carbonyl: for example propargyl, but-1-yn-3-yl, but-1-yn-4-yl, but-2-yn-1-yl, pent-1-yn-3-yl, pent-1-yn-4-yl, pent-1-yn-5-yl, pent-2-yn-1-yl, pent-2-yn-4-yl, pent-2-yn-5-yl, 3-methylbut-1-yn-3-yl, 3-methylbut-1-yn-4-yl, hex-1-yn-3-yl, hex-1-yn-4-yl, hex-1-yn-5-yl, hex-1-yn-6-yl, hex-2-yn-1-yl, hex-2-yn-4-yl, hex-2-yn-5-yl, hex-2-yn-6-yl, hex-3-yn-1-yl, hex-3-yn-2-yl, 3-methylpent-1-yn-3-yl, 3-methylpent-1-yn-4-yl, 3-methylpent-1-yn-5-yl, 4-methylpent-2-yn-4-yl or 4-methylpent-2-yn-5-yl;

$C_2$–$C_6$-alkynyl, and the alkynyl moieties of $C_2$–$C_6$-alkynylcarbonyl: $C_3$–$C_6$-alkynyl as mentioned above, and also ethynyl;

$C_3$–$C_6$-haloalkynyl: a $C_3$–$C_6$-alkynyl radical as mentioned above which is partially or fully substituted by fluorine, chlorine, bromine and/or iodine, i.e., for example, 1,1-difluoroprop-2-yn-1-yl, 3-iodoprop-2-yn-1-yl, 4-fluorobut-2-yn-1-yl, 4-chlorobut-2-yn-1-yl, 1,1-difluorobut-2-yn-1-yl, 4-iodobut-3-yn-1-yl, 5-fluoropent-3-yn-1-yl, 5-iodopent-4-yn-1-yl, 6-fluorohex-4-yn-1-yl or 6-iodohex-5-yn-1-yl;

$C_3$–$C_6$-cycloalkyl, and the cycloalkyl moieties of $C_3$–$C_6$-cycloalkylcarbonyl: for example cyclopropyl, cyclobutyl, cyclopentyl or cyclohexyl;

heterocyclyl, and the heterocyclyl moieties of heterocyclyloxy, heterocyclylcarbonyl, heterocyclyl-$C_1$–$C_6$-alkyl, heterocyclyloxycarbonyl, heterocyclyloxythiocarbonyl, heterocyclyl-$C_2$–$C_6$-alkenylcarbonyl, heterocyclylcarbonyl-$C_1$–$C_6$-alkyl, N-($C_1$–$C_6$-alkyl)-N-(heterocyclyl)aminocarbonyl, heterocyclylaminocarbonyl: a saturated, partially saturated or unsaturated 5- or 6-membered heterocyclic ring which is attached via carbon and contains one to four identical or different heteroatoms selected from the following group: oxygen, sulfur and nitrogen, i.e., for example, 5-membered rings having, for example, one heteroatom, having two heteroatoms, having three heteroatoms or having four heteroatoms or, for example, 6-membered rings having, for example, one heteroatom, having two heteroatoms, having three heteroatoms or having four heteroatoms, i.e. 5-membered rings having one heteroatom, such as:

tetrahydrofuran-2-yl, tetrahydrofuran-3-yl, tetrahydrothien-2-yl, tetrahydrothien-3-yl, tetrahydropyrrol-2-yl, tetrahydropyrrol-3-yl, 2,3-dihydrofuran-2-yl, 2,3-dihydrofuran-3-yl, 2,5-dihydrofuran-2-yl, 2,5-dihydrofuran-3-yl, 4,5-dihydrofuran-2-yl, 4,5-dihydrofuran-3-yl, 2,3-dihydrothien-2-yl, 2,3-dihydrothien-3-yl, 2,5-dihydrothien-2-yl, 2,5-dihydrothien-3-yl, 4,5-dihydrothien-2-yl, 4,5-dihydrothien-3-yl, 2,3-dihydro-1H-pyrrol-2-yl, 2,3-dihydro-1H-pyrrol-3-yl, 2,5-dihydro-1H-pyrrol-2-yl, 2,5-dihydro-1H-pyrrol-3-yl, 4,5-dihydro-1H-pyrrol-2-yl, 4,5-dihydro-1H-pyrrol-3-yl, 3,4-dihydro-2H-pyrrol-2-yl, 3,4-dihydro-2H-pyrrol-3-yl, 3,4-dihydro-5H-pyrrol-2-yl, 3,4-dihydro-5H-pyrrol-3-yl, 2-furyl, 3-furyl, 2-thienyl, 3-thienyl, pyrrol-2-yl or pyrrol-3-yl;

5-membered rings having two heteroatoms such as:

tetrahydropyrazol-3-yl, tetrahydropyrazol-4-yl, tetrahydroisoxazol-3-yl, tetrahydroisoxazol-4-yl, tetrahydroisoxazol-5-yl, 1,2-oxathiolan-3-yl, 1,2-oxathiolan-4-yl, 1,2-oxathiolan-5-yl, tetrahydroisothiazol-3-yl, tetrahydroisothiazol-4-yl, tetrahydroisothiazol-5-yl, 1,2-dithiolan-3-yl, 1,2-dithiolan-4-yl, tetrahydroimidazol-2-yl, tetrahydroimidazol-4-yl, tetrahydrooxazol-2-yl, tetrahydrooxazol-4-yl, tetrahydrooxazol-5-yl, tetrahydrothiazol-2-yl, tetrahydrothiazol-4-yl, tetrahydrothiazol-5-yl, 1,3-dioxolan-2-yl, 1,3-dioxolan-4-yl, 1,3-oxathiolan-2-yl, 1,3-oxathiolan-4-yl, 1,3-oxathiolan-5-yl, 1,3-dithiolan-2-yl, 1,3-dithiolan-4-yl, 4,5-dihydro-1H-pyrazol-3-yl, 4,5-dihydro-1H-pyrazol-4-yl, 4,5-dihydro-1H-pyrazol-5-yl, 2,5-dihydro-1H-pyrazol-3-yl, 2,5-dihydro-1H-pyrazol-4-yl, 2,5-dihydro-1H-pyrazol-5-yl, 4,5-dihydroisoxazol-3-yl, 4,5-dihydroisoxazol-4-yl, 4,5-dihydroisoxazol-5-yl, 2,5-dihydroisoxazol-3-yl, 2,5-dihydroisoxazol-4-yl, 2,5-dihydroisoxazol-5-yl, 2,3-dihydroisoxazol-3-yl, 2,3-dihydroisoxazol-4-yl, 2,3-dihydroisoxazol-5-yl, 4,5-dihydroisothiazol-3-yl, 4,5-dihydroisothiazol-4-yl, 4,5-dihydroisothiazol-5-yl, 2,5-dihydroisothiazol-3-yl, 2,5-dihydroisothiazol-4-yl, 2,5-dihydroisothiazol-5-yl, 2,3-dihydroisothiazol-3-yl, 2,3-dihydroisothiazol-4-yl, 2,3-dihydroisothiazol-5-yl, $\Delta^3$-1,2-dithiol-3-yl, $\Delta^3$-1,2-dithiol-4-yl, $\Delta^3$-1,2-dithiol-5-yl, 4,5-dihydro-1H-imidazol-2-yl, 4,5-dihydro-1H-imidazol-4-yl, 4,5-dihydro-1H-imidazol-5-yl, 2,5-dihydro-1H-imidazol-2-yl, 2,5-dihydro-1H-imidazol-4-yl, 2,5-dihydro-1H-imidazol-5-yl, 2,3-dihydro-1H-imidazol-2-yl, 2,3-dihydro-1H-imidazol-4-yl, 4,5-dihydrooxazol-2-yl, 4,5-dihydrooxazol-4-yl, 4,5-dihydrooxazol-5-yl, 2,5-dihydrooxazol-2-yl, 2,5-dihydrooxazol-4-yl, 2,5-dihydrooxazol-5-yl, 2,3-dihydrooxazol-2-yl, 2,3-dihydrooxazol-4-yl, 2,3-dihydrooxazol-5-yl, 4,5-dihydrothiazol-2-yl, 4,5-dihydrothiazol-4-yl, 4,5-dihydrothiazol-5-yl, 2,5-dihydrothiazol-2-yl, 2,5- dihydrothiazol-4-yl, 2,5-dihydrothiazol-5-yl, 2,3-dihydrothiazol-2-yl, 2,3-dihydrothiazol-4-yl, 2,3-dihydrothiazol-5-yl, 1,3-dioxol-2-yl, 1,3-dioxol-4-yl, 1,3-dithiol-2-yl, 1,3-dithiol-4-yl, 1,3-oxathiol-2-yl, 1,3-oxathiol-4-yl, 1,3-oxathiol-5-yl, pyrazol-3-yl, pyrazol-4-yl, isoxazol-3-yl, isoxazol-4-yl, isoxazol-5-yl, isothiazol-3-yl, isothiazol-4-yl, isothiazol-5-yl, imidazol-2-yl, imidazol-4-yl, oxazol-2-yl, oxazol-4-yl, oxazol-5-yl, thiazol-2-yl, thiazol-4-yl or thiazol-5-yl;

5-membered rings having three heteroatoms such as:
1,2,3-$\Delta^2$-oxadiazolin-4-yl, 1,2,3-$\Delta^2$-oxadiazolin-5-yl, 1,2,4-$\Delta^4$-oxadiazolin-3-yl, 1,2,4-$\Delta^4$-oxadiazolin-5-yl, 1,2,4-$\Delta^2$-oxadiazolin-3-yl, 1,2,4-$\Delta^2$-oxadiazolin-5-yl, 1,2,4-$\Delta^3$-oxadiazolin-3-yl, 1,2,4-$\Delta^3$-oxadiazolin-5-yl, 1,3,4-$\Delta^2$-oxadiazolin-2-yl, 1,3,4-$\Delta^2$-oxadiazolin-5-yl, 1,3,4-$\Delta^3$-oxadiazolin-2-yl, 1,3,4-oxadiazolin-2-yl, 1,2,3-$\Delta^2$-thiadiazolin-4-yl, 1,2,3-$\Delta^2$-thiadiazolin-5-yl, 1,2,4-$\Delta^4$-thiadiazolin-3-yl, 1,2,4-$\Delta^4$-thiadiazolin-5-yl, 1,2,4-$\Delta^3$-thiadiazolin-3-yl, 1,2,4-$\Delta^3$-thiadiazolin-5-yl, 1,2,4-$\Delta^2$-thiadiazolin-3-yl, 1,2,4-$\Delta^2$-thiadiazolin-5-yl, 1,3,4-$\Delta^2$-thiadiazolin-2-yl, 1,3,4-$\Delta^2$-thiadiazolin-5-yl, 1,3,4-$\Delta^3$-thiadiazolin-2-yl, 1,3,4-thiadiazolin-2-yl, 1,3,2-dioxathiolan-4-yl, 1,2,3-$\Delta^2$-triazolin-4-yl, 1,2,3-$\Delta^2$-triazolin-5-yl, 1,2,4-$\Delta^2$-triazolin-3-yl, 1,2,4-$\Delta^2$-triazolin-5-yl, 1,2,4-$\Delta^3$-triazolin-3-yl, 1,2,4-$\Delta^3$-triazolin-5-yl, 1,2,4-$\Delta^1$-triazolin-2-yl, 1,2,4-triazolin-3-yl, 3H-1,2,4-dithiazol-5-yl, 2H-1,3,4-dithiazol-5-yl, 2H-1,3,4-oxathiazol-5-yl, 1,2,3-oxadiazol-4-yl, 1,2,3-oxadiazol-5-yl, 1,2,4-oxadiazol-3-yl, 1,2,4,-oxadiazol-5-yl, 1,3,4-oxadiazol-2-yl, 1,2,3-thiadiazol-4-yl, 1,2,3-thiadiazol-5-yl, 1,2,4-thiadiazol-3-yl, 1,2,4-thiadiazol-5-yl, 1,3,4-thiadiazolyl-2-yl, 1,2,3-triazol-4-yl or 1,2,4-triazol-3-yl;

5-membered rings having four heteroatoms such as:
tetrazol-5-yl;

6-membered rings having one heteroatom such as:
tetrahydropyran-2-yl, tetrahydropyran-3-yl, tetrahydropyran-4-yl, piperidin-2-yl, piperidin-3-yl, piperidin-4-yl, tetrahydrothiopyran-2-yl, tetrahydrothiopyran-3-yl, tetrahydrothiopyran-4-yl, 2H-3,4-dihydropyran-6-yl, 2H-3,4-dihydropyran-5-yl, 2H-3,4-dihydropyran-4-yl, 2H-3,4-dihydropyran-3-yl, 2H-3,4-dihydropyran-2-yl, 2H-3,4-dihydropyran-6-yl, 2H-3,4-dihydrothiopyran-5-yl, 2H-3,4-dihydrothiopyran-4-yl, 2H-3,4-dihydrothiopyran-3-yl, 2H-3,4-dihydropyran-2-yl, 1,2,3,4-tetrahydropyridin-6-yl, 1,2,3,4-tetrahydropyridin-5-yl, 1,2,3,4-tetrahydropyridin-4-yl, 1,2,3,4-tetrahydropyridin-3-yl, 1,2,3,4-tetrahydropyridin-2-yl, 2H-5,6-dihydropyran-2-yl, 2H-5,6-dihydropyran-3-yl, 2H-5,6-dihydropyran-4-yl, 2H-5,6-dihydropyran-5-yl, 2H-5,6-dihydropyran-6-yl, 2H-5,6-dihydrothiopyran-2-yl, 2H-5,6-dihydrothiopyran-3-yl, 2H-5,6-dihydrothiopyran-4-yl, 2H-5,6-dihydrothiopyran-5-yl, 2H-5,6-dihydrothiopyran-6-yl, 1,2,5,6-tetrahydropyridin-2-yl, 1,2,5,6-tetrahydropyridin-3-yl, 1,2,5,6-tetrahydropyridin-4-yl, 1,2,5,6-tetrahydropyridin-5-yl, 1,2,5,6-tetrahydropyridin-6-yl, 2,3,4,5-tetrahydropyridin-2-yl, 2,3,4,5-tetrahydropyridin-3-yl, 2,3,4,5-tetrahydropyridin-4-yl, 2,3,4,5-tetrahydropyridin-5-yl, 2,3,4,5-tetrahydropyridin-6-yl, 4H-pyran-2-yl, 4H-pyran-3-yl, 4H-pyran-4-yl, 4H-thiopyran-2-yl, 4H-thiopyran-3-yl, 4H-thiopyran-4-yl, 1,4-dihydropyridin-2-yl, 1,4-dihydropyridin-3-yl, 1,4-dihydropyridin-4-yl, 2H-pyran-2-yl, 2H-pyran-3-yl, 2H-pyran-4-yl, 2H-pyran-5-yl, 2H-pyran-6-yl, 2H-thiopyran-2-yl, 2H-thiopyran-3-yl, 2H-thiopyran-4-yl, 2H-thiopyran-5-yl, 2H-thiopyran-6-yl, 1,2-dihydropyridin-2-yl, 1,2-dihydropyridin-3-yl, 1,2-dihydropyridin-4-yl, 1,2-dihydropyridin-5-yl, 1,2-dihydropyridin-6-yl, 3,4-dihydropyridin-2-yl, 3,4-dihydropyridin-3-yl, 3,4-dihydropyridin-4-yl, 3,4-dihydropyridin-5-yl, 3,4-dihydropyridin-6-yl, 2,5-dihydropyridin-2-yl, 2,5-dihydropyridin-3-yl, 2,5-dihydropyridin-4-yl, 2,5-dihydropyridin-5-yl, 2,5-dihydropyridin-6-yl, 2,3-dihydropyridin-2-yl, 2,3-dihydropyridin-3-yl, 2,3-dihydropyridin-4-yl, 2,3-dihydropyridin-5-yl, 2,3-dihydropyridin-6-yl, pyridin-2-yl, pyridin-3-yl or pyridin-4-yl;

6-membered rings having two heteroatoms such as:
1,3-dioxan-2-yl, 1,3-dioxan-4-yl, 1,3-dioxan-5-yl, 1,4-dioxan-2-yl, 1,3-dithian-2-yl, 1,3-dithian-4-yl, 1,3-dithian-5-yl, 1,4-dithian-2-yl, 1,3-oxathian-2-yl, 1,3-oxathian-4-yl, 1,3-oxathian-5-yl, 1,3-oxathian-6-yl, 1,4-oxathian-2-yl, 1,4-oxathian-3-yl, 1,2-dithian-3-yl, 1,2-dithian-4-yl, hexahydropyrimidin-2-yl, hexahydropyrimidin-4-yl, hexahydropyrimidin-5-yl, hexahydropyrazin-2-yl, hexahydropyridazin-3-yl, hexahydropyridazin-4-yl, tetrahydro-1,3-oxazin-2-yl, tetrahydro-1,3-oxazin-4-yl, tetrahydro-1,3-oxazin-5-yl, tetrahydro-1,3-oxazin-6-yl, tetrahydro-1,3-thiazin-2-yl, tetrahydro-1,3-thiazin-4-yl, tetrahydro-1,3-thiazin-5-yl, tetrahydro-1,3-thiazin-6-yl, tetrahydro-1,4-thiazin-2-yl, tetrahydro-1,4-thiazin-3-yl, tetrahydro-1,4-oxazin-2-yl, tetrahydro-1,4-oxazin-3-yl, tetrahydro-1,2-oxazin-3-yl, tetrahydro-1,2-oxazin-4-yl, tetrahydro-1,2-oxazin-5-yl, tetrahydro-1,2-oxazin-6-yl, 2H-5,6-dihydro-1,2-oxazin-3-yl, 2H-5,6-dihydro-1,2-oxazin-4-yl, 2H-5,6-dihydro-1,2-oxazin-5-yl, 2H-5,6-dihydro-1,2-oxazin-6-yl, 2H-5,6-dihydro-1,2-thiazin-3-yl, 2H-5,6-dihydro-1,2-thiazin-4-yl, 2H-5,6-dihydro-1,2-thiazin-5-yl, 2H-5,6-dihydro-1,2-thiazin-6-yl, 4H-5,6-dihydro-1,2-oxazin-3-yl, 4H-5,6-dihydro-1,2-oxazin-4-yl, 4H-5,6-dihydro-1,2-oxazin-5-yl, 4H-5,6-dihydro-1,2-oxazin-6-yl, 4H-5,6-dihydro-1,2-thiazin-3-yl, 4H-5,6-dihydro-1,2-thiazin-4-yl, 4H-5,6-dihydro-1,2-thiazin-5-yl, 4H-5,6-dihydro-1,2-thiazin-6-yl, 2H-3,6-dihydro-1,2-oxazin-3-yl, 2H-3,6-dihydro-1,2-oxazin-4-yl, 2H-3,6-dihydro-1,2-oxazin-5-yl, 2H-3,6-dihydro-1,2-oxazin-6-yl, 2H-3,6-dihydro-1,2-thiazin-3-yl, 2H-3,6-dihydro-1,2-thiazin-4-yl, 2H-3,6-dihydro-1,2-thiazin-5-yl, 2H-3,6-dihydro-1,2-thiazin-6-yl, 2H-3,4-dihydro-1,2-oxazin-3-yl, 2H-3,4-dihydro-1,2-oxazin-4-yl, 2H-3,4-dihydro-1,2-oxazin-5-yl, 2H-3,4-dihydro-1,2-oxazin-6-yl, 2H-3,4-dihydro-1,2-thiazin-3-yl, 2H-3,4-dihydro-1,2-thiazin-4-yl, 2H-3,4-dihydro-1,2-thiazin-5-yl, 2H-3,4-dihydro-1,2-thiazin-6-yl, 2,3,4,5-tetrahydropyridazin-3-yl, 2,3,4,5-tetrahydropyridazin-4-yl, 2,3,4,5-tetrahydropyridazin-5-yl, 2,3,4,5-tetrahydropyridazin-6-yl, 3,4,5,6-tetrahydropyridazin-3-yl, 3,4,5,6-tetrahydropyridazin-4-yl, 1,2,5,6-tetrahydropyridazin-3-yl, 1,2,5,6-tetrahydropyridazin-4-yl, 1,2,5,6-tetrahydropyridazin-5-yl, 1,2,5,6-tetrahydropyridazin-6-yl, 1,2,3,6-tetrahydropyridazin-3-yl, 1,2,3,6-tetrahydropyridazin-4-yl, 4H-5,6-dihydro-1,3-oxazin-2-yl, 4H-5,6-dihydro-1,3-oxazin-4-yl, 4H-5,6-dihydro-1,3-oxazin-5-yl, 4H-5,6-dihydro-1,3-oxazin-6-yl, 4H-5,6-dihydro-1,3-thiazin-2-yl, 4H-5,6-dihydro-1,3-thiazin-4-yl, 4H-5,6-dihydro-1,3-thiazin-5-yl, 4H-5,6-dihydro-1,3-thiazin-6-yl, 3,4,5,6-tetrahydropyrimidin-2-yl, 3,4,5,6-tetrahydropyrimidin-4-yl, 3,4,5,6-tetrahydropyrimidin-5-yl, 3,4,5,6-tetrahydropyrimidin-6-yl, 1,2,3,4-tetrahydropyrazin-2-yl, 1,2,3,4-tetrahydropyrazin-5-yl, 1,2,3,4-tetrahydropyrimidin-2-yl, 1,2,3,4-tetrahydropyrimidin-4-yl, 1,2,3,4-tetrahydropyrimidin-5-yl, 1,2,3,4- tetrahydropyrimidin-6-yl, 2,3-dihydro-1,4-thiazin-2-yl, 2,3-dihydro-1,4-thiazin-3-yl, 2,3-dihydro-1,4-thiazin-5-yl, 2,3-dihydro-1,4-thiazin-6-yl, 2H-1,2-oxazin-3-yl, 2H-1,2-oxazin-4-yl, 2H-1,2-oxazin-5-yl, 2H-1,2-oxazin-6-yl, 2H-1,2-thiazin-3-yl, 2H-1,2-thiazin-4-yl, 2H-1,2-thiazin-5-yl, 2H-1,2-thiazin-6-yl, 4H-1,2-oxazin-3-yl, 4H-1,2-oxazin-4-yl, 4H-1,2-oxazin-5-yl, 4H-1,2-oxazin-6-yl, 4H-1,2-thiazin-3-yl, 4H-1,2-thiazin-4-yl, 4H-1,2-thiazin-5-yl, 4H-1,2-thiazin-6-yl, 6H-1,2-oxazin-3-yl, 6H-1,2-oxazin-4-yl, 6H-1,2-oxazin-5-yl, 6H-1,2-oxazin-6-yl, 6H-1,2-thiazin-3-yl, 6H-1,2-thiazin-4-yl, 6H-1,2-thiazin-5-yl, 6H-1,2-thiazin-6-yl, 2H-1,3-oxazin-2-yl, 2H-1,3-oxazin-4-yl, 2H-1,3-oxazin-5-yl, 2H-1,3-oxazin-6-yl, 2H-1,3-thiazin-2-yl, 2H-1,3-thiazin-4-yl, 2H-1,3-thiazin-5-yl, 2H-1,3-thiazin-6-yl, 4H-1,3-oxazin-2-yl, 4H-1,3-oxazin-4-yl, 4H-1,3-oxazin-5-yl, 4H-1,3-oxazin-6-yl, 4H-1,3-thiazin-2-yl, 4H-1,3-thiazin-4-yl, 4H-1,3-thiazin-5-yl, 4H-1,3-thiazin-6-yl, 6H-1,3-oxazin-2-yl, 6H-1,3-oxazin-4-yl, 6H-1,3-oxazin-5-yl, 6H-1,3-oxazin-6-yl, 6H-1,3-thiazin-2-yl, 6H-1,3-oxazin-4-yl, 6H-1,3-oxazin-5-yl, 6H-1,3-thiazin-6-yl, 2H-1,4-oxazin-2-yl, 2H-1,4-oxazin-3-yl, 2H-1,4-oxazin-5-yl, 2H-1,4-oxazin-6-yl, 2H-1,4-thiazin-2-yl, 2H-1,4-thiazin-3-yl, 2H-1,4-thiazin-5-yl, 2H-1,4-thiazin-6-yl, 4H-1,4-oxazin-2-yl, 4H-1,4-oxazin-3-yl, 4H-1,4-thiazin-2-yl, 4H-1,4-thiazin-3-yl, 1,4-dihydropyridazin-3-yl, 1,4-dihydropyridazin-4-yl, 1,4-dihydropyridazin-5-yl, 1,4-dihydropyridazin-6-yl, 1,4-dihydropyrazin-2-yl, 1,2-dihydropyrazin-2-yl, 1,2-dihydropyrazin-3-yl, 1,2-dihydropyrazin-5-yl, 1,2-dihydropyrazin-6-yl, 1,4-dihydropyrimidin-2-yl, 1,4-dihydropyrimidin-4-yl, 1,4-dihydropyrimidin-5-yl, 1,4-dihydropyrimidin-6-yl, 3,4-dihydropyrimidin-2-yl, 3,4-dihydropyrimidin-4-yl, 3,4-dihydropyrimidin-5-yl or 3,4-dihydropyrimidin-6-yl, pyridazin-3-yl, pyridazin-4-yl, pyrimidin-2-yl, pyrimidin-4-yl, pyrimidin-5-yl or pyrazin-2-yl;

6-membered rings having three heteroatoms such as:
1,3,5-triazin-2-yl, 1,2,4-triazin-3-yl, 1,2,4-triazin-5-yl, 1,2,4-triazin-6-yl;

6-membered rings having four heteroatoms such as:
1,2,4,5-tetrazin-3-yl;

where, if appropriate, the sulfur of the abovementioned heterocycles may be oxidized to S=O or S(=O)$_2$ and where a bicyclic ring system may be formed with a fused-on phenyl ring or with a $C_3$–$C_6$-carbocycle or with a further 5- to 6-membered heterocycle.

N-bonded heterocyclyl: a saturated, partially saturated or unsaturated 5- or 6-membered heterocyclic ring which is attached via nitrogen and contains at least one nitrogen and, if appropriate, one to three identical or different heteroatoms selected from the following group: oxygen, sulfur and nitrogen, i.e., for example,
N-bonded 5-membered rings such as:
tetrahydropyrrol-1-yl, 2,3-dihydro-1H-pyrrol-1-yl, 2,5-dihydro-1H-pyrrol-1-yl, pyrrol-1-yl, tetrahydropyrazol-1-yl, tetrahydroisoxazol-2-yl, tetrahydroisothiazol-2-yl, tetrahydroimidazol-1-yl, tetrahydrooxazol-3-yl, tetrahydrothiazol-3-yl, 4,5-dihydro-1H-pyrazol-1-yl, 2,5-dihydro-1H-pyrazol-1-yl, 2,3-dihydro-1H-pyrazol-1-yl, 2,5-dihydroisoxazol-2-yl, 2,3-dihydroisoxazol-2-yl, 2,5-dihydroisothiazol-2-yl, 2,3-dihydroisoxazol-2-yl, 4,5-dihydro-1H-imidazol-1-yl, 2,5-dihydro-1H-imidazol-1-yl, 2,3-dihydro-1H-imidazol-1-yl, 2,3-dihydrooxazol-3-yl, 2,3-dihydrothiazol-3-yl, pyrazol-1-yl, imidazol-1-yl, 1,2,4-$\Delta^4$-oxadiazolin-2-yl, 1,2,4-$\Delta^2$-oxadiazolin-4-yl, 1,2,4-$\Delta^3$-oxadiazolin-2-yl, 1,3,4-$\Delta^2$-oxadiazolin-4-yl, 1,2,4-$\Delta^5$-thiadiazolin-2-yl, 1,2,4-$\Delta^3$-thiadiazolin-2-yl, 1,2,4-$\Delta^2$-thiadiazolin-4-yl, 1,3,4-$\Delta^2$-thiadiazolin-4-yl, 1,2,3-$\Delta^2$-triazolin-1-yl, 1,2,4-$\Delta^2$-triazolin-1-yl, 1,2,4-$\Delta^2$-triazolin-4-yl, 1,2,4-$\Delta^3$-triazolin-1-yl, 1,2,4-$\Delta^1$-triazolin-4-yl, 1,2,3-triazolin-1-yl, 1,2,4-triazol-1-yl, tetrazol-1-yl;

and also N-bonded 6-membered rings such as:
piperidin-1-yl, 1,2,3,4-tetrahydropyridin-1-yl, 1,2,5,6-tetrahydropyridin-1-yl, 1,4-dihydropyridin-1-yl, 1,2-dihydropyridin-1-yl, hexahydropyrimidin-1-yl, hexahydropyrazin-1-yl, hexahydropyridazin-1-yl, tetrahydro-1,3-oxazin-3-yl, tetrahydro-1,3-thiazin-3-yl, tetrahydro-1,4-thiazin-4-yl, tetrahydro-1,4-oxazin-4-yl, tetrahydro-1,2-oxazin-2-yl, 2H-5,6-dihydro-1,2-oxazin-2-yl, 2H-5,6-dihydro-1,2-thiazin-2-yl, 2H-3,6-dihydro-1,2-oxazin-2-yl, 2H-3,6-dihydro-1,2-thiazin-2-yl, 2H-3,4-dihydro-1,2-oxazin-2-yl, 2H-3,4-dihydro-1,2-thiazin-2-yl, 2,3,4,5-tetrahydropyridazin-2-yl, 1,2,5,6-tetrahydropyridazin-1-yl, 1,2,5,6-tetrahydropyridazin-2-yl, 1,2,3,6-tetrahydropyridazin-1-yl, 3,4,5,6-tetrahydropyrimidin-3-yl, 1,2,3,4-tetrahydropyrazin-1-yl, 1,2,3,4-tetrahydropyrimidin-1-yl, 1,2,3,4-tetrahydropyrimidin-3-yl, 2,3-dihydro-1,4-thiazin-4-yl, 2H-1,2-oxazin-2-yl, 2H-1,2-thiazin-2-yl, 4H-1,4-oxazin-4-yl, 4H-1,4-thiazin-4-yl, 1,4-dihydropyridazin-1-yl, 1,4-dihydropyrazin-1-yl, 1,2-dihydropyrazin-1-yl, 1,4-dihydropyrimidin-1-yl or 3,4-dihydropyrimidin-3-yl;

and also N-bonded cyclic imides such as:
phthalimide, tetrahydrophthalimide, succinimide, maleimide, glutarimide, 5-oxotriazolin-1-yl, 5-oxo-1,3,4-oxadiazolin-4-yl or 2,4-dioxo-(1H, 3H)-pyrimidin-3-yl;

where a bicyclic ring system may be formed with a fused-on phenyl ring or with a $C_3$–$C_6$-carbocycle or a further 5- to 6-membered heterocycle.

All phenyl rings, heterocyclyl or N-heterocyclyl radicals and all phenyl components in phenoxy, phenyl-$C_1$–$C_6$-alkyl, phenylcarbonyl-$C_1$–$C_6$-alkyl, phenylcarbonyl, phenylalkenylcarbonyl, phenoxycarbonyl, phenyloxythiocarbonyl, phenylaminocarbonyl and N-($C_1$–$C_6$-alkyl)-N-phenylaminocarbonyl or heterocyclyl components in heterocyclyloxy, heterocyclyl-$C_1$–$C_6$-alkyl, heterocyclylcarbonyl-$C_1$–$C_6$-alkyl, heterocyclylcarbonyl, heterocyclyloxythiocarbonyl, heterocyclylalkenylcarbonyl, heterocyclyloxycarbonyl, heterocyclylaminocarbonyl and N-($C_1$–$C_6$-alkyl)-N-heterocyclylaminocarbonyl are, unless stated otherwise, preferably unsubstituted, or they carry one to three halogen atoms and/or one nitro group, one cyano radical and/or one or two methyl, trifluoromethyl, methoxy or trifluoromethoxy substituents.

Furthermore, the expression "Y together with the two carbons to which it is attached forms a saturated, partially saturated or unsaturated heterocycle which contains one to three identical or different heteroatoms selected from the following group: oxygen, sulfur and nitrogen" denotes, for example, 5-membered rings having one heteroatom such as:

tetrahydrofurandiyl, tetrahydrothienediyl, tetrahydropyrolediyl, dihydrofurandiyl, dihydrothienediyl, dihydropyrolediyl, furandiyl, thienediyl or pyrrolediyl;

or 5-membered rings having two heteroatoms such as:

tetrahydropyrazolediyl, tetrahydroisoxazolediyl, 1,2-oxathiolanediyl, tetrahydroisothiazolediyl, 1,2-dithiolanediyl, tetrahydroimidazolediyl, tetrahydrooxazolediyl, tetrahydrothiazolediyl, 1,3-dioxolanediyl, 1,3-oxathiolanediyl, dihydropyrazolediyl, dihydroisoxazolediyl, dihydroisothiazolediyl, 1,2-dithiolediyl, dihydroimidazolediyl, dihydrooxazolediyl, dihydrothiazolediyl, dioxolediyl, oxathiolediyl, pyrazolediyl, isoxazolediyl, isothiazolediyl, imidazolediyl, oxazolediyl or thiazolediyl;

or 5-membered rings having three heteroatoms such as:

1,2,3-oxadiazolinediyl, 1,2,3-thiadiazolinediyl, 1,2,3-triazolinediyl, 1,2,3-oxadiazolediyl, 1,2,3-thiadiazolediyl or 1,2,3-triazolediyl;

or 6-membered rings having one heteroatom such as:

tetrahydropyrandiyl, piperidinediyl, tetrahydrothiopyrandiyl, dihydropyrandiyl, dihydrothiopyrandiyl, tetrahydropyridinediyl, pyrandiyl, thiopyrandiyl, dihydropyrinediyl or pyridinediyl;

or 6-membered rings having two heteroatoms such as:

1,3-dioxanediyl, 1,4-dioxanediyl, 1,3-dithianediyl, 1,4-dithianediyl, 1,3-oxathianediyl, 1,4-oxathianediyl, 1,2-dithianediyl, hexahydropyrimidinediyl, hexahydropyrazinediyl, hexahydropyridazinediyl, tetrahydro-1,3-oxazinediyl, tetrahydro-1,3-thiazinediyl, tetrahydro-1,4-oxazinediyl, tetrahydro-1,2-oxazinediyl, dihydro-1,2-oxazinediyl, dihydro-1,2-thiazinediyl, tetrahydropyridazinediyl, dihydro-1,3-oxazinediyl, dihydro-1,3-oxazinediyl, dihydro-1,3-thiazinediyl, tetrahydropyrimidinediyl, tetrahydropyrazinediyl, dihydro-1,4-thiazinediyl, dihydro-1,4-oxazinediyl, dihydro-1,4-dioxinediyl, dihydro-1,4-dithiinediyl, 1,2-oxazinediyl, 1,2-thiazinediyl, 1,3-oxazinediyl, 1,3-thiazinediyl, 1,4-oxazinediyl, 1,4-thiazinediyl, dihydropyridazinediyl, dihydropyrazinediyl, dihydropyrimidinediyl, pyridazinediyl, pyrimidinediyl or pyrazinediyl;

or 6-membered rings having 3 heteroatoms such as:

1,2,4-triazinediyl;

where, if appropriate, the sulfur of the abovementioned heterocycles may be oxidized to S=O or S(=O)$_2$;

and where the moiety is fused to the skeleton via two adjacent carbon atoms.

The compounds of the formula I according to the invention where $R^9$=IIa are referred to as compounds of the formula Ia, and compounds of the formula I where $R^9$=IIb are referred to as Ib.

Preference is given to the compounds of the formula I, where $R^{11}$ is hydrogen, $C_1$–$C_6$-alkyl, $C_1$–$C_6$-haloalkyl, hydroxyl, $C_1$–$C_6$-alkoxy or $C_1$–$C_6$-haloalkoxy;

Preference is likewise given to the compounds of the formula Ia.

With respect to the use of the compounds of the formula I according to the invention as herbicides, the variables preferably have the following meanings, in each case alone or in combination:

X is oxygen, sulfur, S=O, S(=O)$_2$, $CR^6R^7$, $NR^8$ or a bond;
Y together with the two carbons to which it is attached forms a saturated, partially saturated or unsaturated 5- or 6-membered heterocycle which contains one or two identical or different heteroatoms selected from the following group: oxygen, sulfur or nitrogen;
$R^1, R^2$ are hydrogen or $C_1$–$C_6$-alkyl;
$R^3$ is halogen, $C_1$–$C_6$-alkyl or $C_1$–$C_6$-alkoxy;
$R^4$ is nitro, halogen, cyano, $C_1$–$C_6$-alkyl, $C_1$–$C_6$-haloalkyl, $C_1$–$C_6$-alkoxy, $C_1$–$C_6$-haloalkoxy, $C_1$–$C_6$-alkylthio, $C_1$–$C_6$-haloalkylthio, $C_1$–$C_6$-alkylsulfinyl, $C_1$–$C_6$-haloalkylsulfinyl, $C_1$–$C_6$-alkylsulfonyl, $C_1$–$C_6$-haloalkylsulfonyl, aminosulfonyl, N-($C_1$–$C_6$-alkyl)aminosulfonyl, N,N-di($C_1$–$C_6$-alkyl)aminosulfonyl, N-($C_1$–$C_6$-alkylsulfonyl)amino, N-($C_1$–$C_6$-haloalkylsulfonyl)amino, N-($C_1$–$C_6$-alkyl)-N-($C_1$–$C_6$-alkylsulfonyl)amino or N-($C_1$–$C_6$-alkyl)-N-($C_1$–$C_6$-haloalkylsulfonyl)amino;
in particular nitro, halogen, $C_1$–$C_6$-alkyl, $C_1$–$C_6$-haloalkyl, $C_1$–$C_6$-alkoxy, $C_1$–$C_6$-haloalkoxy, $C_1$–$C_6$-alkylthio, $C_1$–$C_6$-haloalkylthio, $C_1$–$C_6$-alkylsulfonyl or $C_1$–$C_6$-haloalkylsulfonyl;
$R^5$ is hydrogen;
$R^6, R^7$ are hydrogen or $C_1$–$C_6$-alkyl;
$R^8$ is $C_1$–$C_6$-alkyl, $C_1$–$C_6$-alkylcarbonyl or $C_1$–$C_6$-alkylsulfonyl;
l is 0, 1 or 2;
$R^9$ is a radical IIa

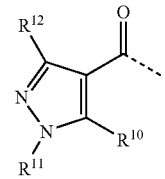

where
$R^{10}$ is hydroxyl, mercapto, halogen, $OR^{13}$, $SR^{13}$, $SO_2R^{14}$ or N-bonded heterocyclyl, where the heterocyclyl radical may be partially or fully halogenated and/or may carry one to three of the following radicals:
nitro, cyano, $C_1$–$C_4$-alkyl, $C_1$–$C_4$-haloalkyl, $C_1$–$C_4$-alkoxy or $C_1$–$C_4$-haloalkoxy;
$R^{11}$ is hydrogen, $C_1$–$C_6$-alkyl, $C_1$–$C_6$-haloalkyl or $C_3$–$C_6$-cycloalkyl;
$R^{12}$ is hydrogen, $C_1$–$C_6$-alkyl or $C_1$–$C_6$-haloalkyl;
$R^{13}$ is $C_1$–$C_6$-alkyl, $C_3$–$C_6$-alkenyl, $C_3$–$C_6$-haloalkenyl, $C_3$–$C_6$-alkynyl, $C_1$–$C_6$-alkylcarbonyl, $C_2$–$C_6$-alkenylcarbonyl, $C_3$–$C_6$-cycloalkylcarbonyl, $C_1$–$C_6$-alkoxycarbonyl, $C_3$–$C_6$-alkenyloxycarbonyl, $C_3$–$C_6$-alkynyloxycarbonyl, $C_1$–$C_6$-alkylthiocarbonyl, $C_1$–$C_6$-alkylaminocarbonyl, $C_3$–$C_6$-alkenylaminocarbonyl, $C_3$–$C_6$-alkynylaminocarbonyl, N,N-di($C_1$–$C_6$-alkyl)aminocarbonyl, N-($C_3$–$C_6$-alkenyl)-N-($C_1$–$C_6$-alkyl)aminocarbonyl, N-($C_3$–$C_6$-alkynyl)-N-($C_1$–$C_6$-alkyl)aminocarbonyl, N-($C_1$–$C_6$-alkoxy)-N-($C_1$–$C_6$-alkyl)aminocarbonyl, N-($C_3$–$C_6$-alkenyl)-N-($C_1$–$C_6$-alkoxy)aminocarbonyl N-($C_3$–$C_6$-alkynyl)-N-($C_1$–$C_6$-alkoxy)aminocarbonyl, di($C_1$–$C_6$-alkyl)aminothiocarbonyl, $C_1$–$C_6$-alkylcarbonyl-$C_1$–$C_6$-alkyl, $C_1$–$C_6$-alkoxyimino-$C_1$–$C_6$-alkyl, N-($C_1$–$C_6$-alkylamino)imino-$C_1$–$C_6$-alkyl or N,N-di($C_1$–$C_6$-alkylamino)imino-$C_1$–$C_6$-alkyl, where the abovementioned alkyl, cycloalkyl and alkoxy radicals may be partially or fully halogenated and/or may carry one to three of the following groups:
cyano, $C_1$–$C_4$-alkoxy, $C_1$–$C_4$-alkylthio, $C_1$–$C_4$-alkylcarbonyl, $C_1$–$C_4$-alkoxycarbonyl, hydroxycarbonyl, di($C_1$–$C_4$-alkyl)aminocarbonyl, $C_1$–$C_4$-alkylcarbonyloxy or $C_3$–$C_6$-cycloalkyl;
is phenyl, heterocyclyl, phenyl-$C_1$–$C_6$-alkyl, heterocyclyl-$C_1$–$C_6$-alkyl, phenylcarbonyl-$C_1$–$C_6$-alkyl, heterocyclylcarbonyl-$C_1$–$C_6$-alkyl, phenylcarbonyl, heterocyclylcarbonyl, phenoxycarbonyl, phenyloxythiocarbonyl, heterocyclyloxycarbonyl, heterocyclyloxythiocarbonyl, phenyl-$C_2$–$C_6$-alkenylcarbonyl or heterocyclyl-$C_2$–$C_6$- alkenylcarbonyl, where the phenyl and the heterocyclyl radical of the 14 lastmentioned substituents may be partially or fully halogenated and/or may carry one to three of the following radicals:

nitro, cyano, $C_1$–$C_4$-alkyl, $C_1$–$C_4$-haloalkyl, $C_1$–$C_4$-alkoxy, $C_1$–$C_4$-haloalkoxy, heterocyclyl or N-bonded heterocyclyl, where the two lastmentioned substituents for their part may be partially or fully halogenated and/or may carry one to three of the following radicals: nitro, cyano, $C_1$–$C_4$-alkyl, $C_1$–$C_4$-haloalkyl, $C_1$–$C_4$-alkoxy or $C_1$–$C_4$-haloalkoxy;

$R^{14}$ is $C_1$–$C_6$-alkyl, $C_3$–$C_6$-alkenyl, $C_3$–$C_6$-haloalkenyl, $C_3$–$C_6$-cycloalkyl, $C_1$–$C_6$-alkoxy or di($C_1$–$C_6$-haloalkyl) amino, where the abovementioned alkyl, cycloalkyl and alkoxy radicals may be partially or fully halogenated and/or may carry one to three of the following groups: cyano, $C_1$–$C_4$-alkoxy, $C_1$–$C_4$-alkylthio, $C_1$–$C_4$-alkylcarbonyl, $C_1$–$C_4$-alkoxycarbonyl, hydroxycarbonyl, di($C_1$–$C_4$-alkyl)aminocarbonyl, $C_1$–$C_4$-alkylcarbonyloxy or $C_3$–$C_6$-cycloalkyl;

is phenyl, heterocyclyl, phenyl-$C_1$–$C_6$-alkyl, heterocyclyl-$C_1$–$C_6$-alkyl, phenoxy, heterocyclyloxy, where the phenyl and the heterocyclyl radical of the lastmentioned substituents may be partially or fully halogenated and/or may carry one to three of the following radicals:

nitro, cyano, $C_1$–$C_4$-alkyl, $C_1$–$C_4$-haloalkyl, $C_1$–$C_4$-alkoxy or $C_1$–$C_4$-haloalkoxy.

Particular preference is given to compounds of the formula I where the variables have the following meanings, either alone or in combination:

X is oxygen, sulfur, S=O, S(=O)$_2$, $CR^6R^7$ or a bond;

Y together with the two carbons to which it is attached forms the following heterocycles:

(in the embodiments of the heterocycles below, the upper undulating line represents in each case the link to the hydrocarbon which carries the radicals $R^1$ and $R^2$, and the lower undulating line represents the link to the meta-carbon of the benzoyl moiety).

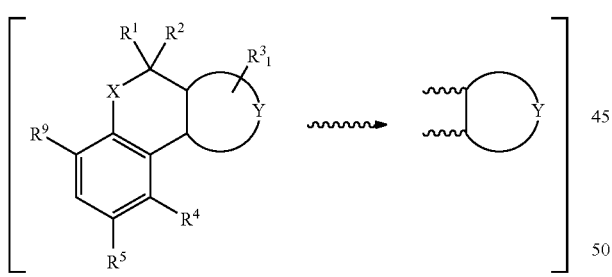

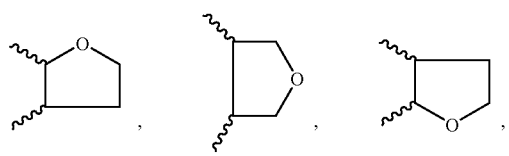

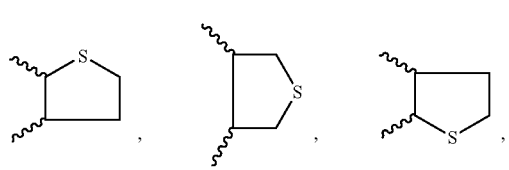

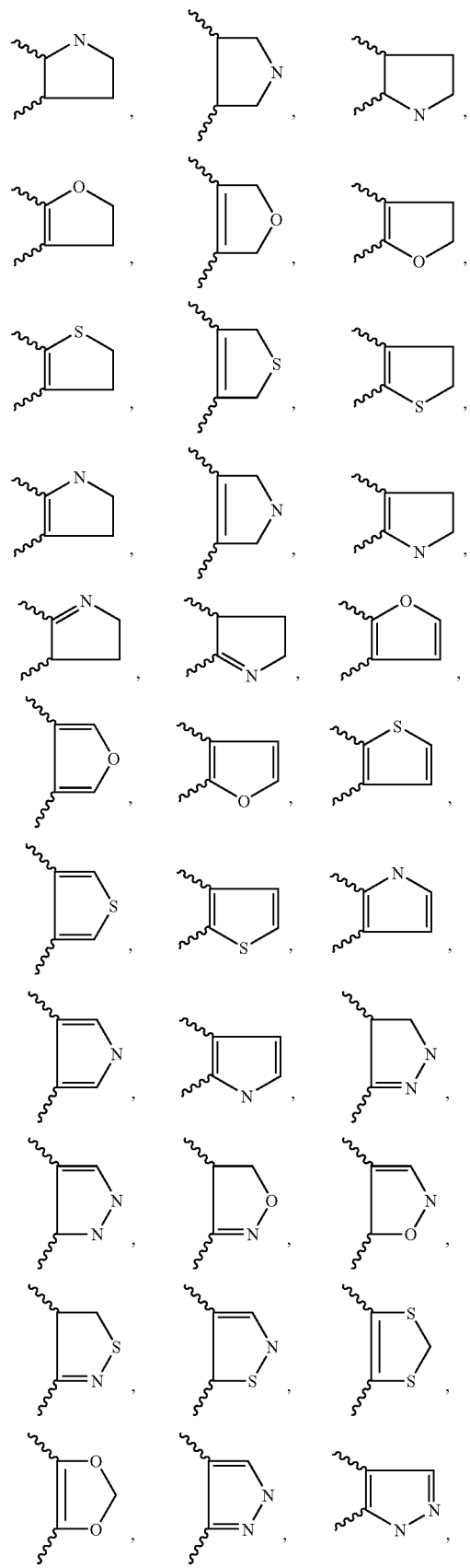

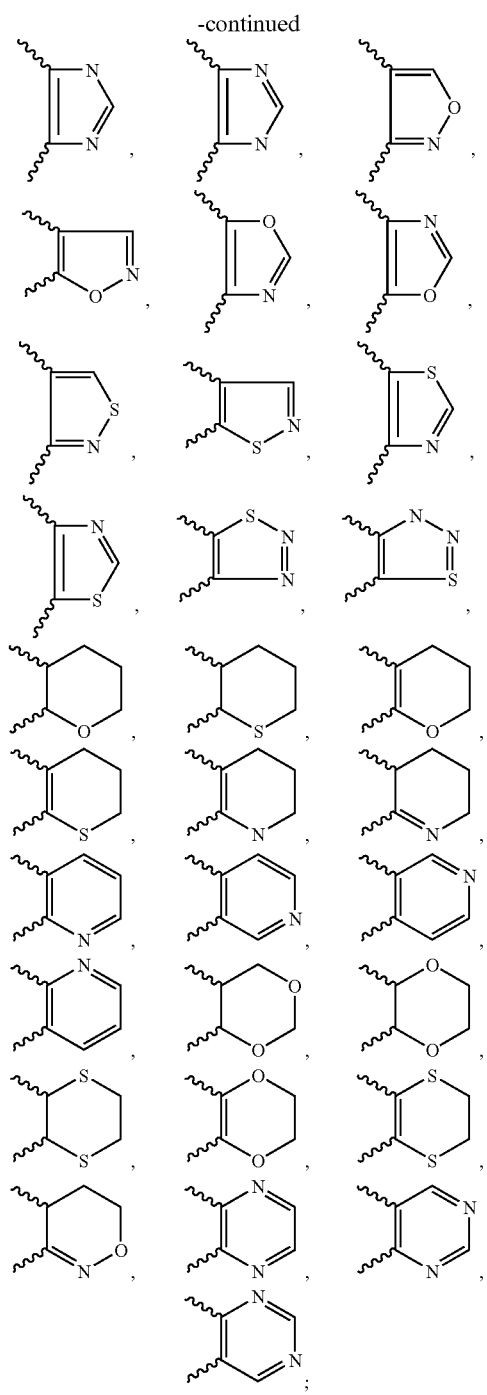
where the sulfur of the abovementioned heterocycles may be oxidized to S=O or S(=O)$_2$;
in particular, Y together with the two carbons to which it is attached forms the following heterocycles:
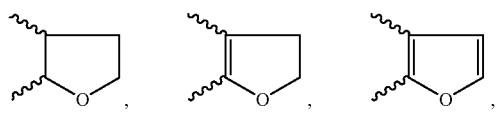
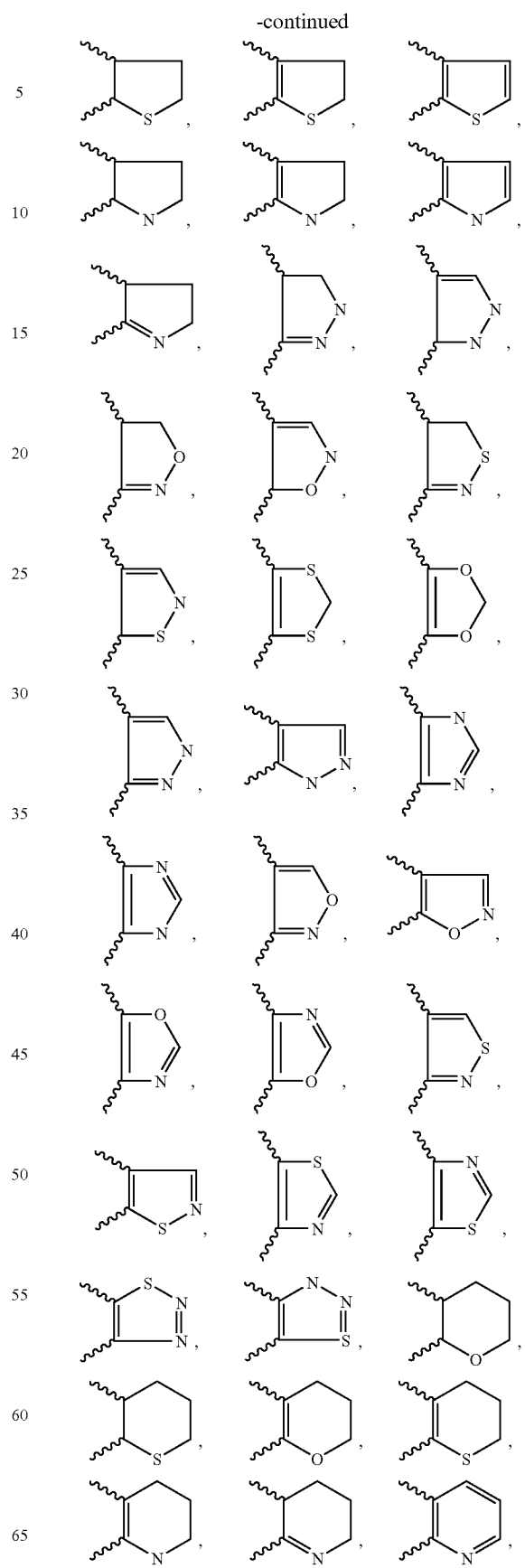

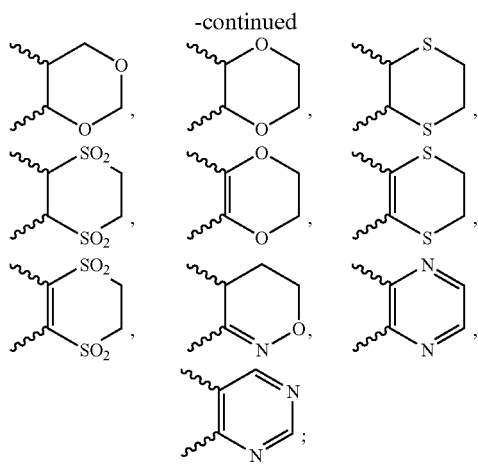

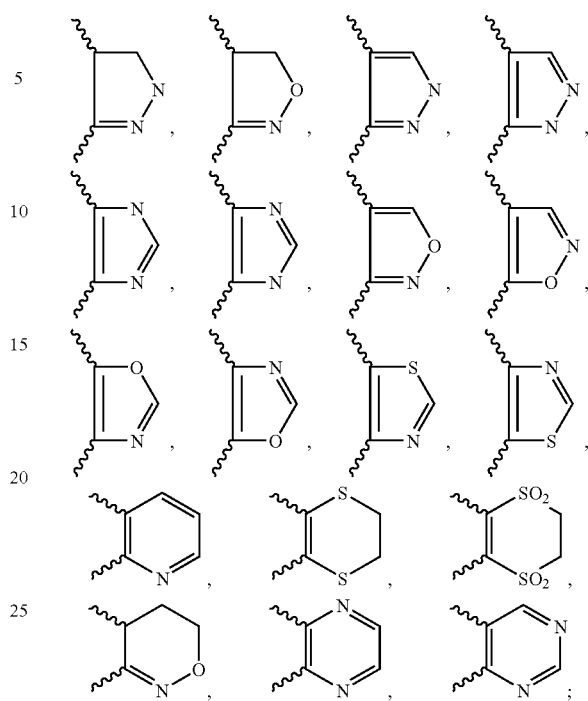

$R^1, R^2$ are hydrogen;
$R^3$ is $C_1$–$C_6$-alkyl, such as methyl, ethyl or n-propyl;
  in particular methyl;
$R^4$ is nitro, halogen, $C_1$–$C_6$-alkyl, $C_1$–$C_6$-haloalkyl, $C_1$–$C_6$-alkoxy, $C_1$–$C_6$-alkylthio or $C_1$–$C_6$-alkylsulfonyl;
  in particular nitro, halogen, such as fluorine, chlorine or bromine, $C_1$–$C_6$-haloalkyl such as trifluoromethyl, $C_1$–$C_6$-alkylthio, such as methylthio or ethylthio, or $C_1$–$C_6$-alkylsulfonyl, such as methylsulfonyl or ethylsulfonyl;
  particularly preferably nitro, chlorine, trifluoromethyl, methylthio or methylsulfonyl;
$R^5$ is hydrogen;
$R^6, R^7$ are hydrogen or $C_1$–$C_6$-alkyl, such as methyl or ethyl;
  in particular hydrogen or methyl;
l is 0, 1 or 2;
  in particular 0 or 1;
$R^9$ is a radical IIa

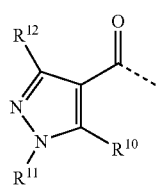

IIa where
$R^{10}$ is hydroxyl;
$R^{11}$ is $C_1$–$C_6$-alkyl, such as methyl, ethyl, n-propyl, 1-methylethyl, n-butyl, 2-methylpropyl or 1,1-dimethylethyl or cyclopropyl;
  in particular methyl or ethyl;
  likewise particularly preferred cyclopropyl;
$R^{12}$ is hydrogen or $C_1$–$C_6$-alkyl, such as methyl, ethyl, n-propyl or 1-methylethyl;
  in particular hydrogen or methyl.

Very particular preference is given to the compounds Ia where
X is oxygen, sulfur, $S(=O)_2$, $CH_2$ or a bond;
Y together with the two carbons to which it is attached forms the following heterocycles:

$R^1, R^2$ are hydrogen;
$R^3$ is $C_1$–$C_4$-alkyl;
$R^4$ is nitro, halogen, $C_1$–$C_6$-alkyl, $C_1$–$C_6$-haloalkyl, $C_1$–$C_6$-alkoxy, $C_1$–$C_6$-alkylthio or $C_1$–$C_6$-alkylsulfonyl;
$R^5$ is hydrogen or $C_1$–$C_6$-alkyl;
l is 0, 1 or 2;
$R^9$ is a radical IIa;
$R^{10}$ is hydroxyl;
$R^{11}$ is hydrogen, $C_1$–$C_6$-alkyl or cyclopropyl;
  in particular $C_1$–$C_6$-alkyl;
$R^{12}$ is hydrogen, $C_1$–$C_6$-alkyl or $C_1$–$C_6$-haloalkyl.

Very particular preference is also given to the compounds Ia where X is oxygen, sulfur or a bond.

Very particular preference is also given to the compounds Ia where
Y together with the two carbons to which it is attached forms a heterocycle selected from the following group: dihydropyrazolediyl, dihydroisoxazolediyl, pyrazolediyl, isoxazolediyl or pyrimidinediyl.

Most preferably, Y together with the two carbons to which it is attached forms the following heterocycles:

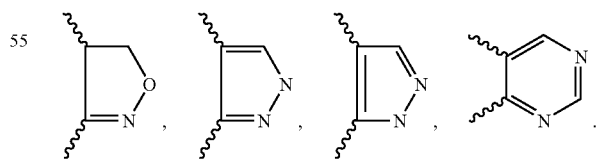

Very particular preference is also given to the compounds of the formula I where
$R^1, R^2$ are hydrogen;
$R^3$ is $C_1$–$C_6$-alkyl;
$R^4$ is nitro, halogen, $C_1$–$C_6$-alkyl, $C_1$–$C_6$-haloalkyl, $C_1$–$C_6$-alkoxy, $C_1$–$C_6$-alkylthio or $C_1$–$C_6$-akylsulfonyl;

in particular halogen, $C_1$–$C_6$-alkoxy, $C_1$–$C_6$-alkylthio or $C_1$–$C_6$-alkylsulfonyl;
$R^5$ is hydrogen;
l is 0 oder 1.

Very particular preference is also given to the compounds of the formula I where
$R^{10}$ is hydroxyl or phenylcarbonyloxy which may be unsubstituted or partially or fully halogenated and/or may carry one to three of the following radicals:
nitro, cyano, $C_1$–$C_4$-alkyl, $C_1$–$C_4$-haloalkyl, $C_1$–$C_4$-alkoxy or $C_1$–$C_4$-haloalkoxy;
in particular hydroxyl;
$R^{11}$ is $C_1$–$C_6$-alkyl or $C_3$–$C_6$-cycloalkyl;
in particular $C_1$–$C_6$-alkyl or
also in particular cyclopropyl;
$R^{12}$ is hydrogen or $C_1$–$C_6$-alkyl;
in particular hydrogen.

Very particular preference is also given to the compounds of the formula Ia1 (=Ia where $R^1$, $R^2$, $R^5$ and $R^{12}$=H, l=0, meaning of the heterocycle according to structural formula), most particularly to compounds Ia1.n where the variables X, $R^4$, $R^{10}$ and $R^{11}$ are as defined in Table 1.

The radical definitions of $R^1$ to $R^{12}$, X, Y and l given above and the meaning of the fused heterocycle are of particular importance for the compounds according to the invention, not only in combination with one another, but also taken on their own. (For reasons of clarity, in the formulae Ia1, Ia2 ..., the meaning of the fused heterocycle is in each case as given in the corresponding structural formula.)

Ia1

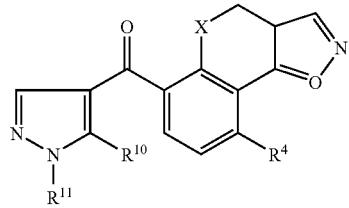

TABLE 1

| n | X | $R^4$ | $R^{10}$ | $R^{11}$ |
|---|---|---|---|---|
| 1 | bond | F | OH | $CH_3$ |
| 2 | bond | Cl | OH | $CH_3$ |
| 3 | bond | Br | OH | $CH_3$ |
| 4 | bond | $NO_2$ | OH | $CH_3$ |
| 5 | bond | $SCH_3$ | OH | $CH_3$ |
| 6 | bond | $SO_2CH_3$ | OH | $CH_3$ |
| 7 | bond | $SO_2CH_2CH_3$ | OH | $CH_3$ |
| 8 | bond | $CH_3$ | OH | $CH_3$ |
| 9 | bond | $CF_3$ | OH | $CH_3$ |
| 10 | bond | $OCHF_2$ | OH | $CH_3$ |
| 11 | $CH_2$ | F | OH | $CH_3$ |
| 12 | $CH_2$ | Cl | OH | $CH_3$ |
| 13 | $CH_2$ | Br | OH | $CH_3$ |
| 14 | $CH_2$ | $NO_2$ | OH | $CH_3$ |
| 15 | $CH_2$ | $SCH_3$ | OH | $CH_3$ |
| 16 | $CH_2$ | $SO_2CH_3$ | OH | $CH_3$ |
| 17 | $CH_2$ | $SO_2CH_2CH_3$ | OH | $CH_3$ |
| 18 | $CH_2$ | $CH_3$ | OH | $CH_3$ |
| 19 | $CH_2$ | $CF_3$ | OH | $CH_3$ |
| 20 | $CH_2$ | $OCHF_2$ | OH | $CH_3$ |
| 21 | O | F | OH | $CH_3$ |
| 22 | O | Cl | OH | $CH_3$ |
| 23 | O | Br | OH | $CH_3$ |
| 24 | O | $NO_2$ | OH | $CH_3$ |
| 25 | O | $SCH_3$ | OH | $CH_3$ |
| 26 | O | $SO_2CH_3$ | OH | $CH_3$ |
| 27 | O | $SO_2CH_2CH_3$ | OH | $CH_3$ |
| 28 | O | $CH_3$ | OH | $CH_3$ |
| 29 | O | $CF_3$ | OH | $CH_3$ |
| 30 | O | $OCHF_2$ | OH | $CH_3$ |
| 31 | S | F | OH | $CH_3$ |
| 32 | S | Cl | OH | $CH_3$ |
| 33 | S | Br | OH | $CH_3$ |
| 34 | S | $NO_2$ | OH | $CH_3$ |
| 35 | S | $SCH_3$ | OH | $CH_3$ |
| 36 | S | $SO_2CH_3$ | OH | $CH_3$ |
| 37 | S | $SO_2CH_2CH_3$ | OH | $CH_3$ |
| 38 | S | $CH_3$ | OH | $CH_3$ |
| 39 | S | $CF_3$ | OH | $CH_3$ |
| 40 | S | $OCHF_2$ | OH | $CH_3$ |
| 41 | $SO_2$ | F | OH | $CH_3$ |
| 42 | $SO_2$ | Cl | OH | $CH_3$ |
| 43 | $SO_2$ | Br | OH | $CH_3$ |
| 44 | $SO_2$ | $NO_2$ | OH | $CH_3$ |
| 45 | $SO_2$ | $SCH_3$ | OH | $CH_3$ |
| 46 | $SO_2$ | $SO_2CH_3$ | OH | $CH_3$ |
| 47 | $SO_2$ | $SO_2CH_2CH_3$ | OH | $CH_3$ |
| 48 | $SO_2$ | $CH_3$ | OH | $CH_3$ |
| 49 | $SO_2$ | $CF_3$ | OH | $CH_3$ |
| 50 | $SO_2$ | $OCHF_2$ | OH | $CH_3$ |
| 51 | bond | F | OH | $CH_2CH_3$ |
| 52 | bond | Cl | OH | $CH_2CH_3$ |
| 53 | bond | Br | OH | $CH_2CH_3$ |
| 54 | bond | $NO_2$ | OH | $CH_2CH_3$ |
| 55 | bond | $SCH_3$ | OH | $CH_2CH_3$ |
| 56 | bond | $SO_2CH_3$ | OH | $CH_2CH_3$ |
| 57 | bond | $SO_2CH_2CH_3$ | OH | $CH_2CH_3$ |
| 58 | bond | $CH_3$ | OH | $CH_2CH_3$ |
| 59 | bond | $CF_3$ | OH | $CH_2CH_3$ |
| 60 | bond | $OCHF_2$ | OH | $CH_2CH_3$ |
| 61 | $CH_2$ | F | OH | $CH_2CH_3$ |
| 62 | $CH_2$ | Cl | OH | $CH_2CH_3$ |
| 63 | $CH_2$ | Br | OH | $CH_2CH_3$ |
| 64 | $CH_2$ | $NO_2$ | OH | $CH_2CH_3$ |
| 65 | $CH_2$ | $SCH_3$ | OH | $CH_2CH_3$ |
| 66 | $CH_2$ | $SO_2CH_3$ | OH | $CH_2CH_3$ |
| 67 | $CH_2$ | $SO_2CH_2CH_3$ | OH | $CH_2CH_3$ |
| 68 | $CH_2$ | $CH_3$ | OH | $CH_2CH_3$ |
| 69 | $CH_2$ | $CF_3$ | OH | $CH_2CH_3$ |
| 70 | $CH_2$ | $OCHF_2$ | OH | $CH_2CH_3$ |
| 71 | O | F | OH | $CH_2CH_3$ |
| 72 | O | Cl | OH | $CH_2CH_3$ |
| 73 | O | Br | OH | $CH_2CH_3$ |
| 74 | O | $NO_2$ | OH | $CH_2CH_3$ |
| 75 | O | $SCH_3$ | OH | $CH_2CH_3$ |
| 76 | O | $SO_2CH_3$ | OH | $CH_2CH_3$ |
| 77 | O | $SO_2CH_2CH_3$ | OH | $CH_2CH_3$ |
| 78 | O | $CH_3$ | OH | $CH_2CH_3$ |
| 79 | O | $CF_3$ | OH | $CH_2CH_3$ |
| 80 | O | $OCHF_2$ | OH | $CH_2CH_3$ |
| 81 | S | F | OH | $CH_2CH_3$ |
| 82 | S | Cl | OH | $CH_2CH_3$ |
| 83 | S | Br | OH | $CH_2CH_3$ |
| 84 | S | $NO_2$ | OH | $CH_2CH_3$ |
| 85 | S | $SCH_3$ | OH | $CH_2CH_3$ |
| 86 | S | $SO_2CH_3$ | OH | $CH_2CH_3$ |
| 87 | S | $SO_2CH_2CH_3$ | OH | $CH_2CH_3$ |
| 88 | S | $CH_3$ | OH | $CH_2CH_3$ |
| 89 | S | $CF_3$ | OH | $CH_2CH_3$ |
| 90 | S | $OCHF_2$ | OH | $CH_2CH_3$ |
| 91 | $SO_2$ | F | OH | $CH_2CH_3$ |
| 92 | $SO_2$ | Cl | OH | $CH_2CH_3$ |
| 93 | $SO_2$ | Br | OH | $CH_2CH_3$ |
| 94 | $SO_2$ | $NO_2$ | OH | $CH_2CH_3$ |
| 95 | $SO_2$ | $SCH_3$ | OH | $CH_2CH_3$ |
| 96 | $SO_2$ | $SO_2CH_3$ | OH | $CH_2CH_3$ |
| 97 | $SO_2$ | $SO_2CH_2CH_3$ | OH | $CH_2CH_3$ |
| 98 | $SO_2$ | $CH_3$ | OH | $CH_2CH_3$ |
| 99 | $SO_2$ | $CF_3$ | OH | $CH_2CH_3$ |
| 100 | $SO_2$ | $OCHF_2$ | OH | $CH_2CH_3$ |
| 101 | bond | F | $OCOC_6H_5$ | $CH_3$ |
| 102 | bond | Cl | $OCOC_6H_5$ | $CH_3$ |

TABLE 1-continued

| n | X | R⁴ | R¹⁰ | R¹¹ |
|---|---|---|---|---|
| 103 | bond | Br | OCOC₆H₅ | CH₃ |
| 104 | bond | NO₂ | OCOC₆H₅ | CH₃ |
| 105 | bond | SCH₃ | OCOC₆H₅ | CH₃ |
| 106 | bond | SO₂CH₃ | OCOC₆H₅ | CH₃ |
| 107 | bond | SO₂CH₂CH₃ | OCOC₆H₅ | CH₃ |
| 108 | bond | CH₃ | OCOC₆H₅ | CH₃ |
| 109 | bond | CF₃ | OCOC₆H₅ | CH₃ |
| 110 | bond | OCHF₂ | OCOC₆H₅ | CH₃ |
| 111 | CH₂ | F | OCOC₆H₅ | CH₃ |
| 112 | CH₂ | Cl | OCOC₆H₅ | CH₃ |
| 113 | CH₂ | Br | OCOC₆H₅ | CH₃ |
| 114 | CH₂ | NO₂ | OCOC₆H₅ | CH₃ |
| 115 | CH₂ | SCH₃ | OCOC₆H₅ | CH₃ |
| 116 | CH₂ | SO₂CH₃ | OCOC₆H₅ | CH₃ |
| 117 | CH₂ | SO₂CH₂CH₃ | OCOC₆H₅ | CH₃ |
| 118 | CH₂ | CH₃ | OCOC₆H₅ | CH₃ |
| 119 | CH₂ | CF₃ | OCOC₆H₅ | CH₃ |
| 120 | CH₂ | OCHF₂ | OCOC₆H₅ | CH₃ |
| 121 | O | F | OCOC₆H₅ | CH₃ |
| 122 | O | Cl | OCOC₆H₅ | CH₃ |
| 123 | O | Br | OCOC₆H₅ | CH₃ |
| 124 | O | NO₂ | OCOC₆H₅ | CH₃ |
| 125 | O | SCH₃ | OCOC₆H₅ | CH₃ |
| 126 | O | SO₂CH₃ | OCOC₆H₅ | CH₃ |
| 127 | O | SO₂CH₂CH₃ | OCOC₆H₅ | CH₃ |
| 128 | O | CH₃ | OCOC₆H₅ | CH₃ |
| 129 | O | CF₃ | OCOC₆H₅ | CH₃ |
| 130 | O | OCHF₂ | OCOC₆H₅ | CH₃ |
| 131 | S | F | OCOC₆H₅ | CH₃ |
| 132 | S | Cl | OCOC₆H₅ | CH₃ |
| 133 | S | Br | OCOC₆H₅ | CH₃ |
| 134 | S | NO₂ | OCOC₆H₅ | CH₃ |
| 135 | S | SCH₃ | OCOC₆H₅ | CH₃ |
| 136 | S | SO₂CH₃ | OCOC₆H₅ | CH₃ |
| 137 | S | SO₂CH₂CH₃ | OCOC₆H₅ | CH₃ |
| 138 | S | CH₃ | OCOC₆H₅ | CH₃ |
| 139 | S | CF₃ | OCOC₆H₅ | CH₃ |
| 140 | S | OCHF₂ | OCOC₆H₅ | CH₃ |
| 141 | SO₂ | F | OCOC₆H₅ | CH₃ |
| 142 | SO₂ | Cl | OCOC₆H₅ | CH₃ |
| 143 | SO₂ | Br | OCOC₆H₅ | CH₃ |
| 144 | SO₂ | NO₂ | OCOC₆H₅ | CH₃ |
| 145 | SO₂ | SCH₃ | OCOC₆H₅ | CH₃ |
| 146 | SO₂ | SO₂CH₃ | OCOC₆H₅ | CH₃ |
| 147 | SO₂ | SO₂CH₂CH₃ | OCOC₆H₅ | CH₃ |
| 148 | SO₂ | CH₃ | OCOC₆H₅ | CH₃ |
| 149 | SO₂ | CF₃ | OCOC₆H₅ | CH₃ |
| 150 | SO₂ | OCHF₂ | OCOC₆H₅ | CH₃ |
| 151 | bond | F | OCOC₆H₅ | CH₂CH₃ |
| 152 | bond | Cl | OCOC₆H₅ | CH₂CH₃ |
| 153 | bond | Br | OCOC₆H₅ | CH₂CH₃ |
| 154 | bond | NO₂ | OCOC₆H₅ | CH₂CH₃ |
| 155 | bond | SCH₃ | OCOC₆H₅ | CH₂CH₃ |
| 156 | bond | SO₂CH₃ | OCOC₆H₅ | CH₂CH₃ |
| 157 | bond | SO₂CH₂CH₃ | OCOC₆H₅ | CH₂CH₃ |
| 158 | bond | CH₃ | OCOC₆H₅ | CH₂CH₃ |
| 159 | bond | CF₃ | OCOC₆H₅ | CH₂CH₃ |
| 160 | bond | OCHF₂ | OCOC₆H₅ | CH₂CH₃ |
| 161 | CH₂ | F | OCOC₆H₅ | CH₂CH₃ |
| 162 | CH₂ | Cl | OCOC₆H₅ | CH₂CH₃ |
| 163 | CH₂ | Br | OCOC₆H₅ | CH₂CH₃ |
| 164 | CH₂ | NO₂ | OCOC₆H₅ | CH₂CH₃ |
| 165 | CH₂ | SCH₃ | OCOC₆H₅ | CH₂CH₃ |
| 166 | CH₂ | SO₂CH₃ | OCOC₆H₅ | CH₂CH₃ |
| 167 | CH₂ | SO₂CH₂CH₃ | OCOC₆H₅ | CH₂CH₃ |
| 168 | CH₂ | CH₃ | OCOC₆H₅ | CH₂CH₃ |
| 169 | CH₂ | CF₃ | OCOC₆H₅ | CH₂CH₃ |
| 170 | CH₂ | OCHF₂ | OCOC₆H₅ | CH₂CH₃ |
| 171 | O | F | OCOC₆H₅ | CH₂CH₃ |
| 172 | O | Cl | OCOC₆H₅ | CH₂CH₃ |
| 173 | O | Br | OCOC₆H₅ | CH₂CH₃ |
| 174 | O | NO₂ | OCOC₆H₅ | CH₂CH₃ |
| 175 | O | SCH₃ | OCOC₆H₅ | CH₂CH₃ |
| 176 | O | SO₂CH₃ | OCOC₆H₅ | CH₂CH₃ |
| 177 | O | SO₂CH₂CH₃ | OCOC₆H₅ | CH₂CH₃ |
| 178 | O | CH₃ | OCOC₆H₅ | CH₂CH₃ |
| 179 | O | CF₃ | OCOC₆H₅ | CH₂CH₃ |
| 180 | O | OCHF₂ | OCOC₆H₅ | CH₂CH₃ |
| 181 | S | F | OCOC₆H₅ | CH₂CH₃ |
| 182 | S | Cl | OCOC₆H₅ | CH₂CH₃ |
| 183 | S | Br | OCOC₆H₅ | CH₂CH₃ |
| 184 | S | NO₂ | OCOC₆H₅ | CH₂CH₃ |
| 185 | S | SCH₃ | OCOC₆H₅ | CH₂CH₃ |
| 186 | S | SO₂CH₃ | OCOC₆H₅ | CH₂CH₃ |
| 187 | S | SO₂CH₂CH₃ | OCOC₆H₅ | CH₂CH₃ |
| 188 | S | CH₃ | OCOC₆H₅ | CH₂CH₃ |
| 189 | S | CF₃ | OCOC₆H₅ | CH₂CH₃ |
| 190 | S | OCHF₂ | OCOC₆H₅ | CH₂CH₃ |
| 191 | SO₂ | F | OCOC₆H₅ | CH₂CH₃ |
| 192 | SO₂ | Cl | OCOC₆H₅ | CH₂CH₃ |
| 193 | SO₂ | Br | OCOC₆H₅ | CH₂CH₃ |
| 194 | SO₂ | NO₂ | OCOC₆H₅ | CH₂CH₃ |
| 195 | SO₂ | SCH₃ | OCOC₆H₅ | CH₂CH₃ |
| 196 | SO₂ | SO₂CH₃ | OCOC₆H₅ | CH₂CH₃ |
| 197 | SO₂ | SO₂CH₂CH₃ | OCOC₆H₅ | CH₂CH₃ |
| 198 | SO₂ | CH₃ | OCOC₆H₅ | CH₂CH₃ |
| 199 | SO₂ | CF₃ | OCOC₆H₅ | CH₂CH₃ |
| 200 | SO₂ | OCHF₂ | OCOC₆H₅ | CH₂CH₃ |
| 201 | bond | F | OCOC(CH₃)₃ | CH₃ |
| 202 | bond | Cl | OCOC(CH₃)₃ | CH₃ |
| 203 | bond | Br | OCOC(CH₃)₃ | CH₃ |
| 204 | bond | NO₂ | OCOC(CH₃)₃ | CH₃ |
| 205 | bond | SCH₃ | OCOC(CH₃)₃ | CH₃ |
| 206 | bond | SO₂CH₃ | OCOC(CH₃)₃ | CH₃ |
| 207 | bond | SO₂CH₂CH₃ | OCOC(CH₃)₃ | CH₃ |
| 208 | bond | CH₃ | OCOC(CH₃)₃ | CH₃ |
| 209 | bond | CF₃ | OCOC(CH₃)₃ | CH₃ |
| 210 | bond | OCHF₂ | OCOC(CH₃)₃ | CH₃ |
| 211 | CH₂ | F | OCOC(CH₃)₃ | CH₃ |
| 212 | CH₂ | Cl | OCOC(CH₃)₃ | CH₃ |
| 213 | CH₂ | Br | OCOC(CH₃)₃ | CH₃ |
| 214 | CH₂ | NO₂ | OCOC(CH₃)₃ | CH₃ |
| 215 | CH₂ | SCH₃ | OCOC(CH₃)₃ | CH₃ |
| 216 | CH₂ | SO₂CH₃ | OCOC(CH₃)₃ | CH₃ |
| 217 | CH₂ | SO₂CH₂CH₃ | OCOC(CH₃)₃ | CH₃ |
| 218 | CH₂ | CH₃ | OCOC(CH₃)₃ | CH₃ |
| 219 | CH₂ | CF₃ | OCOC(CH₃)₃ | CH₃ |
| 220 | CH₂ | OCHF₂ | OCOC(CH₃)₃ | CH₃ |
| 221 | O | F | OCOC(CH₃)₃ | CH₃ |
| 222 | O | Cl | OCOC(CH₃)₃ | CH₃ |
| 223 | O | Br | OCOC(CH₃)₃ | CH₃ |
| 224 | O | NO₂ | OCOC(CH₃)₃ | CH₃ |
| 225 | O | SCH₃ | OCOC(CH₃)₃ | CH₃ |
| 226 | O | SO₂CH₃ | OCOC(CH₃)₃ | CH₃ |
| 227 | O | SO₂CH₂CH₃ | OCOC(CH₃)₃ | CH₃ |
| 228 | O | CH₃ | OCOC(CH₃)₃ | CH₃ |
| 229 | O | CF₃ | OCOC(CH₃)₃ | CH₃ |
| 230 | O | OCHF₂ | OCOC(CH₃)₃ | CH₃ |
| 231 | S | F | OCOC(CH₃)₃ | CH₃ |
| 232 | S | Cl | OCOC(CH₃)₃ | CH₃ |
| 233 | S | Br | OCOC(CH₃)₃ | CH₃ |
| 234 | S | NO₂ | OCOC(CH₃)₃ | CH₃ |
| 235 | S | SCH₃ | OCOC(CH₃)₃ | CH₃ |
| 236 | S | SO₂CH₃ | OCOC(CH₃)₃ | CH₃ |
| 237 | S | SO₂CH₂CH₃ | OCOC(CH₃)₃ | CH₃ |
| 238 | S | CH₃ | OCOC(CH₃)₃ | CH₃ |
| 239 | S | CF₃ | OCOC(CH₃)₃ | CH₃ |
| 240 | S | OCHF₂ | OCOC(CH₃)₃ | CH₃ |
| 241 | SO₂ | F | OCOC(CH₃)₃ | CH₃ |
| 242 | SO₂ | Cl | OCOC(CH₃)₃ | CH₃ |
| 243 | SO₂ | Br | OCOC(CH₃)₃ | CH₃ |
| 244 | SO₂ | NO₂ | OCOC(CH₃)₃ | CH₃ |
| 245 | SO₂ | SCH₃ | OCOC(CH₃)₃ | CH₃ |
| 246 | SO₂ | SO₂CH₃ | OCOC(CH₃)₃ | CH₃ |
| 247 | SO₂ | SO₂CH₂CH₃ | OCOC(CH₃)₃ | CH₃ |
| 248 | SO₂ | CH₃ | OCOC(CH₃)₃ | CH₃ |
| 249 | SO₂ | CF₃ | OCOC(CH₃)₃ | CH₃ |
| 250 | SO₂ | OCHF₂ | OCOC(CH₃)₃ | CH₃ |
| 251 | bond | F | OCOC(CH₃)₃ | CH₂CH₃ |
| 252 | bond | Cl | OCOC(CH₃)₃ | CH₂CH₃ |
| 253 | bond | Br | OCOC(CH₃)₃ | CH₂CH₃ |
| 254 | bond | NO₂ | OCOC(CH₃)₃ | CH₂CH₃ |
| 255 | bond | SCH₃ | OCOC(CH₃)₃ | CH₂CH₃ |
| 256 | bond | SO₂CH₃ | OCOC(CH₃)₃ | CH₂CH₃ |

TABLE 1-continued

| n | X | $R^4$ | $R^{10}$ | $R^{11}$ |
|---|---|---|---|---|
| 257 | bond | $SO_2CH_2CH_3$ | $OCOC(CH_3)_3$ | $CH_2CH_3$ |
| 258 | bond | $CH_3$ | $OCOC(CH_3)_3$ | $CH_2CH_3$ |
| 259 | bond | $CF_3$ | $OCOC(CH_3)_3$ | $CH_2CH_3$ |
| 260 | bond | $OCHF_2$ | $OCOC(CH_3)_3$ | $CH_2CH_3$ |
| 261 | $CH_2$ | F | $OCOC(CH_3)_3$ | $CH_2CH_3$ |
| 262 | $CH_2$ | Cl | $OCOC(CH_3)_3$ | $CH_2CH_3$ |
| 263 | $CH_2$ | Br | $OCOC(CH_3)_3$ | $CH_2CH_3$ |
| 264 | $CH_2$ | $NO_2$ | $OCOC(CH_3)_3$ | $CH_2CH_3$ |
| 265 | $CH_2$ | $SCH_3$ | $OCOC(CH_3)_3$ | $CH_2CH_3$ |
| 266 | $CH_2$ | $SO_2CH_3$ | $OCOC(CH_3)_3$ | $CH_2CH_3$ |
| 267 | $CH_2$ | $SO_2CH_2CH_3$ | $OCOC(CH_3)_3$ | $CH_2CH_3$ |
| 268 | $CH_2$ | $CH_3$ | $OCOC(CH_3)_3$ | $CH_2CH_3$ |
| 269 | $CH_2$ | $CF_3$ | $OCOC(CH_3)_3$ | $CH_2CH_3$ |
| 270 | $CH_2$ | $OCHF_2$ | $OCOC(CH_3)_3$ | $CH_2CH_3$ |
| 271 | O | F | $OCOC(CH_3)_3$ | $CH_2CH_3$ |
| 272 | O | Cl | $OCOC(CH_3)_3$ | $CH_2CH_3$ |
| 273 | O | Br | $OCOC(CH_3)_3$ | $CH_2CH_3$ |
| 274 | O | $NO_2$ | $OCOC(CH_3)_3$ | $CH_2CH_3$ |
| 275 | O | $SCH_3$ | $OCOC(CH_3)_3$ | $CH_2CH_3$ |
| 276 | O | $SO_2CH_3$ | $OCOC(CH_3)_3$ | $CH_2CH_3$ |
| 277 | O | $SO_2CH_2CH_3$ | $OCOC(CH_3)_3$ | $CH_2CH_3$ |
| 278 | O | $CH_3$ | $OCOC(CH_3)_3$ | $CH_2CH_3$ |
| 279 | O | $CF_3$ | $OCOC(CH_3)_3$ | $CH_2CH_3$ |
| 280 | O | $OCHF_2$ | $OCOC(CH_3)_3$ | $CH_2CH_3$ |
| 281 | S | F | $OCOC(CH_3)_3$ | $CH_2CH_3$ |
| 282 | S | Cl | $OCOC(CH_3)_3$ | $CH_2CH_3$ |
| 283 | S | Br | $OCOC(CH_3)_3$ | $CH_2CH_3$ |
| 284 | S | $NO_2$ | $OCOC(CH_3)_3$ | $CH_2CH_3$ |
| 285 | S | $SCH_3$ | $OCOC(CH_3)_3$ | $CH_2CH_3$ |
| 286 | S | $SO_2CH_3$ | $OCOC(CH_3)_3$ | $CH_2CH_3$ |
| 287 | S | $SO_2CH_2CH_3$ | $OCOC(CH_3)_3$ | $CH_2CH_3$ |
| 288 | S | $CH_3$ | $OCOC(CH_3)_3$ | $CH_2CH_3$ |
| 289 | S | $CF_3$ | $OCOC(CH_3)_3$ | $CH_2CH_3$ |
| 290 | S | $OCHF_2$ | $OCOC(CH_3)_3$ | $CH_2CH_3$ |
| 291 | $SO_2$ | F | $OCOC(CH_3)_3$ | $CH_2CH_3$ |
| 292 | $SO_2$ | Cl | $OCOC(CH_3)_3$ | $CH_2CH_3$ |
| 293 | $SO_2$ | Br | $OCOC(CH_3)_3$ | $CH_2CH_3$ |
| 294 | $SO_2$ | $NO_2$ | $OCOC(CH_3)_3$ | $CH_2CH_3$ |
| 295 | $SO_2$ | $SCH_3$ | $OCOC(CH_3)_3$ | $CH_2CH_3$ |
| 296 | $SO_2$ | $SO_2CH_3$ | $OCOC(CH_3)_3$ | $CH_2CH_3$ |
| 297 | $SO_2$ | $SO_2CH_2CH_3$ | $OCOC(CH_3)_3$ | $CH_2CH_3$ |
| 298 | $SO_2$ | $CH_3$ | $OCOC(CH_3)_3$ | $CH_2CH_3$ |
| 299 | $SO_2$ | $CF_3$ | $OCOC(CH_3)_3$ | $CH_2CH_3$ |
| 300 | $SO_2$ | $OCHF_2$ | $OCOC(CH_3)_3$ | $CH_2CH_3$ |
| 301 | bond | F | $OCOSCH_3$ | $CH_3$ |
| 302 | bond | Cl | $OCOSCH_3$ | $CH_3$ |
| 303 | bond | Br | $OCOSCH_3$ | $CH_3$ |
| 304 | bond | $NO_2$ | $OCOSCH_3$ | $CH_3$ |
| 305 | bond | $SCH_3$ | $OCOSCH_3$ | $CH_3$ |
| 306 | bond | $SO_2CH_3$ | $OCOSCH_3$ | $CH_3$ |
| 307 | bond | $SO_2CH_2CH_3$ | $OCOSCH_3$ | $CH_3$ |
| 308 | bond | $CH_3$ | $OCOSCH_3$ | $CH_3$ |
| 309 | bond | $CF_3$ | $OCOSCH_3$ | $CH_3$ |
| 310 | bond | $OCHF_2$ | $OCOSCH_3$ | $CH_3$ |
| 311 | $CH_2$ | F | $OCOSCH_3$ | $CH_3$ |
| 312 | $CH_2$ | Cl | $OCOSCH_3$ | $CH_3$ |
| 313 | $CH_2$ | Br | $OCOSCH_3$ | $CH_3$ |
| 314 | $CH_2$ | $NO_2$ | $OCOSCH_3$ | $CH_3$ |
| 315 | $CH_2$ | $SCH_3$ | $OCOSCH_3$ | $CH_3$ |
| 316 | $CH_2$ | $SO_2CH_3$ | $OCOSCH_3$ | $CH_3$ |
| 317 | $CH_2$ | $SO_2CH_2CH_3$ | $OCOSCH_3$ | $CH_3$ |
| 318 | $CH_2$ | $CH_3$ | $OCOSCH_3$ | $CH_3$ |
| 319 | $CH_2$ | $CF_3$ | $OCOSCH_3$ | $CH_3$ |
| 320 | $CH_2$ | $OCHF_2$ | $OCOSCH_3$ | $CH_3$ |
| 321 | O | F | $OCOSCH_3$ | $CH_3$ |
| 322 | O | Cl | $OCOSCH_3$ | $CH_3$ |
| 323 | O | Br | $OCOSCH_3$ | $CH_3$ |
| 324 | O | $NO_2$ | $OCOSCH_3$ | $CH_3$ |
| 325 | O | $SCH_3$ | $OCOSCH_3$ | $CH_3$ |
| 326 | O | $SO_2CH_3$ | $OCOSCH_3$ | $CH_3$ |
| 327 | O | $SO_2CH_2CH_3$ | $OCOSCH_3$ | $CH_3$ |
| 328 | O | $CH_3$ | $OCOSCH_3$ | $CH_3$ |
| 329 | O | $CF_3$ | $OCOSCH_3$ | $CH_3$ |
| 330 | O | $OCHF_2$ | $OCOSCH_3$ | $CH_3$ |
| 331 | S | F | $OCOSCH_3$ | $CH_3$ |
| 332 | S | Cl | $OCOSCH_3$ | $CH_3$ |
| 333 | S | Br | $OCOSCH_3$ | $CH_3$ |
| 334 | S | $NO_2$ | $OCOSCH_3$ | $CH_3$ |
| 335 | S | $SCH_3$ | $OCOSCH_3$ | $CH_3$ |
| 336 | S | $SO_2CH_3$ | $OCOSCH_3$ | $CH_3$ |
| 337 | S | $SO_2CH_2CH_3$ | $OCOSCH_3$ | $CH_3$ |
| 338 | S | $CH_3$ | $OCOSCH_3$ | $CH_3$ |
| 339 | S | $CF_3$ | $OCOSCH_3$ | $CH_3$ |
| 340 | S | $OCHF_2$ | $OCOSCH_3$ | $CH_3$ |
| 341 | $SO_2$ | F | $OCOSCH_3$ | $CH_3$ |
| 342 | $SO_2$ | Cl | $OCOSCH_3$ | $CH_3$ |
| 343 | $SO_2$ | Br | $OCOSCH_3$ | $CH_3$ |
| 344 | $SO_2$ | $NO_2$ | $OCOSCH_3$ | $CH_3$ |
| 345 | $SO_2$ | $SCH_3$ | $OCOSCH_3$ | $CH_3$ |
| 346 | $SO_2$ | $SO_2CH_3$ | $OCOSCH_3$ | $CH_3$ |
| 347 | $SO_2$ | $SO_2CH_2CH_3$ | $OCOSCH_3$ | $CH_3$ |
| 348 | $SO_2$ | $CH_3$ | $OCOSCH_3$ | $CH_3$ |
| 349 | $SO_2$ | $CF_3$ | $OCOSCH_3$ | $CH_3$ |
| 350 | $SO_2$ | $OCHF_2$ | $OCOSCH_3$ | $CH_3$ |
| 351 | bond | F | $OCOSCH_3$ | $CH_2CH_3$ |
| 352 | bond | Cl | $OCOSCH_3$ | $CH_2CH_3$ |
| 353 | bond | Br | $OCOSCH_3$ | $CH_2CH_3$ |
| 354 | bond | $NO_2$ | $OCOSCH_3$ | $CH_2CH_3$ |
| 355 | bond | $SCH_3$ | $OCOSCH_3$ | $CH_2CH_3$ |
| 356 | bond | $SO_2CH_3$ | $OCOSCH_3$ | $CH_2CH_3$ |
| 357 | bond | $SO_2CH_2CH_3$ | $OCOSCH_3$ | $CH_2CH_3$ |
| 358 | bond | $CH_3$ | $OCOSCH_3$ | $CH_2CH_3$ |
| 359 | bond | $CF_3$ | $OCOSCH_3$ | $CH_2CH_3$ |
| 360 | bond | $OCHF_2$ | $OCOSCH_3$ | $CH_2CH_3$ |
| 361 | $CH_2$ | F | $OCOSCH_3$ | $CH_2CH_3$ |
| 362 | $CH_2$ | Cl | $OCOSCH_3$ | $CH_2CH_3$ |
| 363 | $CH_2$ | Br | $OCOSCH_3$ | $CH_2CH_3$ |
| 364 | $CH_2$ | $NO_2$ | $OCOSCH_3$ | $CH_2CH_3$ |
| 365 | $CH_2$ | $SCH_3$ | $OCOSCH_3$ | $CH_2CH_3$ |
| 366 | $CH_2$ | $SO_2CH_3$ | $OCOSCH_3$ | $CH_2CH_3$ |
| 367 | $CH_2$ | $SO_2CH_2CH_3$ | $OCOSCH_3$ | $CH_2CH_3$ |
| 368 | $CH_2$ | $CH_3$ | $OCOSCH_3$ | $CH_2CH_3$ |
| 369 | $CH_2$ | $CF_3$ | $OCOSCH_3$ | $CH_2CH_3$ |
| 370 | $CH_2$ | $OCHF_2$ | $OCOSCH_3$ | $CH_2CH_3$ |
| 371 | O | F | $OCOSCH_3$ | $CH_2CH_3$ |
| 372 | O | Cl | $OCOSCH_3$ | $CH_2CH_3$ |
| 373 | O | Br | $OCOSCH_3$ | $CH_2CH_3$ |
| 374 | O | $NO_2$ | $OCOSCH_3$ | $CH_2CH_3$ |
| 375 | O | $SCH_3$ | $OCOSCH_3$ | $CH_2CH_3$ |
| 376 | O | $SO_2CH_3$ | $OCOSCH_3$ | $CH_2CH_3$ |
| 377 | O | $SO_2CH_2CH_3$ | $OCOSCH_3$ | $CH_2CH_3$ |
| 378 | O | $CH_3$ | $OCOSCH_3$ | $CH_2CH_3$ |
| 379 | O | $CF_3$ | $OCOSCH_3$ | $CH_2CH_3$ |
| 380 | O | $OCHF_2$ | $OCOSCH_3$ | $CH_2CH_3$ |
| 381 | S | F | $OCOSCH_3$ | $CH_2CH_3$ |
| 382 | S | Cl | $OCOSCH_3$ | $CH_2CH_3$ |
| 383 | S | Br | $OCOSCH_3$ | $CH_2CH_3$ |
| 384 | S | $NO_2$ | $OCOSCH_3$ | $CH_2CH_3$ |
| 385 | S | $SCH_3$ | $OCOSCH_3$ | $CH_2CH_3$ |
| 386 | S | $SO_2CH_3$ | $OCOSCH_3$ | $CH_2CH_3$ |
| 387 | S | $SO_2CH_2CH_3$ | $OCOSCH_3$ | $CH_2CH_3$ |
| 388 | S | $CH_3$ | $OCOSCH_3$ | $CH_2CH_3$ |
| 389 | S | $CF_3$ | $OCOSCH_3$ | $CH_2CH_3$ |
| 390 | S | $OCHF_2$ | $OCOSCH_3$ | $CH_2CH_3$ |
| 391 | $SO_2$ | F | $OCOSCH_3$ | $CH_2CH_3$ |
| 392 | $SO_2$ | Cl | $OCOSCH_3$ | $CH_2CH_3$ |
| 393 | $SO_2$ | Br | $OCOSCH_3$ | $CH_2CH_3$ |
| 394 | $SO_2$ | $NO_2$ | $OCOSCH_3$ | $CH_2CH_3$ |
| 395 | $SO_2$ | $SCH_3$ | $OCOSCH_3$ | $CH_2CH_3$ |
| 396 | $SO_2$ | $SO_2CH_3$ | $OCOSCH_3$ | $CH_2CH_3$ |
| 397 | $SO_2$ | $SO_2CH_2CH_3$ | $OCOSCH_3$ | $CH_2CH_3$ |
| 398 | $SO_2$ | $CH_3$ | $OCOSCH_3$ | $CH_2CH_3$ |
| 399 | $SO_2$ | $CF_3$ | $OCOSCH_3$ | $CH_2CH_3$ |
| 400 | $SO_2$ | $OCHF_2$ | $OCOSCH_3$ | $CH_2CH_3$ |
| 401 | bond | F | $OCH_3$ | $CH_3$ |
| 402 | bond | Cl | $OCH_3$ | $CH_3$ |
| 403 | bond | Br | $OCH_3$ | $CH_3$ |
| 404 | bond | $NO_2$ | $OCH_3$ | $CH_3$ |
| 405 | bond | $SCH_3$ | $OCH_3$ | $CH_3$ |
| 406 | bond | $SO_2CH_3$ | $OCH_3$ | $CH_3$ |
| 407 | bond | $SO_2CH_2CH_3$ | $OCH_3$ | $CH_3$ |
| 408 | bond | $CH_3$ | $OCH_3$ | $CH_3$ |
| 409 | bond | $CF_3$ | $OCH_3$ | $CH_3$ |
| 410 | bond | $OCHF_2$ | $OCH_3$ | $CH_3$ |

TABLE 1-continued

| n | X | R⁴ | R¹⁰ | R¹¹ |
|---|---|---|---|---|
| 411 | CH₂ | F | OCH₃ | CH₃ |
| 412 | CH₂ | Cl | OCH₃ | CH₃ |
| 413 | CH₂ | Br | OCH₃ | CH₃ |
| 414 | CH₂ | NO₂ | OCH₃ | CH₃ |
| 415 | CH₂ | SCH₃ | OCH₃ | CH₃ |
| 416 | CH₂ | SO₂CH₃ | OCH₃ | CH₃ |
| 417 | CH₂ | SO₂CH₂CH₃ | OCH₃ | CH₃ |
| 418 | CH₂ | CH₃ | OCH₃ | CH₃ |
| 419 | CH₂ | CF₃ | OCH₃ | CH₃ |
| 420 | CH₂ | OCHF₂ | OCH₃ | CH₃ |
| 421 | O | F | OCH₃ | CH₃ |
| 422 | O | Cl | OCH₃ | CH₃ |
| 423 | O | Br | OCH₃ | CH₃ |
| 424 | O | NO₂ | OCH₃ | CH₃ |
| 425 | O | SCH₃ | OCH₃ | CH₃ |
| 426 | O | SO₂CH₃ | OCH₃ | CH₃ |
| 427 | O | SO₂CH₂CH₃ | OCH₃ | CH₃ |
| 428 | O | CH₃ | OCH₃ | CH₃ |
| 429 | O | CF₃ | OCH₃ | CH₃ |
| 430 | O | OCHF₂ | OCH₃ | CH₃ |
| 431 | S | F | OCH₃ | CH₃ |
| 432 | S | Cl | OCH₃ | CH₃ |
| 433 | S | Br | OCH₃ | CH₃ |
| 434 | S | NO₂ | OCH₃ | CH₃ |
| 435 | S | SCH₃ | OCH₃ | CH₃ |
| 436 | S | SO₂CH₃ | OCH₃ | CH₃ |
| 437 | S | SO₂CH₂CH₃ | OCH₃ | CH₃ |
| 438 | S | CH₃ | OCH₃ | CH₃ |
| 439 | S | CF₃ | OCH₃ | CH₃ |
| 440 | S | OCHF₂ | OCH₃ | CH₃ |
| 441 | SO₂ | F | OCH₃ | CH₃ |
| 442 | SO₂ | Cl | OCH₃ | CH₃ |
| 443 | SO₂ | Br | OCH₃ | CH₃ |
| 444 | SO₂ | NO₂ | OCH₃ | CH₃ |
| 445 | SO₂ | SCH₃ | OCH₃ | CH₃ |
| 446 | SO₂ | SO₂CH₃ | OCH₃ | CH₃ |
| 447 | SO₂ | SO₂CH₂CH₃ | OCH₃ | CH₃ |
| 448 | SO₂ | CH₃ | OCH₃ | CH₃ |
| 449 | SO₂ | CF₃ | OCH₃ | CH₃ |
| 450 | SO₂ | OCHF₂ | OCH₃ | CH₃ |
| 451 | bond | F | OCH₃ | CH₂CH₃ |
| 452 | bond | Cl | OCH₃ | CH₂CH₃ |
| 453 | bond | Br | OCH₃ | CH₂CH₃ |
| 454 | bond | NO₂ | OCH₃ | CH₂CH₃ |
| 455 | bond | SCH₃ | OCH₃ | CH₂CH₃ |
| 456 | bond | SO₂CH₃ | OCH₃ | CH₂CH₃ |
| 457 | bond | SO₂CH₂CH₃ | OCH₃ | CH₂CH₃ |
| 458 | bond | CH₃ | OCH₃ | CH₂CH₃ |
| 459 | bond | CF₃ | OCH₃ | CH₂CH₃ |
| 460 | bond | OCHF₂ | OCH₃ | CH₂CH₃ |
| 461 | CH₂ | F | OCH₃ | CH₂CH₃ |
| 462 | CH₂ | Cl | OCH₃ | CH₂CH₃ |
| 463 | CH₂ | Br | OCH₃ | CH₂CH₃ |
| 464 | CH₂ | NO₂ | OCH₃ | CH₂CH₃ |
| 465 | CH₂ | SCH₃ | OCH₃ | CH₂CH₃ |
| 466 | CH₂ | SO₂CH₃ | OCH₃ | CH₂CH₃ |
| 467 | CH₂ | SO₂CH₂CH₃ | OCH₃ | CH₂CH₃ |
| 468 | CH₂ | CH₃ | OCH₃ | CH₂CH₃ |
| 469 | CH₂ | CF₃ | OCH₃ | CH₂CH₃ |
| 470 | CH₂ | OCHF₂ | OCH₃ | CH₂CH₃ |
| 471 | O | F | OCH₃ | CH₂CH₃ |
| 472 | O | Cl | OCH₃ | CH₂CH₃ |
| 473 | O | Br | OCH₃ | CH₂CH₃ |
| 474 | O | NO₂ | OCH₃ | CH₂CH₃ |
| 475 | O | SCH₃ | OCH₃ | CH₂CH₃ |
| 476 | O | SO₂CH₃ | OCH₃ | CH₂CH₃ |
| 477 | O | SO₂CH₂CH₃ | OCH₃ | CH₂CH₃ |
| 478 | O | CH₃ | OCH₃ | CH₂CH₃ |
| 479 | O | CF₃ | OCH₃ | CH₂CH₃ |
| 480 | O | OCHF₂ | OCH₃ | CH₂CH₃ |
| 481 | S | F | OCH₃ | CH₂CH₃ |
| 482 | S | Cl | OCH₃ | CH₂CH₃ |
| 483 | S | Br | OCH₃ | CH₂CH₃ |
| 484 | S | NO₂ | OCH₃ | CH₂CH₃ |
| 485 | S | SCH₃ | OCH₃ | CH₂CH₃ |
| 486 | S | SO₂CH₃ | OCH₃ | CH₂CH₃ |
| 487 | S | SO₂CH₂CH₃ | OCH₃ | CH₂CH₃ |
| 488 | S | CH₃ | OCH₃ | CH₂CH₃ |
| 489 | S | CF₃ | OCH₃ | CH₂CH₃ |
| 490 | S | OCHF₂ | OCH₃ | CH₂CH₃ |
| 491 | SO₂ | F | OCH₃ | CH₂CH₃ |
| 492 | SO₂ | Cl | OCH₃ | CH₂CH₃ |
| 493 | SO₂ | Br | OCH₃ | CH₂CH₃ |
| 494 | SO₂ | NO₂ | OCH₃ | CH₂CH₃ |
| 495 | SO₂ | SCH₃ | OCH₃ | CH₂CH₃ |
| 496 | SO₂ | SO₂CH₃ | OCH₃ | CH₂CH₃ |
| 497 | SO₂ | SO₂CH₂CH₃ | OCH₃ | CH₂CH₃ |
| 498 | SO₂ | CH₃ | OCH₃ | CH₂CH₃ |
| 499 | SO₂ | CF₃ | OCH₃ | CH₂CH₃ |
| 500 | SO₂ | OCHF₂ | OCH₃ | CH₂CH₃ |
| 501 | bond | F | OCH(CH₃)₂ | CH₃ |
| 502 | bond | Cl | OCH(CH₃)₂ | CH₃ |
| 503 | bond | Br | OCH(CH₃)₂ | CH₃ |
| 504 | bond | NO₂ | OCH(CH₃)₂ | CH₃ |
| 505 | bond | SCH₃ | OCH(CH₃)₂ | CH₃ |
| 506 | bond | SO₂CH₃ | OCH(CH₃)₂ | CH₃ |
| 507 | bond | SO₂CH₂CH₃ | OCH(CH₃)₂ | CH₃ |
| 508 | bond | CH₃ | OCH(CH₃)₂ | CH₃ |
| 509 | bond | CF₃ | OCH(CH₃)₂ | CH₃ |
| 510 | bond | OCHF₂ | OCH(CH₃)₂ | CH₃ |
| 511 | CH₂ | F | OCH(CH₃)₂ | CH₃ |
| 512 | CH₂ | Cl | OCH(CH₃)₂ | CH₃ |
| 513 | CH₂ | Br | OCH(CH₃)₂ | CH₃ |
| 514 | CH₂ | NO₂ | OCH(CH₃)₂ | CH₃ |
| 515 | CH₂ | SCH₃ | OCH(CH₃)₂ | CH₃ |
| 516 | CH₂ | SO₂CH₃ | OCH(CH₃)₂ | CH₃ |
| 517 | CH₂ | SO₂CH₂CH₃ | OCH(CH₃)₂ | CH₃ |
| 518 | CH₂ | CH₃ | OCH(CH₃)₂ | CH₃ |
| 519 | CH₂ | CF₃ | OCH(CH₃)₂ | CH₃ |
| 520 | CH₂ | OCHF₂ | OCH(CH₃)₂ | CH₃ |
| 521 | O | F | OCH(CH₃)₂ | CH₃ |
| 522 | O | Cl | OCH(CH₃)₂ | CH₃ |
| 523 | O | Br | OCH(CH₃)₂ | CH₃ |
| 524 | O | NO₂ | OCH(CH₃)₂ | CH₃ |
| 525 | O | SCH₃ | OCH(CH₃)₂ | CH₃ |
| 526 | O | SO₂CH₃ | OCH(CH₃)₂ | CH₃ |
| 527 | O | SO₂CH₂CH₃ | OCH(CH₃)₂ | CH₃ |
| 528 | O | CH₃ | OCH(CH₃)₂ | CH₃ |
| 529 | O | CF₃ | OCH(CH₃)₂ | CH₃ |
| 530 | O | OCHF₂ | OCH(CH₃)₂ | CH₃ |
| 531 | S | F | OCH(CH₃)₂ | CH₃ |
| 532 | S | Cl | OCH(CH₃)₂ | CH₃ |
| 533 | S | Br | OCH(CH₃)₂ | CH₃ |
| 534 | S | NO₂ | OCH(CH₃)₂ | CH₃ |
| 535 | S | SCH₃ | OCH(CH₃)₂ | CH₃ |
| 536 | S | SO₂CH₃ | OCH(CH₃)₂ | CH₃ |
| 537 | S | SO₂CH₂CH₃ | OCH(CH₃)₂ | CH₃ |
| 538 | S | CH₃ | OCH(CH₃)₂ | CH₃ |
| 539 | S | CF₃ | OCH(CH₃)₂ | CH₃ |
| 540 | S | OCHF₂ | OCH(CH₃)₂ | CH₃ |
| 541 | SO₂ | F | OCH(CH₃)₂ | CH₃ |
| 542 | SO₂ | Cl | OCH(CH₃)₂ | CH₃ |
| 543 | SO₂ | Br | OCH(CH₃)₂ | CH₃ |
| 544 | SO₂ | NO₂ | OCH(CH₃)₂ | CH₃ |
| 545 | SO₂ | SCH₃ | OCH(CH₃)₂ | CH₃ |
| 546 | SO₂ | SO₂CH₃ | OCH(CH₃)₂ | CH₃ |
| 547 | SO₂ | SO₂CH₂CH₃ | OCH(CH₃)₂ | CH₃ |
| 548 | SO₂ | CH₃ | OCH(CH₃)₂ | CH₃ |
| 549 | SO₂ | CF₃ | OCH(CH₃)₂ | CH₃ |
| 550 | SO₂ | OCHF₂ | OCH(CH₃)₂ | CH₃ |
| 551 | bond | F | OCH(CH₃)₂ | CH₂CH₃ |
| 552 | bond | Cl | OCH(CH₃)₂ | CH₂CH₃ |
| 553 | bond | Br | OCH(CH₃)₂ | CH₂CH₃ |
| 554 | bond | NO₂ | OCH(CH₃)₂ | CH₂CH₃ |
| 555 | bond | SCH₃ | OCH(CH₃)₂ | CH₂CH₃ |
| 556 | bond | SO₂CH₃ | OCH(CH₃)₂ | CH₂CH₃ |
| 557 | bond | SO₂CH₂CH₃ | OCH(CH₃)₂ | CH₂CH₃ |
| 558 | bond | CH₃ | OCH(CH₃)₂ | CH₂CH₃ |
| 559 | bond | CF₃ | OCH(CH₃)₂ | CH₂CH₃ |
| 560 | bond | OCHF₂ | OCH(CH₃)₂ | CH₂CH₃ |
| 561 | CH₂ | F | OCH(CH₃)₂ | CH₂CH₃ |
| 562 | CH₂ | Cl | OCH(CH₃)₂ | CH₂CH₃ |
| 563 | CH₂ | Br | OCH(CH₃)₂ | CH₂CH₃ |
| 564 | CH₂ | NO₂ | OCH(CH₃)₂ | CH₂CH₃ |

TABLE 1-continued

| n | X | R⁴ | R¹⁰ | R¹¹ |
|---|---|---|---|---|
| 565 | CH₂ | SCH₃ | OCH(CH₃)₂ | CH₂CH₃ |
| 566 | CH₂ | SO₂CH₃ | OCH(CH₃)₂ | CH₂CH₃ |
| 567 | CH₂ | SO₂CH₂CH₃ | OCH(CH₃)₂ | CH₂CH₃ |
| 568 | CH₂ | CH₃ | OCH(CH₃)₂ | CH₂CH₃ |
| 569 | CH₂ | CF₃ | OCH(CH₃)₂ | CH₂CH₃ |
| 570 | CH₂ | OCHF₂ | OCH(CH₃)₂ | CH₂CH₃ |
| 571 | O | F | OCH(CH₃)₂ | CH₂CH₃ |
| 572 | O | Cl | OCH(CH₃)₂ | CH₂CH₃ |
| 573 | O | Br | OCH(CH₃)₂ | CH₂CH₃ |
| 574 | O | NO₂ | OCH(CH₃)₂ | CH₂CH₃ |
| 575 | O | SCH₃ | OCH(CH₃)₂ | CH₂CH₃ |
| 576 | O | SO₂CH₃ | OCH(CH₃)₂ | CH₂CH₃ |
| 577 | O | SO₂CH₂CH₃ | OCH(CH₃)₂ | CH₂CH₃ |
| 578 | O | CH₃ | OCH(CH₃)₂ | CH₂CH₃ |
| 579 | O | CF₃ | OCH(CH₃)₂ | CH₂CH₃ |
| 580 | O | OCHF₂ | OCH(CH₃)₂ | CH₂CH₃ |
| 581 | S | F | OCH(CH₃)₂ | CH₂CH₃ |
| 582 | S | Cl | OCH(CH₃)₂ | CH₂CH₃ |
| 583 | S | Br | OCH(CH₃)₂ | CH₂CH₃ |
| 584 | S | NO₂ | OCH(CH₃)₂ | CH₂CH₃ |
| 585 | S | SCH₃ | OCH(CH₃)₂ | CH₂CH₃ |
| 586 | S | SO₂CH₃ | OCH(CH₃)₂ | CH₂CH₃ |
| 587 | S | SO₂CH₂CH₃ | OCH(CH₃)₂ | CH₂CH₃ |
| 588 | S | CH₃ | OCH(CH₃)₂ | CH₂CH₃ |
| 589 | S | CF₃ | OCH(CH₃)₂ | CH₂CH₃ |
| 590 | S | OCHF₂ | OCH(CH₃)₂ | CH₂CH₃ |
| 591 | SO₂ | F | OCH(CH₃)₂ | CH₂CH₃ |
| 592 | SO₂ | Cl | OCH(CH₃)₂ | CH₂CH₃ |
| 593 | SO₂ | Br | OCH(CH₃)₂ | CH₂CH₃ |
| 594 | SO₂ | NO₂ | OCH(CH₃)₂ | CH₂CH₃ |
| 595 | SO₂ | SCH₃ | OCH(CH₃)₂ | CH₂CH₃ |
| 596 | SO₂ | SO₂CH₃ | OCH(CH₃)₂ | CH₂CH₃ |
| 597 | SO₂ | SO₂CH₂CH₃ | OCH(CH₃)₂ | CH₂CH₃ |
| 598 | SO₂ | CH₃ | OCH(CH₃)₂ | CH₂CH₃ |
| 599 | SO₂ | CF₃ | OCH(CH₃)₂ | CH₂CH₃ |
| 600 | SO₂ | OCHF₂ | OCH(CH₃)₂ | CH₂CH₃ |
| 601 | bond | F | OCH₂C₆H₅ | CH₃ |
| 602 | bond | Cl | OCH₂C₆H₅ | CH₃ |
| 603 | bond | Br | OCH₂C₆H₅ | CH₃ |
| 604 | bond | NO₂ | OCH₂C₆H₅ | CH₃ |
| 605 | bond | SCH₃ | OCH₂C₆H₅ | CH₃ |
| 606 | bond | SO₂CH₃ | OCH₂C₆H₅ | CH₃ |
| 607 | bond | SO₂CH₂CH₃ | OCH₂C₆H₅ | CH₃ |
| 608 | bond | CH₃ | OCH₂C₆H₅ | CH₃ |
| 609 | bond | CF₃ | OCH₂C₆H₅ | CH₃ |
| 610 | bond | OCHF₂ | OCH₂C₆H₅ | CH₃ |
| 611 | CH₂ | F | OCH₂C₆H₅ | CH₃ |
| 612 | CH₂ | Cl | OCH₂C₆H₅ | CH₃ |
| 613 | CH₂ | Br | OCH₂C₆H₅ | CH₃ |
| 614 | CH₂ | NO₂ | OCH₂C₆H₅ | CH₃ |
| 615 | CH₂ | SCH₃ | OCH₂C₆H₅ | CH₃ |
| 616 | CH₂ | SO₂CH₃ | OCH₂C₆H₅ | CH₃ |
| 617 | CH₂ | SO₂CH₂CH₃ | OCH₂C₆H₅ | CH₃ |
| 618 | CH₂ | CH₃ | OCH₂C₆H₅ | CH₃ |
| 619 | CH₂ | CF₃ | OCH₂C₆H₅ | CH₃ |
| 620 | CH₂ | OCHF₂ | OCH₂C₆H₅ | CH₃ |
| 621 | O | F | OCH₂C₆H₅ | CH₃ |
| 622 | O | Cl | OCH₂C₆H₅ | CH₃ |
| 623 | O | Br | OCH₂C₆H₅ | CH₃ |
| 624 | O | NO₂ | OCH₂C₆H₅ | CH₃ |
| 625 | O | SCH₃ | OCH₂C₆H₅ | CH₃ |
| 626 | O | SO₂CH₃ | OCH₂C₆H₅ | CH₃ |
| 627 | O | SO₂CH₂CH₃ | OCH₂C₆H₅ | CH₃ |
| 628 | O | CH₃ | OCH₂C₆H₅ | CH₃ |
| 629 | O | CF₃ | OCH₂C₆H₅ | CH₃ |
| 630 | O | OCHF₂ | OCH₂C₆H₅ | CH₃ |
| 631 | S | F | OCH₂C₆H₅ | CH₃ |
| 632 | S | Cl | OCH₂C₆H₅ | CH₃ |
| 633 | S | Br | OCH₂C₆H₅ | CH₃ |
| 634 | S | NO₂ | OCH₂C₆H₅ | CH₃ |
| 635 | S | SCH₃ | OCH₂C₆H₅ | CH₃ |
| 636 | S | SO₂CH₃ | OCH₂C₆H₅ | CH₃ |
| 637 | S | SO₂CH₂CH₃ | OCH₂C₆H₅ | CH₃ |
| 638 | S | CH₃ | OCH₂C₆H₅ | CH₃ |
| 639 | S | CF₃ | OCH₂C₆H₅ | CH₃ |
| 640 | S | OCHF₂ | OCH₂C₆H₅ | CH₃ |
| 641 | SO₂ | F | OCH₂C₆H₅ | CH₃ |
| 642 | SO₂ | Cl | OCH₂C₆H₅ | CH₃ |
| 643 | SO₂ | Br | OCH₂C₆H₅ | CH₃ |
| 644 | SO₂ | NO₂ | OCH₂C₆H₅ | CH₃ |
| 645 | SO₂ | SCH₃ | OCH₂C₆H₅ | CH₃ |
| 646 | SO₂ | SO₂CH₃ | OCH₂C₆H₅ | CH₃ |
| 647 | SO₂ | SO₂CH₂CH₃ | OCH₂C₆H₅ | CH₃ |
| 648 | SO₂ | CH₃ | OCH₂C₆H₅ | CH₃ |
| 649 | SO₂ | CF₃ | OCH₂C₆H₅ | CH₃ |
| 650 | SO₂ | OCHF₂ | OCH₂C₆H₅ | CH₃ |
| 651 | bond | F | OCH₂C₆H₅ | CH₂CH₃ |
| 652 | bond | Cl | OCH₂C₆H₅ | CH₂CH₃ |
| 653 | bond | Br | OCH₂C₆H₅ | CH₂CH₃ |
| 654 | bond | NO₂ | OCH₂C₆H₅ | CH₂CH₃ |
| 655 | bond | SCH₃ | OCH₂C₆H₅ | CH₂CH₃ |
| 656 | bond | SO₂CH₃ | OCH₂C₆H₅ | CH₂CH₃ |
| 657 | bond | SO₂CH₂CH₃ | OCH₂C₆H₅ | CH₂CH₃ |
| 658 | bond | CH₃ | OCH₂C₆H₅ | CH₂CH₃ |
| 659 | bond | CF₃ | OCH₂C₆H₅ | CH₂CH₃ |
| 660 | bond | OCHF₂ | OCH₂C₆H₅ | CH₂CH₃ |
| 661 | CH₂ | F | OCH₂C₆H₅ | CH₂CH₃ |
| 662 | CH₂ | Cl | OCH₂C₆H₅ | CH₂CH₃ |
| 663 | CH₂ | Br | OCH₂C₆H₅ | CH₂CH₃ |
| 664 | CH₂ | NO₂ | OCH₂C₆H₅ | CH₂CH₃ |
| 665 | CH₂ | SCH₃ | OCH₂C₆H₅ | CH₂CH₃ |
| 666 | CH₂ | SO₂CH₃ | OCH₂C₆H₅ | CH₂CH₃ |
| 667 | CH₂ | SO₂CH₂CH₃ | OCH₂C₆H₅ | CH₂CH₃ |
| 668 | CH₂ | CH₃ | OCH₂C₆H₅ | CH₂CH₃ |
| 669 | CH₂ | CF₃ | OCH₂C₆H₅ | CH₂CH₃ |
| 670 | CH₂ | OCHF₂ | OCH₂C₆H₅ | CH₂CH₃ |
| 671 | O | F | OCH₂C₆H₅ | CH₂CH₃ |
| 672 | O | Cl | OCH₂C₆H₅ | CH₂CH₃ |
| 673 | O | Br | OCH₂C₆H₅ | CH₂CH₃ |
| 674 | O | NO₂ | OCH₂C₆H₅ | CH₂CH₃ |
| 675 | O | SCH₃ | OCH₂C₆H₅ | CH₂CH₃ |
| 676 | O | SO₂CH₃ | OCH₂C₆H₅ | CH₂CH₃ |
| 677 | O | SO₂CH₂CH₃ | OCH₂C₆H₅ | CH₂CH₃ |
| 678 | O | CH₃ | OCH₂C₆H₅ | CH₂CH₃ |
| 679 | O | CF₃ | OCH₂C₆H₅ | CH₂CH₃ |
| 680 | O | OCHF₂ | OCH₂C₆H₅ | CH₂CH₃ |
| 681 | S | F | OCH₂C₆H₅ | CH₂CH₃ |
| 682 | S | Cl | OCH₂C₆H₅ | CH₂CH₃ |
| 683 | S | Br | OCH₂C₆H₅ | CH₂CH₃ |
| 684 | S | NO₂ | OCH₂C₆H₅ | CH₂CH₃ |
| 685 | S | SCH₃ | OCH₂C₆H₅ | CH₂CH₃ |
| 686 | S | SO₂CH₃ | OCH₂C₆H₅ | CH₂CH₃ |
| 687 | S | SO₂CH₂CH₃ | OCH₂C₆H₅ | CH₂CH₃ |
| 688 | S | CH₃ | OCH₂C₆H₅ | CH₂CH₃ |
| 689 | S | CF₃ | OCH₂C₆H₅ | CH₂CH₃ |
| 690 | S | OCHF₂ | OCH₂C₆H₅ | CH₂CH₃ |
| 691 | SO₂ | F | OCH₂C₆H₅ | CH₂CH₃ |
| 692 | SO₂ | Cl | OCH₂C₆H₅ | CH₂CH₃ |
| 693 | SO₂ | Br | OCH₂C₆H₅ | CH₂CH₃ |
| 694 | SO₂ | NO₂ | OCH₂C₆H₅ | CH₂CH₃ |
| 695 | SO₂ | SCH₃ | OCH₂C₆H₅ | CH₂CH₃ |
| 696 | SO₂ | SO₂CH₃ | OCH₂C₆H₅ | CH₂CH₃ |
| 697 | SO₂ | SO₂CH₂CH₃ | OCH₂C₆H₅ | CH₂CH₃ |
| 698 | SO₂ | CH₃ | OCH₂C₆H₅ | CH₂CH₃ |
| 699 | SO₂ | CF₃ | OCH₂C₆H₅ | CH₂CH₃ |
| 700 | SO₂ | OCHF₂ | OCH₂C₆H₅ | CH₂CH₃ |
| 701 | bond | F | OSO₂(4-CH₃—C₆H₄) | CH₃ |
| 702 | bond | Cl | OSO₂(4-CH₃—C₆H₄) | CH₃ |
| 703 | bond | Br | OSO₂(4-CH₃—C₆H₄) | CH₃ |
| 704 | bond | NO₂ | OSO₂(4-CH₃—C₆H₄) | CH₃ |
| 705 | bond | SCH₃ | OSO₂(4-CH₃—C₆H₄) | CH₃ |
| 706 | bond | SO₂CH₃ | OSO₂(4-CH₃—C₆H₄) | CH₃ |
| 707 | bond | SO₂CH₂CH₃ | OSO₂(4-CH₃—C₆H₄) | CH₃ |
| 708 | bond | CH₃ | OSO₂(4-CH₃—C₆H₄) | CH₃ |
| 709 | bond | CF₃ | OSO₂(4-CH₃—C₆H₄) | CH₃ |
| 710 | bond | OCHF₂ | OSO₂(4-CH₃—C₆H₄) | CH₃ |
| 711 | CH₂ | F | OSO₂(4-CH₃—C₆H₄) | CH₃ |
| 712 | CH₂ | Cl | OSO₂(4-CH₃—C₆H₄) | CH₃ |
| 713 | CH₂ | Br | OSO₂(4-CH₃—C₆H₄) | CH₃ |
| 714 | CH₂ | NO₂ | OSO₂(4-CH₃—C₆H₄) | CH₃ |
| 715 | CH₂ | SCH₃ | OSO₂(4-CH₃—C₆H₄) | CH₃ |
| 716 | CH₂ | SO₂CH₃ | OSO₂(4-CH₃—C₆H₄) | CH₃ |
| 717 | CH₂ | SO₂CH₂CH₃ | OSO₂(4-CH₃—C₆H₄) | CH₃ |
| 718 | CH₂ | CH₃ | OSO₂(4-CH₃—C₆H₄) | CH₃ |

TABLE 1-continued

| n | X | R⁴ | R¹⁰ | R¹¹ |
|---|---|---|---|---|
| 719 | CH₂ | CF₃ | OSO₂(4-CH₃—C₆H₄) | CH₃ |
| 720 | CH₂ | OCHF₂ | OSO₂(4-CH₃—C₆H₄) | CH₃ |
| 721 | O | F | OSO₂(4-CH₃—C₆H₄) | CH₃ |
| 722 | O | Cl | OSO₂(4-CH₃—C₆H₄) | CH₃ |
| 723 | O | Br | OSO₂(4-CH₃—C₆H₄) | CH₃ |
| 724 | O | NO₂ | OSO₂(4-CH₃—C₆H₄) | CH₃ |
| 725 | O | SCH₃ | OSO₂(4-CH₃—C₆H₄) | CH₃ |
| 726 | O | SO₂CH₃ | OSO₂(4-CH₃—C₆H₄) | CH₃ |
| 727 | O | SO₂CH₂CH₃ | OSO₂(4-CH₃—C₆H₄) | CH₃ |
| 728 | O | CH₃ | OSO₂(4-CH₃—C₆H₄) | CH₃ |
| 729 | O | CF₃ | OSO₂(4-CH₃—C₆H₄) | CH₃ |
| 730 | O | OCHF₂ | OSO₂(4-CH₃—C₆H₄) | CH₃ |
| 731 | S | F | OSO₂(4-CH₃—C₆H₄) | CH₃ |
| 732 | S | Cl | OSO₂(4-CH₃—C₆H₄) | CH₃ |
| 733 | S | Br | OSO₂(4-CH₃—C₆H₄) | CH₃ |
| 734 | S | NO₂ | OSO₂(4-CH₃—C₆H₄) | CH₃ |
| 735 | S | SCH₃ | OSO₂(4-CH₃—C₆H₄) | CH₃ |
| 736 | S | SO₂CH₃ | OSO₂(4-CH₃—C₆H₄) | CH₃ |
| 737 | S | SO₂CH₂CH₃ | OSO₂(4-CH₃—C₆H₄) | CH₃ |
| 738 | S | CH₃ | OSO₂(4-CH₃—C₆H₄) | CH₃ |
| 739 | S | CF₃ | OSO₂(4-CH₃—C₆H₄) | CH₃ |
| 740 | S | OCHF₂ | OSO₂(4-CH₃—C₆H₄) | CH₃ |
| 741 | SO₂ | F | OSO₂(4-CH₃—C₆H₄) | CH₃ |
| 742 | SO₂ | Cl | OSO₂(4-CH₃—C₆H₄) | CH₃ |
| 743 | SO₂ | Br | OSO₂(4-CH₃—C₆H₄) | CH₃ |
| 744 | SO₂ | NO₂ | OSO₂(4-CH₃—C₆H₄) | CH₃ |
| 745 | SO₂ | SCH₃ | OSO₂(4-CH₃—C₆H₄) | CH₃ |
| 746 | SO₂ | SO₂CH₃ | OSO₂(4-CH₃—C₆H₄) | CH₃ |
| 747 | SO₂ | SO₂CH₂CH₃ | OSO₂(4-CH₃—C₆H₄) | CH₃ |
| 748 | SO₂ | CH₃ | OSO₂(4-CH₃—C₆H₄) | CH₃ |
| 749 | SO₂ | CF₃ | OSO₂(4-CH₃—C₆H₄) | CH₃ |
| 750 | SO₂ | OCHF₂ | OSO₂(4-CH₃—C₆H₄) | CH₃ |
| 751 | bond | F | OSO₂(4-CH₃—C₆H₄) | CH₂CH₃ |
| 752 | bond | Cl | OSO₂(4-CH₃—C₆H₄) | CH₂CH₃ |
| 753 | bond | Br | OSO₂(4-CH₃—C₆H₄) | CH₂CH₃ |
| 754 | bond | NO₂ | OSO₂(4-CH₃—C₆H₄) | CH₂CH₃ |
| 755 | bond | SCH₃ | OSO₂(4-CH₃—C₆H₄) | CH₂CH₃ |
| 756 | bond | SO₂CH₃ | OSO₂(4-CH₃—C₆H₄) | CH₂CH₃ |
| 757 | bond | SO₂CH₂CH₃ | OSO₂(4-CH₃—C₆H₄) | CH₂CH₃ |
| 758 | bond | CH₃ | OSO₂(4-CH₃—C₆H₄) | CH₂CH₃ |
| 759 | bond | CF₃ | OSO₂(4-CH₃—C₆H₄) | CH₂CH₃ |
| 760 | bond | OCHF₂ | OSO₂(4-CH₃—C₆H₄) | CH₂CH₃ |
| 761 | CH₂ | F | OSO₂(4-CH₃—C₆H₄) | CH₂CH₃ |
| 762 | CH₂ | Cl | OSO₂(4-CH₃—C₆H₄) | CH₂CH₃ |
| 763 | CH₂ | Br | OSO₂(4-CH₃—C₆H₄) | CH₂CH₃ |
| 764 | CH₂ | NO₂ | OSO₂(4-CH₃—C₆H₄) | CH₂CH₃ |
| 765 | CH₂ | SCH₃ | OSO₂(4-CH₃—C₆H₄) | CH₂CH₃ |
| 766 | CH₂ | SO₂CH₃ | OSO₂(4-CH₃—C₆H₄) | CH₂CH₃ |
| 767 | CH₂ | SO₂CH₂CH₃ | OSO₂(4-CH₃—C₆H₄) | CH₂CH₃ |
| 768 | CH₂ | CH₃ | OSO₂(4-CH₃—C₆H₄) | CH₂CH₃ |
| 769 | CH₂ | CF₃ | OSO₂(4-CH₃—C₆H₄) | CH₂CH₃ |
| 770 | CH₂ | OCHF₂ | OSO₂(4-CH₃—C₆H₄) | CH₂CH₃ |
| 771 | O | F | OSO₂(4-CH₃—C₆H₄) | CH₂CH₃ |
| 772 | O | Cl | OSO₂(4-CH₃—C₆H₄) | CH₂CH₃ |
| 773 | O | Br | OSO₂(4-CH₃—C₆H₄) | CH₂CH₃ |
| 774 | O | NO₂ | OSO₂(4-CH₃—C₆H₄) | CH₂CH₃ |
| 775 | O | SCH₃ | OSO₂(4-CH₃—C₆H₄) | CH₂CH₃ |
| 776 | O | SO₂CH₃ | OSO₂(4-CH₃—C₆H₄) | CH₂CH₃ |
| 777 | O | SO₂CH₂CH₃ | OSO₂(4-CH₃—C₆H₄) | CH₂CH₃ |
| 778 | O | CH₃ | OSO₂(4-CH₃—C₆H₄) | CH₂CH₃ |
| 779 | O | CF₃ | OSO₂(4-CH₃—C₆H₄) | CH₂CH₃ |
| 780 | O | OCHF₂ | OSO₂(4-CH₃—C₆H₄) | CH₂CH₃ |
| 781 | S | F | OSO₂(4-CH₃—C₆H₄) | CH₂CH₃ |
| 782 | S | Cl | OSO₂(4-CH₃—C₆H₄) | CH₂CH₃ |
| 783 | S | Br | OSO₂(4-CH₃—C₆H₄) | CH₂CH₃ |
| 784 | S | NO₂ | OSO₂(4-CH₃—C₆H₄) | CH₂CH₃ |
| 785 | S | SCH₃ | OSO₂(4-CH₃—C₆H₄) | CH₂CH₃ |
| 786 | S | SO₂CH₃ | OSO₂(4-CH₃—C₆H₄) | CH₂CH₃ |
| 787 | S | SO₂CH₂CH₃ | OSO₂(4-CH₃—C₆H₄) | CH₂CH₃ |
| 788 | S | CH₃ | OSO₂(4-CH₃—C₆H₄) | CH₂CH₃ |
| 789 | S | CF₃ | OSO₂(4-CH₃—C₆H₄) | CH₂CH₃ |
| 790 | S | OCHF₂ | OSO₂(4-CH₃—C₆H₄) | CH₂CH₃ |
| 791 | SO₂ | F | OSO₂(4-CH₃—C₆H₄) | CH₂CH₃ |
| 792 | SO₂ | Cl | OSO₂(4-CH₃—C₆H₄) | CH₂CH₃ |
| 793 | SO₂ | Br | OSO₂(4-CH₃—C₆H₄) | CH₂CH₃ |
| 794 | SO₂ | NO₂ | OSO₂(4-CH₃—C₆H₄) | CH₂CH₃ |
| 795 | SO₂ | SCH₃ | OSO₂(4-CH₃—C₆H₄) | CH₂CH₃ |
| 796 | SO₂ | SO₂CH₃ | OSO₂(4-CH₃—C₆H₄) | CH₂CH₃ |
| 797 | SO₂ | SO₂CH₂CH₃ | OSO₂(4-CH₃—C₆H₄) | CH₂CH₃ |
| 798 | SO₂ | CH₃ | OSO₂(4-CH₃—C₆H₄) | CH₂CH₃ |
| 799 | SO₂ | CF₃ | OSO₂(4-CH₃—C₆H₄) | CH₂CH₃ |
| 800 | SO₂ | OCHF₂ | OSO₂(4-CH₃—C₆H₄) | CH₂CH₃ |
| 801 | bond | F | SCH₃ | CH₃ |
| 802 | bond | Cl | SCH₃ | CH₃ |
| 803 | bond | Br | SCH₃ | CH₃ |
| 804 | bond | NO₂ | SCH₃ | CH₃ |
| 805 | bond | SCH₃ | SCH₃ | CH₃ |
| 806 | bond | SO₂CH₃ | SCH₃ | CH₃ |
| 807 | bond | SO₂CH₂CH₃ | SCH₃ | CH₃ |
| 808 | bond | CH₃ | SCH₃ | CH₃ |
| 809 | bond | CF₃ | SCH₃ | CH₃ |
| 810 | bond | OCHF₂ | SCH₃ | CH₃ |
| 811 | CH₂ | F | SCH₃ | CH₃ |
| 812 | CH₂ | Cl | SCH₃ | CH₃ |
| 813 | CH₂ | Br | SCH₃ | CH₃ |
| 814 | CH₂ | NO₂ | SCH₃ | CH₃ |
| 815 | CH₂ | SCH₃ | SCH₃ | CH₃ |
| 816 | CH₂ | SO₂CH₃ | SCH₃ | CH₃ |
| 817 | CH₂ | SO₂CH₂CH₃ | SCH₃ | CH₃ |
| 818 | CH₂ | CH₃ | SCH₃ | CH₃ |
| 819 | CH₂ | CF₃ | SCH₃ | CH₃ |
| 820 | CH₂ | OCHF₂ | SCH₃ | CH₃ |
| 821 | O | F | SCH₃ | CH₃ |
| 822 | O | Cl | SCH₃ | CH₃ |
| 823 | O | Br | SCH₃ | CH₃ |
| 824 | O | NO₂ | SCH₃ | CH₃ |
| 825 | O | SCH₃ | SCH₃ | CH₃ |
| 826 | O | SO₂CH₃ | SCH₃ | CH₃ |
| 827 | O | SO₂CH₂CH₃ | SCH₃ | CH₃ |
| 828 | O | CH₃ | SCH₃ | CH₃ |
| 829 | O | CF₃ | SCH₃ | CH₃ |
| 830 | O | OCHF₂ | SCH₃ | CH₃ |
| 831 | S | F | SCH₃ | CH₃ |
| 832 | S | Cl | SCH₃ | CH₃ |
| 833 | S | Br | SCH₃ | CH₃ |
| 834 | S | NO₂ | SCH₃ | CH₃ |
| 835 | S | SCH₃ | SCH₃ | CH₃ |
| 836 | S | SO₂CH₃ | SCH₃ | CH₃ |
| 837 | S | SO₂CH₂CH₃ | SCH₃ | CH₃ |
| 838 | S | CH₃ | SCH₃ | CH₃ |
| 839 | S | CF₃ | SCH₃ | CH₃ |
| 840 | S | OCHF₂ | SCH₃ | CH₃ |
| 841 | SO₂ | F | SCH₃ | CH₃ |
| 842 | SO₂ | Cl | SCH₃ | CH₃ |
| 843 | SO₂ | Br | SCH₃ | CH₃ |
| 844 | SO₂ | NO₂ | SCH₃ | CH₃ |
| 845 | SO₂ | SCH₃ | SCH₃ | CH₃ |
| 846 | SO₂ | SO₂CH₃ | SCH₃ | CH₃ |
| 847 | SO₂ | SO₂CH₂CH₃ | SCH₃ | CH₃ |
| 848 | SO₂ | CH₃ | SCH₃ | CH₃ |
| 849 | SO₂ | CF₃ | SCH₃ | CH₃ |
| 850 | SO₂ | OCHF₂ | SCH₃ | CH₃ |
| 851 | bond | F | SCH₃ | CH₂CH₃ |
| 852 | bond | Cl | SCH₃ | CH₂CH₃ |
| 853 | bond | Br | SCH₃ | CH₂CH₃ |
| 854 | bond | NO₂ | SCH₃ | CH₂CH₃ |
| 855 | bond | SCH₃ | SCH₃ | CH₂CH₃ |
| 856 | bond | SO₂CH₃ | SCH₃ | CH₂CH₃ |
| 857 | bond | SO₂CH₂CH₃ | SCH₃ | CH₂CH₃ |
| 858 | bond | CH₃ | SCH₃ | CH₂CH₃ |
| 859 | bond | CF₃ | SCH₃ | CH₂CH₃ |
| 860 | bond | OCHF₂ | SCH₃ | CH₂CH₃ |
| 861 | CH₂ | F | SCH₃ | CH₂CH₃ |
| 862 | CH₂ | Cl | SCH₃ | CH₂CH₃ |
| 863 | CH₂ | Br | SCH₃ | CH₂CH₃ |
| 864 | CH₂ | NO₂ | SCH₃ | CH₂CH₃ |
| 865 | CH₂ | SCH₃ | SCH₃ | CH₂CH₃ |
| 866 | CH₂ | SO₂CH₃ | SCH₃ | CH₂CH₃ |
| 867 | CH₂ | SO₂CH₂CH₃ | SCH₃ | CH₂CH₃ |
| 868 | CH₂ | CH₃ | SCH₃ | CH₂CH₃ |
| 869 | CH₂ | CF₃ | SCH₃ | CH₂CH₃ |
| 870 | CH₂ | OCHF₂ | SCH₃ | CH₂CH₃ |
| 871 | O | F | SCH₃ | CH₂CH₃ |
| 872 | O | Cl | SCH₃ | CH₂CH₃ |

TABLE 1-continued

| n | X | R⁴ | R¹⁰ | R¹¹ |
|---|---|---|---|---|
| 873 | O | Br | SCH₃ | CH₂CH₃ |
| 874 | O | NO₂ | SCH₃ | CH₂CH₃ |
| 875 | O | SCH₃ | SCH₃ | CH₂CH₃ |
| 876 | O | SO₂CH₃ | SCH₃ | CH₂CH₃ |
| 877 | O | SO₂CH₂CH₃ | SCH₃ | CH₂CH₃ |
| 878 | O | CH₃ | SCH₃ | CH₂CH₃ |
| 879 | O | CF₃ | SCH₃ | CH₂CH₃ |
| 880 | O | OCHF₂ | SCH₃ | CH₂CH₃ |
| 881 | S | F | SCH₃ | CH₂CH₃ |
| 882 | S | Cl | SCH₃ | CH₂CH₃ |
| 883 | S | Br | SCH₃ | CH₂CH₃ |
| 884 | S | NO₂ | SCH₃ | CH₂CH₃ |
| 885 | S | SCH₃ | SCH₃ | CH₂CH₃ |
| 886 | S | SO₂CH₃ | SCH₃ | CH₂CH₃ |
| 887 | S | SO₂CH₂CH₃ | SCH₃ | CH₂CH₃ |
| 888 | S | CH₃ | SCH₃ | CH₂CH₃ |
| 889 | S | CF₃ | SCH₃ | CH₂CH₃ |
| 890 | S | OCHF₂ | SCH₃ | CH₂CH₃ |
| 891 | SO₂ | F | SCH₃ | CH₂CH₃ |
| 892 | SO₂ | Cl | SCH₃ | CH₂CH₃ |
| 893 | SO₂ | Br | SCH₃ | CH₂CH₃ |
| 894 | SO₂ | NO₂ | SCH₃ | CH₂CH₃ |
| 895 | SO₂ | SCH₃ | SCH₃ | CH₂CH₃ |
| 896 | SO₂ | SO₂CH₃ | SCH₃ | CH₂CH₃ |
| 897 | SO₂ | SO₂CH₂CH₃ | SCH₃ | CH₂CH₃ |
| 898 | SO₂ | CH₃ | SCH₃ | CH₂CH₃ |
| 899 | SO₂ | CF₃ | SCH₃ | CH₂CH₃ |
| 900 | SO₂ | OCHF₂ | SCH₃ | CH₂CH₃ |
| 901 | bond | F | Cl | CH₃ |
| 902 | bond | Cl | Cl | CH₃ |
| 903 | bond | Br | Cl | CH₃ |
| 904 | bond | NO₂ | Cl | CH₃ |
| 905 | bond | SCH₃ | Cl | CH₃ |
| 906 | bond | SO₂CH₃ | Cl | CH₃ |
| 907 | bond | SO₂CH₂CH₃ | Cl | CH₃ |
| 908 | bond | CH₃ | Cl | CH₃ |
| 909 | bond | CF₃ | Cl | CH₃ |
| 910 | bond | OCHF₂ | Cl | CH₃ |
| 911 | CH₂ | F | Cl | CH₃ |
| 912 | CH₂ | Cl | Cl | CH₃ |
| 913 | CH₂ | Br | Cl | CH₃ |
| 914 | CH₂ | NO₂ | Cl | CH₃ |
| 915 | CH₂ | SCH₃ | Cl | CH₃ |
| 916 | CH₂ | SO₂CH₃ | Cl | CH₃ |
| 917 | CH₂ | SO₂CH₂CH₃ | Cl | CH₃ |
| 918 | CH₂ | CH₃ | Cl | CH₃ |
| 919 | CH₂ | CF₃ | Cl | CH₃ |
| 920 | CH₂ | OCHF₂ | Cl | CH₃ |
| 921 | O | F | Cl | CH₃ |
| 922 | O | Cl | Cl | CH₃ |
| 923 | O | Br | Cl | CH₃ |
| 924 | O | NO₂ | Cl | CH₃ |
| 925 | O | SCH₃ | Cl | CH₃ |
| 926 | O | SO₂CH₃ | Cl | CH₃ |
| 927 | O | SO₂CH₂CH₃ | Cl | CH₃ |
| 928 | O | CH₃ | Cl | CH₃ |
| 929 | O | CF₃ | Cl | CH₃ |
| 930 | O | OCHF₂ | Cl | CH₃ |
| 931 | S | F | Cl | CH₃ |
| 932 | S | Cl | Cl | CH₃ |
| 933 | S | Br | Cl | CH₃ |
| 934 | S | NO₂ | Cl | CH₃ |
| 935 | S | SCH₃ | Cl | CH₃ |
| 936 | S | SO₂CH₃ | Cl | CH₃ |
| 937 | S | SO₂CH₂CH₃ | Cl | CH₃ |
| 938 | S | CH₃ | Cl | CH₃ |
| 939 | S | CF₃ | Cl | CH₃ |
| 940 | S | OCHF₂ | Cl | CH₃ |
| 941 | SO₂ | F | Cl | CH₃ |
| 942 | SO₂ | Cl | Cl | CH₃ |
| 943 | SO₂ | Br | Cl | CH₃ |
| 944 | SO₂ | NO₂ | Cl | CH₃ |
| 945 | SO₂ | SCH₃ | Cl | CH₃ |
| 946 | SO₂ | SO₂CH₃ | Cl | CH₃ |
| 947 | SO₂ | SO₂CH₂CH₃ | Cl | CH₃ |
| 948 | SO₂ | CH₃ | Cl | CH₃ |
| 949 | SO₂ | CF₃ | Cl | CH₃ |
| 950 | SO₂ | OCHF₂ | Cl | CH₃ |
| 951 | bond | F | Cl | CH₂CH₃ |
| 952 | bond | Cl | Cl | CH₂CH₃ |
| 953 | bond | Br | Cl | CH₂CH₃ |
| 954 | bond | NO₂ | Cl | CH₂CH₃ |
| 955 | bond | SCH₃ | Cl | CH₂CH₃ |
| 956 | bond | SO₂CH₃ | Cl | CH₂CH₃ |
| 957 | bond | SO₂CH₂CH₃ | Cl | CH₂CH₃ |
| 958 | bond | CH₃ | Cl | CH₂CH₃ |
| 959 | bond | CF₃ | Cl | CH₂CH₃ |
| 960 | bond | OCHF₂ | Cl | CH₂CH₃ |
| 961 | CH₂ | F | Cl | CH₂CH₃ |
| 962 | CH₂ | Cl | Cl | CH₂CH₃ |
| 963 | CH₂ | Br | Cl | CH₂CH₃ |
| 964 | CH₂ | NO₂ | Cl | CH₂CH₃ |
| 965 | CH₂ | SCH₃ | Cl | CH₂CH₃ |
| 966 | CH₂ | SO₂CH₃ | Cl | CH₂CH₃ |
| 967 | CH₂ | SO₂CH₂CH₃ | Cl | CH₂CH₃ |
| 968 | CH₂ | CH₃ | Cl | CH₂CH₃ |
| 969 | CH₂ | CF₃ | Cl | CH₂CH₃ |
| 970 | CH₂ | OCHF₂ | Cl | CH₂CH₃ |
| 971 | O | F | Cl | CH₂CH₃ |
| 972 | O | Cl | Cl | CH₂CH₃ |
| 973 | O | Br | Cl | CH₂CH₃ |
| 974 | O | NO₂ | Cl | CH₂CH₃ |
| 975 | O | SCH₃ | Cl | CH₂CH₃ |
| 976 | O | SO₂CH₃ | Cl | CH₂CH₃ |
| 977 | O | SO₂CH₂CH₃ | Cl | CH₂CH₃ |
| 978 | O | CH₃ | Cl | CH₂CH₃ |
| 979 | O | CF₃ | Cl | CH₂CH₃ |
| 980 | O | OCHF₂ | Cl | CH₂CH₃ |
| 981 | S | F | Cl | CH₂CH₃ |
| 982 | S | Cl | Cl | CH₂CH₃ |
| 983 | S | Br | Cl | CH₂CH₃ |
| 984 | S | NO₂ | Cl | CH₂CH₃ |
| 985 | S | SCH₃ | Cl | CH₂CH₃ |
| 986 | S | SO₂CH₃ | Cl | CH₂CH₃ |
| 987 | S | SO₂CH₂CH₃ | Cl | CH₂CH₃ |
| 988 | S | CH₃ | Cl | CH₂CH₃ |
| 989 | S | CF₃ | Cl | CH₂CH₃ |
| 990 | S | OCHF₂ | Cl | CH₂CH₃ |
| 991 | SO₂ | F | Cl | CH₂CH₃ |
| 992 | SO₂ | Cl | Cl | CH₂CH₃ |
| 993 | SO₂ | Br | Cl | CH₂CH₃ |
| 994 | SO₂ | NO₂ | Cl | CH₂CH₃ |
| 995 | SO₂ | SCH₃ | Cl | CH₂CH₃ |
| 996 | SO₂ | SO₂CH₃ | Cl | CH₂CH₃ |
| 997 | SO₂ | SO₂CH₂CH₃ | Cl | CH₂CH₃ |
| 998 | SO₂ | CH₃ | Cl | CH₂CH₃ |
| 999 | SO₂ | CF₃ | Cl | CH₂CH₃ |
| 1000 | SO₂ | OCHF₂ | Cl | CH₂CH₃ |
| 1001 | bond | F | OH | CH(CH₃)₂ |
| 1002 | bond | Cl | OH | CH(CH₃)₂ |
| 1003 | bond | Br | OH | CH(CH₃)₂ |
| 1004 | bond | NO₂ | OH | CH(CH₃)₂ |
| 1005 | bond | SCH₃ | OH | CH(CH₃)₂ |
| 1006 | bond | SO₂CH₃ | OH | CH(CH₃)₂ |
| 1007 | bond | SO₂CH₂CH₃ | OH | CH(CH₃)₂ |
| 1008 | bond | CH₃ | OH | CH(CH₃)₂ |
| 1009 | bond | CF₃ | OH | CH(CH₃)₂ |
| 1010 | bond | OCHF₂ | OH | CH(CH₃)₂ |
| 1011 | CH₂ | F | OH | CH(CH₃)₂ |
| 1012 | CH₂ | Cl | OH | CH(CH₃)₂ |
| 2025 | CH₂ | Br | OH | CH(CH₃)₂ |
| 2026 | CH₂ | NO₂ | OH | CH(CH₃)₂ |
| 2027 | CH₂ | SCH₃ | OH | CH(CH₃)₂ |
| 2028 | CH₂ | SO₂CH₃ | OH | CH(CH₃)₂ |
| 2029 | CH₂ | SO₂CH₂CH₃ | OH | CH(CH₃)₂ |
| 2030 | CH₂ | CH₃ | OH | CH(CH₃)₂ |
| 2031 | CH₂ | CF₃ | OH | CH(CH₃)₂ |
| 2032 | CH₂ | OCHF₂ | OH | CH(CH₃)₂ |
| 2033 | O | F | OH | CH(CH₃)₂ |
| 2034 | O | Cl | OH | CH(CH₃)₂ |
| 2035 | O | Br | OH | CH(CH₃)₂ |
| 2036 | O | NO₂ | OH | CH(CH₃)₂ |
| 2037 | O | SCH₃ | OH | CH(CH₃)₂ |
| 2038 | O | SO₂CH₃ | OH | CH(CH₃)₂ |

TABLE 1-continued

| n | X | R⁴ | R¹⁰ | R¹¹ |
|---|---|---|---|---|
| 2039 | O | SO$_2$CH$_2$CH$_3$ | OH | CH(CH$_3$)$_2$ |
| 2040 | O | CH$_3$ | OH | CH(CH$_3$)$_2$ |
| 2041 | O | CF$_3$ | OH | CH(CH$_3$)$_2$ |
| 2042 | O | OCHF$_2$ | OH | CH(CH$_3$)$_2$ |
| 2043 | S | F | OH | CH(CH$_3$)$_2$ |
| 2044 | S | Cl | OH | CH(CH$_3$)$_2$ |
| 2045 | S | Br | OH | CH(CH$_3$)$_2$ |
| 2046 | S | NO$_2$ | OH | CH(CH$_3$)$_2$ |
| 2047 | S | SCH$_3$ | OH | CH(CH$_3$)$_2$ |
| 2048 | S | SO$_2$CH$_3$ | OH | CH(CH$_3$)$_2$ |
| 2049 | S | SO$_2$CH$_2$CH$_3$ | OH | CH(CH$_3$)$_2$ |
| 2050 | S | CH$_3$ | OH | CH(CH$_3$)$_2$ |
| 2051 | S | CF$_3$ | OH | CH(CH$_3$)$_2$ |
| 2052 | S | OCHF$_2$ | OH | CH(CH$_3$)$_2$ |
| 2053 | SO$_2$ | F | OH | CH(CH$_3$)$_2$ |
| 2054 | SO$_2$ | Cl | OH | CH(CH$_3$)$_2$ |
| 2055 | SO$_2$ | Br | OH | CH(CH$_3$)$_2$ |
| 2056 | SO$_2$ | NO$_2$ | OH | CH(CH$_3$)$_2$ |
| 2057 | SO$_2$ | SCH$_3$ | OH | CH(CH$_3$)$_2$ |
| 2058 | SO$_2$ | SO$_2$CH$_3$ | OH | CH(CH$_3$)$_2$ |
| 2059 | SO$_2$ | SO$_2$CH$_2$CH$_3$ | OH | CH(CH$_3$)$_2$ |
| 2060 | SO$_2$ | CH$_3$ | OH | CH(CH$_3$)$_2$ |
| 2061 | SO$_2$ | CF$_3$ | OH | CH(CH$_3$)$_2$ |
| 2062 | SO$_2$ | OCHF$_2$ | OH | CH(CH$_3$)$_2$ |
| 2063 | bond | F | OH | C(CH$_3$)$_3$ |
| 2064 | bond | Cl | OH | C(CH$_3$)$_3$ |
| 2065 | bond | Br | OH | C(CH$_3$)$_3$ |
| 2066 | bond | NO$_2$ | OH | C(CH$_3$)$_3$ |
| 2067 | bond | SCH$_3$ | OH | C(CH$_3$)$_3$ |
| 2068 | bond | SO$_2$CH$_3$ | OH | C(CH$_3$)$_3$ |
| 2069 | bond | SO$_2$CH$_2$CH$_3$ | OH | C(CH$_3$)$_3$ |
| 2070 | bond | CH$_3$ | OH | C(CH$_3$)$_3$ |
| 2071 | bond | CF$_3$ | OH | C(CH$_3$)$_3$ |
| 2072 | bond | OCHF$_2$ | OH | C(CH$_3$)$_3$ |
| 2073 | CH$_2$ | F | OH | C(CH$_3$)$_3$ |
| 2074 | CH$_2$ | Cl | OH | C(CH$_3$)$_3$ |
| 2075 | CH$_2$ | Br | OH | C(CH$_3$)$_3$ |
| 2076 | CH$_2$ | NO$_2$ | OH | C(CH$_3$)$_3$ |
| 2077 | CH$_2$ | SCH$_3$ | OH | C(CH$_3$)$_3$ |
| 2078 | CH$_2$ | SO$_2$CH$_3$ | OH | C(CH$_3$)$_3$ |
| 2079 | CH$_2$ | SO$_2$CH$_2$CH$_3$ | OH | C(CH$_3$)$_3$ |
| 2080 | CH$_2$ | CH$_3$ | OH | C(CH$_3$)$_3$ |
| 2081 | CH$_2$ | CF$_3$ | OH | C(CH$_3$)$_3$ |
| 2082 | CH$_2$ | OCHF$_2$ | OH | C(CH$_3$)$_3$ |
| 2083 | O | F | OH | C(CH$_3$)$_3$ |
| 2084 | O | Cl | OH | C(CH$_3$)$_3$ |
| 2085 | O | Br | OH | C(CH$_3$)$_3$ |
| 2086 | O | NO$_2$ | OH | C(CH$_3$)$_3$ |
| 2087 | O | SCH$_3$ | OH | C(CH$_3$)$_3$ |
| 2088 | O | SO$_2$CH$_3$ | OH | C(CH$_3$)$_3$ |
| 2089 | O | SO$_2$CH$_2$CH$_3$ | OH | C(CH$_3$)$_3$ |
| 2090 | O | CH$_3$ | OH | C(CH$_3$)$_3$ |
| 2091 | O | CF$_3$ | OH | C(CH$_3$)$_3$ |
| 2092 | O | OCHF$_2$ | OH | C(CH$_3$)$_3$ |
| 2093 | S | F | OH | C(CH$_3$)$_3$ |
| 2094 | S | Cl | OH | C(CH$_3$)$_3$ |
| 2095 | S | Br | OH | C(CH$_3$)$_3$ |
| 2096 | S | NO$_2$ | OH | C(CH$_3$)$_3$ |
| 2097 | S | SCH$_3$ | OH | C(CH$_3$)$_3$ |
| 2098 | S | SO$_2$CH$_3$ | OH | C(CH$_3$)$_3$ |
| 2099 | S | SO$_2$CH$_2$CH$_3$ | OH | C(CH$_3$)$_3$ |
| 2100 | S | CH$_3$ | OH | C(CH$_3$)$_3$ |
| 2101 | S | CF$_3$ | OH | C(CH$_3$)$_3$ |
| 2102 | S | OCHF$_2$ | OH | C(CH$_3$)$_3$ |
| 2103 | SO$_2$ | F | OH | C(CH$_3$)$_3$ |
| 2104 | SO$_2$ | Cl | OH | C(CH$_3$)$_3$ |
| 2105 | SO$_2$ | Br | OH | C(CH$_3$)$_3$ |
| 2106 | SO$_2$ | NO$_2$ | OH | C(CH$_3$)$_3$ |
| 2107 | SO$_2$ | SCH$_3$ | OH | C(CH$_3$)$_3$ |
| 2108 | SO$_2$ | SO$_2$CH$_3$ | OH | C(CH$_3$)$_3$ |
| 2109 | SO$_2$ | SO$_2$CH$_2$CH$_3$ | OH | C(CH$_3$)$_3$ |
| 2110 | SO$_2$ | CH$_3$ | OH | C(CH$_3$)$_3$ |
| 2111 | SO$_2$ | CF$_3$ | OH | C(CH$_3$)$_3$ |
| 2112 | SO$_2$ | OCHF$_2$ | OH | C(CH$_3$)$_3$ |
| 2113 | bond | F | OCOC$_6$H$_5$ | CH(CH$_3$)$_2$ |
| 2114 | bond | Cl | OCOC$_6$H$_5$ | CH(CH$_3$)$_2$ |
| 2115 | bond | Br | OCOC$_6$H$_5$ | CH(CH$_3$)$_2$ |
| 2116 | bond | NO$_2$ | OCOC$_6$H$_5$ | CH(CH$_3$)$_2$ |
| 2117 | bond | SCH$_3$ | OCOC$_6$H$_5$ | CH(CH$_3$)$_2$ |
| 2118 | bond | SO$_2$CH$_3$ | OCOC$_6$H$_5$ | CH(CH$_3$)$_2$ |
| 2119 | bond | SO$_2$CH$_2$CH$_3$ | OCOC$_6$H$_5$ | CH(CH$_3$)$_2$ |
| 2120 | bond | CH$_3$ | OCOC$_6$H$_5$ | CH(CH$_3$)$_2$ |
| 2121 | bond | CF$_3$ | OCOC$_6$H$_5$ | CH(CH$_3$)$_2$ |
| 2122 | bond | OCHF$_2$ | OCOC$_6$H$_5$ | CH(CH$_3$)$_2$ |
| 2123 | CH$_2$ | F | OCOC$_6$H$_5$ | CH(CH$_3$)$_2$ |
| 2124 | CH$_2$ | Cl | OCOC$_6$H$_5$ | CH(CH$_3$)$_2$ |
| 2125 | CH$_2$ | Br | OCOC$_6$H$_5$ | CH(CH$_3$)$_2$ |
| 2126 | CH$_2$ | NO$_2$ | OCOC$_6$H$_5$ | CH(CH$_3$)$_2$ |
| 2127 | CH$_2$ | SCH$_3$ | OCOC$_6$H$_5$ | CH(CH$_3$)$_2$ |
| 2128 | CH$_2$ | SO$_2$CH$_3$ | OCOC$_6$H$_5$ | CH(CH$_3$)$_2$ |
| 2129 | CH$_2$ | SO$_2$CH$_2$CH$_3$ | OCOC$_6$H$_5$ | CH(CH$_3$)$_2$ |
| 2130 | CH$_2$ | CH$_3$ | OCOC$_6$H$_5$ | CH(CH$_3$)$_2$ |
| 2131 | CH$_2$ | CF$_3$ | OCOC$_6$H$_5$ | CH(CH$_3$)$_2$ |
| 2132 | CH$_2$ | OCHF$_2$ | OCOC$_6$H$_5$ | CH(CH$_3$)$_2$ |
| 2133 | O | F | OCOC$_6$H$_5$ | CH(CH$_3$)$_2$ |
| 2134 | O | Cl | OCOC$_6$H$_5$ | CH(CH$_3$)$_2$ |
| 2135 | O | Br | OCOC$_6$H$_5$ | CH(CH$_3$)$_2$ |
| 2136 | O | NO$_2$ | OCOC$_6$H$_5$ | CH(CH$_3$)$_2$ |
| 2137 | O | SCH$_3$ | OCOC$_6$H$_5$ | CH(CH$_3$)$_2$ |
| 2138 | O | SO$_2$CH$_3$ | OCOC$_6$H$_5$ | CH(CH$_3$)$_2$ |
| 2139 | O | SO$_2$CH$_2$CH$_3$ | OCOC$_6$H$_5$ | CH(CH$_3$)$_2$ |
| 2140 | O | CH$_3$ | OCOC$_6$H$_5$ | CH(CH$_3$)$_2$ |
| 2141 | O | CF$_3$ | OCOC$_6$H$_5$ | CH(CH$_3$)$_2$ |
| 2142 | O | OCHF$_2$ | OCOC$_6$H$_5$ | CH(CH$_3$)$_2$ |
| 2143 | S | F | OCOC$_6$H$_5$ | CH(CH$_3$)$_2$ |
| 2144 | S | Cl | OCOC$_6$H$_5$ | CH(CH$_3$)$_2$ |
| 2145 | S | Br | OCOC$_6$H$_5$ | CH(CH$_3$)$_2$ |
| 2146 | S | NO$_2$ | OCOC$_6$H$_5$ | CH(CH$_3$)$_2$ |
| 2147 | S | SCH$_3$ | OCOC$_6$H$_5$ | CH(CH$_3$)$_2$ |
| 2148 | S | SO$_2$CH$_3$ | OCOC$_6$H$_5$ | CH(CH$_3$)$_2$ |
| 2149 | S | SO$_2$CH$_2$CH$_3$ | OCOC$_6$H$_5$ | CH(CH$_3$)$_2$ |
| 2150 | S | CH$_3$ | OCOC$_6$H$_5$ | CH(CH$_3$)$_2$ |
| 2151 | S | CF$_3$ | OCOC$_6$H$_5$ | CH(CH$_3$)$_2$ |
| 2152 | S | OCHF$_2$ | OCOC$_6$H$_5$ | CH(CH$_3$)$_2$ |
| 2153 | SO$_2$ | F | OCOC$_6$H$_5$ | CH(CH$_3$)$_2$ |
| 2154 | SO$_2$ | Cl | OCOC$_6$H$_5$ | CH(CH$_3$)$_2$ |
| 2155 | SO$_2$ | Br | OCOC$_6$H$_5$ | CH(CH$_3$)$_2$ |
| 2156 | SO$_2$ | NO$_2$ | OCOC$_6$H$_5$ | CH(CH$_3$)$_2$ |
| 2157 | SO$_2$ | SCH$_3$ | OCOC$_6$H$_5$ | CH(CH$_3$)$_2$ |
| 2158 | SO$_2$ | SO$_2$CH$_3$ | OCOC$_6$H$_5$ | CH(CH$_3$)$_2$ |
| 2159 | SO$_2$ | SO$_2$CH$_2$CH$_3$ | OCOC$_6$H$_5$ | CH(CH$_3$)$_2$ |
| 2160 | SO$_2$ | CH$_3$ | OCOC$_6$H$_5$ | CH(CH$_3$)$_2$ |
| 2161 | SO$_2$ | CF$_3$ | OCOC$_6$H$_5$ | CH(CH$_3$)$_2$ |
| 2162 | SO$_2$ | OCHF$_2$ | OCOC$_6$H$_5$ | CH(CH$_3$)$_2$ |
| 2163 | bond | F | OCOC$_6$H$_5$ | C(CH$_3$)$_3$ |
| 2164 | bond | Cl | OCOC$_6$H$_5$ | C(CH$_3$)$_3$ |
| 2165 | bond | Br | OCOC$_6$H$_5$ | C(CH$_3$)$_3$ |
| 2166 | bond | NO$_2$ | OCOC$_6$H$_5$ | C(CH$_3$)$_3$ |
| 2167 | bond | SCH$_3$ | OCOC$_6$H$_5$ | C(CH$_3$)$_3$ |
| 2168 | bond | SO$_2$CH$_3$ | OCOC$_6$H$_5$ | C(CH$_3$)$_3$ |
| 2169 | bond | SO$_2$CH$_2$CH$_3$ | OCOC$_6$H$_5$ | C(CH$_3$)$_3$ |
| 2170 | bond | CH$_3$ | OCOC$_6$H$_5$ | C(CH$_3$)$_3$ |
| 2171 | bond | CF$_3$ | OCOC$_6$H$_5$ | C(CH$_3$)$_3$ |
| 2172 | bond | OCHF$_2$ | OCOC$_6$H$_5$ | C(CH$_3$)$_3$ |
| 2173 | CH$_2$ | F | OCOC$_6$H$_5$ | C(CH$_3$)$_3$ |
| 2174 | CH$_2$ | Cl | OCOC$_6$H$_5$ | C(CH$_3$)$_3$ |
| 2175 | CH$_2$ | Br | OCOC$_6$H$_5$ | C(CH$_3$)$_3$ |
| 2176 | CH$_2$ | NO$_2$ | OCOC$_6$H$_5$ | C(CH$_3$)$_3$ |
| 2177 | CH$_2$ | SCH$_3$ | OCOC$_6$H$_5$ | C(CH$_3$)$_3$ |
| 2178 | CH$_2$ | SO$_2$CH$_3$ | OCOC$_6$H$_5$ | C(CH$_3$)$_3$ |
| 2179 | CH$_2$ | SO$_2$CH$_2$CH$_3$ | OCOC$_6$H$_5$ | C(CH$_3$)$_3$ |
| 2180 | CH$_2$ | CH$_3$ | OCOC$_6$H$_5$ | C(CH$_3$)$_3$ |
| 2181 | CH$_2$ | CF$_3$ | OCOC$_6$H$_5$ | C(CH$_3$)$_3$ |
| 2182 | CH$_2$ | OCHF$_2$ | OCOC$_6$H$_5$ | C(CH$_3$)$_3$ |
| 2183 | O | F | OCOC$_6$H$_5$ | C(CH$_3$)$_3$ |
| 2184 | O | Cl | OCOC$_6$H$_5$ | C(CH$_3$)$_3$ |
| 2185 | O | Br | OCOC$_6$H$_5$ | C(CH$_3$)$_3$ |
| 2186 | O | NO$_2$ | OCOC$_6$H$_5$ | C(CH$_3$)$_3$ |
| 2187 | O | SCH$_3$ | OCOC$_6$H$_5$ | C(CH$_3$)$_3$ |
| 2188 | O | SO$_2$CH$_3$ | OCOC$_6$H$_5$ | C(CH$_3$)$_3$ |
| 2189 | O | SO$_2$CH$_2$CH$_3$ | OCOC$_6$H$_5$ | C(CH$_3$)$_3$ |
| 2190 | O | CH$_3$ | OCOC$_6$H$_5$ | C(CH$_3$)$_3$ |
| 2191 | O | CF$_3$ | OCOC$_6$H$_5$ | C(CH$_3$)$_3$ |
| 2192 | O | OCHF$_2$ | OCOC$_6$H$_5$ | C(CH$_3$)$_3$ |

TABLE 1-continued

| n | X | R⁴ | R¹⁰ | R¹¹ |
|---|---|---|---|---|
| 2193 | S | F | OCOC₆H₅ | C(CH₃)₃ |
| 2194 | S | Cl | OCOC₆H₅ | C(CH₃)₃ |
| 2195 | S | Br | OCOC₆H₅ | C(CH₃)₃ |
| 2196 | S | NO₂ | OCOC₆H₅ | C(CH₃)₃ |
| 2197 | S | SCH₃ | OCOC₆H₅ | C(CH₃)₃ |
| 2198 | S | SO₂CH₃ | OCOC₆H₅ | C(CH₃)₃ |
| 2199 | S | SO₂CH₂CH₃ | OCOC₆H₅ | C(CH₃)₃ |
| 2200 | S | CH₃ | OCOC₆H₅ | C(CH₃)₃ |
| 2201 | S | CF₃ | OCOC₆H₅ | C(CH₃)₃ |
| 2202 | S | OCHF₂ | OCOC₆H₅ | C(CH₃)₃ |
| 2203 | SO₂ | F | OCOC₆H₅ | C(CH₃)₃ |
| 2204 | SO₂ | Cl | OCOC₆H₅ | C(CH₃)₃ |
| 2205 | SO₂ | Br | OCOC₆H₅ | C(CH₃)₃ |
| 2206 | SO₂ | NO₂ | OCOC₆H₅ | C(CH₃)₃ |
| 2207 | SO₂ | SCH₃ | OCOC₆H₅ | C(CH₃)₃ |
| 2208 | SO₂ | SO₂CH₃ | OCOC₆H₅ | C(CH₃)₃ |
| 2209 | SO₂ | SO₂CH₂CH₃ | OCOC₆H₅ | C(CH₃)₃ |
| 2210 | SO₂ | CH₃ | OCOC₆H₅ | C(CH₃)₃ |
| 2211 | SO₂ | CF₃ | OCOC₆H₅ | C(CH₃)₃ |
| 2212 | SO₂ | OCHF₂ | OCOC₆H₅ | C(CH₃)₃ |
| 2213 | bond | F | OCOC(CH₃)₃ | CH(CH₃)₂ |
| 2214 | bond | Cl | OCOC(CH₃)₃ | CH(CH₃)₂ |
| 2215 | bond | Br | OCOC(CH₃)₃ | CH(CH₃)₂ |
| 2216 | bond | NO₂ | OCOC(CH₃)₃ | CH(CH₃)₂ |
| 2217 | bond | SCH₃ | OCOC(CH₃)₃ | CH(CH₃)₂ |
| 2218 | bond | SO₂CH₃ | OCOC(CH₃)₃ | CH(CH₃)₂ |
| 2219 | bond | SO₂CH₂CH₃ | OCOC(CH₃)₃ | CH(CH₃)₂ |
| 2220 | bond | CH₃ | OCOC(CH₃)₃ | CH(CH₃)₂ |
| 2221 | bond | CF₃ | OCOC(CH₃)₃ | CH(CH₃)₂ |
| 2222 | bond | OCHF₂ | OCOC(CH₃)₃ | CH(CH₃)₂ |
| 2223 | CH₂ | F | OCOC(CH₃)₃ | CH(CH₃)₂ |
| 2224 | CH₂ | Cl | OCOC(CH₃)₃ | CH(CH₃)₂ |
| 2225 | CH₂ | Br | OCOC(CH₃)₃ | CH(CH₃)₂ |
| 2226 | CH₂ | NO₂ | OCOC(CH₃)₃ | CH(CH₃)₂ |
| 2227 | CH₂ | SCH₃ | OCOC(CH₃)₃ | CH(CH₃)₂ |
| 2228 | CH₂ | SO₂CH₃ | OCOC(CH₃)₃ | CH(CH₃)₂ |
| 2229 | CH₂ | SO₂CH₂CH₃ | OCOC(CH₃)₃ | CH(CH₃)₂ |
| 2230 | CH₂ | CH₃ | OCOC(CH₃)₃ | CH(CH₃)₂ |
| 2231 | CH₂ | CF₃ | OCOC(CH₃)₃ | CH(CH₃)₂ |
| 2232 | CH₂ | OCHF₂ | OCOC(CH₃)₃ | CH(CH₃)₂ |
| 2233 | O | F | OCOC(CH₃)₃ | CH(CH₃)₂ |
| 2234 | O | Cl | OCOC(CH₃)₃ | CH(CH₃)₂ |
| 2235 | O | Br | OCOC(CH₃)₃ | CH(CH₃)₂ |
| 2236 | O | NO₂ | OCOC(CH₃)₃ | CH(CH₃)₂ |
| 2237 | O | SCH₃ | OCOC(CH₃)₃ | CH(CH₃)₂ |
| 2238 | O | SO₂CH₃ | OCOC(CH₃)₃ | CH(CH₃)₂ |
| 2239 | O | SO₂CH₂CH₃ | OCOC(CH₃)₃ | CH(CH₃)₂ |
| 2240 | O | CH₃ | OCOC(CH₃)₃ | CH(CH₃)₂ |
| 2241 | O | CF₃ | OCOC(CH₃)₃ | CH(CH₃)₂ |
| 2242 | O | OCHF₂ | OCOC(CH₃)₃ | CH(CH₃)₂ |
| 2243 | S | F | OCOC(CH₃)₃ | CH(CH₃)₂ |
| 2244 | S | Cl | OCOC(CH₃)₃ | CH(CH₃)₂ |
| 2245 | S | Br | OCOC(CH₃)₃ | CH(CH₃)₂ |
| 2246 | S | NO₂ | OCOC(CH₃)₃ | CH(CH₃)₂ |
| 2247 | S | SCH₃ | OCOC(CH₃)₃ | CH(CH₃)₂ |
| 2248 | S | SO₂CH₃ | OCOC(CH₃)₃ | CH(CH₃)₂ |
| 2249 | S | SO₂CH₂CH₃ | OCOC(CH₃)₃ | CH(CH₃)₂ |
| 2250 | S | CH₃ | OCOC(CH₃)₃ | CH(CH₃)₂ |
| 2251 | S | CF₃ | OCOC(CH₃)₃ | CH(CH₃)₂ |
| 2252 | S | OCHF₂ | OCOC(CH₃)₃ | CH(CH₃)₂ |
| 2253 | SO₂ | F | OCOC(CH₃)₃ | CH(CH₃)₂ |
| 2254 | SO₂ | Cl | OCOC(CH₃)₃ | CH(CH₃)₂ |
| 2255 | SO₂ | Br | OCOC(CH₃)₃ | CH(CH₃)₂ |
| 2256 | SO₂ | NO₂ | OCOC(CH₃)₃ | CH(CH₃)₂ |
| 2257 | SO₂ | SCH₃ | OCOC(CH₃)₃ | CH(CH₃)₂ |
| 2258 | SO₂ | SO₂CH₃ | OCOC(CH₃)₃ | CH(CH₃)₂ |
| 2259 | SO₂ | SO₂CH₂CH₃ | OCOC(CH₃)₃ | CH(CH₃)₂ |
| 2260 | SO₂ | CH₃ | OCOC(CH₃)₃ | CH(CH₃)₂ |
| 2261 | SO₂ | CF₃ | OCOC(CH₃)₃ | CH(CH₃)₂ |
| 2262 | SO₂ | OCHF₂ | OCOC(CH₃)₃ | CH(CH₃)₂ |
| 2263 | bond | F | OCOC(CH₃)₃ | C(CH₃)₃ |
| 2264 | bond | Cl | OCOC(CH₃)₃ | C(CH₃)₃ |
| 2265 | bond | Br | OCOC(CH₃)₃ | C(CH₃)₃ |
| 2266 | bond | NO₂ | OCOC(CH₃)₃ | C(CH₃)₃ |
| 2267 | bond | SCH₃ | OCOC(CH₃)₃ | C(CH₃)₃ |
| 2268 | bond | SO₂CH₃ | OCOC(CH₃)₃ | C(CH₃)₃ |
| 2269 | bond | SO₂CH₂CH₃ | OCOC(CH₃)₃ | C(CH₃)₃ |
| 2270 | bond | CH₃ | OCOC(CH₃)₃ | C(CH₃)₃ |
| 2271 | bond | CF₃ | OCOC(CH₃)₃ | C(CH₃)₃ |
| 2272 | bond | OCHF₂ | OCOC(CH₃)₃ | C(CH₃)₃ |
| 2273 | CH₂ | F | OCOC(CH₃)₃ | C(CH₃)₃ |
| 2274 | CH₂ | Cl | OCOC(CH₃)₃ | C(CH₃)₃ |
| 2275 | CH₂ | Br | OCOC(CH₃)₃ | C(CH₃)₃ |
| 2276 | CH₂ | NO₂ | OCOC(CH₃)₃ | C(CH₃)₃ |
| 2277 | CH₂ | SCH₃ | OCOC(CH₃)₃ | C(CH₃)₃ |
| 2278 | CH₂ | SO₂CH₃ | OCOC(CH₃)₃ | C(CH₃)₃ |
| 2279 | CH₂ | SO₂CH₂CH₃ | OCOC(CH₃)₃ | C(CH₃)₃ |
| 2280 | CH₂ | CH₃ | OCOC(CH₃)₃ | C(CH₃)₃ |
| 2281 | CH₂ | CF₃ | OCOC(CH₃)₃ | C(CH₃)₃ |
| 2282 | CH₂ | OCHF₂ | OCOC(CH₃)₃ | C(CH₃)₃ |
| 2283 | O | F | OCOC(CH₃)₃ | C(CH₃)₃ |
| 2284 | O | Cl | OCOC(CH₃)₃ | C(CH₃)₃ |
| 2285 | O | Br | OCOC(CH₃)₃ | C(CH₃)₃ |
| 2286 | O | NO₂ | OCOC(CH₃)₃ | C(CH₃)₃ |
| 2287 | O | SCH₃ | OCOC(CH₃)₃ | C(CH₃)₃ |
| 2288 | O | SO₂CH₃ | OCOC(CH₃)₃ | C(CH₃)₃ |
| 2289 | O | SO₂CH₂CH₃ | OCOC(CH₃)₃ | C(CH₃)₃ |
| 2290 | O | CH₃ | OCOC(CH₃)₃ | C(CH₃)₃ |
| 2291 | O | CF₃ | OCOC(CH₃)₃ | C(CH₃)₃ |
| 2292 | O | OCHF₂ | OCOC(CH₃)₃ | C(CH₃)₃ |
| 2293 | S | F | OCOC(CH₃)₃ | C(CH₃)₃ |
| 2294 | S | Cl | OCOC(CH₃)₃ | C(CH₃)₃ |
| 2295 | S | Br | OCOC(CH₃)₃ | C(CH₃)₃ |
| 2296 | S | NO₂ | OCOC(CH₃)₃ | C(CH₃)₃ |
| 2297 | S | SCH₃ | OCOC(CH₃)₃ | C(CH₃)₃ |
| 2298 | S | SO₂CH₃ | OCOC(CH₃)₃ | C(CH₃)₃ |
| 2299 | S | SO₂CH₂CH₃ | OCOC(CH₃)₃ | C(CH₃)₃ |
| 2300 | S | CH₃ | OCOC(CH₃)₃ | C(CH₃)₃ |
| 2301 | S | CF₃ | OCOC(CH₃)₃ | C(CH₃)₃ |
| 2302 | S | OCHF₂ | OCOC(CH₃)₃ | C(CH₃)₃ |
| 2303 | SO₂ | F | OCOC(CH₃)₃ | C(CH₃)₃ |
| 2304 | SO₂ | Cl | OCOC(CH₃)₃ | C(CH₃)₃ |
| 2305 | SO₂ | Br | OCOC(CH₃)₃ | C(CH₃)₃ |
| 2306 | SO₂ | NO₂ | OCOC(CH₃)₃ | C(CH₃)₃ |
| 2307 | SO₂ | SCH₃ | OCOC(CH₃)₃ | C(CH₃)₃ |
| 2308 | SO₂ | SO₂CH₃ | OCOC(CH₃)₃ | C(CH₃)₃ |
| 2309 | SO₂ | SO₂CH₂CH₃ | OCOC(CH₃)₃ | C(CH₃)₃ |
| 2310 | SO₂ | CH₃ | OCOC(CH₃)₃ | C(CH₃)₃ |
| 2311 | SO₂ | CF₃ | OCOC(CH₃)₃ | C(CH₃)₃ |
| 2312 | SO₂ | OCHF₂ | OCOC(CH₃)₃ | C(CH₃)₃ |
| 2313 | bond | F | OCOSCH₃ | CH(CH₃)₂ |
| 2314 | bond | Cl | OCOSCH₃ | CH(CH₃)₂ |
| 2315 | bond | Br | OCOSCH₃ | CH(CH₃)₂ |
| 2316 | bond | NO₂ | OCOSCH₃ | CH(CH₃)₂ |
| 2317 | bond | SCH₃ | OCOSCH₃ | CH(CH₃)₂ |
| 2318 | bond | SO₂CH₃ | OCOSCH₃ | CH(CH₃)₂ |
| 2319 | bond | SO₂CH₂CH₃ | OCOSCH₃ | CH(CH₃)₂ |
| 2320 | bond | CH₃ | OCOSCH₃ | CH(CH₃)₂ |
| 2321 | bond | CF₃ | OCOSCH₃ | CH(CH₃)₂ |
| 2322 | bond | OCHF₂ | OCOSCH₃ | CH(CH₃)₂ |
| 2323 | CH₂ | F | OCOSCH₃ | CH(CH₃)₂ |
| 2324 | CH₂ | Cl | OCOSCH₃ | CH(CH₃)₂ |
| 2325 | CH₂ | Br | OCOSCH₃ | CH(CH₃)₂ |
| 2326 | CH₂ | NO₂ | OCOSCH₃ | CH(CH₃)₂ |
| 2327 | CH₂ | SCH₃ | OCOSCH₃ | CH(CH₃)₂ |
| 2328 | CH₂ | SO₂CH₃ | OCOSCH₃ | CH(CH₃)₂ |
| 2329 | CH₂ | SO₂CH₂CH₃ | OCOSCH₃ | CH(CH₃)₂ |
| 2330 | CH₂ | CH₃ | OCOSCH₃ | CH(CH₃)₂ |
| 2331 | CH₂ | CF₃ | OCOSCH₃ | CH(CH₃)₂ |
| 2332 | CH₂ | OCHF₂ | OCOSCH₃ | CH(CH₃)₂ |
| 2333 | O | F | OCOSCH₃ | CH(CH₃)₂ |
| 2334 | O | Cl | OCOSCH₃ | CH(CH₃)₂ |
| 2335 | O | Br | OCOSCH₃ | CH(CH₃)₂ |
| 2336 | O | NO₂ | OCOSCH₃ | CH(CH₃)₂ |
| 2337 | O | SCH₃ | OCOSCH₃ | CH(CH₃)₂ |
| 2338 | O | SO₂CH₃ | OCOSCH₃ | CH(CH₃)₂ |
| 2339 | O | SO₂CH₂CH₃ | OCOSCH₃ | CH(CH₃)₂ |
| 2340 | O | CH₃ | OCOSCH₃ | CH(CH₃)₂ |
| 2341 | O | CF₃ | OCOSCH₃ | CH(CH₃)₂ |
| 2342 | O | OCHF₂ | OCOSCH₃ | CH(CH₃)₂ |
| 2343 | S | F | OCOSCH₃ | CH(CH₃)₂ |
| 2344 | S | Cl | OCOSCH₃ | CH(CH₃)₂ |
| 2345 | S | Br | OCOSCH₃ | CH(CH₃)₂ |
| 2346 | S | NO₂ | OCOSCH₃ | CH(CH₃)₂ |

TABLE 1-continued

| n | X | R⁴ | R¹⁰ | R¹¹ |
|---|---|---|---|---|
| 2347 | S | SCH₃ | OCOSCH₃ | CH(CH₃)₂ |
| 2348 | S | SO₂CH₃ | OCOSCH₃ | CH(CH₃)₂ |
| 2349 | S | SO₂CH₂CH₃ | OCOSCH₃ | CH(CH₃)₂ |
| 2350 | S | CH₃ | OCOSCH₃ | CH(CH₃)₂ |
| 2351 | S | CF₃ | OCOSCH₃ | CH(CH₃)₂ |
| 2352 | S | OCHF₂ | OCOSCH₃ | CH(CH₃)₂ |
| 2353 | SO₂ | F | OCOSCH₃ | CH(CH₃)₂ |
| 2354 | SO₂ | Cl | OCOSCH₃ | CH(CH₃)₂ |
| 2355 | SO₂ | Br | OCOSCH₃ | CH(CH₃)₂ |
| 2356 | SO₂ | NO₂ | OCOSCH₃ | CH(CH₃)₂ |
| 2357 | SO₂ | SCH₃ | OCOSCH₃ | CH(CH₃)₂ |
| 2358 | SO₂ | SO₂CH₃ | OCOSCH₃ | CH(CH₃)₂ |
| 2359 | SO₂ | SO₂CH₂CH₃ | OCOSCH₃ | CH(CH₃)₂ |
| 2360 | SO₂ | CH₃ | OCOSCH₃ | CH(CH₃)₂ |
| 2361 | SO₂ | CF₃ | OCOSCH₃ | CH(CH₃)₂ |
| 2362 | SO₂ | OCHF₂ | OCOSCH₃ | CH(CH₃)₂ |
| 2363 | bond | F | OCOSCH₃ | C(CH₃)₃ |
| 2364 | bond | Cl | OCOSCH₃ | C(CH₃)₃ |
| 2365 | bond | Br | OCOSCH₃ | C(CH₃)₃ |
| 2366 | bond | NO₂ | OCOSCH₃ | C(CH₃)₃ |
| 2367 | bond | SCH₃ | OCOSCH₃ | C(CH₃)₃ |
| 2368 | bond | SO₂CH₃ | OCOSCH₃ | C(CH₃)₃ |
| 2369 | bond | SO₂CH₂CH₃ | OCOSCH₃ | C(CH₃)₃ |
| 2370 | bond | CH₃ | OCOSCH₃ | C(CH₃)₃ |
| 2371 | bond | CF₃ | OCOSCH₃ | C(CH₃)₃ |
| 2372 | bond | OCHF₂ | OCOSCH₃ | C(CH₃)₃ |
| 2373 | CH₂ | F | OCOSCH₃ | C(CH₃)₃ |
| 2374 | CH₂ | Cl | OCOSCH₃ | C(CH₃)₃ |
| 2375 | CH₂ | Br | OCOSCH₃ | C(CH₃)₃ |
| 2376 | CH₂ | NO₂ | OCOSCH₃ | C(CH₃)₃ |
| 2377 | CH₂ | SCH₃ | OCOSCH₃ | C(CH₃)₃ |
| 2378 | CH₂ | SO₂CH₃ | OCOSCH₃ | C(CH₃)₃ |
| 2379 | CH₂ | SO₂CH₂CH₃ | OCOSCH₃ | C(CH₃)₃ |
| 2380 | CH₂ | CH₃ | OCOSCH₃ | C(CH₃)₃ |
| 2381 | CH₂ | CF₃ | OCOSCH₃ | C(CH₃)₃ |
| 2382 | CH₂ | OCHF₂ | OCOSCH₃ | C(CH₃)₃ |
| 2383 | O | F | OCOSCH₃ | C(CH₃)₃ |
| 2384 | O | Cl | OCOSCH₃ | C(CH₃)₃ |
| 2385 | O | Br | OCOSCH₃ | C(CH₃)₃ |
| 2386 | O | NO₂ | OCOSCH₃ | C(CH₃)₃ |
| 2387 | O | SCH₃ | OCOSCH₃ | C(CH₃)₃ |
| 2388 | O | SO₂CH₃ | OCOSCH₃ | C(CH₃)₃ |
| 2389 | O | SO₂CH₂CH₃ | OCOSCH₃ | C(CH₃)₃ |
| 2390 | O | CH₃ | OCOSCH₃ | C(CH₃)₃ |
| 2391 | O | CF₃ | OCOSCH₃ | C(CH₃)₃ |
| 2392 | O | OCHF₂ | OCOSCH₃ | C(CH₃)₃ |
| 2393 | S | F | OCOSCH₃ | C(CH₃)₃ |
| 2394 | S | Cl | OCOSCH₃ | C(CH₃)₃ |
| 2395 | S | Br | OCOSCH₃ | C(CH₃)₃ |
| 2396 | S | NO₂ | OCOSCH₃ | C(CH₃)₃ |
| 2397 | S | SCH₃ | OCOSCH₃ | C(CH₃)₃ |
| 2398 | S | SO₂CH₃ | OCOSCH₃ | C(CH₃)₃ |
| 2399 | S | SO₂CH₂CH₃ | OCOSCH₃ | C(CH₃)₃ |
| 2400 | S | CH₃ | OCOSCH₃ | C(CH₃)₃ |
| 2401 | S | CF₃ | OCOSCH₃ | C(CH₃)₃ |
| 2402 | S | OCHF₂ | OCOSCH₃ | C(CH₃)₃ |
| 2403 | SO₂ | F | OCOSCH₃ | C(CH₃)₃ |
| 2404 | SO₂ | Cl | OCOSCH₃ | C(CH₃)₃ |
| 2405 | SO₂ | Br | OCOSCH₃ | C(CH₃)₃ |
| 2406 | SO₂ | NO₂ | OCOSCH₃ | C(CH₃)₃ |
| 2407 | SO₂ | SCH₃ | OCOSCH₃ | C(CH₃)₃ |
| 2408 | SO₂ | SO₂CH₃ | OCOSCH₃ | C(CH₃)₃ |
| 2409 | SO₂ | SO₂CH₂CH₃ | OCOSCH₃ | C(CH₃)₃ |
| 2410 | SO₂ | CH₃ | OCOSCH₃ | C(CH₃)₃ |
| 2411 | SO₂ | CF₃ | OCOSCH₃ | C(CH₃)₃ |
| 2412 | SO₂ | OCHF₂ | OCOSCH₃ | C(CH₃)₃ |
| 2413 | bond | F | OCH₃ | CH(CH₃)₂ |
| 2414 | bond | Cl | OCH₃ | CH(CH₃)₂ |
| 2415 | bond | Br | OCH₃ | CH(CH₃)₂ |
| 2416 | bond | NO₂ | OCH₃ | CH(CH₃)₂ |
| 2417 | bond | SCH₃ | OCH₃ | CH(CH₃)₂ |
| 2418 | bond | SO₂CH₃ | OCH₃ | CH(CH₃)₂ |
| 2419 | bond | SO₂CH₂CH₃ | OCH₃ | CH(CH₃)₂ |
| 2420 | bond | CH₃ | OCH₃ | CH(CH₃)₂ |
| 2421 | bond | CF₃ | OCH₃ | CH(CH₃)₂ |
| 2422 | bond | OCHF₂ | OCH₃ | CH(CH₃)₂ |
| 2423 | CH₂ | F | OCH₃ | CH(CH₃)₂ |
| 2424 | CH₂ | Cl | OCH₃ | CH(CH₃)₂ |
| 2425 | CH₂ | Br | OCH₃ | CH(CH₃)₂ |
| 2426 | CH₂ | NO₂ | OCH₃ | CH(CH₃)₂ |
| 2427 | CH₂ | SCH₃ | OCH₃ | CH(CH₃)₂ |
| 2428 | CH₂ | SO₂CH₃ | OCH₃ | CH(CH₃)₂ |
| 2429 | CH₂ | SO₂CH₂CH₃ | OCH₃ | CH(CH₃)₂ |
| 2430 | CH₂ | CH₃ | OCH₃ | CH(CH₃)₂ |
| 2431 | CH₂ | CF₃ | OCH₃ | CH(CH₃)₂ |
| 2432 | CH₂ | OCHF₂ | OCH₃ | CH(CH₃)₂ |
| 2433 | O | F | OCH₃ | CH(CH₃)₂ |
| 2434 | O | Cl | OCH₃ | CH(CH₃)₂ |
| 2435 | O | Br | OCH₃ | CH(CH₃)₂ |
| 2436 | O | NO₂ | OCH₃ | CH(CH₃)₂ |
| 2437 | O | SCH₃ | OCH₃ | CH(CH₃)₂ |
| 2438 | O | SO₂CH₃ | OCH₃ | CH(CH₃)₂ |
| 2439 | O | SO₂CH₂CH₃ | OCH₃ | CH(CH₃)₂ |
| 2440 | O | CH₃ | OCH₃ | CH(CH₃)₂ |
| 2441 | O | CF₃ | OCH₃ | CH(CH₃)₂ |
| 2442 | O | OCHF₂ | OCH₃ | CH(CH₃)₂ |
| 2443 | S | F | OCH₃ | CH(CH₃)₂ |
| 2444 | S | Cl | OCH₃ | CH(CH₃)₂ |
| 2445 | S | Br | OCH₃ | CH(CH₃)₂ |
| 2446 | S | NO₂ | OCH₃ | CH(CH₃)₂ |
| 2447 | S | SCH₃ | OCH₃ | CH(CH₃)₂ |
| 2448 | S | SO₂CH₃ | OCH₃ | CH(CH₃)₂ |
| 2449 | S | SO₂CH₂CH₃ | OCH₃ | CH(CH₃)₂ |
| 2450 | S | CH₃ | OCH₃ | CH(CH₃)₂ |
| 2451 | S | CF₃ | OCH₃ | CH(CH₃)₂ |
| 2452 | S | OCHF₂ | OCH₃ | CH(CH₃)₂ |
| 2453 | SO₂ | F | OCH₃ | CH(CH₃)₂ |
| 2454 | SO₂ | Cl | OCH₃ | CH(CH₃)₂ |
| 2455 | SO₂ | Br | OCH₃ | CH(CH₃)₂ |
| 2456 | SO₂ | NO₂ | OCH₃ | CH(CH₃)₂ |
| 2457 | SO₂ | SCH₃ | OCH₃ | CH(CH₃)₂ |
| 2458 | SO₂ | SO₂CH₃ | OCH₃ | CH(CH₃)₂ |
| 2459 | SO₂ | SO₂CH₂CH₃ | OCH₃ | CH(CH₃)₂ |
| 2460 | SO₂ | CH₃ | OCH₃ | CH(CH₃)₂ |
| 2461 | SO₂ | CF₃ | OCH₃ | CH(CH₃)₂ |
| 2462 | SO₂ | OCHF₂ | OCH₃ | CH(CH₃)₂ |
| 2463 | bond | F | OCH₃ | C(CH₃)₃ |
| 2464 | bond | Cl | OCH₃ | C(CH₃)₃ |
| 2465 | bond | Br | OCH₃ | C(CH₃)₃ |
| 2466 | bond | NO₂ | OCH₃ | C(CH₃)₃ |
| 2467 | bond | SCH₃ | OCH₃ | C(CH₃)₃ |
| 2468 | bond | SO₂CH₃ | OCH₃ | C(CH₃)₃ |
| 2469 | bond | SO₂CH₂CH₃ | OCH₃ | C(CH₃)₃ |
| 2470 | bond | CH₃ | OCH₃ | C(CH₃)₃ |
| 2471 | bond | CF₃ | OCH₃ | C(CH₃)₃ |
| 2472 | bond | OCHF₂ | OCH₃ | C(CH₃)₃ |
| 2473 | CH₂ | F | OCH₃ | C(CH₃)₃ |
| 2474 | CH₂ | Cl | OCH₃ | C(CH₃)₃ |
| 2475 | CH₂ | Br | OCH₃ | C(CH₃)₃ |
| 2476 | CH₂ | NO₂ | OCH₃ | C(CH₃)₃ |
| 2477 | CH₂ | SCH₃ | OCH₃ | C(CH₃)₃ |
| 2478 | CH₂ | SO₂CH₃ | OCH₃ | C(CH₃)₃ |
| 2479 | CH₂ | SO₂CH₂CH₃ | OCH₃ | C(CH₃)₃ |
| 2480 | CH₂ | CH₃ | OCH₃ | C(CH₃)₃ |
| 2481 | CH₂ | CF₃ | OCH₃ | C(CH₃)₃ |
| 2482 | CH₂ | OCHF₂ | OCH₃ | C(CH₃)₃ |
| 2483 | O | F | OCH₃ | C(CH₃)₃ |
| 2484 | O | Cl | OCH₃ | C(CH₃)₃ |
| 2485 | O | Br | OCH₃ | C(CH₃)₃ |
| 2486 | O | NO₂ | OCH₃ | C(CH₃)₃ |
| 2487 | O | SCH₃ | OCH₃ | C(CH₃)₃ |
| 2488 | O | SO₂CH₃ | OCH₃ | C(CH₃)₃ |
| 2489 | O | SO₂CH₂CH₃ | OCH₃ | C(CH₃)₃ |
| 2490 | O | CH₃ | OCH₃ | C(CH₃)₃ |
| 2491 | O | CF₃ | OCH₃ | C(CH₃)₃ |
| 2492 | O | OCHF₂ | OCH₃ | C(CH₃)₃ |
| 2493 | S | F | OCH₃ | C(CH₃)₃ |
| 2494 | S | Cl | OCH₃ | C(CH₃)₃ |
| 2495 | S | Br | OCH₃ | C(CH₃)₃ |
| 2496 | S | NO₂ | OCH₃ | C(CH₃)₃ |
| 2497 | S | SCH₃ | OCH₃ | C(CH₃)₃ |
| 2498 | S | SO₂CH₃ | OCH₃ | C(CH₃)₃ |
| 2499 | S | SO₂CH₂CH₃ | OCH₃ | C(CH₃)₃ |
| 2500 | S | CH₃ | OCH₃ | C(CH₃)₃ |

TABLE 1-continued

| n | X | $R^4$ | $R^{10}$ | $R^{11}$ |
|---|---|---|---|---|
| 2501 | S | $CF_3$ | $OCH_3$ | $C(CH_3)_3$ |
| 2502 | S | $OCHF_2$ | $OCH_3$ | $C(CH_3)_3$ |
| 2503 | $SO_2$ | F | $OCH_3$ | $C(CH_3)_3$ |
| 2504 | $SO_2$ | Cl | $OCH_3$ | $C(CH_3)_3$ |
| 2505 | $SO_2$ | Br | $OCH_3$ | $C(CH_3)_3$ |
| 2506 | $SO_2$ | $NO_2$ | $OCH_3$ | $C(CH_3)_3$ |
| 2507 | $SO_2$ | $SCH_3$ | $OCH_3$ | $C(CH_3)_3$ |
| 2508 | $SO_2$ | $SO_2CH_3$ | $OCH_3$ | $C(CH_3)_3$ |
| 2509 | $SO_2$ | $SO_2CH_2CH_3$ | $OCH_3$ | $C(CH_3)_3$ |
| 2510 | $SO_2$ | $CH_3$ | $OCH_3$ | $C(CH_3)_3$ |
| 2511 | $SO_2$ | $CF_3$ | $OCH_3$ | $C(CH_3)_3$ |
| 2512 | $SO_2$ | $OCHF_2$ | $OCH_3$ | $C(CH_3)_3$ |
| 2513 | bond | F | $OCH(CH_3)_2$ | $CH(CH_3)_2$ |
| 2514 | bond | Cl | $OCH(CH_3)_2$ | $CH(CH_3)_2$ |
| 2515 | bond | Br | $OCH(CH_3)_2$ | $CH(CH_3)_2$ |
| 2516 | bond | $NO_2$ | $OCH(CH_3)_2$ | $CH(CH_3)_2$ |
| 2517 | bond | $SCH_3$ | $OCH(CH_3)_2$ | $CH(CH_3)_2$ |
| 2518 | bond | $SO_2CH_3$ | $OCH(CH_3)_2$ | $CH(CH_3)_2$ |
| 2519 | bond | $SO_2CH_2CH_3$ | $OCH(CH_3)_2$ | $CH(CH_3)_2$ |
| 2520 | bond | $CH_3$ | $OCH(CH_3)_2$ | $CH(CH_3)_2$ |
| 2521 | bond | $CF_3$ | $OCH(CH_3)_2$ | $CH(CH_3)_2$ |
| 2522 | bond | $OCHF_2$ | $OCH(CH_3)_2$ | $CH(CH_3)_2$ |
| 2523 | $CH_2$ | F | $OCH(CH_3)_2$ | $CH(CH_3)_2$ |
| 2524 | $CH_2$ | Cl | $OCH(CH_3)_2$ | $CH(CH_3)_2$ |
| 2525 | $CH_2$ | Br | $OCH(CH_3)_2$ | $CH(CH_3)_2$ |
| 2526 | $CH_2$ | $NO_2$ | $OCH(CH_3)_2$ | $CH(CH_3)_2$ |
| 2527 | $CH_2$ | $SCH_3$ | $OCH(CH_3)_2$ | $CH(CH_3)_2$ |
| 2528 | $CH_2$ | $SO_2CH_3$ | $OCH(CH_3)_2$ | $CH(CH_3)_2$ |
| 2529 | $CH_2$ | $SO_2CH_2CH_3$ | $OCH(CH_3)_2$ | $CH(CH_3)_2$ |
| 2530 | $CH_2$ | $CH_3$ | $OCH(CH_3)_2$ | $CH(CH_3)_2$ |
| 2531 | $CH_2$ | $CF_3$ | $OCH(CH_3)_2$ | $CH(CH_3)_2$ |
| 2532 | $CH_2$ | $OCHF_2$ | $OCH(CH_3)_2$ | $CH(CH_3)_2$ |
| 2533 | O | F | $OCH(CH_3)_2$ | $CH(CH_3)_2$ |
| 2534 | O | Cl | $OCH(CH_3)_2$ | $CH(CH_3)_2$ |
| 2535 | O | Br | $OCH(CH_3)_2$ | $CH(CH_3)_2$ |
| 2536 | O | $NO_2$ | $OCH(CH_3)_2$ | $CH(CH_3)_2$ |
| 2537 | O | $SCH_3$ | $OCH(CH_3)_2$ | $CH(CH_3)_2$ |
| 2538 | O | $SO_2CH_3$ | $OCH(CH_3)_2$ | $CH(CH_3)_2$ |
| 2539 | O | $SO_2CH_2CH_3$ | $OCH(CH_3)_2$ | $CH(CH_3)_2$ |
| 2540 | O | $CH_3$ | $OCH(CH_3)_2$ | $CH(CH_3)_2$ |
| 2541 | O | $CF_3$ | $OCH(CH_3)_2$ | $CH(CH_3)_2$ |
| 2542 | O | $OCHF_2$ | $OCH(CH_3)_2$ | $CH(CH_3)_2$ |
| 2543 | S | F | $OCH(CH_3)_2$ | $CH(CH_3)_2$ |
| 2544 | S | Cl | $OCH(CH_3)_2$ | $CH(CH_3)_2$ |
| 2545 | S | Br | $OCH(CH_3)_2$ | $CH(CH_3)_2$ |
| 2546 | S | $NO_2$ | $OCH(CH_3)_2$ | $CH(CH_3)_2$ |
| 2547 | S | $SCH_3$ | $OCH(CH_3)_2$ | $CH(CH_3)_2$ |
| 2548 | S | $SO_2CH_3$ | $OCH(CH_3)_2$ | $CH(CH_3)_2$ |
| 2549 | S | $SO_2CH_2CH_3$ | $OCH(CH_3)_2$ | $CH(CH_3)_2$ |
| 2550 | S | $CH_3$ | $OCH(CH_3)_2$ | $CH(CH_3)_2$ |
| 2551 | S | $CF_3$ | $OCH(CH_3)_2$ | $CH(CH_3)_2$ |
| 2552 | S | $OCHF_2$ | $OCH(CH_3)_2$ | $CH(CH_3)_2$ |
| 2553 | $SO_2$ | F | $OCH(CH_3)_2$ | $CH(CH_3)_2$ |
| 2554 | $SO_2$ | Cl | $OCH(CH_3)_2$ | $CH(CH_3)_2$ |
| 2555 | $SO_2$ | Br | $OCH(CH_3)_2$ | $CH(CH_3)_2$ |
| 2556 | $SO_2$ | $NO_2$ | $OCH(CH_3)_2$ | $CH(CH_3)_2$ |
| 2557 | $SO_2$ | $SCH_3$ | $OCH(CH_3)_2$ | $CH(CH_3)_2$ |
| 2558 | $SO_2$ | $SO_2CH_3$ | $OCH(CH_3)_2$ | $CH(CH_3)_2$ |
| 2559 | $SO_2$ | $SO_2CH_2CH_3$ | $OCH(CH_3)_2$ | $CH(CH_3)_2$ |
| 2560 | $SO_2$ | $CH_3$ | $OCH(CH_3)_2$ | $CH(CH_3)_2$ |
| 2561 | $SO_2$ | $CF_3$ | $OCH(CH_3)_2$ | $CH(CH_3)_2$ |
| 2562 | $SO_2$ | $OCHF_2$ | $OCH(CH_3)_2$ | $CH(CH_3)_2$ |
| 2563 | bond | F | $OCH(CH_3)_2$ | $C(CH_3)_3$ |
| 2564 | bond | Cl | $OCH(CH_3)_2$ | $C(CH_3)_3$ |
| 2565 | bond | Br | $OCH(CH_3)_2$ | $C(CH_3)_3$ |
| 2566 | bond | $NO_2$ | $OCH(CH_3)_2$ | $C(CH_3)_3$ |
| 2567 | bond | $SCH_3$ | $OCH(CH_3)_2$ | $C(CH_3)_3$ |
| 2568 | bond | $SO_2CH_3$ | $OCH(CH_3)_2$ | $C(CH_3)_3$ |
| 2569 | bond | $SO_2CH_2CH_3$ | $OCH(CH_3)_2$ | $C(CH_3)_3$ |
| 2570 | bond | $CH_3$ | $OCH(CH_3)_2$ | $C(CH_3)_3$ |
| 2571 | bond | $CF_3$ | $OCH(CH_3)_2$ | $C(CH_3)_3$ |
| 2572 | bond | $OCHF_2$ | $OCH(CH_3)_2$ | $C(CH_3)_3$ |
| 2573 | $CH_2$ | F | $OCH(CH_3)_2$ | $C(CH_3)_3$ |
| 2574 | $CH_2$ | Cl | $OCH(CH_3)_2$ | $C(CH_3)_3$ |
| 2575 | $CH_2$ | Br | $OCH(CH_3)_2$ | $C(CH_3)_3$ |
| 2576 | $CH_2$ | $NO_2$ | $OCH(CH_3)_2$ | $C(CH_3)_3$ |
| 2577 | $CH_2$ | $SCH_3$ | $OCH(CH_3)_2$ | $C(CH_3)_3$ |
| 2578 | $CH_2$ | $SO_2CH_3$ | $OCH(CH_3)_2$ | $C(CH_3)_3$ |
| 2579 | $CH_2$ | $SO_2CH_2CH_3$ | $OCH(CH_3)_2$ | $C(CH_3)_3$ |
| 2580 | $CH_2$ | $CH_3$ | $OCH(CH_3)_2$ | $C(CH_3)_3$ |
| 2581 | $CH_2$ | $CF_3$ | $OCH(CH_3)_2$ | $C(CH_3)_3$ |
| 2582 | $CH_2$ | $OCHF_2$ | $OCH(CH_3)_2$ | $C(CH_3)_3$ |
| 2583 | O | F | $OCH(CH_3)_2$ | $C(CH_3)_3$ |
| 2584 | O | Cl | $OCH(CH_3)_2$ | $C(CH_3)_3$ |
| 2585 | O | Br | $OCH(CH_3)_2$ | $C(CH_3)_3$ |
| 2586 | O | $NO_2$ | $OCH(CH_3)_2$ | $C(CH_3)_3$ |
| 2587 | O | $SCH_3$ | $OCH(CH_3)_2$ | $C(CH_3)_3$ |
| 2588 | O | $SO_2CH_3$ | $OCH(CH_3)_2$ | $C(CH_3)_3$ |
| 2589 | O | $SO_2CH_2CH_3$ | $OCH(CH_3)_2$ | $C(CH_3)_3$ |
| 2590 | O | $CH_3$ | $OCH(CH_3)_2$ | $C(CH_3)_3$ |
| 2591 | O | $CF_3$ | $OCH(CH_3)_2$ | $C(CH_3)_3$ |
| 2592 | O | $OCHF_2$ | $OCH(CH_3)_2$ | $C(CH_3)_3$ |
| 2593 | S | F | $OCH(CH_3)_2$ | $C(CH_3)_3$ |
| 2594 | S | Cl | $OCH(CH_3)_2$ | $C(CH_3)_3$ |
| 2595 | S | Br | $OCH(CH_3)_2$ | $C(CH_3)_3$ |
| 2596 | S | $NO_2$ | $OCH(CH_3)_2$ | $C(CH_3)_3$ |
| 2597 | S | $SCH_3$ | $OCH(CH_3)_2$ | $C(CH_3)_3$ |
| 2598 | S | $SO_2CH_3$ | $OCH(CH_3)_2$ | $C(CH_3)_3$ |
| 2599 | S | $SO_2CH_2CH_3$ | $OCH(CH_3)_2$ | $C(CH_3)_3$ |
| 2600 | S | $CH_3$ | $OCH(CH_3)_2$ | $C(CH_3)_3$ |
| 2601 | S | $CF_3$ | $OCH(CH_3)_2$ | $C(CH_3)_3$ |
| 2602 | S | $OCHF_2$ | $OCH(CH_3)_2$ | $C(CH_3)_3$ |
| 2603 | $SO_2$ | F | $OCH(CH_3)_2$ | $C(CH_3)_3$ |
| 2604 | $SO_2$ | Cl | $OCH(CH_3)_2$ | $C(CH_3)_3$ |
| 2605 | $SO_2$ | Br | $OCH(CH_3)_2$ | $C(CH_3)_3$ |
| 2606 | $SO_2$ | $NO_2$ | $OCH(CH_3)_2$ | $C(CH_3)_3$ |
| 2607 | $SO_2$ | $SCH_3$ | $OCH(CH_3)_2$ | $C(CH_3)_3$ |
| 2608 | $SO_2$ | $SO_2CH_3$ | $OCH(CH_3)_2$ | $C(CH_3)_3$ |
| 2609 | $SO_2$ | $SO_2CH_2CH_3$ | $OCH(CH_3)_2$ | $C(CH_3)_3$ |
| 2610 | $SO_2$ | $CH_3$ | $OCH(CH_3)_2$ | $C(CH_3)_3$ |
| 2611 | $SO_2$ | $CF_3$ | $OCH(CH_3)_2$ | $C(CH_3)_3$ |
| 2612 | $SO_2$ | $OCHF_2$ | $OCH(CH_3)_2$ | $C(CH_3)_3$ |
| 2613 | bond | F | $OCH_2C_6H_5$ | $CH(CH_3)_2$ |
| 2614 | bond | Cl | $OCH_2C_6H_5$ | $CH(CH_3)_2$ |
| 2615 | bond | Br | $OCH_2C_6H_5$ | $CH(CH_3)_2$ |
| 2616 | bond | $NO_2$ | $OCH_2C_6H_5$ | $CH(CH_3)_2$ |
| 2617 | bond | $SCH_3$ | $OCH_2C_6H_5$ | $CH(CH_3)_2$ |
| 2618 | bond | $SO_2CH_3$ | $OCH_2C_6H_5$ | $CH(CH_3)_2$ |
| 2619 | bond | $SO_2CH_2CH_3$ | $OCH_2C_6H_5$ | $CH(CH_3)_2$ |
| 2620 | bond | $CH_3$ | $OCH_2C_6H_5$ | $CH(CH_3)_2$ |
| 2621 | bond | $CF_3$ | $OCH_2C_6H_5$ | $CH(CH_3)_2$ |
| 2622 | bond | $OCHF_2$ | $OCH_2C_6H_5$ | $CH(CH_3)_2$ |
| 2623 | $CH_2$ | F | $OCH_2C_6H_5$ | $CH(CH_3)_2$ |
| 2624 | $CH_2$ | Cl | $OCH_2C_6H_5$ | $CH(CH_3)_2$ |
| 2625 | $CH_2$ | Br | $OCH_2C_6H_5$ | $CH(CH_3)_2$ |
| 2626 | $CH_2$ | $NO_2$ | $OCH_2C_6H_5$ | $CH(CH_3)_2$ |
| 2627 | $CH_2$ | $SCH_3$ | $OCH_2C_6H_5$ | $CH(CH_3)_2$ |
| 2628 | $CH_2$ | $SO_2CH_3$ | $OCH_2C_6H_5$ | $CH(CH_3)_2$ |
| 2629 | $CH_2$ | $SO_2CH_2CH_3$ | $OCH_2C_6H_5$ | $CH(CH_3)_2$ |
| 2630 | $CH_2$ | $CH_3$ | $OCH_2C_6H_5$ | $CH(CH_3)_2$ |
| 2631 | $CH_2$ | $CF_3$ | $OCH_2C_6H_5$ | $CH(CH_3)_2$ |
| 2632 | $CH_2$ | $OCHF_2$ | $OCH_2C_6H_5$ | $CH(CH_3)_2$ |
| 2633 | O | F | $OCH_2C_6H_5$ | $CH(CH_3)_2$ |
| 2634 | O | Cl | $OCH_2C_6H_5$ | $CH(CH_3)_2$ |
| 2635 | O | Br | $OCH_2C_6H_5$ | $CH(CH_3)_2$ |
| 2636 | O | $NO_2$ | $OCH_2C_6H_5$ | $CH(CH_3)_2$ |
| 2637 | O | $SCH_3$ | $OCH_2C_6H_5$ | $CH(CH_3)_2$ |
| 2638 | O | $SO_2CH_3$ | $OCH_2C_6H_5$ | $CH(CH_3)_2$ |
| 2639 | O | $SO_2CH_2CH_3$ | $OCH_2C_6H_5$ | $CH(CH_3)_2$ |
| 2640 | O | $CH_3$ | $OCH_2C_6H_5$ | $CH(CH_3)_2$ |
| 2641 | O | $CF_3$ | $OCH_2C_6H_5$ | $CH(CH_3)_2$ |
| 2642 | O | $OCHF_2$ | $OCH_2C_6H_5$ | $CH(CH_3)_2$ |
| 2643 | S | F | $OCH_2C_6H_5$ | $CH(CH_3)_2$ |
| 2644 | S | Cl | $OCH_2C_6H_5$ | $CH(CH_3)_2$ |
| 2645 | S | Br | $OCH_2C_6H_5$ | $CH(CH_3)_2$ |
| 2646 | S | $NO_2$ | $OCH_2C_6H_5$ | $CH(CH_3)_2$ |
| 2647 | S | $SCH_3$ | $OCH_2C_6H_5$ | $CH(CH_3)_2$ |
| 2648 | S | $SO_2CH_3$ | $OCH_2C_6H_5$ | $CH(CH_3)_2$ |
| 2649 | S | $SO_2CH_2CH_3$ | $OCH_2C_6H_5$ | $CH(CH_3)_2$ |
| 2650 | S | $CH_3$ | $OCH_2C_6H_5$ | $CH(CH_3)_2$ |
| 2651 | S | $CF_3$ | $OCH_2C_6H_5$ | $CH(CH_3)_2$ |
| 2652 | S | $OCHF_2$ | $OCH_2C_6H_5$ | $CH(CH_3)_2$ |
| 2653 | $SO_2$ | F | $OCH_2C_6H_5$ | $CH(CH_3)_2$ |
| 2654 | $SO_2$ | Cl | $OCH_2C_6H_5$ | $CH(CH_3)_2$ |

TABLE 1-continued

| n | X | R⁴ | R¹⁰ | R¹¹ |
|---|---|---|---|---|
| 2655 | SO₂ | Br | OCH₂C₆H₅ | CH(CH₃)₂ |
| 2656 | SO₂ | NO₂ | OCH₂C₆H₅ | CH(CH₃)₂ |
| 2657 | SO₂ | SCH₃ | OCH₂C₆H₅ | CH(CH₃)₂ |
| 2658 | SO₂ | SO₂CH₃ | OCH₂C₆H₅ | CH(CH₃)₂ |
| 2659 | SO₂ | SO₂CH₂CH₃ | OCH₂C₆H₅ | CH(CH₃)₂ |
| 2660 | SO₂ | CH₃ | OCH₂C₆H₅ | CH(CH₃)₂ |
| 2661 | SO₂ | CF₃ | OCH₂C₆H₅ | CH(CH₃)₂ |
| 2662 | SO₂ | OCHF₂ | OCH₂C₆H₅ | CH(CH₃)₂ |
| 2663 | bond | F | OCH₂C₆H₅ | C(CH₃)₃ |
| 2664 | bond | Cl | OCH₂C₆H₅ | C(CH₃)₃ |
| 2665 | bond | Br | OCH₂C₆H₅ | C(CH₃)₃ |
| 2666 | bond | NO₂ | OCH₂C₆H₅ | C(CH₃)₃ |
| 2667 | bond | SCH₃ | OCH₂C₆H₅ | C(CH₃)₃ |
| 2668 | bond | SO₂CH₃ | OCH₂C₆H₅ | C(CH₃)₃ |
| 2669 | bond | SO₂CH₂CH₃ | OCH₂C₆H₅ | C(CH₃)₃ |
| 2670 | bond | CH₃ | OCH₂C₆H₅ | C(CH₃)₃ |
| 2671 | bond | CF₃ | OCH₂C₆H₅ | C(CH₃)₃ |
| 2672 | bond | OCHF₂ | OCH₂C₆H₅ | C(CH₃)₃ |
| 2673 | CH₂ | F | OCH₂C₆H₅ | C(CH₃)₃ |
| 2674 | CH₂ | Cl | OCH₂C₆H₅ | C(CH₃)₃ |
| 2675 | CH₂ | Br | OCH₂C₆H₅ | C(CH₃)₃ |
| 2676 | CH₂ | NO₂ | OCH₂C₆H₅ | C(CH₃)₃ |
| 2677 | CH₂ | SCH₃ | OCH₂C₆H₅ | C(CH₃)₃ |
| 2678 | CH₂ | SO₂CH₃ | OCH₂C₆H₅ | C(CH₃)₃ |
| 2679 | CH₂ | SO₂CH₂CH₃ | OCH₂C₆H₅ | C(CH₃)₃ |
| 2680 | CH₂ | CH₃ | OCH₂C₆H₅ | C(CH₃)₃ |
| 2681 | CH₂ | CF₃ | OCH₂C₆H₅ | C(CH₃)₃ |
| 2682 | CH₂ | OCHF₂ | OCH₂C₆H₅ | C(CH₃)₃ |
| 2683 | O | F | OCH₂C₆H₅ | C(CH₃)₃ |
| 2684 | O | Cl | OCH₂C₆H₅ | C(CH₃)₃ |
| 2685 | O | Br | OCH₂C₆H₅ | C(CH₃)₃ |
| 2686 | O | NO₂ | OCH₂C₆H₅ | C(CH₃)₃ |
| 2687 | O | SCH₃ | OCH₂C₆H₅ | C(CH₃)₃ |
| 2688 | O | SO₂CH₃ | OCH₂C₆H₅ | C(CH₃)₃ |
| 2689 | O | SO₂CH₂CH₃ | OCH₂C₆H₅ | C(CH₃)₃ |
| 2690 | O | CH₃ | OCH₂C₆H₅ | C(CH₃)₃ |
| 2691 | O | CF₃ | OCH₂C₆H₅ | C(CH₃)₃ |
| 2692 | O | OCHF₂ | OCH₂C₆H₅ | C(CH₃)₃ |
| 2693 | S | F | OCH₂C₆H₅ | C(CH₃)₃ |
| 2694 | S | Cl | OCH₂C₆H₅ | C(CH₃)₃ |
| 2695 | S | Br | OCH₂C₆H₅ | C(CH₃)₃ |
| 2696 | S | NO₂ | OCH₂C₆H₅ | C(CH₃)₃ |
| 2697 | S | SCH₃ | OCH₂C₆H₅ | C(CH₃)₃ |
| 2698 | S | SO₂CH₃ | OCH₂C₆H₅ | C(CH₃)₃ |
| 2699 | S | SO₂CH₂CH₃ | OCH₂C₆H₅ | C(CH₃)₃ |
| 2700 | S | CH₃ | OCH₂C₆H₅ | C(CH₃)₃ |
| 2701 | S | CF₃ | OCH₂C₆H₅ | C(CH₃)₃ |
| 2702 | S | OCHF₂ | OCH₂C₆H₅ | C(CH₃)₃ |
| 2703 | SO₂ | F | OCH₂C₆H₅ | C(CH₃)₃ |
| 2704 | SO₂ | Cl | OCH₂C₆H₅ | C(CH₃)₃ |
| 2705 | SO₂ | Br | OCH₂C₆H₅ | C(CH₃)₃ |
| 2706 | SO₂ | NO₂ | OCH₂C₆H₅ | C(CH₃)₃ |
| 2707 | SO₂ | SCH₃ | OCH₂C₆H₅ | C(CH₃)₃ |
| 2708 | SO₂ | SO₂CH₃ | OCH₂C₆H₅ | C(CH₃)₃ |
| 2709 | SO₂ | SO₂CH₂CH₃ | OCH₂C₆H₅ | C(CH₃)₃ |
| 2710 | SO₂ | CH₃ | OCH₂C₆H₅ | C(CH₃)₃ |
| 2711 | SO₂ | CF₃ | OCH₂C₆H₅ | C(CH₃)₃ |
| 2712 | SO₂ | OCHF₂ | OCH₂C₆H₅ | C(CH₃)₃ |
| 2713 | bond | F | OSO₂(4-CH₃—C₆H₄) | CH(CH₃)₂ |
| 2714 | bond | Cl | OSO₂(4-CH₃—C₆H₄) | CH(CH₃)₂ |
| 2715 | bond | Br | OSO₂(4-CH₃—C₆H₄) | CH(CH₃)₂ |
| 2716 | bond | NO₂ | OSO₂(4-CH₃—C₆H₄) | CH(CH₃)₂ |
| 2717 | bond | SCH₃ | OSO₂(4-CH₃—C₆H₄) | CH(CH₃)₂ |
| 2718 | bond | SO₂CH₃ | OSO₂(4-CH₃—C₆H₄) | CH(CH₃)₂ |
| 2719 | bond | SO₂CH₂CH₃ | OSO₂(4-CH₃—C₆H₄) | CH(CH₃)₂ |
| 2720 | bond | CH₃ | OSO₂(4-CH₃—C₆H₄) | CH(CH₃)₂ |
| 2721 | bond | CF₃ | OSO₂(4-CH₃—C₆H₄) | CH(CH₃)₂ |
| 2722 | bond | OCHF₂ | OSO₂(4-CH₃—C₆H₄) | CH(CH₃)₂ |
| 2723 | CH₂ | F | OSO₂(4-CH₃—C₆H₄) | CH(CH₃)₂ |
| 2724 | CH₂ | Cl | OSO₂(4-CH₃—C₆H₄) | CH(CH₃)₂ |
| 2725 | CH₂ | Br | OSO₂(4-CH₃—C₆H₄) | CH(CH₃)₂ |
| 2726 | CH₂ | NO₂ | OSO₂(4-CH₃—C₆H₄) | CH(CH₃)₂ |
| 2727 | CH₂ | SCH₃ | OSO₂(4-CH₃—C₆H₄) | CH(CH₃)₂ |
| 2728 | CH₂ | SO₂CH₃ | OSO₂(4-CH₃—C₆H₄) | CH(CH₃)₂ |
| 2729 | CH₂ | SO₂CH₂CH₃ | OSO₂(4-CH₃—C₆H₄) | CH(CH₃)₂ |
| 2730 | CH₂ | CH₃ | OSO₂(4-CH₃—C₆H₄) | CH(CH₃)₂ |
| 2731 | CH₂ | CF₃ | OSO₂(4-CH₃—C₆H₄) | CH(CH₃)₂ |
| 2732 | CH₂ | OCHF₂ | OSO₂(4-CH₃—C₆H₄) | CH(CH₃)₂ |
| 2733 | O | F | OSO₂(4-CH₃—C₆H₄) | CH(CH₃)₂ |
| 2734 | O | Cl | OSO₂(4-CH₃—C₆H₄) | CH(CH₃)₂ |
| 2735 | O | Br | OSO₂(4-CH₃—C₆H₄) | CH(CH₃)₂ |
| 2736 | O | NO₂ | OSO₂(4-CH₃—C₆H₄) | CH(CH₃)₂ |
| 2737 | O | SCH₃ | OSO₂(4-CH₃—C₆H₄) | CH(CH₃)₂ |
| 2738 | O | SO₂CH₃ | OSO₂(4-CH₃—C₆H₄) | CH(CH₃)₂ |
| 2739 | O | SO₂CH₂CH₃ | OSO₂(4-CH₃—C₆H₄) | CH(CH₃)₂ |
| 2740 | O | CH₃ | OSO₂(4-CH₃—C₆H₄) | CH(CH₃)₂ |
| 2741 | O | CF₃ | OSO₂(4-CH₃—C₆H₄) | CH(CH₃)₂ |
| 2742 | O | OCHF₂ | OSO₂(4-CH₃—C₆H₄) | CH(CH₃)₂ |
| 2743 | S | F | OSO₂(4-CH₃—C₆H₄) | CH(CH₃)₂ |
| 2744 | S | Cl | OSO₂(4-CH₃—C₆H₄) | CH(CH₃)₂ |
| 2745 | S | Br | OSO₂(4-CH₃—C₆H₄) | CH(CH₃)₂ |
| 2746 | S | NO₂ | OSO₂(4-CH₃—C₆H₄) | CH(CH₃)₂ |
| 2747 | S | SCH₃ | OSO₂(4-CH₃—C₆H₄) | CH(CH₃)₂ |
| 2748 | S | SO₂CH₃ | OSO₂(4-CH₃—C₆H₄) | CH(CH₃)₂ |
| 2749 | S | SO₂CH₂CH₃ | OSO₂(4-CH₃—C₆H₄) | CH(CH₃)₂ |
| 2750 | S | CH₃ | OSO₂(4-CH₃—C₆H₄) | CH(CH₃)₂ |
| 2751 | S | CF₃ | OSO₂(4-CH₃—C₆H₄) | CH(CH₃)₂ |
| 2752 | S | OCHF₂ | OSO₂(4-CH₃—C₆H₄) | CH(CH₃)₂ |
| 2753 | SO₂ | F | OSO₂(4-CH₃—C₆H₄) | CH(CH₃)₂ |
| 2754 | SO₂ | Cl | OSO₂(4-CH₃—C₆H₄) | CH(CH₃)₂ |
| 2755 | SO₂ | Br | OSO₂(4-CH₃—C₆H₄) | CH(CH₃)₂ |
| 2756 | SO₂ | NO₂ | OSO₂(4-CH₃—C₆H₄) | CH(CH₃)₂ |
| 2757 | SO₂ | SCH₃ | OSO₂(4-CH₃—C₆H₄) | CH(CH₃)₂ |
| 2758 | SO₂ | SO₂CH₃ | OSO₂(4-CH₃—C₆H₄) | CH(CH₃)₂ |
| 2759 | SO₂ | SO₂CH₂CH₃ | OSO₂(4-CH₃—C₆H₄) | CH(CH₃)₂ |
| 2760 | SO₂ | CH₃ | OSO₂(4-CH₃—C₆H₄) | CH(CH₃)₂ |
| 2761 | SO₂ | CF₃ | OSO₂(4-CH₃—C₆H₄) | CH(CH₃)₂ |
| 2762 | SO₂ | OCHF₂ | OSO₂(4-CH₃—C₆H₄) | CH(CH₃)₂ |
| 2763 | bond | F | OSO₂(4-CH₃—C₆H₄) | C(CH₃)₃ |
| 2764 | bond | Cl | OSO₂(4-CH₃—C₆H₄) | C(CH₃)₃ |
| 2765 | bond | Br | OSO₂(4-CH₃—C₆H₄) | C(CH₃)₃ |
| 2766 | bond | NO₂ | OSO₂(4-CH₃—C₆H₄) | C(CH₃)₃ |
| 2767 | bond | SCH₃ | OSO₂(4-CH₃—C₆H₄) | C(CH₃)₃ |
| 2768 | bond | SO₂CH₃ | OSO₂(4-CH₃—C₆H₄) | C(CH₃)₃ |
| 2769 | bond | SO₂CH₂CH₃ | OSO₂(4-CH₃—C₆H₄) | C(CH₃)₃ |
| 2770 | bond | CH₃ | OSO₂(4-CH₃—C₆H₄) | C(CH₃)₃ |
| 2771 | bond | CF₃ | OSO₂(4-CH₃—C₆H₄) | C(CH₃)₃ |
| 2772 | bond | OCHF₂ | OSO₂(4-CH₃—C₆H₄) | C(CH₃)₃ |
| 2773 | CH₂ | F | OSO₂(4-CH₃—C₆H₄) | C(CH₃)₃ |
| 2774 | CH₂ | Cl | OSO₂(4-CH₃—C₆H₄) | C(CH₃)₃ |
| 2775 | CH₂ | Br | OSO₂(4-CH₃—C₆H₄) | C(CH₃)₃ |
| 2776 | CH₂ | NO₂ | OSO₂(4-CH₃—C₆H₄) | C(CH₃)₃ |
| 2777 | CH₂ | SCH₃ | OSO₂(4-CH₃—C₆H₄) | C(CH₃)₃ |
| 2778 | CH₂ | SO₂CH₃ | OSO₂(4-CH₃—C₆H₄) | C(CH₃)₃ |
| 2779 | CH₂ | SO₂CH₂CH₃ | OSO₂(4-CH₃—C₆H₄) | C(CH₃)₃ |
| 2780 | CH₂ | CH₃ | OSO₂(4-CH₃—C₆H₄) | C(CH₃)₃ |
| 2781 | CH₂ | CF₃ | OSO₂(4-CH₃—C₆H₄) | C(CH₃)₃ |
| 2782 | CH₂ | OCHF₂ | OSO₂(4-CH₃—C₆H₄) | C(CH₃)₃ |
| 2783 | O | F | OSO₂(4-CH₃—C₆H₄) | C(CH₃)₃ |
| 2784 | O | Cl | OSO₂(4-CH₃—C₆H₄) | C(CH₃)₃ |
| 2785 | O | Br | OSO₂(4-CH₃—C₆H₄) | C(CH₃)₃ |
| 2786 | O | NO₂ | OSO₂(4-CH₃—C₆H₄) | C(CH₃)₃ |
| 2787 | O | SCH₃ | OSO₂(4-CH₃—C₆H₄) | C(CH₃)₃ |
| 2788 | O | SO₂CH₃ | OSO₂(4-CH₃—C₆H₄) | C(CH₃)₃ |
| 2789 | O | SO₂CH₂CH₃ | OSO₂(4-CH₃—C₆H₄) | C(CH₃)₃ |
| 2790 | O | CH₃ | OSO₂(4-CH₃—C₆H₄) | C(CH₃)₃ |
| 2791 | O | CF₃ | OSO₂(4-CH₃—C₆H₄) | C(CH₃)₃ |
| 2792 | O | OCHF₂ | OSO₂(4-CH₃—C₆H₄) | C(CH₃)₃ |
| 2793 | S | F | OSO₂(4-CH₃—C₆H₄) | C(CH₃)₃ |
| 2794 | S | Cl | OSO₂(4-CH₃—C₆H₄) | C(CH₃)₃ |
| 2795 | S | Br | OSO₂(4-CH₃—C₆H₄) | C(CH₃)₃ |
| 2796 | S | NO₂ | OSO₂(4-CH₃—C₆H₄) | C(CH₃)₃ |
| 2797 | S | SCH₃ | OSO₂(4-CH₃—C₆H₄) | C(CH₃)₃ |
| 2798 | S | SO₂CH₃ | OSO₂(4-CH₃—C₆H₄) | C(CH₃)₃ |
| 2799 | S | SO₂CH₂CH₃ | OSO₂(4-CH₃—C₆H₄) | C(CH₃)₃ |
| 2800 | S | CH₃ | OSO₂(4-CH₃—C₆H₄) | C(CH₃)₃ |
| 2801 | S | CF₃ | OSO₂(4-CH₃—C₆H₄) | C(CH₃)₃ |
| 2802 | S | OCHF₂ | OSO₂(4-CH₃—C₆H₄) | C(CH₃)₃ |
| 2803 | SO₂ | F | OSO₂(4-CH₃—C₆H₄) | C(CH₃)₃ |
| 2804 | SO₂ | Cl | OSO₂(4-CH₃—C₆H₄) | C(CH₃)₃ |
| 2805 | SO₂ | Br | OSO₂(4-CH₃—C₆H₄) | C(CH₃)₃ |
| 2806 | SO₂ | NO₂ | OSO₂(4-CH₃—C₆H₄) | C(CH₃)₃ |
| 2807 | SO₂ | SCH₃ | OSO₂(4-CH₃—C₆H₄) | C(CH₃)₃ |
| 2808 | SO₂ | SO₂CH₃ | OSO₂(4-CH₃—C₆H₄) | C(CH₃)₃ |

TABLE 1-continued

| n | X | R⁴ | R¹⁰ | R¹¹ |
|---|---|---|---|---|
| 2809 | SO₂ | SO₂CH₂CH₃ | OSO₂(4-CH₃—C₆H₄) | C(CH₃)₃ |
| 2810 | SO₂ | CH₃ | OSO₂(4-CH₃—C₆H₄) | C(CH₃)₃ |
| 2811 | SO₂ | CF₃ | OSO₂(4-CH₃—C₆H₄) | C(CH₃)₃ |
| 2812 | SO₂ | OCHF₂ | OSO₂(4-CH₃—C₆H₄) | C(CH₃)₃ |
| 2813 | bond | F | SCH₃ | CH(CH₃)₂ |
| 2814 | bond | Cl | SCH₃ | CH(CH₃)₂ |
| 2815 | bond | Br | SCH₃ | CH(CH₃)₂ |
| 2816 | bond | NO₂ | SCH₃ | CH(CH₃)₂ |
| 2817 | bond | SCH₃ | SCH₃ | CH(CH₃)₂ |
| 2818 | bond | SO₂CH₃ | SCH₃ | CH(CH₃)₂ |
| 2819 | bond | SO₂CH₂CH₃ | SCH₃ | CH(CH₃)₂ |
| 2820 | bond | CH₃ | SCH₃ | CH(CH₃)₂ |
| 2821 | bond | CF₃ | SCH₃ | CH(CH₃)₂ |
| 2822 | bond | OCHF₂ | SCH₃ | CH(CH₃)₂ |
| 2823 | CH₂ | F | SCH₃ | CH(CH₃)₂ |
| 2824 | CH₂ | Cl | SCH₃ | CH(CH₃)₂ |
| 2825 | CH₂ | Br | SCH₃ | CH(CH₃)₂ |
| 2826 | CH₂ | NO₂ | SCH₃ | CH(CH₃)₂ |
| 2827 | CH₂ | SCH₃ | SCH₃ | CH(CH₃)₂ |
| 2828 | CH₂ | SO₂CH₃ | SCH₃ | CH(CH₃)₂ |
| 2829 | CH₂ | SO₂CH₂CH₃ | SCH₃ | CH(CH₃)₂ |
| 2830 | CH₂ | CH₃ | SCH₃ | CH(CH₃)₂ |
| 2831 | CH₂ | CF₃ | SCH₃ | CH(CH₃)₂ |
| 2832 | CH₂ | OCHF₂ | SCH₃ | CH(CH₃)₂ |
| 2833 | O | F | SCH₃ | CH(CH₃)₂ |
| 2834 | O | Cl | SCH₃ | CH(CH₃)₂ |
| 2835 | O | Br | SCH₃ | CH(CH₃)₂ |
| 2836 | O | NO₂ | SCH₃ | CH(CH₃)₂ |
| 2837 | O | SCH₃ | SCH₃ | CH(CH₃)₂ |
| 2838 | O | SO₂CH₃ | SCH₃ | CH(CH₃)₂ |
| 2839 | O | SO₂CH₂CH₃ | SCH₃ | CH(CH₃)₂ |
| 2840 | O | CH₃ | SCH₃ | CH(CH₃)₂ |
| 2841 | O | CF₃ | SCH₃ | CH(CH₃)₂ |
| 2842 | O | OCHF₂ | SCH₃ | CH(CH₃)₂ |
| 2843 | S | F | SCH₃ | CH(CH₃)₂ |
| 2844 | S | Cl | SCH₃ | CH(CH₃)₂ |
| 2845 | S | Br | SCH₃ | CH(CH₃)₂ |
| 2846 | S | NO₂ | SCH₃ | CH(CH₃)₂ |
| 2847 | S | SCH₃ | SCH₃ | CH(CH₃)₂ |
| 2848 | S | SO₂CH₃ | SCH₃ | CH(CH₃)₂ |
| 2849 | S | SO₂CH₂CH₃ | SCH₃ | CH(CH₃)₂ |
| 2850 | S | CH₃ | SCH₃ | CH(CH₃)₂ |
| 2851 | S | CF₃ | SCH₃ | CH(CH₃)₂ |
| 2852 | S | OCHF₂ | SCH₃ | CH(CH₃)₂ |
| 2853 | SO₂ | F | SCH₃ | CH(CH₃)₂ |
| 2854 | SO₂ | Cl | SCH₃ | CH(CH₃)₂ |
| 2855 | SO₂ | Br | SCH₃ | CH(CH₃)₂ |
| 2856 | SO₂ | NO₂ | SCH₃ | CH(CH₃)₂ |
| 2857 | SO₂ | SCH₃ | SCH₃ | CH(CH₃)₂ |
| 2858 | SO₂ | SO₂CH₃ | SCH₃ | CH(CH₃)₂ |
| 2859 | SO₂ | SO₂CH₂CH₃ | SCH₃ | CH(CH₃)₂ |
| 2860 | SO₂ | CH₃ | SCH₃ | CH(CH₃)₂ |
| 2861 | SO₂ | CF₃ | SCH₃ | CH(CH₃)₂ |
| 2862 | SO₂ | OCHF₂ | SCH₃ | CH(CH₃)₂ |
| 2863 | bond | F | SCH₃ | C(CH₃)₃ |
| 2864 | bond | Cl | SCH₃ | C(CH₃)₃ |
| 2865 | bond | Br | SCH₃ | C(CH₃)₃ |
| 2866 | bond | NO₂ | SCH₃ | C(CH₃)₃ |
| 2867 | bond | SCH₃ | SCH₃ | C(CH₃)₃ |
| 2868 | bond | SO₂CH₃ | SCH₃ | C(CH₃)₃ |
| 2869 | bond | SO₂CH₂CH₃ | SCH₃ | C(CH₃)₃ |
| 2870 | bond | CH₃ | SCH₃ | C(CH₃)₃ |
| 2871 | bond | CF₃ | SCH₃ | C(CH₃)₃ |
| 2872 | bond | OCHF₂ | SCH₃ | C(CH₃)₃ |
| 2873 | CH₂ | F | SCH₃ | C(CH₃)₃ |
| 2874 | CH₂ | Cl | SCH₃ | C(CH₃)₃ |
| 2875 | CH₂ | Br | SCH₃ | C(CH₃)₃ |
| 2876 | CH₂ | NO₂ | SCH₃ | C(CH₃)₃ |
| 2877 | CH₂ | SCH₃ | SCH₃ | C(CH₃)₃ |
| 2878 | CH₂ | SO₂CH₃ | SCH₃ | C(CH₃)₃ |
| 2879 | CH₂ | SO₂CH₂CH₃ | SCH₃ | C(CH₃)₃ |
| 2880 | CH₂ | CH₃ | SCH₃ | C(CH₃)₃ |
| 2881 | CH₂ | CF₃ | SCH₃ | C(CH₃)₃ |
| 2882 | CH₂ | OCHF₂ | SCH₃ | C(CH₃)₃ |
| 2883 | O | F | SCH₃ | C(CH₃)₃ |
| 2884 | O | Cl | SCH₃ | C(CH₃)₃ |
| 2885 | O | Br | SCH₃ | C(CH₃)₃ |
| 2886 | O | NO₂ | SCH₃ | C(CH₃)₃ |
| 2887 | O | SCH₃ | SCH₃ | C(CH₃)₃ |
| 2888 | O | SO₂CH₃ | SCH₃ | C(CH₃)₃ |
| 2889 | O | SO₂CH₂CH₃ | SCH₃ | C(CH₃)₃ |
| 2890 | O | CH₃ | SCH₃ | C(CH₃)₃ |
| 2891 | O | CF₃ | SCH₃ | C(CH₃)₃ |
| 2892 | O | OCHF₂ | SCH₃ | C(CH₃)₃ |
| 2893 | S | F | SCH₃ | C(CH₃)₃ |
| 2894 | S | Cl | SCH₃ | C(CH₃)₃ |
| 2895 | S | Br | SCH₃ | C(CH₃)₃ |
| 2896 | S | NO₂ | SCH₃ | C(CH₃)₃ |
| 2897 | S | SCH₃ | SCH₃ | C(CH₃)₃ |
| 2898 | S | SO₂CH₃ | SCH₃ | C(CH₃)₃ |
| 2899 | S | SO₂CH₂CH₃ | SCH₃ | C(CH₃)₃ |
| 2900 | S | CH₃ | SCH₃ | C(CH₃)₃ |
| 2901 | S | CF₃ | SCH₃ | C(CH₃)₃ |
| 2902 | S | OCHF₂ | SCH₃ | C(CH₃)₃ |
| 2903 | SO₂ | F | SCH₃ | C(CH₃)₃ |
| 2904 | SO₂ | Cl | SCH₃ | C(CH₃)₃ |
| 2905 | SO₂ | Br | SCH₃ | C(CH₃)₃ |
| 2906 | SO₂ | NO₂ | SCH₃ | C(CH₃)₃ |
| 2907 | SO₂ | SCH₃ | SCH₃ | C(CH₃)₃ |
| 2908 | SO₂ | SO₂CH₃ | SCH₃ | C(CH₃)₃ |
| 2909 | SO₂ | SO₂CH₂CH₃ | SCH₃ | C(CH₃)₃ |
| 2910 | SO₂ | CH₃ | SCH₃ | C(CH₃)₃ |
| 2911 | SO₂ | CF₃ | SCH₃ | C(CH₃)₃ |
| 2912 | SO₂ | OCHF₂ | SCH₃ | C(CH₃)₃ |
| 2913 | bond | F | Cl | CH(CH₃)₂ |
| 2914 | bond | Cl | Cl | CH(CH₃)₂ |
| 2915 | bond | Br | Cl | CH(CH₃)₂ |
| 2916 | bond | NO₂ | Cl | CH(CH₃)₂ |
| 2917 | bond | SCH₃ | Cl | CH(CH₃)₂ |
| 2918 | bond | SO₂CH₃ | Cl | CH(CH₃)₂ |
| 2919 | bond | SO₂CH₂CH₃ | Cl | CH(CH₃)₂ |
| 2920 | bond | CH₃ | Cl | CH(CH₃)₂ |
| 2921 | bond | CF₃ | Cl | CH(CH₃)₂ |
| 2922 | bond | OCHF₂ | Cl | CH(CH₃)₂ |
| 2923 | CH₂ | F | Cl | CH(CH₃)₂ |
| 2924 | CH₂ | Cl | Cl | CH(CH₃)₂ |
| 2925 | CH₂ | Br | Cl | CH(CH₃)₂ |
| 2926 | CH₂ | NO₂ | Cl | CH(CH₃)₂ |
| 2927 | CH₂ | SCH₃ | Cl | CH(CH₃)₂ |
| 2928 | CH₂ | SO₂CH₃ | Cl | CH(CH₃)₂ |
| 2929 | CH₂ | SO₂CH₂CH₃ | Cl | CH(CH₃)₂ |
| 2930 | CH₂ | CH₃ | Cl | CH(CH₃)₂ |
| 2931 | CH₂ | CF₃ | Cl | CH(CH₃)₂ |
| 2932 | CH₂ | OCHF₂ | Cl | CH(CH₃)₂ |
| 2933 | O | F | Cl | CH(CH₃)₂ |
| 2934 | O | Cl | Cl | CH(CH₃)₂ |
| 2935 | O | Br | Cl | CH(CH₃)₂ |
| 2936 | O | NO₂ | Cl | CH(CH₃)₂ |
| 2937 | O | SCH₃ | Cl | CH(CH₃)₂ |
| 2938 | O | SO₂CH₃ | Cl | CH(CH₃)₂ |
| 2939 | O | SO₂CH₂CH₃ | Cl | CH(CH₃)₂ |
| 2940 | O | CH₃ | Cl | CH(CH₃)₂ |
| 2941 | O | CF₃ | Cl | CH(CH₃)₂ |
| 2942 | O | OCHF₂ | Cl | CH(CH₃)₂ |
| 2943 | S | F | Cl | CH(CH₃)₂ |
| 2944 | S | Cl | Cl | CH(CH₃)₂ |
| 2945 | S | Br | Cl | CH(CH₃)₂ |
| 2946 | S | NO₂ | Cl | CH(CH₃)₂ |
| 2947 | S | SCH₃ | Cl | CH(CH₃)₂ |
| 2948 | S | SO₂CH₃ | Cl | CH(CH₃)₂ |
| 2949 | S | SO₂CH₂CH₃ | Cl | CH(CH₃)₂ |
| 2950 | S | CH₃ | Cl | CH(CH₃)₂ |
| 2951 | S | CF₃ | Cl | CH(CH₃)₂ |
| 2952 | S | OCHF₂ | Cl | CH(CH₃)₂ |
| 2953 | SO₂ | F | Cl | CH(CH₃)₂ |
| 2954 | SO₂ | Cl | Cl | CH(CH₃)₂ |
| 2955 | SO₂ | Br | Cl | CH(CH₃)₂ |
| 2956 | SO₂ | NO₂ | Cl | CH(CH₃)₂ |
| 2957 | SO₂ | SCH₃ | Cl | CH(CH₃)₂ |
| 2958 | SO₂ | SO₂CH₃ | Cl | CH(CH₃)₂ |
| 2959 | SO₂ | SO₂CH₂CH₃ | Cl | CH(CH₃)₂ |
| 2960 | SO₂ | CH₃ | Cl | CH(CH₃)₂ |
| 2961 | SO₂ | CF₃ | Cl | CH(CH₃)₂ |
| 2962 | SO₂ | OCHF₂ | Cl | CH(CH₃)₂ |

TABLE 1-continued

| n | X | $R^4$ | $R^{10}$ | $R^{11}$ |
|---|---|---|---|---|
| 2963 | bond | F | Cl | $C(CH_3)_3$ |
| 2964 | bond | Cl | Cl | $C(CH_3)_3$ |
| 2965 | bond | Br | Cl | $C(CH_3)_3$ |
| 2966 | bond | $NO_2$ | Cl | $C(CH_3)_3$ |
| 2967 | bond | $SCH_3$ | Cl | $C(CH_3)_3$ |
| 2968 | bond | $SO_2CH_3$ | Cl | $C(CH_3)_3$ |
| 2969 | bond | $SO_2CH_2CH_3$ | Cl | $C(CH_3)_3$ |
| 2970 | bond | $CH_3$ | Cl | $C(CH_3)_3$ |
| 2971 | bond | $CF_3$ | Cl | $C(CH_3)_3$ |
| 2972 | bond | $OCHF_2$ | Cl | $C(CH_3)_3$ |
| 2973 | $CH_2$ | F | Cl | $C(CH_3)_3$ |
| 2974 | $CH_2$ | Cl | Cl | $C(CH_3)_3$ |
| 2975 | $CH_2$ | Br | Cl | $C(CH_3)_3$ |
| 2976 | $CH_2$ | $NO_2$ | Cl | $C(CH_3)_3$ |
| 2977 | $CH_2$ | $SCH_3$ | Cl | $C(CH_3)_3$ |
| 2978 | $CH_2$ | $SO_2CH_3$ | Cl | $C(CH_3)_3$ |
| 2979 | $CH_2$ | $SO_2CH_2CH_3$ | Cl | $C(CH_3)_3$ |
| 2980 | $CH_2$ | $CH_3$ | Cl | $C(CH_3)_3$ |
| 2981 | $CH_2$ | $CF_3$ | Cl | $C(CH_3)_3$ |
| 2982 | $CH_2$ | $OCHF_2$ | Cl | $C(CH_3)_3$ |
| 2983 | O | F | Cl | $C(CH_3)_3$ |
| 2984 | O | Cl | Cl | $C(CH_3)_3$ |
| 2985 | O | Br | Cl | $C(CH_3)_3$ |
| 2986 | O | $NO_2$ | Cl | $C(CH_3)_3$ |
| 2987 | O | $SCH_3$ | Cl | $C(CH_3)_3$ |
| 2988 | O | $SO_2CH_3$ | Cl | $C(CH_3)_3$ |
| 2989 | O | $SO_2CH_2CH_3$ | Cl | $C(CH_3)_3$ |
| 2990 | O | $CH_3$ | Cl | $C(CH_3)_3$ |
| 2991 | O | $CF_3$ | Cl | $C(CH_3)_3$ |
| 2992 | O | $OCHF_2$ | Cl | $C(CH_3)_3$ |
| 2993 | S | F | Cl | $C(CH_3)_3$ |
| 2994 | S | Cl | Cl | $C(CH_3)_3$ |
| 2995 | S | Br | Cl | $C(CH_3)_3$ |
| 2996 | S | $NO_2$ | Cl | $C(CH_3)_3$ |
| 2997 | S | $SCH_3$ | Cl | $C(CH_3)_3$ |
| 2998 | S | $SO_2CH_3$ | Cl | $C(CH_3)_3$ |
| 2999 | S | $SO_2CH_2CH_3$ | Cl | $C(CH_3)_3$ |
| 3000 | S | $CH_3$ | Cl | $C(CH_3)_3$ |
| 3001 | S | $CF_3$ | Cl | $C(CH_3)_3$ |
| 3002 | S | $OCHF_2$ | Cl | $C(CH_3)_3$ |
| 3003 | $SO_2$ | F | Cl | $C(CH_3)_3$ |
| 3004 | $SO_2$ | Cl | Cl | $C(CH_3)_3$ |
| 3005 | $SO_2$ | Br | Cl | $C(CH_3)_3$ |
| 3006 | $SO_2$ | $NO_2$ | Cl | $C(CH_3)_3$ |
| 3007 | $SO_2$ | $SCH_3$ | Cl | $C(CH_3)_3$ |
| 3008 | $SO_2$ | $SO_2CH_3$ | Cl | $C(CH_3)_3$ |
| 3009 | $SO_2$ | $SO_2CH_2CH_3$ | Cl | $C(CH_3)_3$ |
| 3010 | $SO_2$ | $CH_3$ | Cl | $C(CH_3)_3$ |
| 3011 | $SO_2$ | $CF_3$ | Cl | $C(CH_3)_3$ |
| 3012 | $SO_2$ | $OCHF_2$ | Cl | $C(CH_3)_3$ |

Very particular preference is also given to the compounds of the formula Ia2 (=Ia where $R^1$, $R^2$, $R^5$ and $R^{12}$=H, $R^3$=$CH_3$, l=1), in particular to the compounds Ia2.n, where the variables X, $R^4$, $R^{10}$ and $R^{11}$ are as defined in Table 1.

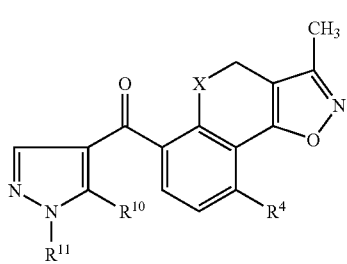

Very particular preference is also given to the compounds of the formula Ia3 (=Ia where $R^1$, $R^2$, $R^5$ and $R^{12}$=H, $R^3$=$CH_3$, l=1), in particular to the compounds Ia3.n, where the variables X, $R^4$, $R^{10}$ and $R^{11}$ are as defined in Table 1.

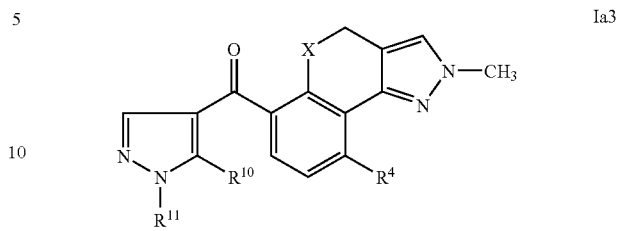

Very particular preference is also given to the compounds of the formula Ia4 (=Ia where $R^1$, $R^2$, $R^5$ and $R^{12}$=H, $R^3$=$CH_3$, l=2), in particular to the compounds Ia4.n, where the variables X, $R^4$, $R^{10}$ and $R^{11}$ are as defined in Table 1.

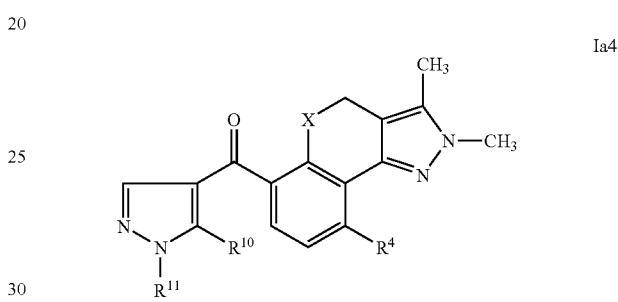

Very particular preference is also given to the compounds of the formula Ia5 (=Ia where $R^1$, $R^2$, $R^5$ and $R^{12}$=H, $R^3$=$CH_3$, l=1), in particular to the compounds Ia5.n, where the variables X, $R^4$, $R^{10}$ and $R^{11}$ are as defined in Table 1.

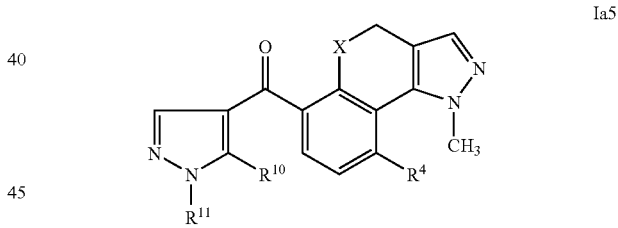

Very particular preference is also given to the compounds of the formula Ia6 (=Ia where $R^1$, $R^2$, $R^5$ and $R^{12}$=H, $R^3$=$CH_3$, l=2), in particular to the compounds Ia6.n, where the variables X, $R^4$, $R^{10}$ and $R^{11}$ are as defined in Table 1.

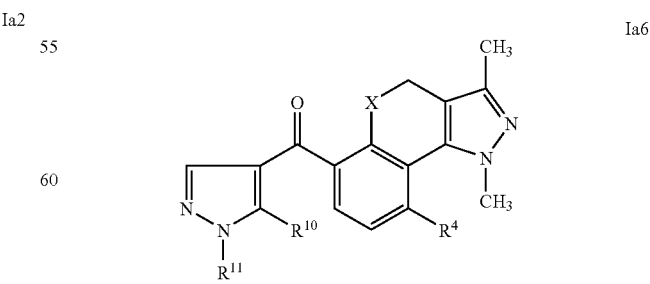

Very particular preference is also given to the compounds of the formula Ia7 (=Ia where $R^1$, $R^2$, $R^5$ and $R^{12}$=H, l=0), in particular to the compounds Ia7.n, where the variables X, $R^4$, $R^{10}$ and $R^{11}$ are as defined in Table 1.

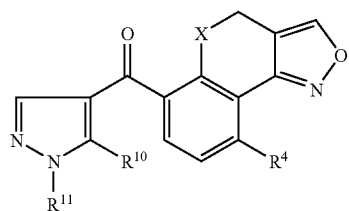

Ia7

Very particular preference is also given to the compounds of the formula Ia8 (≡Ia where $R^1$, $R^2$, $R^5$ and $R^{12}$=H, $R^3$=CH$^3$, l=1), in particular to the compounds Ia8.n, where the variables X, $R^4$, $R^{10}$ and $R^{11}$ are as defined in Table 1.

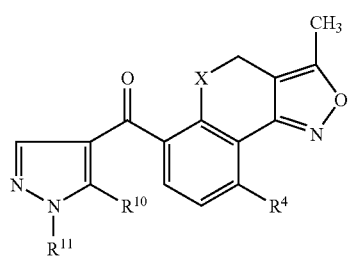

Ia8

Very particular preference is also given to the compounds of the formula Ia9 (≡Ia where $R^1$, $R^2$, $R^5$ and $R^{12}$=H, l=0), in particular to the compounds Ia9.n, where the variables X, $R^4$, $R^{10}$ and $R^{11}$ are as defined in Table 1.

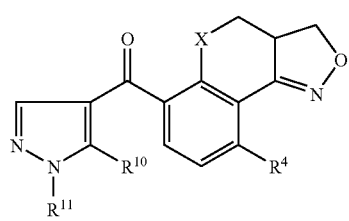

Ia9

Very particular preference is also given to the compounds of the formula Ia10 (≡Ia where $R^1$, $R^2$, $R^5$ and $R^{12}$=H, l=0), in particular to the compounds Ia10.n, where the variables X, $R^4$, $R^{10}$ and $R^{11}$ are as defined in Table 1.

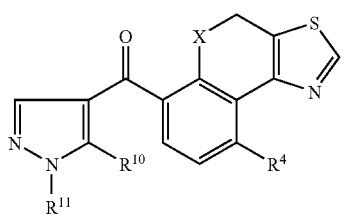

Ia10

Very particular preference is also given to the compounds of the formula Ia11 (≡Ia where $R^1$, $R^2$, $R^5$ and $R^{12}$=H, l=0), in particular to the compounds Ia11.n, where the variables X, $R^4$, $R^{10}$ and $R^{11}$ are as defined in Table 1.

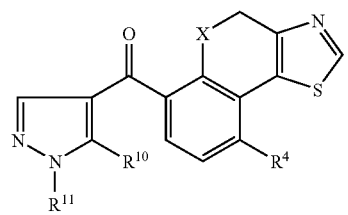

Ia11

Very particular preference is also given to the compounds of the formula Ia12 (≡Ia where $R^1$, $R^2$, $R^5$ and $R^{12}$=H, l=0), in particular to the compounds Ia12.n, where the variables X, $R^4$, $R^{10}$ and $R^{11}$ are as defined in Table 1.

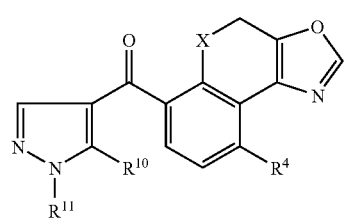

Ia12

Very particular preference is also given to the compounds of the formula Ia13 (≡Ia where $R^1$, $R^2$, $R^5$ and $R^{12}$=H, l=0), in particular to the compounds Ia13.n, where the variables X, $R^4$, $R^{10}$ and $R^{11}$ are as defined in Table 1.

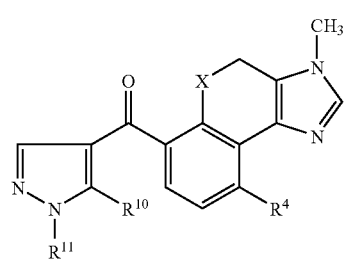

Ia13

Very particular preference is also given to the compounds of the formula Ia14 (≡Ia where $R^1$, $R^2$, $R^5$ and $R^{12}$=H, $R^3$=CH$_3$, l=1), in particular to the compounds Ia14.n, where the variables X, $R^4$, $R^{10}$ and $R^{11}$ are as defined in Table 1.

Ia14

Very particular preference is also given to the compounds of the formula Ia15 (≡Ia where $R^1$, $R^2$, $R^5$ and $R^{12}$=H, $R^3=CH_3$, l=1), in particular to the compounds Ia15.n, where the variables X, $R^4$, $R^{10}$ and $R^{11}$ are as defined in Table 1.

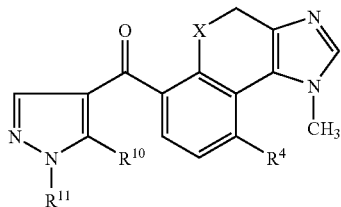

Ia15

Very particular preference is also given to the compounds of the formula Ia16 (=Ia where $R^1$, $R^2$, $R^5$ and $R^{12}$=H, l=0), in particular to the compounds Ia16.n, where the variables X, $R^4$, $R^{10}$ and $R^{11}$ are as defined in Table 1.

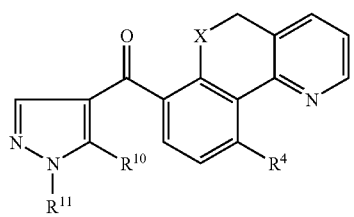

Ia16

Very particular preference is also given to the compounds of the formula Ia17 (=Ia where $R^1$, $R^2$, $R^5$ and $R^{12}$=H, l=0), in particular to the compounds Ia17.n, where the variables X, $R^4$, $R^{10}$ and $R^{11}$ are as defined in Table 1.

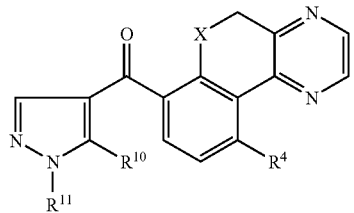

Ia17

Very particular preference is also given to the compounds of the formula Ia18 (=Ia where $R^1$, $R^2$, $R^5$ and $R^{12}$=H, $R^{13}$=CH$_3$, l=1), in particular to the compounds Ia18.n, where the variables X, $R^4$, $R^{10}$ and $R^{11}$ are as defined in Table 1.

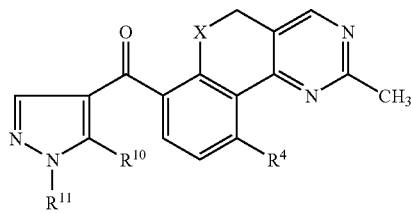

Ia18

Very particular preference is also given to the compounds of the formula Ia19 (=Ia where $R^1$, $R^2$, $R^5$ and $R^{12}$=H, l=0), in particular to the compounds Ia19.n, where the variables X, $R^4$, $R^{10}$ and $R^{11}$ are as defined in Table 1.

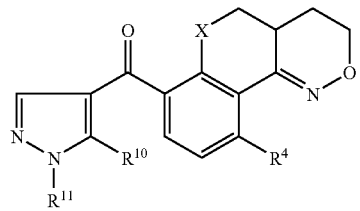

Ia19

Very particular preference is also given to the compounds of the formula Ia20 (=Ia where $R^1$, $R^2$, $R^5$ and $R^{12}$=H, l=0), in particular to the compounds Ia20.n, where the variables X, $R^4$, $R^{10}$ and $R^{11}$ are as defined in Table 1.

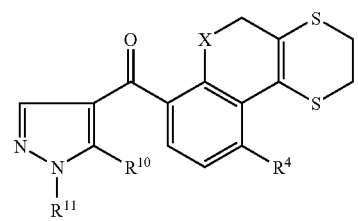

Ia20

Very particular preference is also given to the compounds of the formula Ia21 (=Ia where $R^1$, $R^2$, $R^5$ and $R^{12}$=H, l=0), in particular to the compounds Ia21.n, where the variables X, $R^4$, $R^{10}$ and $R^{11}$ are as defined in Table 1.

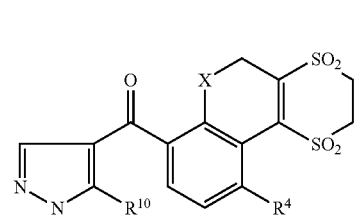

Ia21

Very particular preference is also given to the compounds of the formula Ia22 (=Ia where $R^1$, $R^2$, $R^5$ and $R^{12}$=H, $R^3$=CH$_3$, l=1), in particular to the compounds Ia22.n, where the variables X, $R^4$, $R^{10}$ and $R^{11}$ are as defined in Table 1.

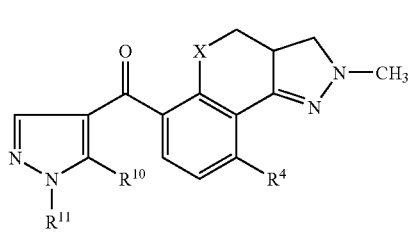

Ia22

The tricyclic benzoylpyrazole derivatives of the formula I can be obtained by various routes, for example by one of the following processes:

A. Preparation of compounds of the formula I where $R^{10}$=halogen by reacting a tricyclic benzoylpyrazole derivative of the formula Iα (≡I where $R^{10}$=hydroxyl) with a halogenating agent:

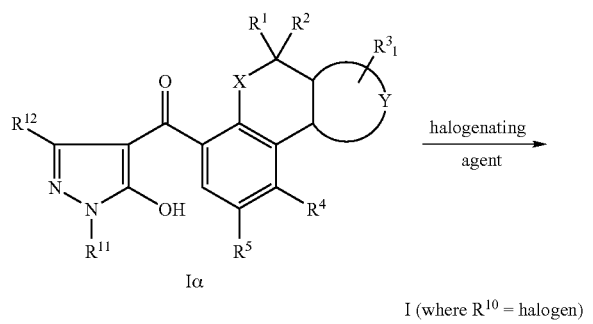

Suitable halogenating agents are, for example, phosgene, diphosgene, triphosgene, thionyl chloride, oxalyl chloride, phosphorus oxychloride, phosphorus pentachloride, mesyl chloride, chloromethylene-N,N-dimethylammonium chloride, oxalyl bromide, phosphorus oxybromide, etc.

The starting materials are generally employed in equimolar amounts. However, it may also be advantageous to employ an excess of one or the other component.

Suitable solvents are, for example, chlorinated hydrocarbons, such as methylene chloride or 1,2-dichloroethane, aromatic hydrocarbons, for example toluene, xylene or chlorobenzene, polar aprotic solvents, such as acetonitrile, dimethylformamide or dimethyl sulfoxide, or mixtures of these. However, it is also possible to carry out the reaction in the absence of solvent.

The reaction temperature is generally in the range from 0° C. to the boiling point of the reaction mixture.

Work-up can be carried out in a manner known per se to afford the product.

B. Preparation of compounds of the formula I where $R^{10}$=$OR^{13}$, by reacting a tricyclic benzoylpyrazole derivative of the formula Iα (≡I where $R^{10}$=hydroxyl) with an alkylating agent III.

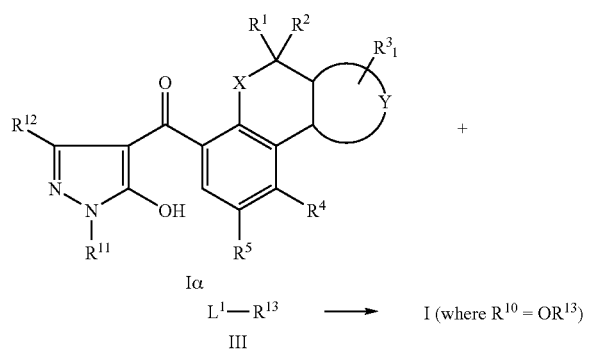

$L^1$ is a nucleophilically replaceable leaving group, such as halogen, for example chlorine or bromine, hetaryl, for example imidazolyl, carboxylate, for example acetate, or sulfonate, for example mesylate or triflate, etc.

The compounds of the formula III can be employed directly, such as, for example, in the case of the carbonyl halides, or be generated in situ, for example activated carboxylic acids (using carboxylic acid and dicyclohexylcarbodiimide etc.).

The starting materials are generally employed in equimolar amounts. However, it may also be advantageous to employ an excess of one or the other component.

If appropriate, it may also be advantageous to carry out the reaction in the presence of a base. Here, the reactants and the base are advantageously employed in equimolar amounts. In certain cases, an excess of base, for example from 1.5 to 3 molar equivalents, may be advantageous.

Suitable bases are tertiary alkylamines, such as triethylamine, aromatic amines, such as pyridine, alkali metal carbonates, for example sodium carbonate or potassium carbonate, alkali metal bicarbonates, for example sodium bicarbonate and potassium bicarbonate, alkali metal alkoxides, such as sodium methoxide, sodium ethoxide, potassium tert-butoxide, or alkali metal hydrides, for example sodium hydride. Preference is given to using triethylamine or pyridine.

Suitable solvents are, for example, chlorinated hydrocarbons, such as methylene chloride or 1,2-dichloroethane, aromatic hydrocarbons, for example toluene, xylene or chlorobenzene, ethers, such as diethyl ether, methyl tert-butyl ether, tetrahydrofuran or dioxane, polar aprotic solvents, such as acetonitrile, dimethylformamide or dimethyl sulfoxide, or esters, such as ethyl acetate, or mixtures of these.

The reaction temperature is generally in the range from 0° C. to the boiling point of the reaction mixture.

Work-up can be carried out in a manner known per se to afford the product.

C. Preparation of compounds of the formula I where $R^{10}$=$OR^{13}$, $SR^{13}$, $NR^{15}R^{16}$ or N-bonded heterocyclyl by reacting compounds of the formula Iβ (≡I where $R^{10}$=halogen) with a compound of the formula IVα, IVβ, IVγ or IVδ, if appropriate in the presence of a base or with prior formation of salt.

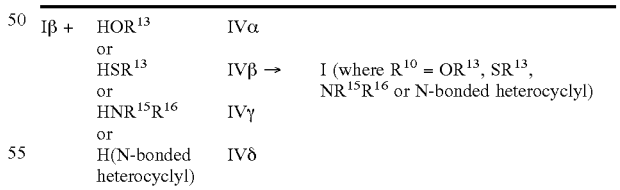

| Iβ + | HOR¹³ | IVα | |
|---|---|---|---|
| | or | | |
| | HSR¹³ | IVβ | → I (where $R^{10}$ = $OR^{13}$, $SR^{13}$, |
| | or | | $NR^{15}R^{16}$ or N-bonded heterocyclyl) |
| | HNR¹⁵R¹⁶ | IVγ | |
| | or | | |
| | H(N-bonded heterocyclyl) | IVδ | |

The starting materials are generally employed in equimolar amounts. However, it may also be advantageous to employ an excess of one or the other component.

If appropriate, it may also be advantageous to carry out the reaction in the presence of a base. Here, the reactants and the base are advantageously employed in equimolar amounts. An excess of base, for example from 1.5 to 3 molar equivalents, based on Iβ (where $R^{10}$=halogen), may be advantageous in certain cases.

Suitable bases are tertiary alkylamines, such as triethylamine, aromatic amines, such as pyridine, alkali metal carbonates, for example sodium carbonate or potassium carbonate, alkali metal bicarbonates, for example sodium bicarbonate and potassium bicarbonate, alkali metal alkoxides, such as sodium methoxide, sodium ethoxide, potassium tert-butoxide, or alkali metal hydrides, for example sodium hydride. Preference is given to using sodium hydride or potassium tert-butoxide.

Suitable solvents are, for example, chlorinated hydrocarbons, such as methylene chloride or 1,2-dichloroethane, aromatic hydrocarbons, for example toluene, xylene or chlorobenzene, ethers, such as diethyl ether, methyl tert-butyl ether, tetrahydrofuran or dioxane, polar aprotic solvents, such as acetonitrile, dimethylformamide or dimethyl sulfoxide, or mixtures of these.

The reaction temperature is generally in the range from 0° C. to the boiling point of the reaction mixture.

Work-up can be carried out in a manner known per se to afford the product.

D. Preparation of compounds of the formula I where $R^{10}$ $SO_2R^{14}$ by reacting compounds of the formula I where $R^{10}=SR^{10}$ (Iγ) with an oxidizing agent.

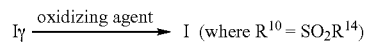

Suitable oxidizing agents are, for example, m-chloroperbenzoic acid, peroxyacetic acid, trifluoroperoxyacetic acid, hydrogen peroxide, if appropriate in the presence of a catalyst, such as tungstate.

The starting materials are generally employed in equimolar amounts. However, it may also be advantageous to employ an excess of one or the other component.

Suitable solvents are, for example, chlorinated hydrocarbons, such as methylene chloride or 1,2-dichloroethane, aromatic hydrocarbons, for example toluene, xylene or chlorobenzene, ethers, such as diethyl ether, methyltert-butyl ether, tetrahydrofuran or dioxane, polar aprotic solvents, such as acetonitrile or dimethylformamide, or esters, such as ethyl acetate, or mixtures of these.

The reaction temperature is generally in the range from 0° C. to the boiling point of the reaction mixture.

Work-up can be carried out in a manner known per se to afford the product.

E. Preparation of compounds of the formula I where $R^9$=IIa (where $R^{10}$≠hydroxyl or mercapto) by reacting a metalated pyrazole derivative of the formula V with a tricyclic benzoic acid derivative of the formula VIα:

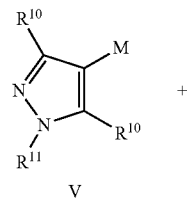

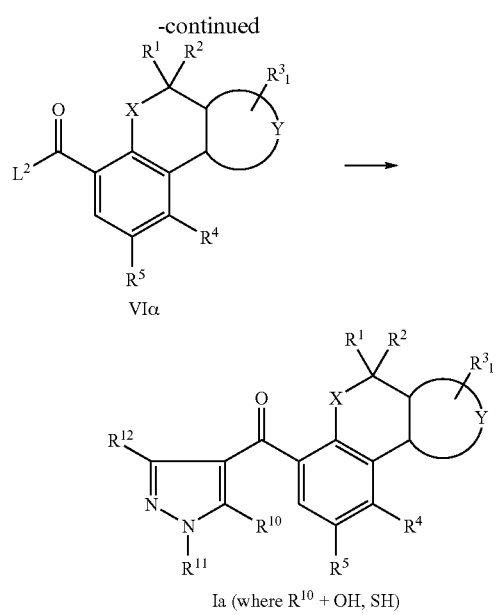

Here, M is a metal, in particular an alkali metal, such as lithium or sodium, an alkaline earth metal, such as, for example, magnesium, or a transition metal, such as palladium, nickel, etc. and $L^2$ is a nucleophilically replaceable leaving group, such as halogen, for example chlorine or bromine, alkylsulfonate, such as mesylate, haloalkylsulfonate, such as triflate, or cyanide.

The reaction is generally carried out at temperatures of from –100° C. to the reflux temperature of the reaction mixture. Suitable solvents are inert aprotic solvents, such as ethers, for example diethyl ether, tetrahydrofuran. The compounds of the formula VIα are generally employed in excess, but it may also be advantageous to employ them in equimolar amounts or in substoichiometric amounts. Work-up is carried out to afford the product.

The metalated pyrazole derivatives of the formula V can be formed in a manner known per se by reacting pyrazoles which are halogenated in the 4-position with metals, such as lithium, sodium, magnesium, etc., or with organometallic compounds, such as, for example, butyllithium. However, it is also possible to metalate pyrazoles which are linked in the 4 position to hydrogen directly, for example with the abovementioned metals or organometallic compounds. The reactions are generally carried out in an inert aprotic solvent, preferably in ether, such as diethyl ether, tetrahydrofuran, etc. The reaction temperature is in the range from –100° C. to the boiling point of the reaction mixture. The compounds of the formula V are generally directly reacted further or generated in situ.

F. Preparation of compounds of the formula Iα (=I where $R^{10}$=hydroxyl) by reacting an activated tricyclic benzoic acid of the formula VIβ or a tricyclic benzoic acid VIγ, preferably activated in situ, with a pyrazole of the formula VII to give the acylation product, followed by rearrangement.

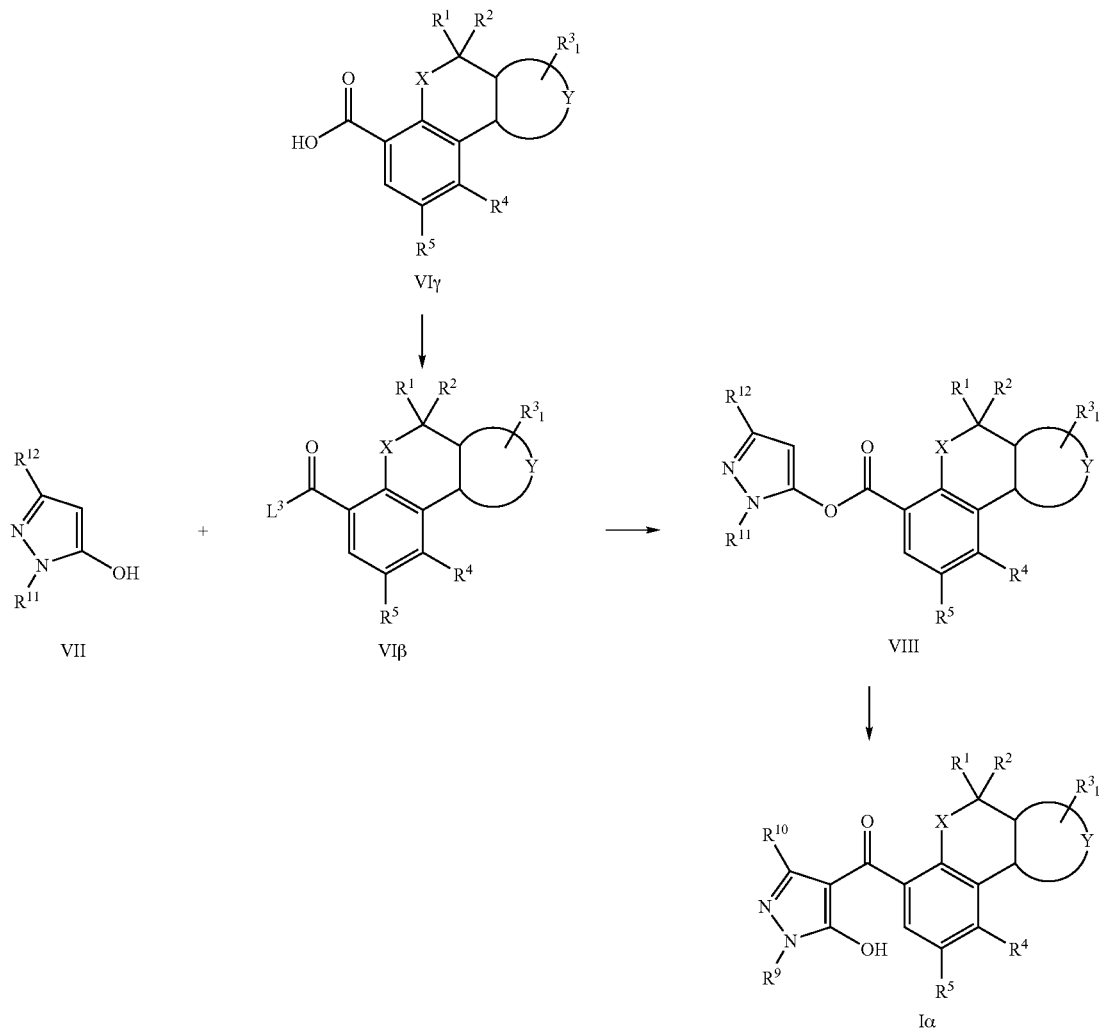

$L^3$ is a nucleophilically replaceable leaving group, such as halogen, for example bromine or chlorine, hetaryl, for example imidazolyl or pyridyl, carboxylate, for example acetate or trifluoroacetate, etc.

The activated tricyclic benzoic acid VIβ can be employed directly, such as in the case of the tricyclic benzoyl halides, or be generated in situ, for example using dicyclohexylcarbodiimide, triphenylphosphine/azodicarboxylic ester, 2-pyridine disulfide/triphenylphosphine, carbonyldiimidazole, etc.

If appropriate, it may be advantageous to carry out the acylation reaction in the presence of a base. Here, the reactants and the auxiliary base are advantageously employed in equimolar amounts. A slight excess of auxiliary base, for example from 1.2 to 1.5 molar equivalents, based on VI, may be advantageous in certain cases.

Suitable auxiliary bases are tertiary alkylamines, pyridine, or alkali metal carbonates. Suitable solvents are, for example, chlorinated hydrocarbons, such as methylene chloride or 1,2-dichloroethane, aromatic hydrocarbons, such as toluene, xylene or chlorobenzene, ethers, such as diethyl ether, methyl tert-butyl ether, tetrahydrofuran or dioxane, polar aprotic solvents, such as acetonitrile, dimethylformamide or dimethyl sulfoxide, or esters, such as ethyl acetate, or mixtures of these.

If tricyclic benzoyl halides are employed as activated carboxylic acid components, it may be advantageous to cool the reaction mixture to 0–10° C. when adding this reaction partner. The mixture is subsequently stirred at 20–100° C., preferably at 25–50° C., until the reaction has gone to completion. Work-up is carried out in a customary manner, for example by pouring the reaction mixture into water and extracting the product of value. Solvents which are suitable for this purpose are, in particular, methylene chloride, diethyl ether and ethyl acetate. The organic phase is dried and the solvent removed, and the crude ester can then be employed for the rearrangement without further purification.

The rearrangement of the esters VIII to give the compounds of the formula Iα is advantageously carried out at from 20 to 100° C. in a solvent and in the presence of a base and, if appropriate, using a cyano compound as catalyst.

Solvents which may be used are, for example, acetonitrile, methylene chloride, 1,2-dichloroethane, dioxane, ethyl acetate, toluene or mixtures of these. Preferred solvents are acetonitrile and dioxane.

Suitable bases are tertiary amines, such as triethylamine, aromatic amines, such as pyridine, or alkali metal carbonates, such as sodium carbonate or potassium carbonate, which are preferably employed in equimolar amounts or in an up to four-fold excess, based on the ester. Preference is given to using triethylamine or alkali metal carbonate, preferably in double the equimolar ratio, based on the ester.

Suitable cyano compounds are inorganic cyanides, such as sodium cyanide or potassium cyanide, and organic cyano compounds, such as acetone cyanohydrin or trimethylsilyl cyanide. They are employed in an amount of from 1 to 50 mol percent, based on the ester. Preference is given to using acetone cyanohydrin or trimethylsilyl cyanide, for example in an amount of from 5 to 15, preferably 10, mol percent, based on the ester.

Work-up may be carried out in a manner known per se. The reaction mixture is, for example, acidified using dilute mineral acid, such as 5% strength hydrochloric acid or sulfuric acid, and extracted with an organic solvent, for example methylene chloride or ethyl acetate. The organic extract can be extracted with 5–10% strength alkali metal carbonate solution, for example sodium carbonate or potassium carbonate solution. The aqueous phase is acidified and the resulting precipitate is filtered off with suction and/or extracted with methylene chloride or ethyl acetate, the extract being dried and concentrated.

However, it is also possible to generate the ester VIII in situ by reacting a pyrazole of the formula VII, or an alkali metal salt thereof, with a tricyclic benzene derivative of the formula IX in the presence of carbon monoxide, a catalyst and a base.

A suitable palladium(0) ligand complex is, for example, tetrakis(triphenylphosphane)palladium.

Metallic palladium is preferably applied to an inert carrier, such as, for example, activated carbon, silica, alumina, barium sulfate or calcium carbonate. The reaction is preferably carried out in the presence of complex ligands, such as, for example, triphenylphosphane.

Suitable palladium(II) salts are, for example, palladium acetate and palladium chloride. Preference is given to carrying out the reaction in the presence of complex ligands such as, for example, triphenylphosphane.

Suitable complex ligands for the palladium ligand complexes, or complex ligands in whose presence the reaction with metallic palladium or palladium(II) salts is preferably carried out are tertiary phosphanes whose structure is represented by the following formulae:

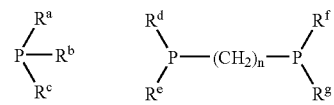

where n is a number from 1 to 4 and the radicals $R^a$ to $R^g$ are $C_1$–$C_6$-alkyl, aryl-$C_1$–$C_2$-alkyl or preferably aryl. Aryl is, for example, naphthyl and unsubstituted or substituted phenyl such as, for example, 2-tolyl and in particular unsubstituted phenyl.

The complex palladium salts can be prepared in a manner known per se starting from commercially available palla-

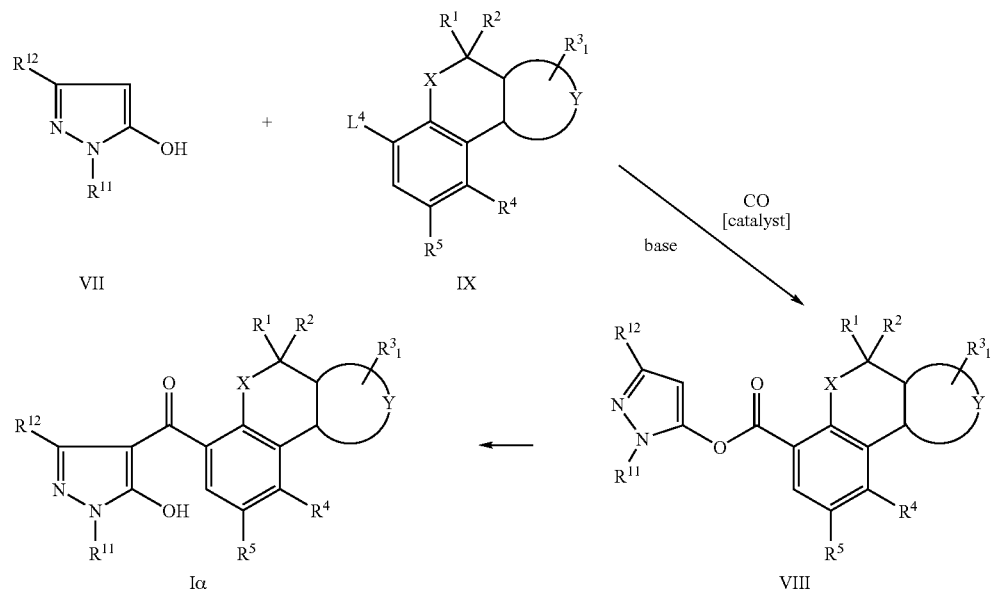

$L^4$ is a leaving group, such as halogen, for example chlorine, bromine or iodine, or sulfonate such as mesylate or triflate; preference is given to bromine or triflate.

If appropriate, the ester VIII reacts directly to give the tricyclic benzoylpyrazole derivative of the formula Iα.

Suitable catalysts are palladium ligand complexes in which the palladium is present in oxidation state 0, metallic palladium, if appropriate applied to a support, and preferably palladium(II) salts. The reaction with palladium(II) salts and metallic palladium is preferably carried out in the presence of complex ligands.

dium salts, such as palladium chloride or palladium acetate, and the corresponding phosphanes, such as, for example, triphenylphosphane or 1,2-bis(diphenylphosphano)ethane. A large number of complexed palladium salts is also commercially available. Preferred palladium salts are [(R)-(+)-2,2'-bis(diphenylphosphano)-1,1'-binaphthyl]palladium (II) chloride, bis(triphenylphosphane)palladium(II)acetate and in particular bis(triphenylphosphane)palladium(II) chloride.

The palladium catalyst is generally employed in a concentration of from 0.05 to 5 mol %, and preferably of 1–3 mol %.

Suitable bases are tertiary amines, such as, for example, N-methylpiperidine, ethyldiisopropylamine, 1,8-bisdimethylaminonaphthalene and in particular triethylamine. Also suitable are alkali metal carbonates, such as sodium carbonate or potassium carbonate. However, mixtures of potassium carbonate and triethylamine are also suitable.

In general, from 2 to 4 molar equivalents, in particular 2 molar equivalents, of the alkali metal carbonate, and from 1 to 4 molar equivalents, in particular 2 molar equivalents, of the tertiary amine are employed, based on the tricyclic benzene derivative of the formula IX.

Suitable solvents are nitriles, such as benzonitrile and acetonitrile, amides, such as dimethylformamide, dimethylacetamide, tetra-$C_1$–$C_4$-alkylureas or N-methylpyrrolidone, and preferably ethers, such as tetrahydrofuran, methyl tert-butyl ether. Particular preference is given to using, as solvents, ethers such as 1,4-dioxane and dimethoxyethane.

The tricyclic benzoyl halides of the formula VIβ where $L^3$=Cl, Br can be prepared in a manner known per se by reacting the tricyclic benzoic acids of the formula VIγ (≡VIb) with halogenating agents such as thionyl chloride, thionyl bromide, phosgene, diphosgene, triphosgene, oxalyl chloride and oxalyl bromide.

In a known manner, the tricyclic benzoic acids of the formula VIγ (≡VIb) can be prepared by acidic or basic hydrolysis from the corresponding esters VIc.

Tricyclic benzoic acid derivatives of the formula VI

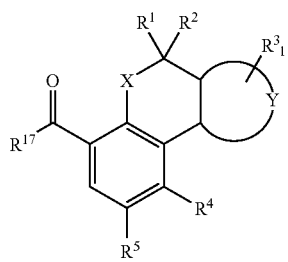

VI where:
x is oxygen, sulfur, S=O, S(=O)$_2$, CR$^6$R$^7$, NR$^8$ or a bond;
Y together with the two carbons to which it is attached forms a saturated, partially saturated or unsaturated 5- or 6-membered heterocycle which contains one to three identical or different heteroatoms selected from the following group:
oxygen, sulfur or nitrogen;
$R^1,R^2,R^6,R^7$ are hydrogen, $C_1$–$C_6$-alkyl, $C_1$–$C_6$-haloalkyl, $C_1$–$C_6$-alkoxy or $C_1$–$C_6$-haloalkoxy;
$R^3$ is halogen, $C_1$–$C_6$-alkyl, $C_1$–$C_6$-haloalkyl, $C_1$–$C_6$-alkoxy or $C_1$–$C_6$-haloalkoxy;
$R^4$ is nitro, halogen, cyano, $C_1$–$C_6$-alkyl, $C_1$–$C_6$-haloalkyl, $C_1$–$C_6$-alkoxy, $C_1$–$C_6$-haloalkoxy, $C_1$–$C_6$-alkylthio, $C_1$–$C_6$-haloalkylthio, $C_1$–$C_6$-alkylsulfinyl, $C_1$–$C_6$-haloalkylsulfinyl, $C_1$–$C_6$-alkylsulfonyl, $C_1$–$C_6$-haloalkylsulfonyl, aminosulfonyl, N-($C_1$–$C_6$-alkyl)-aminosulfonyl, N,N-di($C_1$–$C_6$-alkyl)aminosulfonyl, N-($C_1$–$C_6$-alkylsulfonyl)amino, N-($C_1$–$C_6$-haloalkylsulfonyl)amino, N-($C_1$–$C_6$-alkyl)-N-($C_1$–$C_6$-alkylsulfonyl)amino or N-($C_1$–$C_6$-alkyl)-N-($C_1$–$C_6$-haloalkylsulfonyl)amino;
$R^5$ is hydrogen, $C_1$–$C_6$-alkyl or halogen;
$R^8$ is hydrogen, $C_1$–$C_6$-alkyl, $C_1$–$C_6$-haloalkyl, $C_1$–$C_6$-alkylcarbonyl, formyl, $C_1$–$C_6$-alkoxycarbonyl, $C_1$–$C_6$-haloalkoxycarbonyl, $C_1$–$C_6$-alkylsulfonyl or $C_1$–$C_6$-haloalkylsulfonyl;

l is 0, 1 or 2;
$R^{17}$ is hydroxyl or a radical which can be removed by hydrolysis;
are novel.

Examples of radicals which can be removed by hydrolysis are alkoxy, phenoxy, alkylthio and phenylthio radicals which can be unsubstituted or substituted, halides, heteroaryl radicals which are attached via nitrogen, amino and imino radicals which may be unsubstituted or substituted, etc.

Preference is given to tricyclic benzoyl halides VIa (VI where $R^{17}$=halogen)

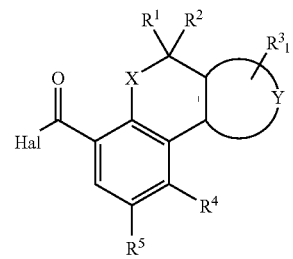

VIa where the variables X, Y, $R^1$ to $R^5$ and l are as defined under formula VI and
Hal is halogen, in particular chloride or bromide.

Preference is also given to tricyclic benzoic acids of the formula VIb (VI where $R^{17}$=hydroxyl; ≡VIγ),

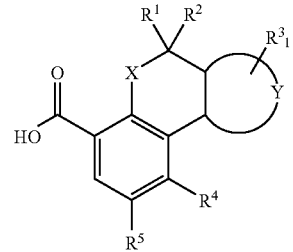

VIb where the variables X, Y, $R^1$ to $R^5$ and l are as defined under formula VI.

Preference is also given to tricyclic benzoic esters of the formula VIc (VI where $R^{17}$=T=$C_1$–$C_6$-alkoxy),

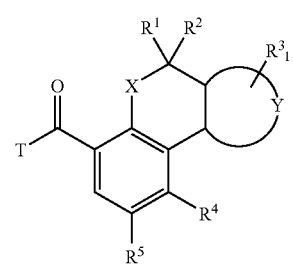

VIc where the variables X, Y, $R^1$ to $R^5$ and l are as defined under formula VI and
T is $C_1$–$C_6$-alkoxy.

With respect to the variables X, Y, $R^1$ to $R^5$ and l, the particularly preferred embodiments of the tricyclic benzoic acid derivatives of the formulae VI, VIa, VIb and VIc correspond to those of the tricyclic benzoylpyrazole derivatives of the formula I.

Particular preference is given to the compounds VI, VIa, VIb and VIc where Y together with the two carbons to which it is attached forms the following heterocycles:

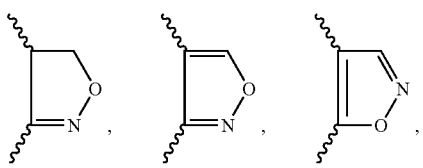

Here, extraordinary preference is given to the compounds VI, VIa, VIb and VIc where $R^4$ is nitro, halogen, $C_1$–$C_6$-alkyl, $C_1$–$C_6$-haloalkyl, $C_1$–$C_6$-alkoxy, $C_1$–$C_6$-alkylthio or $C_1$–$C_6$-alkylsulfonyl; in particular $C_1$–$C_6$-alkylsulfonyl.

The tricyclic benzoic esters VIc can be obtained in different ways.

For example, benzoic esters of the formula X, which are prepared in a manner known per se (cf., for example, Chem. Pharm. Bull. 1985, 33 (8), 3336; Helv. Chim. Acta 1987, 70, 1326; J. Chem. Soc. Perkin Trans. 1972, 2019; J. Chem. Soc. Perkin Trans. 1991, 2763; Tetrahydron Asymmetry 1998, 9, 1137), can be cyclized to cyclic ketones of the formula XI (cf., for example, Chem. Ber. 1923, 56, 1819; J. Chem. Soc. Perkin 11991, 2763; J. Med. Chem. 1988, 31, 230; Tetrahedron 1987, 43, 4549; Synlett 1991, 6, 443; Chem. Pharm. Bull. 1985, 33 (8), 3336). Analogously to known processes (cf., for example, J. Heterocyclic Chem. 1976, 13, 545; J. Heterocyclic Chem. 1972, 9, 1341; J. Org. Chem. 1978, 43, 3015; J. Chem. Soc. Perkin Trans. 11978, 86; J. Org. Chem. 1986, 51, 2021), these can be converted into the tricyclic benzoic esters of the formula VIc.

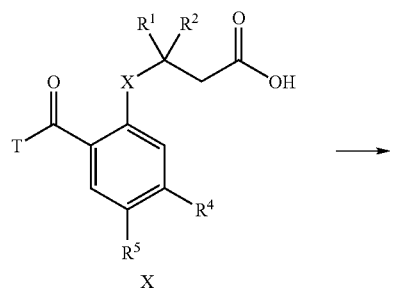

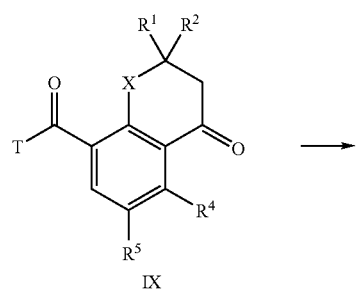

Furthermore, it may be suitable to cyclize the cyclic ketone of the formula XI in a manner known per se (XII), for example using an anhydride or acid anhydride, if appropriate in the presence of catalytic amounts of a Lewis acid, such as boron trifluoride (cf., for example, Can. J. Chem. 1979, 57, 3292; J. Am. Chem. Soc. 1953, 75, 626), followed by reaction with a hydrazine (cf. A. R. Katritzky et al., Comprehensive Heterocyclic Chemistry, Vol. 5, p. 121, 277–280 (1984), Pergamon Press; J. Org. Chem. 1961, 26, 451; Org. Synth. 1949, 29, 54), where the resulting pyrazole radical can be modified further by customary processes.

Furthermore, the diketone XII can be reacted with hydroxylamine or equivalents thereof (cf. A. R. Katritzky et al., Comprehensive Heterocyclic Chemistry, Vol. 6, p. 61–64, 118 (1984), Pergamon Press; Chem. Ber. 1967, 100, 3326). This gives the corresponding isoxazole derivatives which can be modified further by customary processes.

It is also possible to react the diketone XII with amidines (cf., for example, A. R. Katritzky et al., Comprehensive Heterocyclic Chemistry, Vol. 3, p. 112–114 (1924), Pergamon Press; J. Chem. Soc. C 1967, 1922; Org. Synth. 1963, IV, 182). If required, the resulting pyrimidine derivatives can be modified further by customary processes.

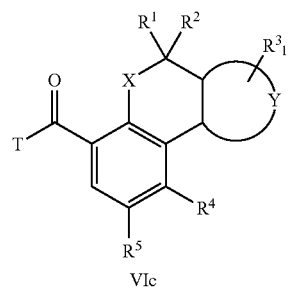

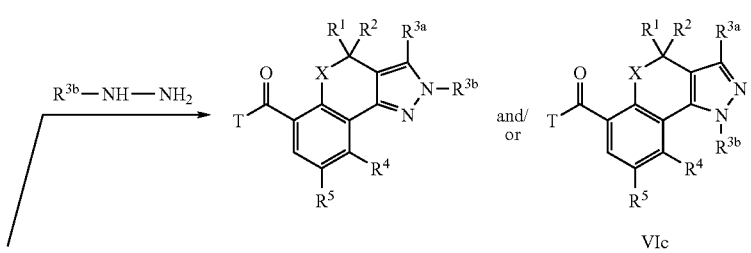

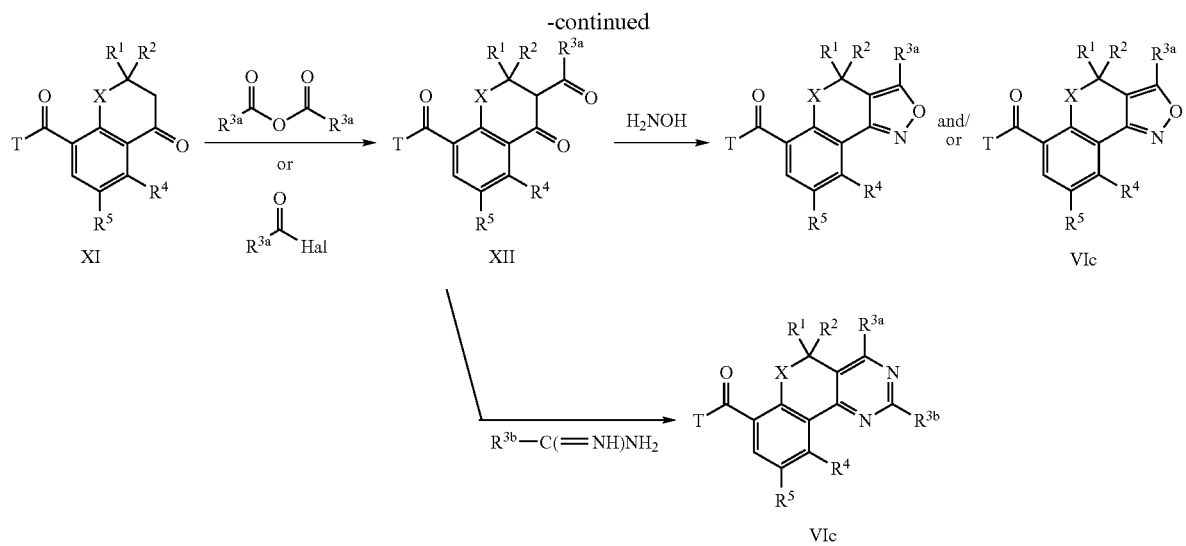

In the reactions mentioned above, it is also possible to employ, instead of the diketone XII, equivalents thereof, such as enol ethers or enamines, which can be prepared analogously to known processes.

It may also be possible to react the cyclic ketone of the formula XI analogously to known processes with an aldehyde or ketone to give (XIII) (cf., for example, Tetrahedron Lett. 1978, 2111; Tetrahedron Lett. 1981, 5251; Chem. Ber. 1960, 2294; J. Chem. Soc. Perkin Trans. 1, 1991, 1467; Tetrahedron Lett. 1992, 8091). The resulting unsaturated cyclic ketone of the formula XIII can be reacted with a hydrazine in a manner known per se (cf., for example, A. R. Katritzky et al. Comprehensive Heterocyclic Chemistry, Vol. 2, 6 (1984), Pergamon Press; J. Heterocyclic Chem. 1969, 533; J. Heterocyclic Chem. 1968, 853), where the resulting pyrazoline can be modified further by customary processes.

It is furthermore possible to react the unsaturated cyclic ketone of the formula XIII with hydroxylamine or equivalents thereof (Z. Chem. 1980, 20, 19). This gives the corresponding isoxazoline derivatives, which can be modified further by customary processes.

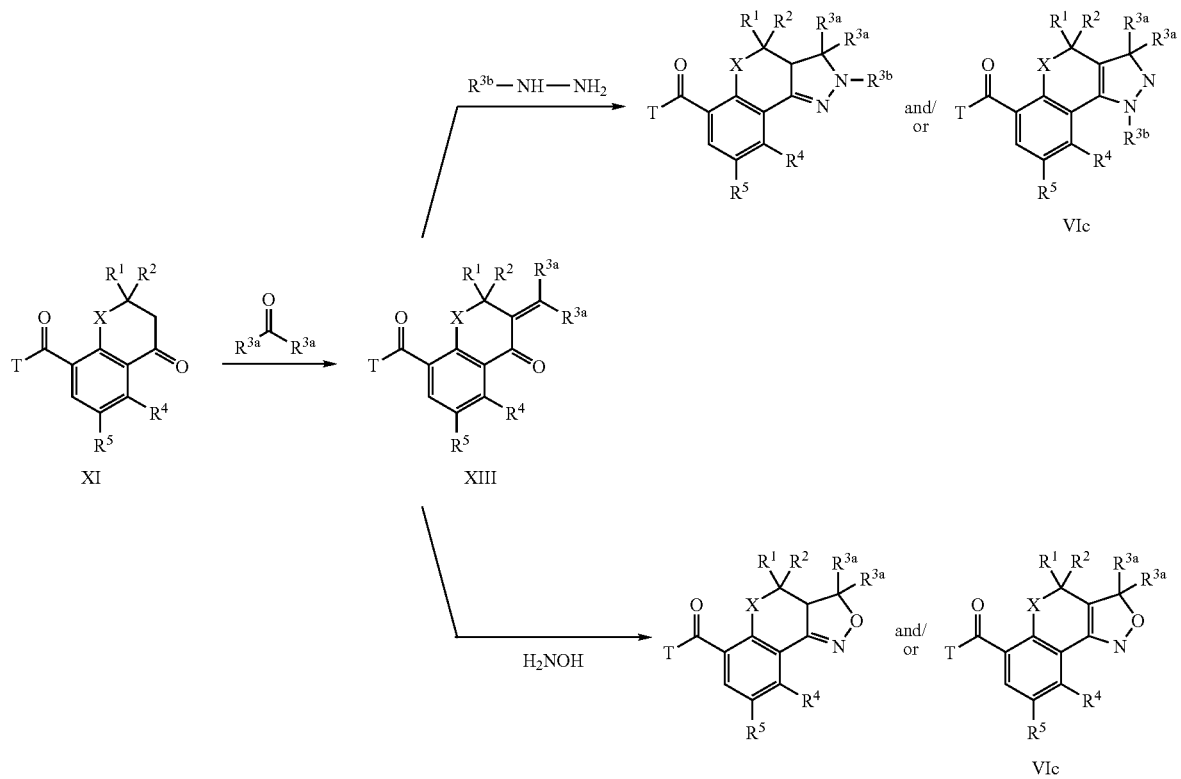

Furthermore, it is possible to convert aldehydes of the formula XIV, which can be prepared in a manner known per se, analogously to processes known from the literature by reaction with a hydrazine or hydroxylamine (or equivalents of these) into the corresponding hydrazones or oximes (cf., for example, Synth. Commun. 1990, 20, 1373; J. Org. Chem. 1980, 45, 3756). These in turn can be converted in a manner known per se into the corresponding 1,3-dipoles, which then react in a [3+2]-cycloaddition to give the compounds VIc (cf., for example, Synth. Commun. 1990, 20, 1373; EP-A 386 892; J. Org. Chem. 1980, 45, 3756; Tetrahedron Lett. 1981, 22, 1333.)

The resulting pyrazoles or pyrazolines and isoxazoles or isoxazolines can be modified further by customary processes.

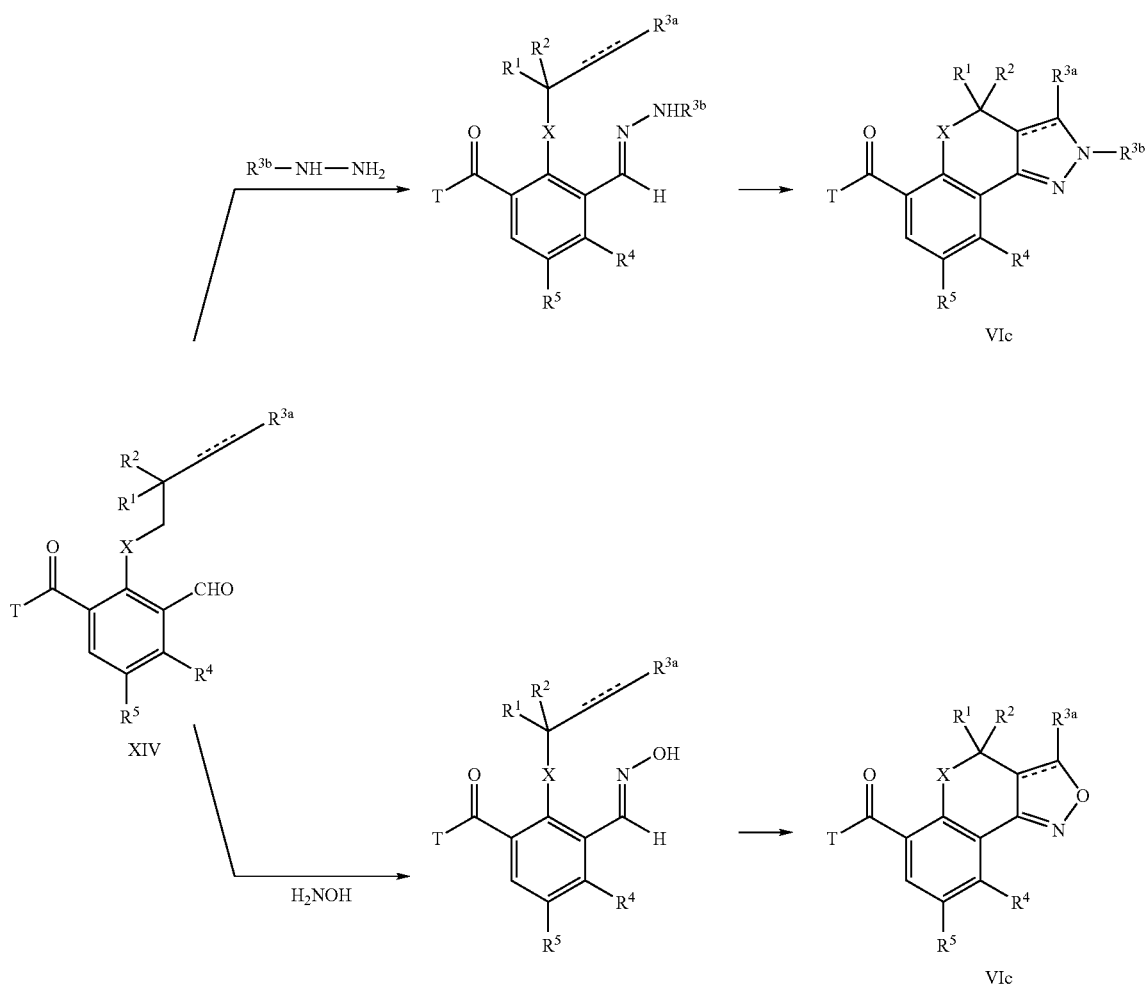

It is also possible to react the cyclic ketone of the formula XI with a dithiol or a "mixed alcohol" analogously to processes known from the literature (cf., for example, T. W. Greene et al., Protective Groups in Organic Synthesis, John Wiley & Sons, 133–140), and to subject it subsequently to a rearrangement in the presence of bromine or a suitable Lewis acid, such as, for example, tellurium tetrachloride (cf. Tetrahedron 1991, 47, 4187; Synthesis 1991, 223; J. Chem. Soc. Chem. Commun. 1985, 1645).

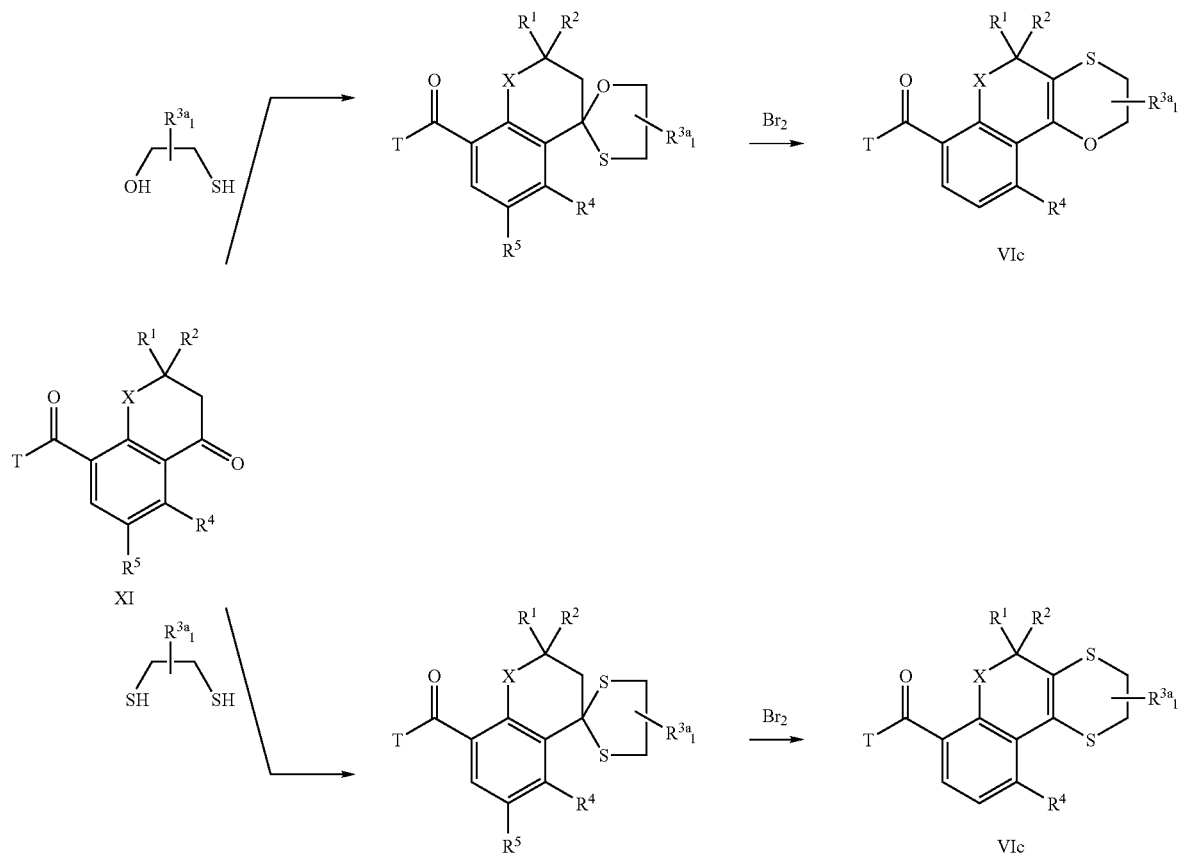

The resulting heterocycles can, if desired, be modified further by processes known per se.

The abovementioned substituents $R^{3a}$ are hydrogen, $C_1$–$C_6$-alkyl, $C_1$–$C_6$-haloalkyl, hydroxyl, $C_1$–$C_6$-alkoxy or $C_1$–$C_6$-haloalkoxy; furthermore, the abovementioned radicals $R^{3b}$ are hydrogen, $C_1$–$C_6$-alkyl or $C_1$–$C_6$-haloalkyl.

The tricyclic benzoic esters of the formula VIc or the tricyclic benzoic acids of the formula VIb can be obtained by reacting a tricyclic benzene derivative of the formula IX with a $C_1$–$C_6$-alcohol or water in the presence of carbon monoxide, a catalyst and a base. In general, the conditions mentioned under process F apply.

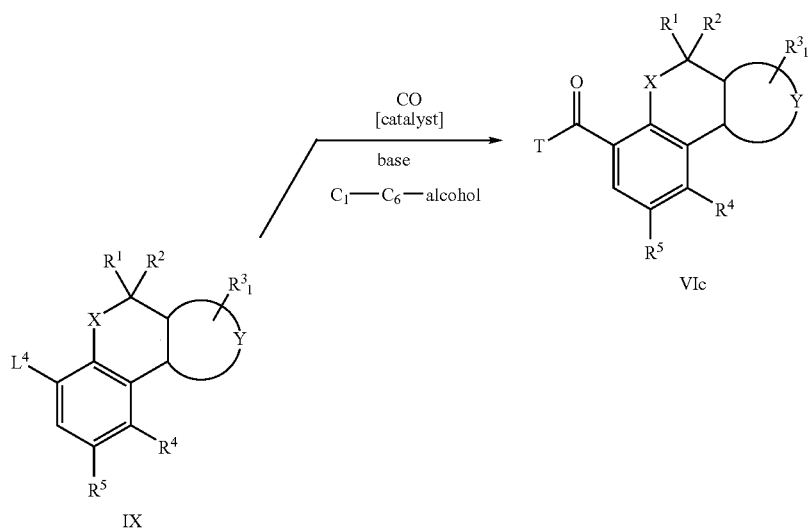

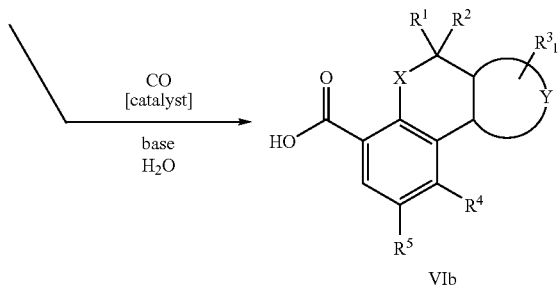

$L^4$ is a leaving group, such as halogen, for example chlorine, bromine or iodine, or sulfate, such as mesylate or triflate; preference is given to bromine or triflate.

Furthermore, the tricyclic benzoic acids of the formula VIb can be obtained by converting a tricyclic benzene derivative of the formula IX where $L^4$ is halogen, such as chlorine or bromine, in particular bromine, by reaction with, for example, n-butyllithium or magnesium into the metalated derivative, followed by quenching with carbon dioxide (cf., for example, J. Org. Chem. 1990, 55, 773; Angew. Chem. Int. Ed. 1969, 8, 68).

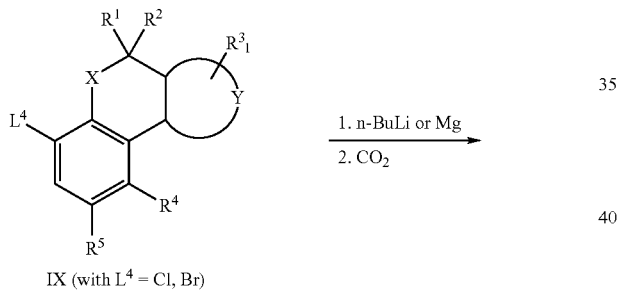

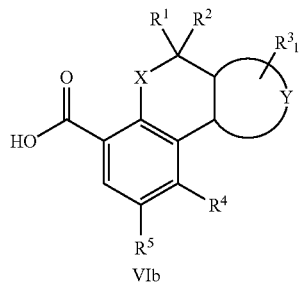

It is also possible to obtain the tricyclic benzoic acids VIb by hydrolyzing the corresponding nitriles, analogously to processes known from the literature. The nitriles for their part can be obtained by halogen/nitrile exchange or by Sandmeyer reaction from the corresponding anilines XV.

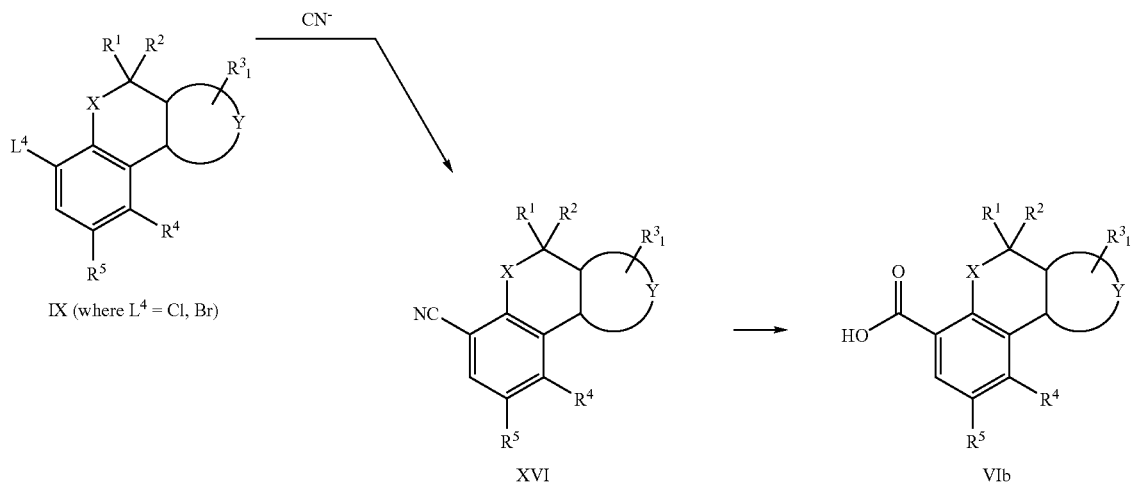

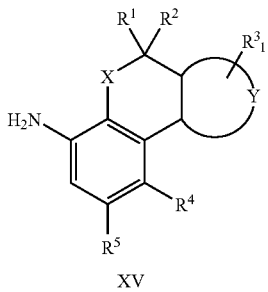

The compounds of the formula IX, where:
- X is oxygen, sulfur, S=O, S(=O)$_2$, CR$^6$R$^7$, NR$^8$ or a bond;
- Y together with the two carbons to which it is attached forms a saturated, partially saturated or unsaturated 5- or 6-membered heterocycle which contains one to three identical or different heteroatoms selected from the following group: oxygen, sulfur or nitrogen;
- R$^1$,R$^2$,R$^6$,R$^7$ are hydrogen, C$_1$–C$_6$-alkyl, C$_1$–C$_6$-haloalkyl, C$_1$–C$_6$-alkoxy or C$_1$–C$_6$-haloalkoxy;
- R$^3$ is halogen, C$_1$–C$_6$-alkyl, C$_1$–C$_6$-haloalkyl, C$_1$–C$_6$-alkoxy or C$_1$–C$_6$-haloalkoxy;
- R$^4$ is nitro, halogen, cyano, C$_1$–C$_6$-alkyl, C$_1$–C$_6$-haloalkyl, C$_1$–C$_6$-alkoxy, C$_1$–C$_6$-haloalkoxy, C$_1$–C$_6$-alkylthio, C$_1$–C$_6$-haloalkylthio, C$_1$–C$_6$-alkylsulfinyl, C$_1$–C$_6$-haloalkylsulfinyl, C$_1$–C$_6$-alkylsulfonyl, C$_1$–C$_6$-haloalkylsulfonyl, aminosulfonyl, N-(C$_1$–C$_6$-alkyl)aminosulfonyl, N,N-di(C$_1$–C$_6$-alkyl)aminosulfonyl, N-(C$_1$–C$_6$-alkylsulfonyl)amino, N-(C$_1$–C$_6$-haloalkylsulfonyl)amino, N-(C$_1$–C$_6$-alkyl)-N-(C$_1$–C$_6$-alkylsulfonyl)amino or N-(C$_1$–C$_6$-alkyl)-N-(C$_1$–C$_6$-haloalkylsulfonyl)amino;
- R$^5$ is hydrogen, C$_1$–C$_6$-alkyl or halogen;
- R$^8$ is hydrogen, C$_1$–C$_6$-alkyl, C$_1$–C$_6$-haloalkyl, C$_1$–C$_6$-alkylcarbonyl, formyl, C$_1$–C$_6$-alkoxycarbonyl, C$_1$–C$_6$-haloalkoxycarbonyl, C$_1$–C$_6$-alkylsulfonyl or C$_1$–C$_6$-haloalkylsulfonyl;
- l is 0, 1 or 2;
- L$^4$ is halogen, C$_1$–C$_6$-alkylsulfonyloxy, C$_1$–C$_6$-haloalkylsulfonyloxy or phenylsulfonyloxy, where the phenyl ring of the lastmentioned radical may be unsubstituted or partially or fully halogenated and/or may carry one to three of the following radicals: nitro, cyano, C$_1$–C$_6$-alkyl, C$_1$–C$_6$-haloalkyl, C$_1$–C$_4$-alkoxy or C$_1$–C$_4$-haloalkoxy;

are novel.

Preference is given to compounds of the formula IX where L$^4$ is halogen, in particular bromine.

The particularly preferred embodiments of the compounds of the formula IX with respect to the variables X, Y, R$^1$ to R$^5$ and l correspond to those of the tricyclic benzoylpyrazole derivatives of the formula I.

Particular preference is given to the compounds of the formula IX where
- Y together with the two carbons to which it is attached forms the following heterocycles:

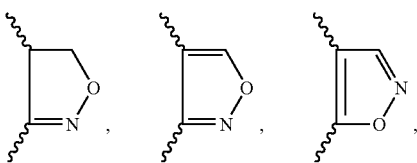

Here, extraordinary preference is given to the compounds IX where
- R$^4$ is nitro, halogen, C$_1$–C$_6$-alkyl, C$_1$–C$_6$-haloalkyl, C$_1$–C$_6$-alkoxy, C$_1$–C$_6$-alkylthio or C$_1$–C$_6$-alkylsulfonyl; in particular C$_1$–C$_6$-alkylsulfonyl.

The compounds of the formula IX can be obtained in different ways, the fused system, for example, can be constructed analogously to the processes described for the compounds of the formula VIc.

However, it is also possible to construct the fused system from a suitable parent compound (analogously to the processes described for compounds of the formula VIc) and to introduce L$^4$=halogen subsequently by customary halogenating reactions.

The anilines of the formula XV and the nitriles of the formula XVI

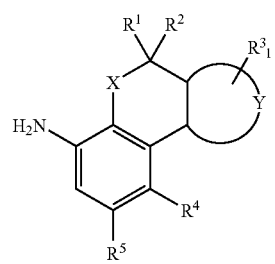

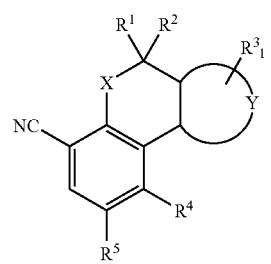

where:
- X is oxygen, sulfur, S=O, S(=O)$_2$, CR$^6$R$^7$, NR$^8$ or a bond;

Y together with the two carbons to which it is attached forms a saturated, partially saturated or unsaturated 5- or 6-membered heterocycle which contains one to three identical or different heteroatoms selected from the following group:
oxygen, sulfur or nitrogen;
$R^1, R^2, R^6, R^7$ are hydrogen, $C_1$–$C_6$-alkyl, $C_1$–$C_6$-haloalkyl, $C_1$–$C_6$-alkoxy or $C_1$–$C_6$-haloalkoxy;
$R^3$ is halogen, $C_1$–$C_6$-alkyl, $C_1$–$C_6$-haloalkyl, $C_1$–$C_6$-alkoxy or $C_1$–$C_6$-haloalkoxy;
$R^4$ is nitro, halogen, cyano, $C_1$–$C_6$-alkyl, $C_1$–$C_6$-haloalkyl, $C_1$–$C_6$-alkoxy, $C_1$–$C_6$-haloalkoxy, $C_1$–$C_6$-alkylthio, $C_1$–$C_6$-haloalkylthio, $C_1$–$C_6$-alkylsulfinyl, $C_1$–$C_6$-haloalkylsulfinyl, $C_1$–$C_6$-alkylsulfonyl, $C_1$–$C_6$-haloalkylsulfonyl, aminosulfonyl, N-($C_1$–$C_6$-alkyl)aminosulfonyl, N,N-di($C_1$–$C_6$-alkyl)aminosulfonyl, N-($C_1$–$C_6$-alkylsulfonyl)amino, N-($C_1$–$C_6$-haloalkylsulfonyl)amino, N-($C_1$–$C_6$-alkyl)-N-($C_1$–$C_6$-alkylsulfonyl)amino or N-($C_1$–$C_6$-alkyl)-N-($C_1$–$C_6$-haloalkylsulfonyl)amino;
$R^5$ is hydrogen, $C_1$–$C_6$-alkyl or halogen;
$R^8$ is hydrogen, $C_1$–$C_6$-alkyl, $C_1$–$C_6$-haloalkyl, $C_1$–$C_6$-alkylcarbonyl, formyl, $C_1$–$C_6$-alkoxycarbonyl, $C_1$–$C_6$-haloalkoxycarbonyl, $C_1$–$C_6$-alkylsulfonyl or $C_1$–$C_6$-haloalkylsulfonyl;
l is 0, 1 or 2;

are also novel.

The particularly preferred embodiments of the compounds of the formulae XV and XVI with respect to the variables X, Y, $R^1$ to $R^5$ and l correspond to those of the tricyclic benzoylpyrazole derivatives of the formula I.

Particular preference is given to the compounds of the formula XV or XVI where
Y together with the two carbons to which it is attached forms the following heterocycles:

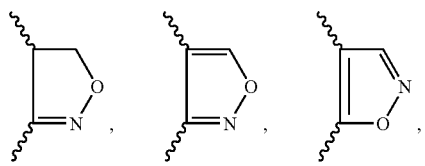

Here, extraordinary preference is given to the compounds XV or XVI where
$R^4$ is nitro, halogen, $C_1$–$C_6$-alkyl, $C_1$–$C_6$-haloalkyl, $C_1$–$C_6$-alkoxy, $C_1$–$C_6$-alkylthio or $C_1$–$C_6$-alkylsulfonyl; in particular $C_1$–$C_6$-alkylsulfonyl.

The compounds of the formula XV can be obtained in different ways; for example, the fused system can be constructed analogously to the processes described for the compounds of the formula VIc.

However, it is also possible to construct the fused system from a suitable parent compound (analogously to the processes described for the compounds of the formula VIc) and to introduce a nitro group subsequently by nitration para to $R^4$, analogously to processes known from the literature, and to convert this group in a manner known per se by reduction into the amino group.

If appropriate, it may be advantageous in the synthesis variants described above to introduce protective groups for certain functionalities if the functionalities are not compatible with the reaction conditions required.

The selection of the protective groups depends both on the reaction conditions and on the structure of the molecule. The protective groups, their introduction and their removal are generally known from the literature (cf., for example, T. W. Greene et al., "Protective Groups in Organic Synthesis", $2^{nd}$ edition, Wiley, New York, 1991), and they can be employed analogously to processes known from the literature.

Furthermore, it may be necessary to carry out a combination of the synthesis variants described above.

It is also possible to introduce further substituents or to modify the substituents present by electrophilic, nucleophilic, free-radical or organometallic reactions and by oxidation or reduction reactions.

PREPARATION EXAMPLES 1. (5-Phenylcarbonyloxy-1-methyl-1H-pyrazol-4-yl)-(8-methyl-sulfonyl-3a,4-dihydro-3H-indeno[1,2-c]isoxazol-5-yl)methanone (compound 2.2)

2-Allyl-6-chlorobenzaldehyde

Under an atmosphere of protective gas, a solution of 10.89 g (0.107 mol) of trimethylethylenediamine in 50 ml of anhydrous tetrahydrofuran was cooled to –10° C. and admixed dropwise with 66.6 ml of a 1.6 molar solution of n-butyllithium in hexane (0.107 mol). After 10 minutes, 15 g (0.107 mol) of 6-chlorobenzaldehyde in 70 ml of tetrahydrofuran were added dropwise, and the mixture was admixed with a further 0.214 mol of n-butyllithium in hexane (146.8 ml) and stirred at 0° C. for 2.5 hours. The mixture was cooled to –200° C., 12.42 g (0.139 mol) of copper(I) cyanide were added, the mixture was stirred at –10° C. for 30 minutes, and 28.42 g of allyl bromide in 100 ml of tetrahydrofuran were then added dropwise. The mixture was stirred at 0° C. for another 2.5 hours, and 230 ml of saturated ammonium chloride solution were then added dropwise. The resulting solid was separated off and the aqueous phase was extracted with diethyl ether. The combined organic phases were then washed with saturated ammonium chloride solution and dried, and the solvent was removed under reduced pressure. This gave 17.0 g of 2-allyl-6-chlorobenzaldehyde (89%) in the form of a dark oil.

$^1$H NMR (CDCl$_3$, δ in ppm): 3.73 (d, 2H); 5.05 (dd, 2H); 5.96 (m, 1H); 7.05–7.48 (m, 3H); 10.58 (s, 1H).

2-Allyl-6-chlorobenzaldehyde oxime 5.58 g of sodium bicarbonate were added to a solution of 4.62 g of hydroxylamine hydrochloride in 50 ml of water, and the mixture was cooled to 0° C. A solution of 9.7 g (44.32 mmol) of 2-allyl-6-chlorobenzaldehyde in 50 ml of methanol was then added dropwise, and the mixture was stirred at room temperature overnight. The methanol was subsequently removed under reduced pressure and the residue was stirred into 300 ml of water. The aqueous phase was extracted with diethyl ether and the combined organic phases were washed with saturated ammonium chloride solution and dried, and the solvent was removed. This gave 8.7 g (quantitative) of 2-allyl-6-chlorobenzaldehyde oxime in the form of a viscous oil.

$^1$H NMR (CDCl$_3$, δ in ppm): 3.58 (d, 2H); 5.02 (2d, 2H); 5.95 (m, 1H); 7.08–7.36 (m, 3H); 8.49 (s, 1H).

8-Chloro-3a,4-dihydro-3H-indeno[1,2-c]isoxazole

At room temperature, 37.0 ml of a sodium hypochlorite solution (12.5% of active chlorine) were added dropwise to a solution of 8.4 g (42.9 mmol) of 2-allyl-6-chlorobenzaldehyde oxime in 100 ml of methylene chloride, and a spatula tip of sodium acetate was added. The mixture was stirred at room temperature for 2 hours, the organic phase was separated off, the aqueous phase was extracted with methylene chloride and the combined organic phases were washed with saturated ammonium chloride solution. The organic phase was dried and the solvent was removed. This gave 7.0 g (94%) of 8-chloro-3a,4-dihydro-3H-indeno-[1,2-c]isoxazole in the form of a viscous oil.

$^1$H NMR (CDCl$_3$, δ in ppm): 2.81 (dd, 1H); 3.24 (dd, 1H); 3.78–4.03 (s, 2H); 4.78 (t, 1H); 7.23–7.41 (m, 3H).

8-Methylthio-3a,4-dihydro-3H-indeno[1,2c]isoxazole

At room temperature, 3.6 g (52.0 mmol) of sodium thiomethoxide were added to a solution of 5.0 g (25.8 mmol) of 8-chloro-3a,4-dihydro-3H-indeno-[1,2-c]isoxazole in 60 ml of N-methylpyrrolidone, and the mixture was stirred overnight. The mixture was subsequently stirred into 800 ml of water, the aqueous phase was extracted with diethyl ether, the combined organic phases were washed with saturated ammonium chloride solution and dried, and the solvent was removed. This gave 4.6 g (87%) of 8-methylthio-3a,4-dihydro-3H-indeno[1,2-c]isoxazole in the form of a dark brown solid.

$^1$H NMR (CDCl$_3$, δ in ppm): 2.54 (s, 3H); 2.78 (dd, 1H); 3.21 (dd, 1H); 3.72–3.93 (s, 2H); 4.64 (t, 1H); 7.09–7.38 (m, 3H).

5-Bromo-8-methylthio-3a,4-dihydro-3H-indeno[1,2-c]isoxazole 120 ml of sulfuric acid (98 percent strength) were cooled to 0° C., and 11.2 g (54.8 mmol) of 8-methylthio-3a,4-dihydro-3H-indeno[1,2-c]isoxazole were added a little at a time. 9.2 g (57.5 mmol) of bromine were then added dropwise, and stirring was continued at 0° C. for another 2 hours. The resulting solution was poured into 2 l of a mixture of water and ice, this mixture was stirred for 1.5 hours and the precipitated solid was filtered off with suction and then washed and dried. This gave 11.4 g (73%) of 5-bromo-8-methylthio-3a,4-dihydro-3H-indeno[1,2-c]isoxazole of a brown solid having a m.p. of 127–135° C.

$^1$H NMR (CDCl$_3$, δ in ppm): 2.53 (s, 3H); 2.71 (dd, 1H); 3.24 (dd, 1H); 3.81–4.02 (s, 2H); 4.71 (t, 1H); 7.01 (d, 1H); 7.47 (d, 1H).

5-Bromo-8-methylsulfonyl-3a,4-dihydro-3H-indeno[1,2-c]-isoxazole

A solution of 11.2 g (39.4 mmol) of 5-bromo-8-methylthio-3a,4-dihydro-3H-indeno[1,2-c]isoxazole and 1.55 g of sodium tungstate in 250 ml of toluene and 50 ml of glacial acetic acid was heated to 70° C. and mixed dropwise with 10.73 g (39 percent strength, 86.8 mmol) of hydrogen peroxide. Stirring was continued at 70° C. for another 3 hours, and a solid precipitated out. The mixture was allowed to cool to room temperature and stirred into 1 l of water, and the white solid was filtered off with suction. The organic phase of the filtrate was separated off and the aqueous phase was extracted with ethyl acetate. The combined organic phases were washed with water and dried, and the solvent was removed. This gave a viscous brown oil which was stirred with hexane/ethyl acetate (4:1). The resulting precipitate was filtered off with suction and combined with the solid obtained above. This gave 7.3 g (59%) of 5-bromo-8-methylsulfonyl-3a,4-dihydro-3H-indeno[1,2-c]-isoxazole.

$^1$H-NMR (d$^6$-DMSO, δ in ppm): 2.93 (dd, 1H); 3.23 (dd, 1H); 3.41 (s, 3H); 3.94 (dd, 1H); 4.16 (m, 1H); 4.81 (t, 1H); 7.82 (d, 1H); 8.03 (d, 1H).

(5-Hydroxy-1-methyl-1H-pyrazol-4-yl)-(8-methyl-sulfonyl-3a,4-dihydro-3H-indeno[1,2-c]isoxazol-5-yl)methanone (compound 2.1)

0.62 g (6.33 mmol) of 5-hydroxy-1-methylpyrazole, 1.75 g (12.66 mmol) of dry potassium carbonate, 1.28 g (12.67 mmol) of triethylamine and 0.22 g (0.30 mmol) of bis-(triphenylphosphane)palladium dichloride were added to a suspension of 2.0 g (6.33 mmol) of 5-bromo-8-methylsulfonyl-3a,4-dihydro-3H-indeno[1,2-c]-isoxazole in 100 ml of dioxane. In a miniautoclave, a carbon monoxide pressure of 20 bar was applied, the mixture was stirred for 5 minutes and the autoclave was vented. This procedure was repeated 3 times. The autoclave was subsequently heated to 1300° C., a carbon monoxide pressure of 20 bar was applied once more and the mixture was stirred for 24 hours. After cooling and venting, the solvent was removed, and the residue was taken up in water, adjusted to pH 11 and washed with methylene chloride. The mixture was subsequently acidified to pH 4 using 10 percent strength hydrochloric acid and extracted with methylene chloride. The combined organic phases were washed with saturated ammonium chloride solution and dried, and the solvent was removed. This gave 0.58 g (25%) of (5-hydroxy-1-methyl-1H-pyrazol-4-yl)-(8-methylsulfonyl-3a,4-dihydro-3H-indeno[1,2-c]isoxazole)-methanone in the form of a dark oil.

$^1$H NMR (CDCl$_3$, δ in ppm): 3.03 (dd, 1H); 3.42 (s, 3H); 3.40 (m, 1H); 3.51 (s, 3H); 4.05 (m, 2H); 4.85 (t, 1H); 7.57 (s, 1H); 7.92 (d, 1H); 8.22 (d, 1H).

(5-Phenylcarbonyloxy-1-methyl-1H-pyrazol-4-yl)-(8-methyl-sulfonyl-3a,4-dihydro-3H-indeno[1,2-c]isoxazol-5-yl)methanone (compound 2.2)

Under an atmosphere of protective gas, 0.18 g of triethylamine and 0.26 g (1.82 mmol) of benzoyl chloride in 10 ml of tetrahydrofuran were added at 0° C. to a suspension of 0.55 g (1.52 mmol) of (5-hydroxy-1-methyl-1H-pyrazol-4-yl)-(8-methylsulfonyl-3a,4-dihydro-3H-indeno[1,2-c]-isoxazol-5-yl)methanone in 10 ml of tetrahydrofuran. The mixture was stirred overnight at room temperature, the solvent was removed, the residue was taken up in ethyl acetate, washed with water and dried, and the solvent was removed. The crude product was purified by silica gel chromatography (mobile phase: ethyl acetate: hexane=1:1). This gave 0.22 g (31%) of (5-phenylcarbonyloxy-1-methyl-1H-pyrazol-4-yl)-(8-methylsulfonyl-3a,4-dihydro-3H-indeno[1,2-c]isoxazol-5-yl)methanone in the form of a yellow solid having a m.p. of 86–93° C.

$^1$H NMR (CDCl$_3$, δ in ppm): 3.22 (s, 3H); 3.34 (m, 2H); 3.81 (s, 3H); 3.98 (m, 2H); 4.81 (t, 1H); 7.20–8.21 (m, 8H).

2. 4-(2-Methyl-9-chloro-[1]-thiochromano[4,3-c] pyrazol-6-yl) carbonyl-5-hydroxy-1-methyl-1H-pyrazole (compound 3.1)

Methyl 2-chlorosulfonyl-4-chlorobenzoate

At from 0 to 5° C., a solution of 60.9 g (0.88 mol) of sodium nitrite in 100 ml of water was added dropwise to a solution of 139 g (0.75 mol) of methyl 2-amino-4-chlorobenzoate in 400 ml of concentrated hydrochloric acid and the mixture was stirred at 0° C. for another hour.

In a second apparatus, 3 g of copper(II) chloride, 3 g of benzyltriethylammonium chloride, 10 ml of water and 400 ml of 1,2-dichloroethane were combined and 64 g (1 mol) of sulfur dioxide were introduced.

The diazonium salt described above was subsequently added at from 10 to 150° C., and the mixture was slowly heated to 50° C. A further 54 g (0.84 mol) of sulfur dioxide were then introduced, and stirring was continued at 500° C. for another 30 minutes. After cooling, 7.4 g (0.1 mol) of chlorine gas were then introduced at room temperature, stirring was continued for 15 minutes and the phases which had formed were then separated. The organic phase was dried and the solvent was removed. This gave 207 g of methyl 2-chlorosulfonyl-4-chlorobenzoate.

$^1$H NMR (CDCl$_3$, δ in ppm): 4.00 (s, 3H); 7.75 (m, 2H); 8.18 (m, 1H)

Methyl 2-mercapto-4-chlorobenzoate

Over a period of 1.5 hours, 243.5 g (3.7 mol) of zinc powder were added a little at a time to a suspension of 205 g (0.75 mol) of methyl 2-chlorosulfonyl-4-chlorobenzoate in 1 l of concentrated hydrochloric acid and 375 g of ice. The mixture was stirred for another 3 hours and slowly heated to 70° C. After 2 hours at this temperature, the mixture was cooled. The reaction mixture was allowed to stand at room temperature for 12 hours and then extracted with ethyl acetate, the combined organic phases were dried and the solvent was removed. This gave 125.4 g (83%) of methyl 2-mercapto-4-chlorobenzoate.

$^1$H NMR (CDCl$_3$, δ in ppm): 3.95 (s, 3H); 4.88 (s, 1H); 7.10 (m, 1H); 7.30 (m, 1H); 7.96 (d, 1H).

Methyl 2-(2-hydroxycarbonyleth-1-yl)thio-4-chlorobenzoate 179.5 g (1.3 mol) of potassium carbonate and, a little at a time, 94.5 g (0.62 mol) of 3-bromopropionic acid were added to a solution of 125.4 g (0.62 mol) of methyl 2-mercapto-4-chlorobenzoate in 1.5 l of acetone, and the reaction mixture was stirred at room temperature for 12 hours. The solvent was distilled off, the residue was taken up in water and the mixture was extracted with diethyl ether. The aqueous phase was then made acidic using concentrated hydrochloric acid and the resulting precipitate was filtered off with suction and dried. This gave 150 g (88%) of methyl 2-(2-hydroxycarbonyleth-1-yl)thio-4-chlorobenzoate.

M.p.: 133 to 1360° C.

Methyl 5-chloro-4-oxothiochromane-8-carboxylate

At 70° C., 50 g (0.18 mol) of methyl 2-(2-hydroxycarbonyleth-1-yl)thio-4-chlorobenzoate were added to 500 g of polyphosphoric acid, and the mixture was stirred for a further 30 minutes. The reaction mixture was then stirred into water and the resulting precipitate was filtered off with suction and dried. This gave 41.1 g (88%) of methyl 5-chloro-4-oxothiochromane-8-carboxylate.

$^1$H NMR (CDCl$_3$, δ in ppm): 3.08 (m, 4H); 3.96 (s, 3H); 7.14 (d, 1H); 7.95 (d, 1H).

Methyl 5-chloro-3-(N,N-dimethylaminomethylidene)-4-oxothiochromane-8-carboxylate 30 g (0.078 mol) of methyl 5-chloro-4-oxothiochromane-8-carboxylate in 300 ml of N,N-dimethylformamide dimethyl acetal were refluxed for 6 hours. Volatile components were then distilled off, the residue was taken up in methylene chloride and the organic phase was washed with water. Drying and removal of the solvent gave 35.3 g (97%) of methyl 5-chloro-3-(N,N-dimethylaminomethylidene)-4-oxothiochromane-8-carboxylate.

$^1$H NMR (CDCl$_3$, δ in ppm): 3.18 (s, 6H); 3.80 (s, 2H); 3.95 (s, 3H); 7.24 (d, 1H); 7.64 (s, 1H); 7.82 (d, 1H).

2-Methyl-6-methoxycarbonyl-9-chloro-[1]-thiochromano[4,3-c]-pyrazole 1.3 g (29.2 mmol) of methylhydrazine were added dropwise to a solution of 7.0 g (22.5 mmol) of methyl 5-chloro-3-(N,N-dimethylaminomethylidene)-4-oxothiochromane-8-carboxylate in 700 ml of ethanol, and the mixture was refluxed for 2 hours. The solvent was removed and the residue was chromatographed over silica gel using ethyl acetate/cyclohexane (2:3) as mobile phase. This gave 4.0 g (60%) of 2-methyl-6-methoxycarbonyl-9-chloro-[1]-thiochromano[4,3-c]pyrazole.

$^1$H NMR (CDCl$_3$, δ in ppm): 3.76 (s, 2H); 3.95 (s, 3H); 4.00 (s, 3H); 7.24 (s, 1H); 7.36 (d, 1H); 7.70 (d, 1H).

2-Methyl-6-hydroxycarbonyl-9-chloro-[1]-thiochromano[4,3-c]pyrazole 4.0 g (13.6 mmol) of 2-methyl-6-methoxycarbonyl-9-chloro-[1]-thiochromano[4,3-c]pyrazole in 100 ml of methanol/water (1:1) were refluxed with 0.8 g (20 mmol) of sodium hydroxide for 1 hour. The organic solvent was removed under reduced pressure and the residue was extracted with ethyl acetate. The aqueous phase was acidified using concentrated hydrochloric acid and the resulting precipitate was filtered off with suction and dried. This gave 3.5 g (92%) of 2-methyl-6-hydroxycarbonyl-9-chloro-[1]-thiochromano[4,3-c]-pyrazole $^1$H NMR (CDCl$_3$, δ in ppm): 3.80 (s, 2H); 3.96 (s, 3H); 7.40 (d, 1H); 7.65 (m, 2H).

4-(2-Methyl-9-chloro-[1]-thiochromano[4,3-c]pyrazol-6-yl)-carbonyl-5-hydroxy-1-methyl-1H-pyrazole (compound 3.1)

A mixture of 0.60 g (2.1 mmol) of 2-methyl-6-hydroxycarbonyl-9-chloro-[1]-thiochromano[4,3-c]-pyrazole and 0.21 g (2.1 mmol) of N,N-dicyclohexylcarbodiimide in 20 ml of acetonitrile was stirred at room temperature overnight. The mixture was admixed with in each case 500 ml of ethyl acetate and 2% strength sodium carbonate solution, the resulting precipitate was filtered off, the organic phase was dried and the solvent was removed. The residue was then refluxed with 0.59 g (4.3 mmol) of potassium carbonate in 5 ml of 1,4-dioxane for 3 hours. After cooling, the mixture was extracted with diethyl ether and the aqueous phase was acidified to pH 3. The resulting precipitate was filtered off with suction and dried. This gave 0.14 g of 4-(2-methyl-9-chloro-[1]-thiochromano[4,3-c]pyrazol-6-yl)-carbonyl-5-hydroxy-1-methyl-1H-pyrazole.

M.p.: 168–1710° C.

3. (5-Hydroxy-1-methyl-1H-pyrazol-4-yl)-(6-methoxy-3a,4-dihydro-3H-chromeno[4,3-c]isoxazolin-9-yl)methanone (compound 2.3)

Methyl 2-hydroxy-3-formyl-4-methoxybenzoate

At from 0 to 5° C., a solution of 209.0 g (1.1 mol) of titanium tetrachloride in 150 ml of methylene chloride was added dropwise to a solution of 50.1 g (0.275 mol) of methyl 2-hydroxy-4-methoxybenzoate and 88 g (0.725 mol) of dichloromethoxymethane in 400 ml of methylene chloride, and the mixture was stirred at room temperature overnight.

The mixture was then stirred into ice-water and extracted with methylene chloride. The combined organic phases were washed with sodium bicarbonate solution, water and sodium chloride solution and dried, and the solvent was then removed. Silica gel chromatography using cyclohexane/ethyl acetate=1:1 gave 24.5 g (42%) of methyl 2-hydroxy-3-formyl-4-methoxybenzoate in the form of a colorless solid of m.p.: 123–1240° C.

$^1$H NMR (CDCl$_3$, δ in ppm): 3.92 (s, 3H); 3.98 (s, 3H); 6.49 (d, 1H); 8.19 (d, 1H); 10.39 (s, 1H).

Methyl 2-allyloxy-3-formyl-4-methoxybenzoate

At room temperature, 23.2 g (0.192 mol) of allyl bromide were added dropwise to a mixture of 21.0 g (0.375 mol) of potassium hydroxide and 20.2 g (0.096 mol) of methyl 2-hydroxy-3-formyl-4-methoxybenzoate in 500 ml of dimethyl sulfoxide, and the mixture was stirred at room temperature for 4 hours. The mixture was subsequently stirred into 1.5 l of 3% strength aqueous hydrochloric acid and extracted with ethyl acetate. The combined organic phases were washed with water and dried, and the solvent was removed. Silica gel chromatography using cyclohexane/ethyl acetate=1:2 gave 7.7 g (36%) of methyl 2-allyloxy-3-formyl-4-methoxybenzoate in the form of a yellowish oil.

$^1$H NMR (CDCl$_3$, δ in ppm): 3.86 (s, 3H); 3.93 (s, 3H); 4.58 (d, 2H); 5.32 (d, 1H); 5.39 (d, 1H); 6.15 (m, 1H); 6.79 (d, 1H); 8.04 (d, 1H); 10.41 (s, 1H).

6-Methoxy-9-methoxycarbonyl-3a,4-dihydro-3H-chromeno[4,3-c]isoxazoline

Step a)

At room temperature, 4.6 g (18.4 mmol) of methyl 2-allyloxy-3-formyl-4-methoxybenzoate in 70 ml of methanol were added dropwise to a solution of 2.25 g (32.3 mmol) of hydroxylammonium chloride and 2.7 g of pyridine in 70 ml of water. The mixture was stirred at room temperature overnight, 150 ml of water were added, the mixture was extracted with methylene chloride, the combined organic phases were washed with 3% strength aqueous hydrochloric acid and dried, and the solvent was removed. The resulting oxime has a melting point of 126–1290° C.

Step b)

This oxime was reacted further without any further purification by dissolving it in 40 ml of methylene chloride, followed by dropwise addition of 15.0 ml (25.0 mmol) of sodium hypochlorite solution (12.5% of active chlorine). A spatula tip of sodium acetate was added and the mixture was stirred at room temperature for 12 hours. The organic phase was separated off, the aqueous phase was extracted with methylene chloride, the combined organic phases were washed with water and dried, and the solvent was removed. Silica gel chromatography using cyclohexane/ethyl acetate=1:1 gave 2.2 g (49%) of 6-methoxy-9-methoxycarbonyl-3a,4-dihydro-3H-chromeno[4,3-c]-isoxazoline in the form of a colorless solid of m.p: 199–203° C.

$^1$H NMR (CDCl$_3$, δ in ppm): 3.84 (s, 3H); 3.98 (s, 3H); 3.8–4.0 (m, 2H); 4.16 (dt, 1H); 4.63 (t, 1H); 4.84 (dd, 1H); 6.61 (d, 1H); 7.93 (d, 1H).

6-Methoxy-9-hydroxycarbonyl-3a,4-dihydro-3H-chromeno[4,3-c]isoxazoline

At room temperature, a solution of 0.8 g (20.0 mmol) of sodium hydroxide in 7 ml of water was added dropwise to a solution of 2.1 g (8.0 mmol) of 6-methoxy-9-methoxycarbonyl-3a,4-dihydro-3H-chromeno[4,3-c]isoxazoline in 40 ml of methanol, and the mixture was refluxed for 6 hours. After cooling, the solvent was removed and the residue was taken up in about 50 ml of water and washed with methylene chloride. The aqueous phase was subsequently acidified using 10% strength hydrochloric acid (pH=1–2), and the precipitate was filtered off with suction, washed with water and dried at 600° C. This gave 1.7 g (86%) of 6-methoxy-9-hydroxycarbonyl-3a,4-dihydro-3H-chromeno[4,3-c]-isoxazoline in the form of colorless crystals.

$^1$H NMR (CDCl$_3$, δ in ppm): 3.73 (dd, 1H); 3.89 (s, 3H); 3.84–3.95 (m, 1H); 4.11 (dd, 1H); 4.54 (dd, 1H); 4.79 (dd, 1H); 6.61 (d, 1H); 7.81 (d, 1H).

(5-Hydroxy-1-methyl-1H-pyrazol-4-yl)-(6-methoxy-3a,4-dihydro-3H-chromeno[4,3-c]isoxazolin-9-yl) methanone (compound 2.3)

Step a)

At room temperature, 0.26 g (2.2 mmol) of thionyl chloride and a drop of dimethylformamide were added to a solution of 0.50 g (2.0 mmol) of 6-methoxy-9-hydroxycarbonyl-3a,4-dihydro-3H-chromeno[(4,3-c)]isoxazoline in 30 ml of carbon tetrachloride, and the mixture was stirred at 40–50° C. for 3 hours. The solvent was subsequently removed under reduced pressure. This gave, in quantitative yield, 6-methoxy-9-chloroformyl-3a,4-dihydro-3H-chromeno[4,3-c] isoxazoline (0.54 g) as a brownish oil.

Step b)

0.54 g (2 mmol) of 6-methoxy-9-chloroformyl-3a,4-dihydro-3H-chromeno[4,3-c]isoxazoline was dissolved in 30 ml of acetonitrile and, at 0° C., added dropwise to a solution of 0.2 g (2.0 mmol) of 1-methyl-5-hydroxypyrazole and 0.6 g (6.0 mmol) of triethylamine in 20 ml of acetonitrile. The mixture was stirred at room temperature overnight, the solvent was removed, and the residue was taken up in methylene chloride and washed with water. The solution was dried and the solvent was distilled off. The residue was dissolved in 30 ml of dioxane and admixed with 0.42 g (3.0 mmol) of potassium carbonate, and the mixture was refluxed for 7 hours. After cooling, the solvent was distilled off under reduced pressure, the residue was taken up in water and the solution was adjusted to pH=1 using 10% strength hydrochloric acid. The solution was extracted with methylene chloride, the combined organic phases were dried and the solvent was subsequently removed. This gave 0.45 g (68%) of (5-hydroxy-1-methyl-1H-pyrazol-4-yl)-(6-methoxy-3a,4-dihydro-3H-chromeno[4,3-c]isoxazolin-9-yl)methanone of m.p. 236–238° C.

$^1$H NMR (CDCl$_3$, δ in ppm): 3.66 (s, 3H); 3.84–4.2 (m, 2H); 4.02 (s, 3H); 4.12 (dd, 1H); 4.63–4.77 (m, 2H); 6.68 (d, 1H); 7.24 (s, 1H); 7.61 (d, 1H).

4. [5-Hydroxy-1-(1,1-dimethyleth-1-yl)-1H-pyrazol-4-yl]-[6-methoxy-3a,4-dihydro-3H-chromeno[4,3-c] isoxazolin-9-yl]methanone (compound 2.4)

0.54 g (2 mmol) of 6-methoxy-9-chloroformyl-3a,4-dihydro-3H-chromeno[4,3-c]-isoxazoline was dissolved in 30 ml of acetonitrile and, at 0° C., added dropwise to a solution of 0.28 g (2.0 mmol) of 1-(1,1-dimethyleth-1-yl)-5-hydroxy-1H-pyrazole and 0.6 g (6.0 mmol) of triethylamine in 20 ml of acetonitrile. The mixture was stirred at room temperature overnight, the solvent was removed, and the residue was taken up in methylene chloride and washed with water. The solution was dried, and the solvent was distilled off. The residue was dissolved in 30 ml of dioxane and admixed with 0.42 g (3.0 mmol) of potassium carbonate, and the mixture was refluxed for 7 hours. After cooling, the solvent was distilled off under reduced pressure, the residue was taken up in water and the solution was adjusted to pH=1 using 10% strength hydrochloric acid. The solution was extracted with methylene chloride, the combined organic phases were dried, and the solvent was subsequently removed. This gave 0.3 g (40%) of [5-hydroxy-1-(1,1-dimethyleth-1-yl)-1H-pyrazol-4-yl]-[6-methoxy-3a,4-dihydro-3H-chromeno[4,3-c]isoxazolin-9-yl]methanone having a melting point of 223° C.–2250° C.

$^1$H NMR (CDCl$_3$, δ in ppm): 1.64 (s, 9H); 3.8–4.2 (m, 6H); 4.6–4.8 (m, 2H); 6.68 (d, 1H); 7.44 (s, 1H); 7.62 (d, 1H).

In addition to the compounds above, other tricyclic benzoylpyrazole derivatives of the formula I which were prepared or are preparable in a similar manner are listed in Tables 2 to

TABLE 2

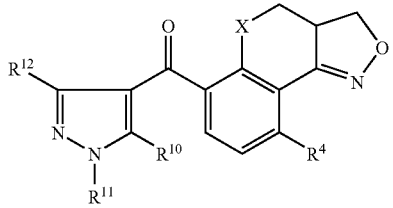

Ia where 1 = 0, R$^5$ = H,
Y together with the two carbons to which it is attached forms the following isoxazoline:

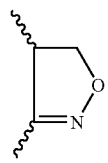

| No. | X | R$^4$ | R$^{10}$ | R$^{11}$ | R$^{12}$ | physical data (m.p.[° C.]; $^1$H NMR [ppm]) |
|---|---|---|---|---|---|---|
| 2.1 | Bond | SO$_2$CH$_3$ | OH | CH$_3$ | H | 3.03(dd, 1H); 3.42(s, 3H); 3.51(s, 3H); 4.05(m, 2H); 4.85(t, 1H); 7.57(s, 1H); 7.92(d, 1H); 8.22(d, 1H) |
| 2.2 | Bond | SO$_2$CH$_3$ | OCOC$_6$H$_5$ | CH$_3$ | H | 3.22(s, 3H); 3.34(m, 2H); 3.81(s, 3H); 3.98(m, 2H); 4.81(t, 1H); 7.20–8.21(m, 8H); |
| 2.3 | O | OCH$_3$ | OH | CH$_3$ | H | 236–238 |
| 2.4 | O | OCH$_3$ | OH | C(CH$_3$)$_3$ | H | 223–225 |
| 2.5 | O | OCH$_3$ | OCO(3-F—C$_6$H$_4$) | CH$_3$ | H | oil |

TABLE 3

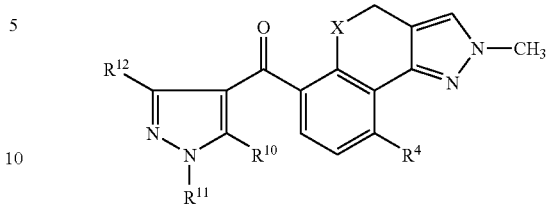

Ia where R$^5$ = H,
Y together with the two carbons to which it is attached forms the following methyl-substituted pyrazole:

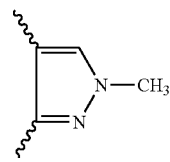

| No. | X | R$^4$ | R$^{10}$ | R$^{11}$ | R$^{12}$ | physical data (m.p.[° C.]) |
|---|---|---|---|---|---|---|
| 3.1 | S | Cl | OH | CH$_3$ | H | 168–171 |
| 3.2 | S | Cl | OH | CH$_2$CH$_3$ | H | 115 |
| 3.3 | S | SCH$_3$ | OH | CH$_3$ | H | 245 |
| 3.4 | S | SCH$_3$ | OH | CH$_2$CH$_3$ | H | 222 |

TABLE 4

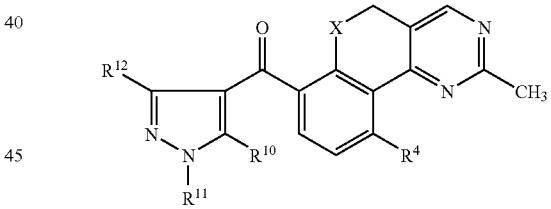

Ia where R$^5$ = H,
Y together with the two carbons to which it is attached forms the following methyl-substituted pyrimidine:

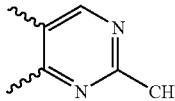

| No. | X | R$^4$ | R$^{10}$ | R$^{11}$ | R$^{12}$ | physical data (m.p.[° C.]; $^1$H NMR [ppm]) |
|---|---|---|---|---|---|---|
| 4.1 | S | Cl | OH | CH$_3$ | H | 180° C. |
| 4.2 | S | Cl | OH | CH$_2$CH$_3$ | H | 112° C. |

TABLE 5

| Nr. | X | R⁴ | R¹⁰ | R¹¹ | R¹² | physical data (m.p.[° C.]; ¹H NMR [ppm]) |
|---|---|---|---|---|---|---|
| 5.1 | O | SCH₃ | OH | CH₃ | H | 201 |

The compounds of the formula I and their agriculturally useful salts are suitable, both in the form of isomer mixtures and in the form of the pure isomers, as herbicides. The herbicidal compositions comprising compounds of the formula I control vegetation on non-crop areas very efficiently, especially at high rates of application. They act against broad-leaved weeds and grass weeds in crops such as wheat, rice, maize, soya and cotton without causing any significant damage to the crop plants. This effect is mainly observed at low rates of application.

Depending on the application method in question, the compounds of the formula I, or herbicidal compositions comprising them, can additionally be employed in a further number of crop plants for eliminating undesirable plants. Examples of suitable crops are the following:

*Allium cepa, Ananas comosus, Arachis hypogaea, Asparagus officinalis, Beta vulgaris* spec. *altissima, Beta vulgaris* spec. *rapa, Brassica napus* var. *napus, Brassica napus* var. *napobrassica, Brassica rapa* var. *silvestris, Camellia sinensis, Carthamus tinctorius, Carya illinoinensis, Citrus limon, Citrus sinensis, Coffea arabica* (*Coffea canephora, Coffea liberica*), *Cucumis sativus, Cynodon dactylon, Daucus carota, Elaeis guineensis, Fragaria vesca, Glycine max, Gossypium hirsutum,* (*Gossypium arboreum, Gossypium herbaceum, Gossypium vitifolium*), *Helianthus annuus, Hevea brasiliensis, Hordeum vulgare, Humulus lupulus, Ipomoea batatas, Juglans regia, Lens culinaris, Linum usitatissimum, Lycopersicon lycopersicum, Malus* spec., *Manihot esculenta, Medicago sativa, Musa* spec., *Nicotiana tabacum* (*N.rustica*), *Olea europaea, Oryza sativa, Phaseolus lunatus, Phaseolus vulgaris, Picea abies, Pinus* spec., *Pisum sativum, Prunus avium, Prunus persica, Pyrus communis, Ribes sylvestre, Ricinus communis, Saccharum officinarum, Secale cereale, Solanum tuberosum, Sorghum bicolor* (*s. vulgare*), *Theobroma cacao, Trifolium pratense, Triticum aestivum, Triticum durum, Vicia faba, Vitis vinifera* and *Zea mays.*

In addition, the compounds of the formula I may also be used in crops which tolerate the action of herbicides owing to breeding, including genetic engineering methods.

The compounds of the formula I, or the herbicidal compositions comprising them, can be used for example in the form of ready-to-spray aqueous solutions, powders, suspensions, also highly-concentrated aqueous, oily or other suspensions or dispersions, emulsions, oil dispersions, pastes, dusts, materials for broadcasting, or granules, by means of spraying, atomizing, dusting, spreading or watering. The use forms depend on the intended purpose; in any case, they should guarantee the finest possible distribution of the active compounds according to the invention.

The herbicidal compositions comprise a herbicidally effective amount of at least one compound of the formula I or an agriculturally useful salt of I and auxiliaries which are customarily used for formulating crop protection agents.

Suitable for use as inert auxiliaries are essentially the following:

mineral oil fractions of medium to high boiling point, such as kerosene and diesel oil, furthermore coal-tar oils and oils of vegetable or animal origin, aliphatic, cyclic and aromatic hydrocarbons, for example paraffin, tetrahydronaphthalene, alkylated naphthalenes and their derivatives, alkylated benzenes or their derivatives, alcohols such as methanol, ethanol, propanol, butanol and cyclohexanol, ketones such as cyclohexanone, strongly polar solvents, for example amines such as N-methylpyrrolidone, and water.

Aqueous use forms can be prepared from emulsion concentrates, suspensions, pastes, wettable powders or water-dispersible granules by adding water. To prepare emulsions, pastes or oil dispersions, the tricyclic benzoylpyrazole derivatives of the formula I, either as such or dissolved in an oil or solvent, can be homogenized in water by means of a wetting agent, tackifier, dispersant or emulsifier. Alternatively, it is possible to prepare concentrates comprising active compound, wetting agent, tackifier, dispersant or emulsifier and, if desired, solvent or oil, which are suitable for dilution with water.

Suitable surfactants are the alkali metal salts, alkaline earth metal salts and ammonium salts of aromatic sulfonic acids, e.g. ligno-, phenol-, naphthalene- and dibutylnaphthalenesulfonic acid, and of fatty acids, alkyl- and alkylarylsulfonates, alkyl sulfates, lauryl ether sulfates and fatty alcohol sulfates, and salts of sulfated hexa-, hepta- and octadecanols, and also of fatty alcohol glycol ethers, condensates of sulfonated naphthalene and its derivatives with formaldehyde, condensates of naphthalene or of the naphthalenesulfonic acids with phenol and formaldehyde, polyoxyethylene octylphenol ether, ethoxylated isooctyl-, octyl- or nonylphenol, alkylphenyl or tributylphenyl polyglycol ether, alkylaryl polyether alcohols, isotridecyl alcohol, fatty alcohol/ethylene oxide condensates, ethoxylated castor oil, polyoxyethylene alkyl ethers or polyoxypropylene alkyl ethers, lauryl alcohol polyglycol ether acetate, sorbitol esters, lignin-sulfite waste liquors or methylcellulose.

Powders, materials for broadcasting and dusts can be prepared by mixing or grinding the active compounds together with a solid carrier.

Granules, e.g. coated granules, impregnated granules and homogeneous granules, can be prepared by binding the active compounds to solid carriers. Solid carriers are mineral earths such as silicas, silica gels, silicates, talc, kaolin, limestone, lime, chalk, bole, loess, clay, dolomite, diatomaceous earth, calcium sulfate, magnesium sulfate and magnesium oxide, ground synthetic materials, fertilizers such as ammonium sulfate, ammonium phosphate, ammonium nitrate and ureas, and products of vegetable origin, such as cereal meal, tree bark meal, wood meal and nutshell meal, cellulose powders, or other solid carriers.

The concentrations of the compounds of the formula I in the ready-to-use preparations can be varied within wide ranges. In general, the formulations comprise approximately from 0.001 to 98% by weight, preferably 0.01 to 95% by weight, of at least one active compound. The active compounds are employed in a purity of from 90% to 100%, preferably 95% to 100% (according to NMR spectrum).

The following formulation examples illustrate the preparation of such formulations:

I. 20 parts by weight of the compound No. 2.2 are dissolved in a mixture composed of 80 parts by weight of alkylated benzene, 10 parts by weight of the adduct of from 8 to 10 mol of ethylene oxide to 1 mol of oleic acid N-monoethanolamide, 5 parts by weight of calcium salt of dodecylbenzenesulfonic acid and 5 parts by weight of the adduct of 40 mol of ethylene oxide to 1 mol of castor oil. Pouring the solution into 100,000 parts by weight of water and finely distributing it therein gives an aqueous dispersion which comprises 0.02% by weight of the active compound.

II. 20 parts by weight of the compound No. 3.1 are dissolved in a mixture composed of 40 parts by weight of cyclohexanone, 30 parts by weight of isobutanol, 20 parts by weight of the adduct of 7 mol of ethylene oxide to 1 mol of isooctylphenol and 10 parts by weight of the adduct of 40 mol of ethylene oxide to 1 mol of castor oil. Pouring the solution into 100,000 parts by weight of water and finely distributing it therein gives an aqueous dispersion which comprises 0.02% by weight of the active compound.

III. 20 parts by weight of the compound No. 2.3 are dissolved in a mixture composed of 25 parts by weight of cyclohexanone, 65 parts by weight of a mineral oil fraction of boiling point 210 to 280° C. and 10 parts by weight of the adduct of 40 mol of ethylene oxide to 1 mol of castor oil. Pouring the solution into 100,000 parts by weight of water and finely distributing it therein gives an aqueous dispersion which comprises 0.02% by weight of the active compound.

IV. 20 parts by weight of the compound No. 2.4 are mixed thoroughly with 3 parts by weight of the sodium salt of diisobutylnaphthalenesulfonic acid, 17 parts by weight of the sodium salt of a lignosulfonic acid from a sulfite waste liquor and 60 parts by weight of pulverulent silica gel, and the mixture is ground in a hammer mill. Finely distributing the mixture in 20,000 parts by weight of water gives a spray mixture which comprises 0.1% by weight of the active compound.

V. 3 parts by weight of the compound No. 2.3 are mixed with 97 parts by weight of finely divided kaolin. This gives a dust which comprises 3% by weight of the active compound.

VI. 20 parts by weight of the compound No. 2.4 are mixed intimately with 2 parts by weight of calcium salt of dodecylbenzenesulfonic acid, 8 parts by weight of fatty alcohol polyglycol ether, 2 parts by weight of sodium salt of a phenol/urea/formaldehyde condensate and 68 parts by weight of a paraffinic mineral oil. This gives a stable oily dispersion.

VII. 1 part by weight of the compound No. 2.2 is dissolved in a mixture composed of 70 parts by weight of cyclohexanone, 20 parts by weight of ethoxylated isooctylphenol and 10 parts by weight of ethoxylated castor oil. This gives a stable emulsion concentrate.

VIII. 1 part by weight of the compound No. 3.1 is dissolved in a mixture composed of 80 parts by weight of cyclohexanone and 20 parts by weight of Wettol® EM 31 (=nonionic emulsifier based on ethoxylated castor oil). This gives a stable emulsion concentrate.

The compounds of the formula I or the herbicidal compositions can be applied pre- or post-emergence. If the active compounds are less well tolerated by certain crop plants, application techniques may be used in which the herbicidal compositions are sprayed, with the aid of the spraying equipment, in such a way that as far as possible they do not come into contact with the leaves of the sensitive crop plants, while the active compounds reach the leaves of undesirable plants growing underneath, or the bare soil surface (post-directed, lay-by).

The rates of application of the compound of the formula I are from 0.001 to 3.0, preferably 0.01 to 1.0, kg/ha of active substance (a.s.), depending on the control target, the season, the target plants and the growth stage.

To widen the spectrum of action and to achieve synergistic effects, the tricyclic benzylpyrazole derivatives of the formula I may be mixed with a large number of representatives of other herbicidal or growth-regulating active compound groups and applied concomitantly. Suitable components for mixtures are, for example, 1,2,4-thiadiazoles, 1,3, 4-thiadiazoles, amides, aminophosphoric acid and its derivatives, aminotriazoles, anilides, aryloxy-/heteroaryloxyalkanoic acids and their derivatives, benzoic acid and its derivatives, benzothiadiazinones, 2-aroyl-1,3-cyclohexanediones, heteroaryl aryl ketones, benzylisoxazolidinones, meta-$CF_3$-phenyl derivatives, carbamates, quinoline carboxylic acid and its derivatives, chloroacetanilides, cyclohexenone oxime ether derivatives, diazines, dichloropropionic acid and its derivatives, dihydrobenzofurans, dihydrofuran-3-ones, dinitroanilines, dinitrophenols, diphenyl ethers, dipyridyls, halocarboxylic acids and their derivatives, ureas, 3-phenyluracils, imidazoles, imidazolinones, N-phenyl-3,4,5,6-tetrahydrophthalimides, oxadiazoles, oxiranes, phenols, aryloxy- and hetaryloxyphenoxypropionic esters, phenylacetic acid and its derivatives, 2-phenylpropionic acid and its derivatives, pyrazoles, phenylpyrazoles, pyridazines, pyridinecarboxylic acid and its derivatives, pyrimidyl ethers, sulfonamides, sulfonylureas, triazines, triazinones, triazolinones, triazolecarboxamides and uracils.

It may furthermore be advantageous to apply the compounds of the formula I, alone or in combination with other herbicides, in the form of a mixture with other crop protection agents, for example together with agents for controlling pests or phytopathogenic fungi or bacteria. Also of interest is the miscibility with mineral salt solutions, which are employed for treating nutritional and trace element deficiencies. Non-phytotoxic oils and oil concentrates may also be added.

Use Examples

The herbicidal activity of the tricyclic benzylpyrazole derivatives of the formula I was demonstrated by the following greenhouse experiments:

The culture containers used were plastic pots containing loamy sand with approximately 3.0% of humus as the substrate. The seeds of the test plants were sown separately for each species.

For the pre-emergence treatment, the active compounds, which had been suspended or emulsified in water, were applied directly after sowing by means of finely distributing nozzles. The containers were irrigated gently to promote germination and growth and subsequently covered with transparent plastic hoods until the plants had rooted. This cover causes uniform germination of the test plants, unless this was adversely affected by the active compounds.

For post-emergence treatment, the test plants were first grown to a plant height of from 3 to 15 cm, depending on the plant habit, and only then treated with the active compounds which had been suspended or emulsified in water. For this purpose, the test plants were either sown directly and grown in the same containers, or they were first grown separately as seedlings and transplanted into the test containers a few days prior to the treatment. The application rate for the post-emergence treatment was 0.5 or 0.25 kg of a.s./ha.

Depending on the species, the plants were kept at 10–25° C. or 20–35° C. The test period extended over 2 to 4 weeks. During this time, the plants were tended, and their response to the individual treatments was evaluated.

Evaluation was carried out using a scale from 0 to 100. 100 means no emergence of the plants, or complete destruction of at least the above-ground parts, and 0 means no damage, or normal course of growth.

The plants used in the greenhouse trials were of the following species:

| Scientific Name | Common Name |
| --- | --- |
| Chenopodium album | lambsquarters (goosefoot) |
| Echinochloa crusgalli | barnyardgrass |
| Setaria viridis | green foxtail |
| Solanum nigrum | black nightshade |
| Veronica ssp. | speadwell |

At application rates of 0.5 or 0.25 kg/ha, the compound 2.2 shows very good activity against the abovementioned undesired broad-leaved weeds and weed grasses when applied by the post-emergence method.

We claim:

1. A tricyclic benzoylpyrazole compound of formula I

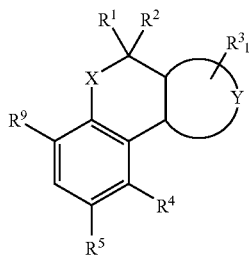

where:

X is a bond;

Y together with the two carbons to which it is attached forms a 1,2-isoxazole ring which is saturated, partially saturated or unsaturated;

$R^1$, $R^2$, $R^6$, $R^7$ are hydrogen, $C_1$–$C_6$-alkyl, $C_1$–$C_6$-haloalkyl, $C_1$–$C_6$-alkoxy or $C_1$–$C_6$-haloalkoxy;

$R^3$ is halogen, $C_1$–$C_6$-alkyl, $C_1$–$C_6$-haloalkyl, $C_1$–$C_6$-alkoxy or $C_1$–$C_6$-haloalkoxy;

$R^4$ is hydrogen, nitro, halogen, cyano, $C_1$–$C_6$-alkyl, $C_1$–$C_6$-haloalkyl, $C_1$–$C_6$-alkoxy, $C_1$–$C_6$-haloalkoxy, $C_1$–$C_6$-alkylthio, $C_1$–$C_6$-haloalkylthio, $C_1$–$C_6$-alkylsulfinyl, $C_1$–$C_6$-haloalkylsulfinyl, $C_1$–$C_6$-alkylsulfonyl, $C_1$–$C_6$-haloalkylsulfonyl, aminosulfonyl, N-($C_1$–$C_6$-alkyl)aminosulfonyl, N,N-di($C_1$–$C_6$-alkyl)aminosulfonyl, N-($C_1$–$C_6$-alkylsulfonyl)amino, N-($C_1$–$C_6$-haloalkylsulfonyl)amino, N-($C_1$–$C_6$-alkyl)-N-($C_1$–$C_6$-alkylsulfonyl)amino or N-($C_1$–$C_6$-alkyl)-N-($C_1$–$C_6$-haloalkylsulfonyl)amino;

$R^5$ is hydrogen, $C_1$–$C_6$-alkyl or halogen;

$R^8$ is hydrogen, $C_1$–$C_6$-alkyl, $C_1$–$C_6$-haloalkyl, $C_1$–$C_6$-alkylcarbonyl, formyl, $C_1$–$C_6$-alkoxycarbonyl, $C_1$–$C_6$-haloalkoxycarbonyl, $C_1$–$C_6$-alkylsulfonyl or $C_1$–$C_6$-haloalkylsulfonyl;

l is 0, 1 or 2;

$R^9$ is a radical IIa

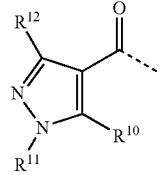

where $R^{10}$ is hydroxyl, mercapto, halogen, $OR^{13}$, $SR^{13}$, $SO_2R^{14}$, $NR^{15}R^{16}$ or N-bonded heterocyclyl, where the heterocyclyl radical may be partially or fully halogenated and/or may carry one to three of the following radicals: nitro, cyano, $C_1$–$C_4$-alkyl, $C_1$–$C_4$-haloalkyl, $C_1$–$C_4$-alkoxy or $C_1$–$C_4$-haloalkoxy;

$R^{11}$ is hydrogen, $C_1$–$C_6$-alkyl, $C_1$–$C_6$-haloalkyl, $C_3$–$C_6$-cycloalkyl, hydroxyl, $C_1$–$C_6$-alkoxy or $C_1$–$C_6$-haloalkoxy;

$R^{12}$ is hydrogen, halogen, $C_1$–$C_6$-alkyl, $C_1$–$C_6$-haloalkyl, hydroxyl, $C_1$–$C_6$-alkoxy, $C_1$–$C_6$-haloalkoxy, $C_1$–$C_6$-alkylthio or $C_1$–$C_6$-haloalkylthio;

$R^{13}$ is $C_1$–$C_6$-alkyl, $C_3$–$C_6$-alkenyl, $C_3$–$C_6$-haloalkenyl, $C_3$–$C_6$-alkynyl, $C_3$–$C_6$-haloalkynyl, $C_3$–$C_6$-cycloalkyl, $C_1$–$C_{20}$-alkylcarbonyl, $C_2$–$C_{20}$-alkenylcarbonyl, $C_2$–$C_6$-alkynylcarbonyl, $C_3$–$C_6$-Cycloalkylcarbonyl, $C_1$–$C_6$-alkoxycarbonyl, $C_3$–$C_6$-alkenyloxycarbonyl, $C_3$–$C_6$-alkynyloxycarbonyl, $C_1$–$C_6$-alkylthiocarbonyl, $C_1$–$C_6$-alkylaminocarbonyl, $C_3$–$C_6$-alkenylaminocarbonyl, $C_3$–$C_6$-alkynylaminocarbonyl, N,N-di($C_1$–$C_6$-alkyl)aminocarbonyl, N-($C_3$–$C_6$-alkenyl)-N-($C_1$–$C_6$-alkyl)aminocarbonyl, N-($C_3$–$C_6$-alkynyl)-N-($C_1$–$C_6$-alkyl)aminocarbonyl, N-($C_1$–$C_6$-alkoxy)-N-($C_1$–$C_6$-alkyl)aminocarbonyl, N-($C_3$–$C_6$-alkenyl)-N-($C_1$–$C_6$-alkoxy)aminocarbonyl, N-($C_3$–$C_6$-alkynyl)-N-($C_1$–$C_6$-alkoxy)aminocarbonyl, di($C_1$–$C_6$-alkyl) aminothiocarbonyl, $C_1$–$C_6$-alkylcarbonyl-$C_1$–$C_6$-alkyl, $C_1$–$C_6$-alkoxyimino-$C_1$–$C_6$-alkyl, N-($C_1$–$C_6$-alkylamino)imino-$C_1$–$C_6$-alkyl or N,N-di($C_1$–$C_6$-alkylamino)imino-$C_1$–$C_6$-alkyl, where the abovementioned alkyl, cycloalkyl and alkoxy radicals may be partially or fully halogenated and/or may carry one to three of the following groups:

cyano, $C_1$–$C_4$-alkoxy, $C_1$–$C_4$-alkylthio, di($C_1$–$C_4$-alkyl)amino, $C_1$–$C_4$-alkylcarbonyl, $C_1$–$C_4$-alkoxycarbonyl, $C_1$–$C_4$-alkoxy-$C_1$–$C_4$-alkoxycarbonyl, di($C_1$–$C_4$-alkyl)amino-$C_1$–$C_4$-alkoxycarbonyl, hydroxycarbonyl, $C_1$–$C_4$-alkylaminocarbonyl, di($C_1$–$C_4$-alkyl)aminocarbonyl, aminocarbonyl, $C_1$–$C_4$-alkylcarbonyloxy or $C_3$–$C_6$-cycloalkyl;

is phenyl, heterocyclyl, phenyl-$C_1$–$C_6$-alkyl, heterocyclyl-$C_1$–$C_6$-alkyl, phenylcarbonyl-$C_1$–$C_6$-alkyl, heterocyclylcarbonyl-$C_1$–$C_6$-alkyl, phenylcarbonyl, heterocyclylcarbonyl, phenoxycarbonyl, phenyloxythiocarbonyl, heterocyclyloxycarbonyl, heterocyclyloxythiocarbonyl, phenylaminocarbonyl, N-($C_1$–$C_6$-alkyl)-N-(phenyl)aminocarbonyl, heterocyclylaminocarbonyl, N-($C_1$–$C_6$-alkyl)-N-(heterocyclyl) aminocarbonyl, phenyl-$C_2$–$C_6$-alkenylcarbonyl or heterocyclyl-$C_2$–$C_6$-alkenylcarbonyl, where the phenyl and the heterocyclyl radical of the 18 lastmentioned substituents may be partially or fully halogenated and/or may carry one to three of the following radicals:

nitro, cyano, $C_1$–$C_4$-alkyl, $C_1$–$C_4$-haloalkyl, $C_1$–$C_4$-alkoxy, $C_1$–$C_4$-haloalkoxy, heterocyclyl or N-bonded heterocyclyl, where the two lastmentioned substituents for their part may be partially or fully halogenated and/or may carry one to three of the following radicals:

nitro, cyano, $C_1$–$C_4$-alkyl, $C_1$–$C_4$-haloalkyl, $C_1$–$C_4$-alkoxy or $C_1$–$C_4$-haloalkoxy;

$R^{14}$ is $C_1$–$C_6$-alkyl, $C_3$–$C_6$-alkenyl, $C_3$–$C_6$-haloalkenyl, $C_3$–$C_6$-alkynyl, $C_3$–$C_6$-haloalkynyl, $C_3$–$C_6$-cycloalkyl, $C_1$–$C_6$-alkoxy, di($C_1$–$C_6$-alkyl)amino or di($C_1$–$C_6$-haloalkyl)amino, where the abovementioned alkyl, cycloalkyl and alkoxy radicals may be partially or fully halogenated and/or may carry one to three of the following groups:

cyano, $C_1$–$C_4$-alkoxy, $C_1$–$C_4$-alkylthio, di($C_1$–$C_4$-alkyl)amino, $C_1$–$C_4$-alkylcarbonyl, $C_1$–$C_4$-alkoxycarbonyl, $C_1$–$C_4$-alkoxy-$C_1$–$C_4$-alkoxycarbonyl, di($C_1$–$C_4$-alkyl)amino-$C_1$–$C_4$-alkoxycarbonyl, hydroxycarbonyl, $C_1$–$C_4$-alkylaminocarbonyl, di($C_1$–$C_4$-alkyl)aminocarbonyl, aminocarbonyl, $C_1$–$C_4$-alkylcarbonyloxy or $C_3$–$C_6$-cycloalkyl;

is phenyl, heterocyclyl, phenyl-$C_1$–$C_6$-alkyl, heterocyclyl-$C_1$–$C_6$-alkyl, phenoxy, heterocyclyloxy, where the phenyl and the heterocyclyl radical of the lastmentioned substituents may be partially or fully halogenated and/or may carry one to three of the following radicals:

nitro, cyano, $C_1$–$C_4$-alkyl, $C_1$–$C_4$-haloalkyl, $C_1$–$C_4$-alkoxy or $C_1$–$C_4$-haloalkoxy;

$R^{15}$ is $C_1$–$C_6$-alkyl, $C_3$–$C_6$-alkenyl, $C_3$–$C_6$-haloalkenyl, $C_3$–$C_6$-alkynyl, $C_3$–$C_6$-haloalkynyl, $C_3$–$C_6$-cycloalkyl, $C_1$–$C_6$-alkoxy, $C_3$–$C_6$-alkenyloxy, $C_3$–$C_6$-alkynyloxy, di($C_1$–$C_6$-alkyl)amino or $C_1$–$C_6$-alkylcarbonylamino, where the abovementioned alkyl, cycloalkyl and alkoxy radicals may be partially or fully halogenated and/or may carry one to three radicals of the following group:

cyano, $C_1$–$C_4$-alkoxy, $C_1$–$C_4$-alkylthio, di($C_1$–$C_4$-alkyl)amino, $C_1$–$C_4$-alkylcarbonyl, $C_1$–$C_4$-alkoxycarbonyl, $C_1$–$C_4$-alkoxy-$C_1$–$C_4$-alkoxycarbonyl, di($C_1$–$C_4$-alkyl)amino-$C_1$–$C_4$-alkoxycarbonyl, hydroxycarbonyl, $C_1$–$C_4$-alkylaminocarbonyl, di($C_1$–$C_4$-alkyl)aminocarbonyl, aminocarbonyl, $C_1$–$C_4$-alkylcarbonyloxy or $C_3$–$C_6$-cycloalkyl;

is phenyl, heterocyclyl, phenyl-$C_1$–$C_6$-alkyl or heterocyclyl-$C_1$–$C_6$-alkyl, where the phenyl or heterocyclyl radical of the four lastmentioned substituents may be partially or fully halogenated and/or may carry one to three of the following radicals:

nitro, cyano, $C_1$–$C_4$-alkyl, $C_1$–$C_4$-haloalkyl, $C_1$–$C_4$-alkoxy or $C_1$–$C_4$-haloalkoxy;

$R^{16}$ is $C_1$–$C_6$-alkyl, $C_3$–$C_6$-alkenyl, $C_3$–$C_6$-alkynyl or $C_1$–$C_6$-alkylcarbonyl;

or an agriculturally useful salt thereof.

2. The tricyclic benzoylpyrazole compound of formula I defined in claim 1 where $R^1$, $R^2$ are hydrogen;

$R^3$ is $C_1$–$C_6$-alkyl;

$R^4$ is nitro, halogen, $C_1$–$C_6$-alkyl, $C_1$–$C_6$-haloalkyl, $C_1$–$C_6$-alkoxy, $C_1$–$C_6$-alkylthio or $C_1$–$C_6$-alkylsulfonyl;

$R^5$ is hydrogen;

l is 0 or 1.

3. The tricyclic benzoylpyrazole compound of formula I defined in claim 1 where $R^{10}$ is hydroxyl;

$R^{11}$ is $C_1$–$C_6$-alkyl or $C_3$–$C_6$-cycloalkyl;

$R^{12}$ is hydrogen or $C_1$–$C_6$-alkyl.

4. A process for preparing the compound of formula I where $R^{10}$=halogen as claimed in claim 1, which comprises reacting a tricyclic benzoylpyrazole compound of formula Iα (=I where $R^{10}$=hydroxyl),

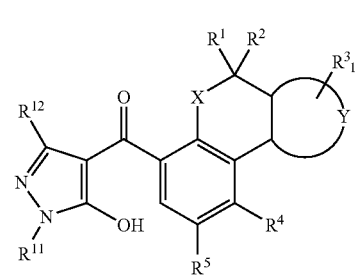

where the variables $R^1$ to $R^3$, $R^{11}$ and $R^{12}$, X, Y and l are as defined in claim 1, with a halogenating agent.

5. A process for preparing the compound of formula I where $R^{10}$=$OR^{13}$ as claimed in claim 1, which comprises reacting a tricyclic benzoylpyrazole compound of formula Iα (=I where $R^{10}$=hydroxyl),

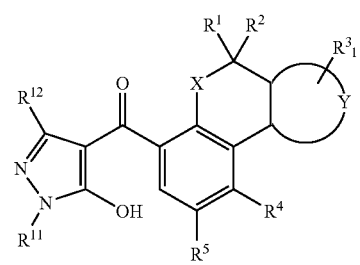

where the variables $R^1$ to $R^5$, $R^{11}$ and $R^{12}$, X, Y and l are as defined in claim 1, with a compound of formula III $$L^1\text{—}R^{13} \qquad \text{III}$$

where the variable $R^{13}$ is as defined in claim 1 and $L^1$ is a nucleophilically replaceable leaving group.

6. A process for preparing the compound of formula I where $R^{10}$=$OR^{13}$, $SR^{13}$, $NR^{15}R^{16}$ or N-bonded heterocyclyl as claimed in claim 1, which comprises reacting a compound of formula Iβ (=I where $R^{10}$=halogen),

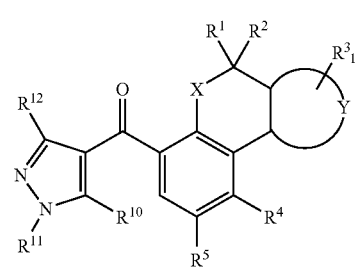

-continued

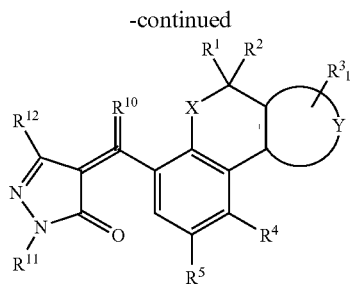

where the variables $R^1$ to $R^5$, $R^{11}$ and $R^{12}$, X, Y and l are as defined in claim 1, with a compound of formula IVα, IVβ, IVγ or IVδ

| HOR$^{13}$ | HSR$^{13}$ | NHR$^{15}$R$^{16}$ | H(N-bonded heterocyclyl) |
|---|---|---|---|
| IVα | IVβ | IVγ | IVδ | where the variables $R^{13}$ to $R^{16}$ are as defined in claim 1, optionally in the presence of a base.

7. A process for preparing the compound of formula I where $R^{10}=SO_2R^{14}$ as claimed in claim 1, which comprises reacting a compound of formula Iγ (=I where $R^{10}=SR^{14}$),

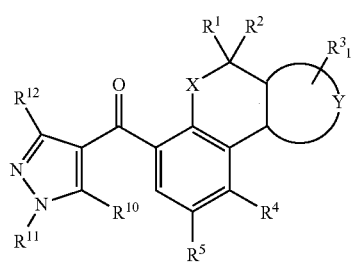

where the variables $R^1$ to $R^5$, $R^{11}$ and $R^{12}$, X, Y and l are as defined in claim 1, with an oxidizing agent.

8. A process for preparing the compound of formula I as claimed in claim 1, which comprises reacting a metalated pyrazole compound of formula V where M is a metal and $R^{10}$ to $R^{12}$ are as defined in claim 1, except for $R^{10}$=hydroxyl and mercapto, with a tricyclic benzoic acid compound of formula VIα where $R^1$ to $R^5$, X, Y and l are as defined in claim 1 and $L^2$ is a nucleophilically replaceable leaving group

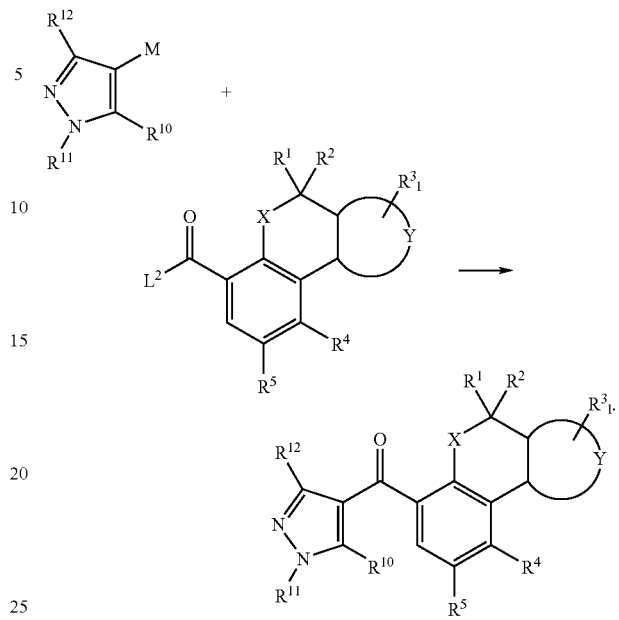

9. A process for preparing the compound of formula Iα (=I where $R^{10}$=hydroxyl) as claimed in claim 1, which comprises acylating a pyrazole of formula VII in which the variables $R^{11}$ and $R^{12}$ are as defined in claim 1

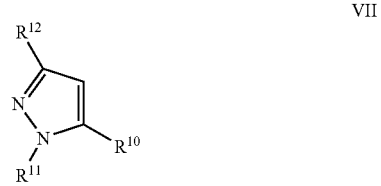

with an activated tricyclic benzoic acid of formula VIβ or with a tricyclic benzoic acid of formula VIγ,

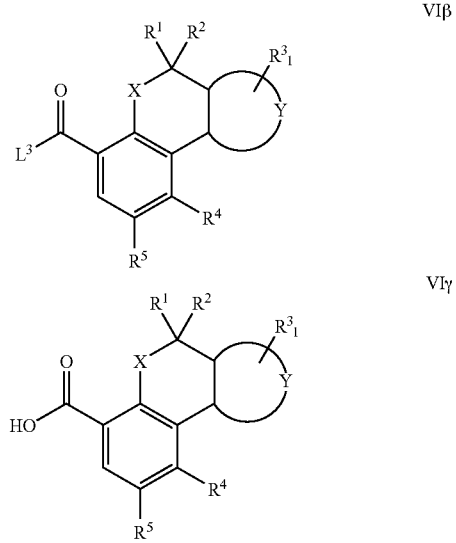

where the variables $R^1$ to $R^5$, X, Y and l are as defined in claim 1 and $L^3$ is a nucleophilically replaceable leaving group, and rearranging the acylation product, optionally in the presence of a catalyst.

10. A process for preparing the compound of formula Iα (=I where $R^{10}$=hydroxyl) as claimed in claim 1, which comprises reacting a pyrazole of formula VII in which the variables $R^{11}$ and $R^{12}$ are as defined in claim 1, or an alkali metal salt thereof,

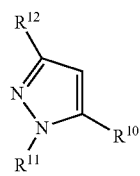

VII with a tricyclic benzene compound of formula IX where $L^4$ is a leaving group and the variables X, Y, $R^1$ to $R^5$ and l are as defined in claim 1

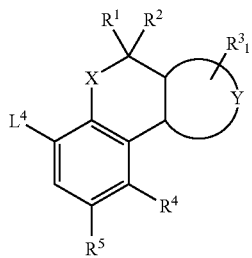

IX in the presence of carbon monoxide, a catalyst and a base.

11. A composition, comprising a herbicidally effective amount of at least one compound of formula I or an agriculturally useful salt thereof as claimed in claim 1 and auxiliaries which are customary for formulating crop protection agents.

12. A process for preparing the composition defined in claim 11, which comprises mixing a herbicidally effective amount of at least one compound of formula I or an agriculturally useful salt thereof and auxiliaries which are customary for formulating crop protection agents.

13. A method for controlling undesirable vegetation, which comprises allowing a herbicidally effective amount of at least one compound of formula I or an agriculturally useful salt thereof as claimed in claim 1 to act on plants, their habitat or on seed.

14. A tricyclic benzoic acid compound of formula VI

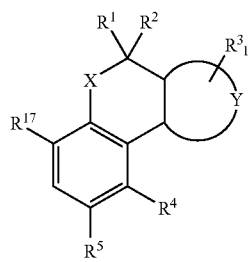

VI in which the variables X, Y, $R^1$ to $R^3$ and $R^5$ and l are as defined in claim 1 and $R^4$ is nitro, halogen, cyano, $C_1$–$C_6$-alkyl, $C_1$–$C_6$-haloalkyl, $C_1$–$C_6$-alkoxy, $C_1$–$C_6$-haloalkoxy, $C_1$–$C_6$-alkylthio, $C_1$–$C_6$-haloalkylthio, $C_1$–$C_6$-alkylsulfinyl, $C_1$–$C_6$-haloalkylsulfinyl, $C_1$–$C_6$-alkylsulfonyl, $C_1$–$C_6$-haloalkylsulfonyl, aminosulfonyl, N-($C_1$–$C_6$-alkyl)aminosulfonyl, N,N-di($C_1$–$C_6$-alkyl)aminosulfonyl, N-($C_1$–$C_6$-alkylsulfonyl)amino, N-($C_1$–$C_6$-haloalkylsulfonyl)amino, N-($C_1$–$C_6$-alkyl)-N-($C_1$–$C_6$-alkylsulfonyl)amino or N-($C_1$–$C_6$-alkyl)-N-($C_1$–$C_6$-haloalkylsulfonyl)amino;

$R^{17}$ is hydroxyl or a radical which can be removed by hydrolysis.

15. A tricyclic benzene compound of formula IX

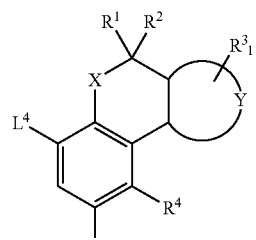

IX in which the variables X, Y, $R^1$ to $R^3$ and $R^5$ and l are as defined in claim 1 and $R^4$ is nitro, halogen, cyano, $C_1$–$C_6$-alkyl, $C_1$–$C_6$-haloalkyl, $C_1$–$C_6$-alkylthio, $C_1$–$C_6$-haloalkylthio, $C_1$–$C_6$-alkylsulfinyl, $C_1$–$C_6$-haloalkylsulfinyl, $C_1$–$C_6$-alkylsulfonyl, $C_1$–$C_6$-haloalkylsulfonyl, aminosulfonyl, N-($C_1$–$C_6$-alkyl)aminosulfonyl, N,N-di($C_1$–$C_6$-alkyl) aminosulfonyl, N-($C_1$–$C_6$-alkylsulfonyl)amino, N-($C_1$–$C_6$-haloalkylsulfonyl)amino, N-($C_1$–$C_6$-alkyl)-N-($C_1$–$C_6$-alkylsulfonyl)amino or N-($C_1$–$C_6$-alkyl)-N-($C_1$–$C_6$-haloalkylsulfonyl)amino;

$R^5$ is hydrogen or $C_1$–$C_6$-alkyl;

$L^4$ is halogen, $C_1$–$C_6$-alkylsulfonyloxy, $C_1$–$C_6$-haloalkylsulfonyloxy or phenylsulfonyloxy, where the phenyl ring of the lastmentioned radical may be unsubstituted or partially or fully halogenated and/or may carry one to three of the following radicals:

nitro, cyano, $C_1$–$C_4$-alkyl, $C_1$–$C_4$-haloalkyl, $C_1$–$C_4$-alkoxy or $C_1$–$C_4$-haloalkoxy.

16. An aniline compound of formula XV

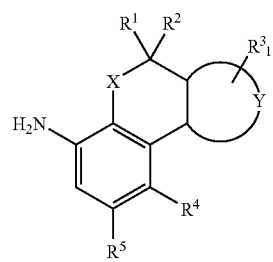

XV in which the variables X, Y, $R^1$ to $R^3$ and $R^5$ and l are in each case as defined in claim 1 and $R^4$ is nitro, halogen, cyano, $C_1$–$C_6$-haloalkyl, $C_1$–$C_6$-alkoxy, $C_1$–$C_6$-haloalkoxy, $C_1$–$C_6$-alkylthio, $C_1$–$C_6$-haloalkylthio, $C_1$–$C_6$-alkylsulfinyl, $C_1$–$C_6$-haloalkylsulfinyl, $C_1$–$C_6$-alkylsulfonyl, $C_1$–$C_6$-haloalkylsulfonyl, aminosulfonyl, N-($C_1$–$C_6$-alkyl)aminosulfonyl, N,N-di($C_1$–$C_6$-alkyl)aminosulfonyl, N-($C_1$–$C_6$-alkylsulfonyl)amino, N-($C_1$–$C_6$-haloalkylsulfonyl)amino, N-($C_1$–$C_6$-alkyl)-N-($C_1$–$C_6$-alkylsulfonyl)amino or N-($C_1$–$C_6$-alkyl)-N-($C_1$–$C_6$-haloalkylsulfonyl)amino.

17. A nitrile compound of formula XVI

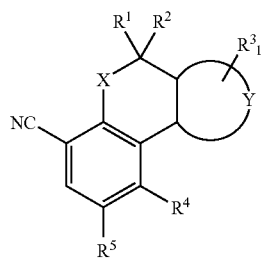

XVI in which the variables X, Y, $R^1$ to $R^3$ and l are in each case as defined in claim 1 and $R^4$ is nitro, halogen, cyano, $C_1$–$C_6$-haloalkyl, $C_1$–$C_6$-alkylthio, $C_1$–$C_6$-haloalkylthio, $C_1$–$C_6$-alkylsulfinyl, $C_1$–$C_6$-haloalkinylsulfinyl, $C_1$–$C_6$-alkylsulfonyl, $C_1$–$C_6$-haloalkylsulfonyl, aminosulfonyl, N-($C_1$–$C_6$-alkyl)aminosulfonyl, N,N-di-($C_1$–$C_6$-alkyl)aminosulfonyl, N-($C_1$–$C_6$-alkylsulfonyl)amino, N-($C_1$–$C_6$-haloalkylsulfonyl)amino, N-($C_1$–$C_6$-alkyl)-N-($C_1$–$C_6$-alkylsulfonyl)amino or N-($C_1$–$C_6$-alkyl)-N-($C_1$–$C_6$-haloalkylsulfonyl)amino;

$R^5$ is hydrogen or $C_1$–$C_6$-alkyl.

18. The compound of formula I defined in claim 1, wherein $R^{10}$ is hydroxyl, mercapto, halogen, $OR^{13}$, $SR^{13}$, $SO_2R^{14}$ or $NR^{15}R^{16}$.

\* \* \* \* \*